(12) United States Patent
Narayanan et al.

(10) Patent No.: US 10,662,148 B2
(45) Date of Patent: May 26, 2020

(54) SELECTIVE ANDROGEN RECEPTOR MODULATOR AND METHODS OF USE THEREOF

(71) Applicant: University of Tennessee Research Foundation, Knoxville, TN (US)

(72) Inventors: Ramesh Narayanan, Cordova, TN (US); Thamarai Ponnusamy, Memphis, TN (US); James T. Dalton, Ann Arbor, MI (US); Duane D. Miller, Collierville, TN (US)

(73) Assignee: UNIVERSITY OF TENNESSEE RESEARCH FOUNDATION, Knoxville, TN (US)

( * ) Notice: Subject to any disclaimer, the term of this patent is extended or adjusted under 35 U.S.C. 154(b) by 13 days.

(21) Appl. No.: 15/887,076

(22) Filed: Feb. 2, 2018

(65) Prior Publication Data

US 2018/0273470 A1     Sep. 27, 2018

Related U.S. Application Data

(60) Continuation of application No. 15/398,672, filed on Jan. 4, 2017, now Pat. No. 10,053,418, which is a continuation of application No. 14/963,130, filed on Dec. 8, 2015, now Pat. No. 9,884,038, said application No. 15/887,076 is a division of application No. 14/963,130, filed on Dec. 8, 2015, now Pat. No. 9,884,038, which is a continuation-in-part of application No. 14/062,748, filed on Oct. 24, 2013, now Pat. No. 9,889,110, which is a continuation-in-part of application No. 13/557,885, filed on Jul. 25, 2012, which is a continuation-in-part of application No. 13/082,830, filed on Apr. 8, 2011, which is a continuation-in-part of application No. 11/785,064, filed on Apr. 13, 2007, now Pat. No. 8,853,266, which is a continuation-in-part of application No. 11/634,380, filed on Dec. 6, 2006, which is a continuation-in-part of application No. 11/505,499, filed on Aug. 17, 2006, now Pat. No. 7,645,898, which is a continuation-in-part of application No. 11/505,363, filed on Aug. 17, 2006, which is a continuation-in-part of application No. 11/355,187, filed on Feb. 16, 2006, now Pat. No. 7,919,647, which is a continuation-in-part of application No. 11/220,414, filed on Sep. 7, 2005, now Pat. No. 7,855,229, which is a continuation-in-part of application No. 11/146,427, filed on Jun. 7, 2005, now Pat. No. 7,622,503, which is a continuation-in-part of application No. 10/863,524, filed on Jun. 9, 2004, which is a continuation-in-part of application No. 10/861,923, filed on Jun. 7, 2004, now Pat. No. 8,008,348.

(51) Int. Cl.
*A61K 31/277* (2006.01)
*C07C 255/54* (2006.01)

(52) U.S. Cl.
CPC ........... *C07C 255/54* (2013.01); *A61K 31/277* (2013.01)

(58) Field of Classification Search
CPC ........................... A61K 31/277; C07C 255/54
See application file for complete search history.

(56) References Cited

U.S. PATENT DOCUMENTS

| | | |
|---|---|---|
| 3,239,345 A | 3/1966 | Hodge et al. |
| 3,865,801 A | 2/1975 | Chiba et al. |
| 3,875,229 A | 4/1975 | Gold |
| 4,036,979 A | 7/1977 | Asato |
| 4,139,638 A | 2/1979 | Neri et al. |
| 4,191,775 A | 3/1980 | Glen |
| 4,239,776 A | 12/1980 | Glen et al. |
| 4,282,218 A | 8/1981 | Glen et al. |
| 4,386,080 A | 5/1983 | Crossley et al. |
| 4,411,890 A | 10/1983 | Momany et al. |
| 4,465,507 A | 8/1984 | Konno et al. |
| 4,636,505 A | 1/1987 | Tucker |
| 4,880,839 A | 11/1989 | Tucker |
| 4,977,288 A | 12/1990 | Kassis et al. |
| 5,162,504 A | 11/1992 | Horoszewicz |
| 5,179,080 A | 1/1993 | Rothkopf et al. |
| 5,441,868 A | 8/1995 | Lin et al. |
| 5,547,933 A | 8/1996 | Lin et al. |
| 5,609,849 A | 3/1997 | Kung |
| 5,612,359 A | 3/1997 | Murugesan et al. |
| 5,618,698 A | 4/1997 | Lin et al. |
| 5,621,080 A | 4/1997 | Lin et al. |

(Continued)

FOREIGN PATENT DOCUMENTS

| | | |
|---|---|---|
| AU | 2002364949 | 6/2003 |
| AU | 2003216174 | 9/2003 |

(Continued)

OTHER PUBLICATIONS

Bach (Chest, 1997, 112, 1024-28). (Year: 1997).*
Abuchowski et al. "Immunosuppressive properties and circulating life of Achromobacter glutaminase-asparaginase covalently attached to polyethylene glycol in man" Cancer Treat Rep. 65(11-12):1077-81. Nov.-Dec. 1981.
Baird et al. "Hormonal Contraception—Drug Therapy", The New England Journal of Medicine , May 27, 1993, pp. 1543-1549.
Balthasar. "Bioequivalence and Bioequivalency Testing" Am. J. Pharm. Educ., 63, 194-198, (1999).

(Continued)

*Primary Examiner* — Umamaheswari Ramachandran
(74) *Attorney, Agent, or Firm* — Mark S. Cohen; Pearl Cohen Zedek Latzer Baratz LLP

(57) ABSTRACT

This invention provides substituted acylanilide compounds and uses thereof in treating a variety of diseases or conditions in a subject including, inter alia, a muscle wasting disease and/or disorder such as Duchenne muscular dystrophy or Becker muscular dystrophy.

5 Claims, 49 Drawing Sheets

Specification includes a Sequence Listing.

(56) References Cited

U.S. PATENT DOCUMENTS

| | | |
|---|---|---|
| 5,656,651 A | 8/1997 | Sovak et al. |
| 5,735,105 A | 4/1998 | Stroud et al. |
| 6,019,957 A | 2/2000 | Miller et al. |
| 6,043,265 A | 3/2000 | Murugesan et al. |
| 6,071,957 A | 6/2000 | Miller et al. |
| 6,160,011 A | 12/2000 | Miller et al. |
| 6,482,861 B2 | 11/2002 | Miller et al. |
| 6,492,554 B2 | 12/2002 | Dalton et al. |
| 6,548,529 B1 | 4/2003 | Robl et al. |
| 6,569,896 B2 | 5/2003 | Dalton et al. |
| 6,769,226 B2 | 8/2004 | Holland et al. |
| 6,777,427 B2 | 8/2004 | Miyakawa et al. |
| 6,838,484 B2 | 1/2005 | Steiner et al. |
| 6,899,888 B2 | 5/2005 | Steiner et al. |
| 6,960,474 B2 | 11/2005 | Salvati et al. |
| 6,995,284 B2 | 2/2006 | Dalton et al. |
| 6,998,500 B2 | 2/2006 | Dalton et al. |
| 7,022,870 B2 | 4/2006 | Dalton et al. |
| 7,026,500 B2 | 4/2006 | Dalton et al. |
| 7,041,844 B2 | 5/2006 | Miller et al. |
| 7,129,377 B2 | 10/2006 | Miller |
| 7,205,437 B2 | 4/2007 | Dalton et al. |
| 7,213,511 B2 | 5/2007 | Cruttenden et al. |
| 7,214,693 B2 | 5/2007 | Dalton et al. |
| 7,344,700 B2 | 3/2008 | Dalton et al. |
| 7,365,202 B2 | 4/2008 | Tan et al. |
| 7,518,013 B2 | 4/2009 | Dalton et al. |
| 7,547,728 B2 | 6/2009 | Steiner et al. |
| 7,622,503 B2 | 11/2009 | Dalton et al. |
| 7,645,898 B2 | 1/2010 | Dalton et al. |
| 7,705,182 B2 | 4/2010 | Dalton et al. |
| 7,759,520 B2 | 7/2010 | Dalton et al. |
| 7,772,433 B2 | 8/2010 | Dalton et al. |
| 7,825,229 B2 | 11/2010 | Itzhak et al. |
| 8,080,682 B2 | 12/2011 | Dalton et al. |
| 8,354,446 B2 | 1/2013 | Zhi |
| 8,426,465 B2 | 4/2013 | Dalton et al. |
| 8,563,606 B2 | 10/2013 | Dalton et al. |
| 9,150,501 B2 | 10/2015 | Dalton et al. |
| 2001/0012839 A1 | 8/2001 | Miller et al. |
| 2002/0099036 A1 | 7/2002 | Dalton et al. |
| 2002/0099096 A1 | 7/2002 | Dalton et al. |
| 2002/0173445 A1 | 11/2002 | Salvati et al. |
| 2003/0162761 A1 | 8/2003 | Steiner et al. |
| 2003/0225040 A1 | 12/2003 | Dalton et al. |
| 2003/0229099 A1 | 12/2003 | Zhu et al. |
| 2003/0232792 A1 | 12/2003 | Dalton et al. |
| 2003/0232882 A1 | 12/2003 | Miller et al. |
| 2004/0014975 A1 | 1/2004 | Dalton et al. |
| 2004/0029913 A1 | 2/2004 | Dalton et al. |
| 2004/0053897 A1 | 3/2004 | Steiner et al. |
| 2004/0087557 A1 | 5/2004 | Steiner et al. |
| 2004/0087810 A1 | 5/2004 | Dalton et al. |
| 2004/0147489 A1 | 7/2004 | Dalton et al. |
| 2004/0197928 A1 | 10/2004 | Dalton et al. |
| 2004/0214790 A1 | 10/2004 | Borgens et al. |
| 2004/0224979 A1 | 11/2004 | Dalton et al. |
| 2004/0260092 A1 | 12/2004 | Miller et al. |
| 2004/0260108 A1 | 12/2004 | Dalton et al. |
| 2004/0265916 A1 | 12/2004 | Dalton et al. |
| 2005/0033074 A1 | 2/2005 | Dalton et al. |
| 2005/0038110 A1 | 2/2005 | Steiner et al. |
| 2005/0137172 A1 | 6/2005 | Dalton et al. |
| 2005/0154043 A1 | 7/2005 | Zhai et al. |
| 2006/0004042 A1 | 1/2006 | Dalton et al. |
| 2006/0009488 A1 | 1/2006 | Miller et al. |
| 2006/0019931 A1 | 1/2006 | Dalton et al. |
| 2006/0035965 A1 | 2/2006 | Dalton et al. |
| 2006/0088590 A1 | 4/2006 | Sukuru et al. |
| 2006/0111441 A1 | 5/2006 | Dalton et al. |
| 2006/0165744 A1 | 7/2006 | Jamil et al. |
| 2006/0183931 A1 | 8/2006 | Dalton et al. |
| 2006/0229362 A1 | 10/2006 | Dalton et al. |
| 2006/0276539 A1 | 12/2006 | Dalton et al. |
| 2006/0287349 A1 | 12/2006 | Meissner et al. |
| 2007/0066568 A1 | 3/2007 | Dalton et al. |
| 2007/0123563 A1 | 5/2007 | Dalton et al. |
| 2007/0161608 A1 | 7/2007 | Dalton et al. |
| 2007/0173546 A1 | 7/2007 | Dalton et al. |
| 2007/0281906 A1 | 12/2007 | Dalton et al. |
| 2008/0076828 A1 | 3/2008 | Dalton et al. |
| 2009/0088480 A1 | 4/2009 | Dalton et al. |
| 2009/0264534 A1 | 10/2009 | Dalton et al. |
| 2010/0022641 A1 | 1/2010 | Dalton et al. |
| 2010/0137430 A1 | 6/2010 | Dalton et al. |
| 2010/0144871 A1 | 6/2010 | Steiner et al. |
| 2010/0249228 A1 | 9/2010 | Dalton et al. |
| 2010/0280107 A1 | 11/2010 | Dalton et al. |
| 2013/0034562 A1 | 2/2013 | Dalton et al. |
| 2014/0018433 A1 | 1/2014 | Dalton et al. |
| 2014/0080905 A1 | 3/2014 | Dalton et al. |
| 2014/0350102 A1 | 11/2014 | Dalton et al. |
| 2016/0128968 A1 | 5/2016 | Dalton et al. |

FOREIGN PATENT DOCUMENTS

| | | |
|---|---|---|
| CA | 1305665 | 7/1992 |
| CA | 2149240 | 5/1994 |
| CA | 2247946 | 10/1997 |
| CA | 2281570 | 9/1998 |
| CA | 2313089 | 6/1999 |
| CA | 2344316 | 3/2000 |
| CA | 2420279 | 2/2002 |
| CA | 2458452 A1 | 2/2003 |
| CA | 2477737 | 9/2003 |
| CA | 2502209 | 4/2004 |
| CA | 2502355 | 4/2004 |
| CA | 2538095 | 4/2004 |
| CA | 2529464 | 1/2005 |
| CA | 2536518 | 2/2005 |
| CN | 1825959 A | 8/2006 |
| EA | 200602278 | 4/2007 |
| EP | 0040932 | 2/1981 |
| EP | 0100172 | 2/1984 |
| EP | 0002892 | 2/1985 |
| EP | 0253503 | 12/1991 |
| EP | 668351 | 8/1995 |
| EP | 1221439 | 7/2002 |
| EP | 1401801 | 11/2006 |
| EP | 1801140 | 6/2007 |
| GB | 1360001 | 3/1970 |
| JP | 52-128329 | 10/1977 |
| JP | 54-63047 | 12/1980 |
| JP | 59-033250 | 2/1984 |
| JP | 2006-199704 | 3/2006 |
| KR | 20040101251 | 12/2004 |
| WO | WO 1989/007110 | 8/1989 |
| WO | WO 1989/007111 | 8/1989 |
| WO | WO 1991/005867 | 5/1991 |
| WO | WO 1993/004081 | 3/1993 |
| WO | WO 1995/019770 | 7/1995 |
| WO | WO 1998/005962 | 2/1998 |
| WO | WO 1998/053826 A1 | 12/1998 |
| WO | WO 1998/055153 | 12/1998 |
| WO | WO 2000/001389 | 1/2000 |
| WO | WO 2001/27086 | 4/2001 |
| WO | WO 2001/027622 | 4/2001 |
| WO | WO 2001/028990 | 4/2001 |
| WO | WO 2001/034563 | 5/2001 |
| WO | WO 2001/068603 | 9/2001 |
| WO | WO 2002/000617 | 1/2002 |
| WO | WO 2002/016310 | 2/2002 |
| WO | WO 2002/22585 | 3/2002 |
| WO | WO 2003/011302 | 2/2003 |
| WO | WO 2003/049675 | 6/2003 |
| WO | WO 2003/065992 | 8/2003 |
| WO | WO 2003/074449 | 9/2003 |
| WO | WO 2003/074471 | 9/2003 |
| WO | WO 2003/077919 | 9/2003 |
| WO | WO 2004/034978 | 4/2004 |
| WO | WO 2004/035736 | 4/2004 |
| WO | WO 2004/035738 | 4/2004 |
| WO | WO 2004/062612 | 7/2004 |
| WO | WO 2004/064747 A2 | 8/2004 |

(56) References Cited

FOREIGN PATENT DOCUMENTS

| WO | WO 2005/000794 | 1/2005 |
|---|---|---|
| WO | WO 2005/037201 | 4/2005 |
| WO | WO 2005/037205 | 4/2005 |
| WO | WO 2005/037206 | 4/2005 |
| WO | WO 2005/060647 | 7/2005 |
| WO | WO 2005/120483 | 8/2006 |
| WO | WO 2007/027582 A2 | 3/2007 |
| WO | WO 2008/024456 | 7/2008 |
| WO | WO 2008/127717 | 10/2008 |
| WO | WO 2009/036206 | 3/2009 |
| WO | WO 2009/137602 A1 | 11/2009 |
| WO | WO 2009/155481 | 12/2009 |
| WO | WO 2012/139093 A2 | 10/2012 |

OTHER PUBLICATIONS

Belani, C.P. et al, "Development of docetaxel in advanced non-small-cell lung cancer." Lung Cancer, 46, pp. S3-S11, 2004.
Belani; "Development of dosetoxel in advanced non-small-cell lung cancer", Lung Cancer, 46, Suppl 2, 2004, S3-S11.
Belikov "Pharmaceutical chemistry", high school, 1993, vol. 1, pp. 43-47.
Berger et al., "Concepts and limitations in the application of radiolabeled antiandrogens, estrogens, or androgens as isotropic scanning agents for the prostate", Invest. Urol, (1975), 1391, 10-16.
Bhasin et al. "Drug insight: Testosterone and selective androgen receptor modulators as anabolic therapies for chronic illness and aging" Nature, Clinical Practice in Endocrinology and Metabolism, 2(3): 146-159,2006.
Bisson et al. "Discovery of antiandrogen activity of nonsteroidal scaffolds of marketed drugs" Proceedings of the National Academy of Sciences, U S A. 104(29): 1192741932, 2007.
Bohl et al. "A Ligand-based Approach to Identify Quantitative Structure Activity Relationships for the Androgen Receptor". The AAPS Journal, vol. 6, No. 4, Abstract #W4111, Nov. 2004.
Bohl et al. "A Ligand-Based Approach to Identify Quantitative Structure-Activity Relationships for the Androgen Receptor" Journal of Medicinal Chemistry, 47(15):3765-3776, 2004.
Bohl et al. "Structural Basis for Antagonism and Resistance of Bicalutamide in Prostate Cancer" Proc Natl Acad Sci USA. 102(17): 6201-6206, 2005.
Bohl et al. "Structural Basis for Accomodation of Nonsteroidal Ligaiids in the Androgen Receptor". Journal of Biological Chemistry, 280(45):37747-37754, 2005.
Bohl et al. "Crystal structure of the TS77A human androgen receptor Ugand-binding domain completed to cyproterone acetate provides insight for ligand-induced conformational changes and structure-based drug design". Journal of Biological Chemistry, 282(18):13648-13655,2007.
Boyanov MA et al. "Testosterone supplementation in men with type 2 diabetes,visceral obesity and partial androgen deficiency" Aging Male., vol. 6 No. 1, pp. 1-7, Mar. 2003.
Brittain et al., editors "Polymorphism in pharmaceutical solids", Chapter 1 pp. 1-10 and Guillory Chapter 5 pp. 183-226, 1999.
Brown et al. Nonsteroidal Selective Androgen Receptors Modulators (SARMs) Designer Androgens with Flexible Structures Provide Clinical Promise Endocrinology 145: 5417-5419, (2004).
Bruera et al. ABC of palliative care. Anorexia, cachexia, and nutrition. BMJ, 315: 1219-1222, (1997).
Buchwald et al. "Long-term, continuous intravenous heparin administration by an implantable infusion pump in ambulatory patients with recurrent venous thrombosis."Surgery 88:507 (1980).
Byrn et al.; "Pharmaceutical Solids: A Strategic Approach to Regulatory Considerations"; Pharmaceutical research, vol. 12, No. 7. p. 945-954 (1995).
Cabrespine et al. "Randomized phase II study comparing paclitaxel and carboplatin versus mitoxantrone in patients with hormone-refractory prostate cancer" Urology. Feb. 28, 2006;67(2):354-9.
Caira et al. "Crystalline Polymorphism of Organic Compounds", Topic in current chemistry vol., 1998, 198:163-208.

Campfield et al., 1995, "Recombinant mouse OB protein: evidence for a peripheral signal linking adiposity and central neural networks" Science 269:546-549.
Caprio et al.; "Fat distribution and cardiovascular risk factors in obese adolescent girls: importance of the intraabodomina fat dept", Am J Clin Nutr 1996;64:12-7.
Chen et al. "A Selective Androgen Receptor Modulator (SARM) for Hormonal Male Contraception". Journal of Pharmacology and Experimental Therapeutics, 312(2): 546-553,2005.
Chen et al. "Discovery and Therapeutic Promise of Selective Androgen Receptor Modulators" Molecular Interventions, 5(3):173-188I 2005.
Chen et al. "In vitro and in vivo structure-activity relationships of novel androgen receptor ligands with multiple substituents in the B-ring". Endocrinology, 146(12):5444-54, 2005.
Considine et al., 1995, "Evidence against either a premature stop codon or the absence of obese gene mRNA in human obesity." J. Clin. Invest. 95:2986-2988.
Corey (1987) "Asymmetric Bromolactonization Reaction: Synthesis of Optically Active 2-hydroxy-2-Methylalkanoic Acids from 2-Methylalkanoic Acids" Tetrahedron Letters vol. 28, No. 25 2801-2804.
Dalton et al., "Therapeutic Promise of Selective Androgen Receptor Modulators (SARS): Preclinical and Clinical Proof-of-Concept Studies"—The Endocrine Society—Programs and Abstracts—89th Annual meeting—Paper S41-2.
Dalton et al. Discovery of Nonsteroidal Androgens. Biochem. Biophys. Res. Commun.,244(1):1-4, 1998.
Dalton et al "Pharmacokinetics of Aminolevulinic Acid after Oral and Intravenous Dosing in Dogs." Drug Metabolism and Disposition, 27 (4):432-435, 1999.
De Amicis et al. "Androgen receptor overexpression induces tamoxifen resistance in human breast cancer cells", Breast Cancer Res Treat. May 2010;121(1):1-11.
Dewys et al. "Prognostic effect of weight loss prior to chemotherapy in cancer patients" Eastern Cooperative Oncology Group. Am J Med.; 69(4): 491-7. (1980).
Diebold et al. "Innate antiviral responses by means of TLR7-mediated recognition of single-stranded RNA". Science. Mar. 5, 2004;303(5663):1529-31.
Djerassi et al. "A new look at male contraception", Nature, vol. 370, pp. 11-12.
Edwards et al. "Nonsteroidal androgen receptor agonists based on 4-(trifluoromethyl)-2H-pyrano[3,2-g]quinolin-2-one. Bioorg" Med. Chem. Lett., 9: 1003, 1999.
Edwards et al. "New nonsteroidal androgen receptor modulators based on 4-(trifluoromethyl)-2-(1H)-Pyrololidino[3,2-g]quinolone". Bioorg. Med. Chem. Lett., 8: 745, 1998.
Eliason et al., "High Throughput Fluorescence Polarization-Based Screening Assays for the Identification of Novel Nuclear Receptor Ligands," Abstracts of Papers, 223rd ACS National Meeting, Orlando, FL, United States, (2002), Apr. 7, 2002.
Fisher et al. "Preclinical Pharmacology and Pharmacokinetics of a Novel A-ring Substituted Selective Androgen Receptor Modulator (SARM) in Rats" The AAPS Journal, vol. 6, No. 4, Abstract #T2256, Nov. 2004.
Faulkner et al (1991) "Noninvasive measurements of bone mass, structure, and strength: current methods and experimental techniques." Am J Rosentgenology 157:1229-1237.
Foulks et al. "Blepharitis: A Review for Clinicians", Refractive Eyecare vol. 13, No. 3, Mar. 2009.
Francisco et al., "Long-acting contraceptive agents: testosterone esters of unsaturated acids", Steroids, Jan. 1990, vol. 55, Butterworths.
Fukui et al. "Role of endogenous androgen against insulin resistance and atherosclerosis in men with type 2 diabetes" Curr Diabetes Rev., vol. 3 No. 1, pp. 25-31, Feb. 2007.
Gao et al. "Difference in the Metabolism of Selective Androgen Receptor Modulators (SARMs)" PharmSci 5 (4): T3336, 2003.
Gao et al. "Regulation of Cytochrome P450s by Selective Androgen Receptor Modulators (SARMs) in Primary Culture of Human Hepatocytes". PharmSci 5 (4): T3 3 3 8, 2003.

(56) References Cited

OTHER PUBLICATIONS

Gao et al. "Effects of a Novel Selective Androgen Receptor Modulator (SARM) on Skeletal Muscle Mass and Strength in Castrated Male Rats" The Endocrine Society, New Orleans, Abstract # P2-120, Jun. 2005.

Gao et al. "Pharmacologic Effects of a Novel Selective Androgen Receptor Modulator (SARM), Flutamide and Finasteride in Intact Male Rats" The Endocrine Society, Philadelphia, Jun. 2003, Abstract #P3-221.

Gao et al. "In Vitro Metabolism and In Vivo Tissue Selectivity of Andarine" PharmSci 4(4): 2002.

Gao, et al. "Comparison of the Pharmacological Effects of a Novel Selective Androgen Receptor Modulator (SARM), the 5{alpha}-Reductase Inhibitor Finasteride, and the Antiandrogeo Hydroxyflutamide in Intact Rats: New Approach for Benign Prostate Hyperplasia (BPH)" Endocrinology, 145(12): 5420-5428, 2004.

Gao et al. "Selective Androgen Receptor Modulator (SARM) Treatment Improves Muscle Strength and Body Composition, and Prevents Bone Loss in Orchidectomized Rats" Endocrinology, 146(11):4887-4897, 2005.

Gao et al. "Chemistry and structural biology of androgen receptor" Chemical Reviews, 1G5(9):3352-70,2005.

Gao et al. "Inter-Species Differences in Pharmacokinetics and Metabolism of S-3-(4-acelylamino-phenoxy)-2-hydroxy-2-methyl-N-(4-nitro- 3-trifluoromethyi-phenyl>propionamide: The Role of N-Acetyltransferase" Drug Metabolism and Disposition, 34(2):254-260, 2006.

Gao et al. "Characterization of the In vitro Metabolism of Selective Androgen Receptor Modulator (SARM) Using Human, Rat and Dog Liver Enzyme Preparations". Drug Metabolism and Disposition, 34(2):243-253, 2006.

Gao et al. "Pharmacokinetics and Pharmacodynamics of Nonsteroidal Androgen Receptor Ligands"Pharmaceutical Research, 23(8):1641-165B, 2006.

Gao et al. "Expanding the therapeutic use of androgens via selective androgen receptor modulators (SARMs)". Drug Discovery Today, 12(5-6):241-248, 2007.

Gao et al. "Ockham's razor and selective androgen receptor modulators (SARMs): are we overlooking the role of 5a-reductase?"Molecular Interventions, 7(1):1Q-13, 2007.

Garay et al. "Androgen receptor as a targeted therapy for breast cancer", Am J Cancer Res. 2012;2(4):434-45.

Goodson, in Medical Applications of controlled Release, supra, vol. 2, pp. 115-138 (1984).

Grundy, Metabolic and health complications of obesity, 1990, Disease-a-Month 36:Dec.; 36(12):641-731.

Hamann et al. "Discovery of a potent, orally active nonsteroidal androgen receptor agonist: 4-ethyl-1,2,3,4-tetrahydro-6-(trifluoromethyl)-8-pyridono[5,6-g]-quinoline (LG121071)" J. Med. Chem., 42: 210, 1999.

Hanada et al (2003) "Bone anabolic effects of S-40503, a novel nonsteroidal selective androgen receptor modulator (SARM), in rat models of osteoporosis." Biol. Pharm. Bull. 26:1563-1569.

Halaas et al., 1995, "Weight-reducing effects of the plasma protein encoded by the obese gene." Science 269:543-546.

Hamilton et al., 1995, Increased obese mRNA expression in omental fat cells from massively obese humans. Nature Med. 1:953.

Handelsman "Bridging the gender gap in contraception: another hurdle cleared" The Medical Journal of Australia, vol. 154, Feb. 18, 1996, pp. 230-233.

He et al. "Novel Nonsteroidal Ligands with High Affinity and Potent Functional Activity for the Human Androgen Receptor" European Journal of Medicinal Chemistry, 37: 619-634, 2002.

Heil et al. "Pecies-specific recognition of single-stranded RNA via toll-like receptor 7 and 8" Science. Mar. 5, 2004;303(5663):1526-9.

Higuchi et al. "4-Alkyl- and 3,4-diaklyl-1,2,3,4-tetrahydro-8-pyridono[5,6-g]quinolines: potent, nonsteroidal androgen receptor agonists". Bioorg. Med. Chem. Lett., 9:1335,1999.

Hoberman et al. "The History of Synthetic Testosterone", Scientific American, Feb. 1995, pp. 76-81.

Hwang et al. "Synthesis and testing of both reversible and irreversible selective androgen receptor modulators (SARMs) for prostate cancer" Abstracts of Papers of the American Chemical Society, 231: 274-MEDI, Mar. 26 2006.

Hwang et al. "Synthesis and biological testing of (2S)-multU halogenated B-ring 2-hydroxy-2-methylpropionamide selective androgen receptor modulators (SARMs): Probing the B-ring pocket" Abstracts of Papers of the American Chemical Society, 229: U140-U140 176-MEDI Part 2, Mar. 13, 2005.

Hwang et al. "Synthesis of isothiocyanate derivatives of irreversible selective androgen receptor modulators (SARMs) and biological testing in prostate cancer cell lines" Abstracts of Papers of the American Chemical Society, 229: U140-U140 177-MEDI Part 2, Mar. 13, 2005.

Hwang et al. "Aryl isothiocyanato selective androgen receptor modulators (SARMs) for prostate cancer". Bioorganic and Medicinal Chemistry, 14(19):6525-6538, 2006.

International Search Report Application No. PCT/US 12/63048 dated Jan, 8, 2013.

International Search Report for PCT Application No. PCT/US14/62239 dated Feb. 4, 2015.

International Search Report for Application No. PCT/US08/04816 dated Jul. 8, 2008.

International Search Report for Application No. PCT/US05/19788 dated Jun. 16, 2006.

International Search Report for PCT/US2012/032707 dated Jun. 21, 2012.

Joffre et al. "Differences in meibomian fatty acid composition in patients with meibomian gland dysfunction and aqueous-deficient dry eye", Br J Ophthalmol. Jan. 2008;92(1):116-9.

Kalu, DN, (1991) "The ovariectomized rat model of postmenopausal bone loss. Bone Miner." 15 175-91.

Katre et al. "Chemical modification of recombinant interleukin 2 by polyethylene glycol increases its potency in the murine Meth A sarcoma model" Proc Natl Acad Sci U S A. 84(6):1487-91. Mar. 1987.

Kearbey et al. "Selective androgen receptor modulators inhibit bone resorption in rats" PharmSci 5 (4): R6167, 2003.

Kearbey et al. "Selective Androgen Receptor Modulator (SARM) Treatment Prevents Bone Loss and Reduces Body Fat in Ovariectomized Rats" Pharmaceutical Research, 24(2):328-335, 2006.

Kearbey et al. (2004) "Pharmacokinetics of S-3-(4-acetylamino-phenoxy)-2-hydroxy-2-methyl-N-(4-nitro- 3-trifluoromethyl-phenyl)-propionamide in rats, a non-steroidal selective androgen receptor modulator" Xenobiotica 34(3), 273-80.

Kelly et al. "Dose escalation study of intravenous estramustine phosphate in combination with Paclitaxel and Carboplatin in patients with advanced prostate cancer" Clinical cancer research. Jun. 1, 2003;9(6):2098-107.

Kim et al. "Structure-Activity Relationships for Modification of the Linkage Group and B-Ring of Selective Androgen Receptor Modulators" The AAPS Journal, vol. 7(S2):T2117,2005.

Kim et al. "In vitro and In vivo Pharmacologic Activity of 4-Halo Substituted SARMs" The Endocrine Society, Philadelphia, Jun. 2003, Abstract #P3-198.

Kim et al. "The 4-Para-Substituent of S-3-(Phenoxy)-2-hydroxy-2-methyl-N-(4-nitro-3-trifluoromethyl-phenyl-propionamides is a Major Structural Determinant of In Vivo Disposition and Activity of Selective Androgen Receptor Modulators" Journal of Pharmacology and Experimental Therapeutics, 315(I):230-239, 2005.

Kirkovsky et al., "[125I]-Radionated Bicalutamide Analogs as Potential Imaging Agents for Prostate Cancer", Poster Presentation MEDI 155, 214th ACS National Meeting, Las Vegas, NV, Sep. 7-11, 1997, Department of Pharmaceutical Sciences, University of Tennessee, Memphis, TN 38163.

Kirkovsky et al. "Approaches to Irreversible non-steroidal chiral antiandrogens" Department of Pharmaceutical Sciences, University of Tennessee, 47th Southeast/51st Southwest Joint Regional Meeting of the American Chemical Society, Memphis, TN, Nov. 29-Dec. 1, 1995.

(56) References Cited

OTHER PUBLICATIONS

Kirkovsky et al. "Chiral Nonsteroidal Affinity Ligands for the Androgen Receptor. 1. Bicalutamide Analogs bearing Electrophilic Groups at the Aromatic Ring B" Journal of Medicinal Chemistry, 43: 581-590, 2000.

Kori et al. "Early Phase II Study of Combination Chemotherapy of Docetaxel and Carboplatin in Patients With Postoperative Recurrent Adenocarcinoma of the Lung", Apr. 20, 2002, Japanese Journal of Jung Cancer, vol. 42, No. 2, pp. 85-91.

Koski GK et al. "Cutting edge: innate immune system discriminates between RNA containing bacterial versus eukaryotic structural features that prime for high-level IL-12 secretion by dendritic cells" J Immunol. Apr. 1, 2004;172(7):3989-93.

Laaksonen et al., "Sex hormones, inflammation and the metabolic syndrome: a population-based study", European Journal of Endocrinology, Dec. 2003, vol. 149, No. 6, pp. 601-608.

Langer (1990) "New methods of drug delivery" Science 249:1527-1533.

Lönnqvist et al. "Overexpression of the obese (ob) gene in adipose tissue of human obese subjects" Nature medicine. Sep. 1995;1(9):950-3.

Lopez-Berestein in Liposomes in the Therapy of Infectious Disease and Cancer, Lopez-Berestein and Fidler (eds.), Liss, New York, pp. 317-327. (1984).

MacDonald et al. "Understanding and managing cancer cachexia", J. American College of Surgeons, vol. 197, pp. 143-161, 2003.

Marhefka et al. "Homology Modeling Using Multiple Molecular Dynamics Simulations and Docking Studies of the Human Androgen Receptor Ligand Binding Domain Bound to Testosterone and Nonsteroidal Ligands" Journal of Medicinal Chemistry, 44: 1729-1740, 2001.

Marhefka et al. (2004) "Design, synthesis, and biological characterization of metabolically stable selective androgen receptor modulators" J Med Chem 47(4), 993-8.

Matsumoto, 1994, "Hormonal therapy of male hypogonadism" Endocrinol. Met. Clin. N. Am. 23:857-75.

McKillop et al., "Enantioselective metabolism and pharmacokinetics of Casodex in the male rat", Xenobiotica, 1995, vol. 25, No. 6, 623-634.

Mishra et al. "Expression of androgen receptor in breast cancer & its correlation with other steroid receptors & growth factors", Indian J Med Res. Jun. 2012;135(6):843-52.

Monaco et al. "Cloning of the Duchenne/Becker muscular dystrophy locus", Adv Hum Genet. 1988;17:61-98.

Mukherjee et al. Enantioselective Binding of Casodex to the Androgen Receptor. Xenobiotica 26(2): 117-122, 1996.

Mukherjee et al. "Affinity Labeling of the Androgen Receptor with Nonsteroidal Chemoaffinity Ligands" Biochemical Pharmacology, 58: 1259-1267, 1999.

Mukherjee et al. "Development of Nonsteroidal Androgen Receptor Ligands for Imaging Prostate Tumors". PharmSci, 1(1):S-681, 1998.

Nair et al. "Synthesis of Novel Iodo Derived Bicalutamide Analogs" Tetrahedron Letters, 45: 9475-9477, 2004.

Nair et al. "Synthesis of irreversibly binding bicalutamide analogs for imaging studies" Tetrahedron Letters. 46:4821-4823, 2005.

Nair et al. "Synthesis of oxazolidinedione derived bicalutamide analogs" Tetrahedron Letters, 47 (23): 3953-3955, 2006.

Narayanan et al "Steroidal Androgens and Nonsteroidal, Tissue Selective Androgen Receptor Modulators (SARM) Regulate Androgen Receptor Function Through Distinct Genomic and Non-Genomic Signaling Pathways." The Endocrine Society—Programs and Abstracts—89th Annual Meeting—Paper P1-595.

Narayanan et al. "Molecular Mechanism for the Tissue Selectivity of a Novel Non-Steroidal Selective Androgen Receptor Modulator: Genome-Wide Mapping of Androgen Receptor Binding Sites" The Endocrine Society, Boston, Abstract # OR49-1, Jun. 2006.

Narayanan et al. "Steroidal Androgens and Nonsteroidal, Tissue Selective Androgen Receptor Modulators (SARM) Regulate Androgen Receptor Function Through Distinct Genomic and Non-Genomic Signaling Pathways" The Endocrine Society, Toronto, Abstract #PI-595, Jun. 2007.

Negro-Vilar, A. (1999) "Selective androgen receptor modulators (SARMs): a novel approach to androgen therapy for the new illennium." J. Clin. Endocrin Metabol. 84: 3459-3462.

Nelson, S. D. (2001). Structure Toxicity Relationships—How Useful Are They in Predicting Toxicities of New Drugs? In Biological reactive intermediates VI (pp. 33-43). Springer US.

Njelekela et al.; "Obesity and lipid Profiles in Middle Aged Men and Women in Tanzania", East African Medical Journal, Vo. 79 No. 2, Feb. 2002.

Office Action for Japanese Application No. 2014-005551 dated Jan. 27, 2015.

Office Action for Russian Patent Application No. 2011137324 dated Jan. 30, 2014.

Patil et al. Cesium fluoride and tetra-n-butylammonium fluoride mediated 1,4-N—O shift of disubstituted phenyl ring of a bicalutamide derivative. Tetrahedron Letters, 47:3941-3944, 2006.

Pelleymounter et al. 1995, "Effects of the obese gene product on body weight regulation in ob/ob mice" Science 269:540-543.

Perera et al. "Pharmacokinetics and Allometric Scaling of Andarine" PharmSci 4(4): 2002.

Rosen et al. "Intracellular receptors and signal transducers and activators of transcription superfamilies: novel targets for small-molecule drug discovery" J. Med. Chem., 38: 4855, 1995.

Rosen et al. "Novel, non-steroidal, selective androgen receptor modulators (SARMs) with anabolic activity in bone and muscle and improved safety profile", J Musculoskel Neuron Interact 2002, 2(3):222-224.

Saudek et al."A preliminary trial of the programmable implantable medication system for insulin delivery." N. Engl. J. Med. 321:574 (1989).

Sefton, 1987, "Implantable pumps." CRC Crit. Ref. Biomed. Eng. 14:201.

Segal et al. "Therapeutic potential of the SARMs: revisiting the androgen receptor for drug discovery" Expert Opinion in Investigational Drugs. 15(4):377-87, 2006.

Sharifi et al. "A bifunctional colchicinoid that binds to the androgen receptor" Molecular Cancer Therapeutics, 6(8):2328-2336, 2007.

Silverman "The Organic Chemistry of Drug Design and Drug Action", Academic Press, 1992, pp. 15-22.

Singh et al., 2003, "Androgens stimulate myogenic differentiation and inhibit adipogenesis in C3H 10T1/2 pluripotent cells through an androgen receptor-mediated pathway." Endocrinology, 144(11):5081-8.

Steinberger et al. "Effect of chronic Administration of Testosterone Enanthate on Sperm Production and Plasma Testosterone, Follicle Stimulating Hormone, and Luteinizing Hormone Levels: a Preliminary Evaluation of possible Male Contraceptive" Fertility and Sterility 28:1320-28 (1977).

Sullivan et al. "Androgen deficiency, meibomian gland dysfunction, and evaporative dry eye" Annals of the New York Academy of Sciences. Jun. 1, 2002:966(1)211-22.

Sundaram et al. "7 Alpha-Methyl-Nortestosterone (MENT): The Optimal Androgen for Male Contraception", Ann. Med., 25:199-205 (1993).

Supplementary European Search Report of Application No. EP 05 75 8756 dated May 29, 2008.

Treat et al., in Liposomes in the Therapy of infections disease and cancer, Lopez-Berestein and Fidler (eds.), Liss New York, pp. 353-365 (1989).

Tucker et al. "Resolution of the non steroidal antiandrogen 4'-cyano-3-[(4-fluorophenyl) sulfonyl]-2-hydroxy-2-methyl-3'-(trifluoromethyl) propionanilide and the determination of the absolute configuration of the active enantiomer" Journal of medicinal chemistry. Apr. 1988;31(4):885-7.

Wu et al. "The Favorable Effects of Weak Acids on Negative-Ion Electrospray Mass Spectrometry" Analytical Chemistry, 76(3):839-847, 2004.

Wu "Effects of Testosterone Enanthate in Normal Men: Experience from a Multicenter contraceptive efficacy study", Fertility and Sterility 65:626-36 (1996).

(56) References Cited

OTHER PUBLICATIONS

Wu et al. "Pharmacokinetics and metabolism of a selective androgen receptor modulator (SARM) in rats—implication of molecular properties and intensive metabolic profile to investigate ideal pharmacokinetic characteristics of a propanamide in preclinical study" Drug Metabolism and Disposition, 34(3):483-494, 2006.
Xu et al. "In Vitro and In Vivo Anticancer Activity of S-NTBA for Prostate Cancer" PharmSci 5 (4): T2378, 2003.
Tucker et al "Nonsteroidal antiandrogens. Synthesis and structure-activity relationships of 3-substituted derivatives of 2-hydroxypropionanilides." J. Med Chem (1988), 31, 954-959.
Vippagunta et al. "Crystalline solids", Adv Drug Deliv Rev. May 16, 2001;48(1):3-26.
Watkins, "Cardiovascular disease, hypertension, and lipids", BMJ. Apr. 19, 2003;326(7394):874-6.
Wahner, et al (1985) "Bone Mineral Density of the Radius" J. Nucl Medicine 26 13-39.
Wahner, et al (1984) "Assesment of Bone Mineral Part 1 " J Nucl. Medicine, 1134-1141.
Wang et al. "Androgen Receptor Mediated Transcriptional Activation of SARMs is Enhanced by Nuclear Receptor Coactivators" The Endocrine Society, Philadelphia, Jun. 2003, Abstract #P2-95.
World Health Organisation Task Force on Methods for the Regulation of Male Fertility, "Contraceptive efficacy of testosterone-induced azoospermia in normal men", The Lancet, vol. 336, Oct. 20, 1990, pp. 955-959and 1517-1518.
World Health Organization Task Force on Methods and Regulation of Male Fertility "Contraceptive Efficacy of Testosterone-Induced Azoospermia and Oligospermia in Normal Men", Fertility & Sterility 65:821-29 (1996).
Wu "Male Contraception: Current Status and Future Prospects" Clinical Endocrinology, (1988), 29, pp. 443-465.
Wu et al. "Urinary Metabolites of S-I, ANovel Selective Androgen Receptor Modulator (SARM), in Rats" The AAPS Journal, vol. 6, No. 4, Abstract #W53OO, Nov. 2004.
Xu et al. "Pharmacodynamics of Electrophilic Androgen Receptor Ligands in Prostate Cancer Cell Lines" PharmSci 4(4): 2002.
Yang et al. "Preclinical pharmacology of a nonsteroidal ligand for androgen receptor mediated imaging of prostate cancer" Journal of Pharmacology and Experimental Therapeutics, 317(I):402-408, 2006.
Yepuru et al "AN Angrogen Receptor-b Specific Selective Estrogen Receptor Modulator (SERM) Inhibits the Growth of the Prostate Cancer Cells and Stromal-Epithilial Tumor Xenograft" The Endocrine Society—Programs and Abstracts—89th Annual Meeting—Paper OR6-3.
Yin et al. "Key Structural Features of Nonsteroidal Ligands for Binding and Activation of the Androgen Receptor" Molecular Pharmacology, 63:211-223, 2003.
Yin et al. "Pharmacology, Pharmacokinetics and Metabolism of Acetothiolutamide, A Novel Nonsteroidal Agonist for the Androgen Receptor" Journal of Pharmacology and Experimental Therapeutics, 304(3):1323-1333, 2003.
Yin et al. "Pharmacodynamics of Selective Androgen Receptor Modulators" Journal of Pharmacology and Experimental Therapeutics, 304(3): 1334-1340, 2003.
Yin et al. "In Vitro Pharmacology and In Vivo Pharmacokinetics of (R)-Para-Acetamido-Bicalutamide" PharmSci, 1(4):S-3185, 1999.
Zhi et al. "Switching androgen receptor antagonists to agonists by modifying C-ring substituents on piperidino[3,2-g]quinolone "Bioorg. Med. Chem. Lett., 9: 1009, 1999.
Zhou et al, "Pecificity of ligand-dependent androgen receptor stabilization: receptor domain interactions influence ligand dissociation and receptor stability" Molecular Endocrinology. Feb. 1995;9(2):208-18.
Zilbermint et al. "Nonsteroidal selective androgen receptor modulator Ostarine in cancer cachexia" Future Oncol. (2009) 5(8) pp. 1211-1220.

\* cited by examiner

- $p < 0.05$; **$p<0.01$

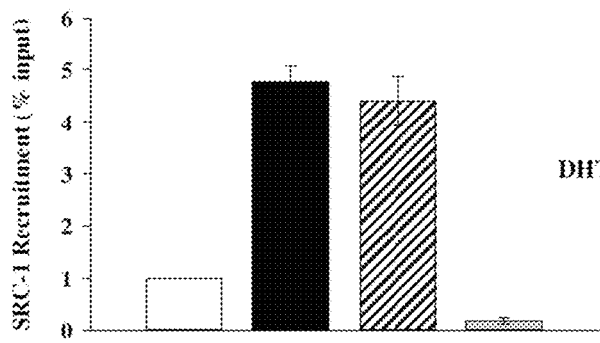
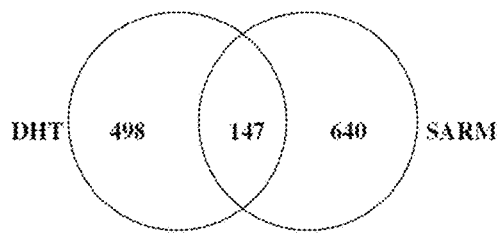
FIGURE 15A  FIGURE 15B
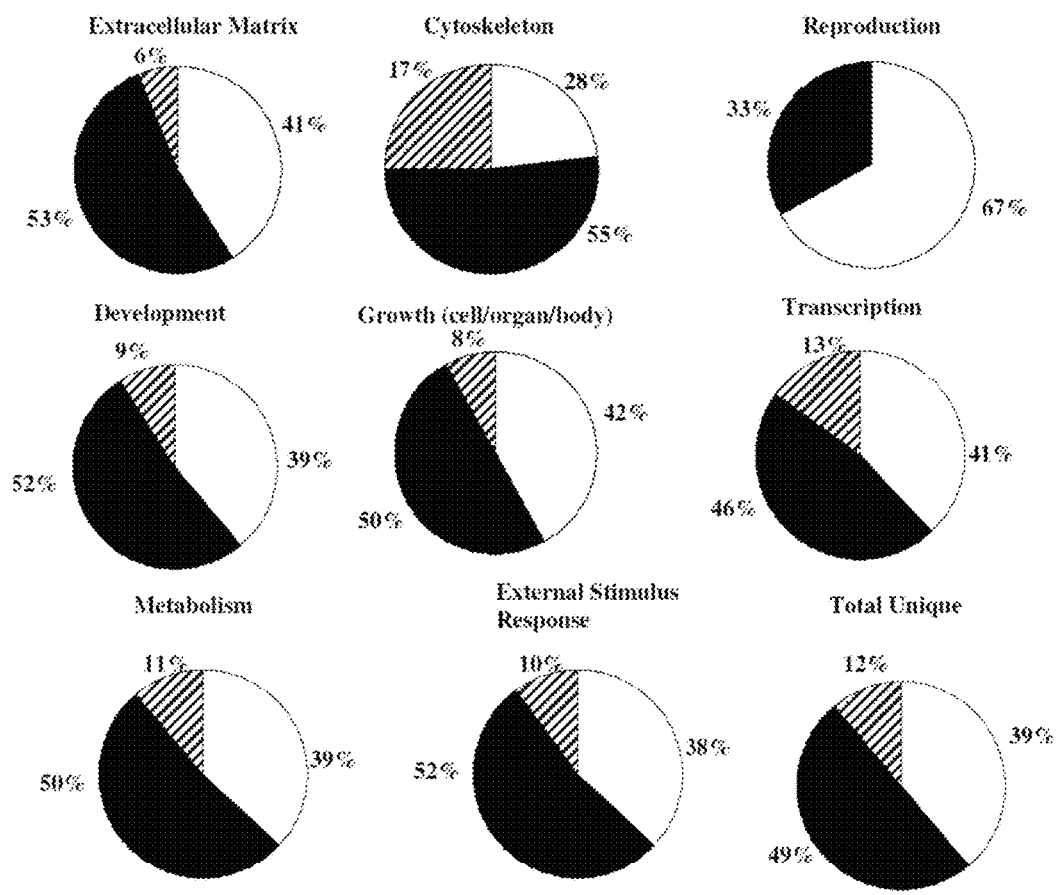
FIGURE 15C

SELECTIVE ANDROGEN RECEPTOR MODULATOR AND METHODS OF USE THEREOF

CROSS-REFERENCE TO RELATED APPLICATIONS

This application is a Divisional of U.S. patent application Ser. No. 14/963,130, filed Dec. 8, 2015 and this application is a Continuation of U.S. patent application Ser. No. 15/398,672, filed Jan. 4, 2017; which is a Continuation of U.S. patent application Ser. No. 14/963,130, filed Dec. 8, 2015; which is a Continuation-in-Part of U.S. patent application Ser. No. 14/062,748, filed Oct. 24, 2013; which is a Continuation-In-Part of U.S. patent application Ser. No. 13/557,885, filed Jul. 25, 2012, now abandoned; which is a Continuation-In-Part of U.S. patent application Ser. No. 13/082,830, filed Apr. 8, 2011, now abandoned; which is a Continuation-In-Part of U.S. patent application Ser. No. 11/785,064, now U.S. Pat. No. 8,853,266, filed Apr. 13, 2007; which is a Continuation-In-Part of U.S. patent application Ser. No. 11/634,380, filed Dec. 6, 2006, now abandoned; which is a Continuation-In-Part Application of U.S. patent application Ser. No. 11/505,499, filed on Aug. 17, 2006, now U.S. Pat. No. 7,645,898, and of U.S. patent application Ser. No. 11/505,363, filed Aug. 17, 2006, now abandoned; which are Continuation-In-Part Applications of U.S. patent application Ser. No. 11/355,187, filed Feb. 16, 2006, now U.S. Pat. No. 7,919,647; which is a Continuation-In-Part of U.S. patent application Ser. No. 11/220,414, filed Sep. 7, 2005, now U.S. Pat. No. 7,855,229; which is a Continuation-In-Part of U.S. patent application Ser. No. 11/146,427, filed Jun. 7, 2005, now U.S. Pat. No. 7,622,503; which is a Continuation-In-Part of U.S. patent application Ser. No. 10/863,524, filed Jun. 9, 2004, which is now abandoned; and is Continuation-In-Part Application of U.S. patent application Ser. No. 10/861,923, filed Jun. 7, 2004, now abandoned, all of which are incorporated herein by reference in their entirety.

FIELD OF THE INVENTION

This invention provides substituted acylanilide compounds and uses thereof in treating a variety of diseases or conditions in a subject, including, inter alia, a muscle wasting disease and/or disorder such as muscular dystrophies including Duchenne muscular dystrophy and Becker muscular dystrophy.

BACKGROUND OF THE INVENTION

Muscle wasting refers to the progressive loss of muscle mass and/or to the progressive weakening and degeneration of muscles, including the skeletal or voluntary muscles, which control movement, cardiac muscles, which control the heart (cardiomyopathies), and smooth muscles. Chronic muscle wasting is a chronic condition (i.e. persisting over a long period of time) characterized by progressive loss of muscle mass, and weakening and degeneration of muscle.

The loss of muscle mass that occurs during muscle wasting can be characterized by muscle protein degradation by catabolism. Protein catabolism occurs because of an unusually high rate of protein degradation, an unusually low rate of protein synthesis, or a combination of both. Muscle protein catabolism, whether caused by a high degree of protein degradation or a low degree of protein synthesis, leads to a decrease in muscle mass and to muscle wasting.

Muscle wasting is associated with chronic, neurological, genetic or infectious pathologies, diseases, illnesses or conditions. These include muscular dystrophies such as Duchenne muscular dystrophy, Becker muscular dystrophy, limb-girdle disease, and myotonic dystrophy; muscle atrophies such as post-polio muscle atrophy (PPMA); cachexias such as cardiac cachexia, AIDS cachexia and cancer cachexia; and malnutrition, leprosy, diabetes, renal disease, chronic obstructive pulmonary disease (COPD), cancer, end stage renal failure, sarcopenia, emphysema, osteomalacia, HIV infection, AIDS, and cardiomyopathy.

In addition, other circumstances and conditions are linked to and can cause muscle wasting. These include chronic lower back pain, advanced age, central nervous system (CNS) injury, peripheral nerve injury, spinal cord injury, chemical injury, central nervous system (CNS) damage, peripheral nerve damage, spinal cord damage, chemical damage, burns, disuse deconditioning that occurs when a limb is immobilized, long term hospitalization due to illness or injury, and alcoholism.

An intact androgen receptor (AR) signaling pathway is crucial for appropriate development of skeletal muscles. Furthermore, an intact AR-signaling pathway increases lean muscle mass, muscle strength and muscle protein synthesis.

Muscle wasting, if left unabated, can have dire health consequences. For example, the changes that occur during muscle wasting can lead to a weakened physical state that is detrimental to an individual's health, resulting in increased susceptibility to hone fracture and poor physical performance status. In addition, muscle wasting is a strong predictor of morbidity and mortality in patients suffering from cachexia and AIDS.

Duchenne muscular dystrophy is the most common of nine muscular dystrophies and occurs in 1/3500 to 1/5000 males around the world. Duchenne muscular dystrophy patients experience difficulty with walking at 3-5 years of age, progressive worsening of symptoms, and death in the teens to $3^{rd}$ decade. Discovered in the 1860's, little was known about the pathogenesis of Duchenne muscular dystrophy until 1986 when the gene underlying this X-linked autosomal recessive disease was cloned and characterized. The gene was named dystrophin (DMD) and found to be part of a sarcolemma (i.e. myocte plasma membrane) protein complex (dystrophin-glycoprotein complex) which connects the myofibril (muscle cell) cytoskeleton to the extracellular matrix, thereby protecting the muscle cell membrane from physical trauma during muscle exertion and exercise. Duchenne muscular dystrophy is predominantly a disease in males and is associated with a variety of mutations of the DMD gene which leads to a wide variation of disease severities. Sarcolemma fragility produces progressive calcium permeability, protease activation, oxidative stress, and inflammation which causes progressive replacement of muscle cells by fibrous tissue and/or conversion to fat. Gross pathology includes weakness and degeneration of skeletal and voluntary muscle which is exacerbated by high impact exercise, muscle contractures that worsen mobility if not corrected, and scoliosis. Although braces and walkers provide some protection, declines in physical function result in loss of ambulation during childhood leading to wheelchair confinement, and eventually impaired cardiac (cardiomyopathy) or respiratory (diaphragm fibrosis) function leads to death. Average life expectancy has improved (and rare cases of men living into their $4^{th}$ or $5^{th}$ decade) as a result of better respiratory (glucocorticoids) and cardiac (ACE inhibitors, angiotensin receptor blockers, and beta-blockers) supportive care, but no disease-modifying therapeutics exist. Anabolics (steroidal androgens, IGF-I, etc.) to slow the rate of physical function decline have been proposed and were shown to provide some benefit in small clinical trials, but no non-steroidal or tissue-selective androgen receptor modulator (SARM) has entered clinical testing for Duchenne muscular dystrophy. The loss of gene function etiology has attracted great interest toward gene therapy approaches to treat the disease; however, such treatments have not completely reversed the phenotype and suffer from difficulties inherent in nucleotide polymer based therapeutics which are exacerbated by the large and complex nature of the dystrophin gene. The above suggests that other therapeutic targets are urgently needed. Consequently, there is increasing interest in further improving the quality of life and length of life via symptom directed supportive care. Aryl propanamide SARMs have been shown to increase global anabolic tone in multiple clinical trials through increases in muscle mass (lean body mass by DEXA) and physical function (e.g., leg press, grip strength, stair climb power) suggesting that they may have therapeutic effects on dystrophic skeletal and specifically diaphragm muscle, cardiac, and smooth muscle, or may delay onset or improve symptoms of loss of mobility/autonomy, cardiomyopathy, or respiratory insufficiency in Duchenne muscular dystrophy or Becker muscular dystrophy and other muscular dystrophy patients.

Becker muscular dystrophy is a rarer and milder variation of Duchenne muscular dystrophy caused by DMD mutants that do not completely abrogate dystrophin glycoprotein complex function in males or more commonly it is observed in some female carriers (Duchenne muscular dystrophy is often asymptomatic in females). Becker muscular dystrophy has a phenotype with less functional impairment and longer life expectancy, but clinical cardiomyopathies and respiratory insufficiencies must be closely monitored.

Interest in drug design for Duchenne muscular dystrophy was hampered by the lack of good models of this disease, however several in vivo disease models now exist. These include the dystrophin gene deletion in mice (mdx mice; denoted by DMD (−/−)) which presents a phenotype representative of the early stages of the disease in humans however, is not progressive in symptomology and much less severe in the later stages of the disease. Double-knockout (knock-down) mice lacking dystrophin (DMD) and utrophin (MN, a protein that can partially compensate for lack of dystrophin) (i.e., DMD (−/−) UTRN (−/−)) present a phenotype more representative of the natural history of Duchenne muscular dystrophy in humans including progressive worsening of symptoms, loss of ambulation at 12 weeks, and early death by ~20 weeks. [A severe phenotype can also be derived from the mdx model by forced treadmill running.] Golden retriever muscular dystrophy is another disease model that matches the human phenotype in, some ways but suffers from a high level of interindividual variation even among littermates, complicating the interpretation of results. Although the pathogenesis of other muscular dystrophies is not related to Duchenne and Becker muscular dystrophies, the phenotypes therein suggest that activity in the mdx and double knockout models may be indicative of therapeutic efficacies in those disease states as well.

While there are many treatments and therapies for these conditions, none are ideal. Since the androgen receptor (AR) signaling pathway has been shown to increase lean muscle mass, muscle strength and muscle protein synthesis, and since hypogonadism accompanies these conditions, molecules targeting the AR signaling pathway may be useful in treating these diseases and/or conditions.

SUMMARY OF THE INVENTION

The present invention is directed to a method of treating, reducing the severity, reducing the incidence, delaying the onset, or reducing the pathogenesis of Duchenne muscular dystrophy in a subject in need thereof, comprising the step of administering to said subject a selective androgen receptor modulator (SARM) compound represented by the structure of formula S-(III):

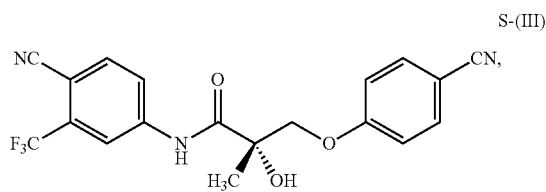 [SMILES: C[C@](O)(COc1ccc(C#N)cc1)C(=O)Nc1ccc(C#N)c(C(F)(F)F)c1]

S-(III)

or its isomer, pharmaceutically acceptable salt, hydrate, N-oxide, or any combination thereof.

In one embodiment, the administering of the present invention comprises administering a pharmaceutical composition comprising said compound and/or its isomer, pharmaceutically acceptable salt, hydrate, N-oxide, or any combination thereof; and a pharmaceutically acceptable carrier.

In one embodiment, the present invention further increases the physical function of said subject.

In one embodiment, the present invention further increases the quality of life of said subject.

In one embodiment, the present invention increases the survival of said subject.

In one embodiment, the present invention delays onset or improves symptoms of cardiomyopathy and/or respiratory function.

In one embodiment, the present invention provides a method of treating, reducing the severity, reducing the incidence, delaying the onset, or reducing the pathogenesis of myotonic dystrophy, limb-girdle muscular dystrophy, facioscapulhumeral muscular dystrophy, congenital muscular dystrophy, oculopharyngeal muscular dystrophy, distal muscular dystrophy, or Emery-Dreifuss muscular dystrophy in a subject in need thereof, comprising the step of administering to said subject a selective androgen receptor modulator (SARM) compound represented by the structure of formula S-(III):

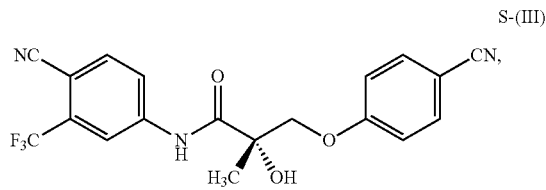

S-(III)

or its isomer, pharmaceutically acceptable salt, hydrate, N-oxide, or any combination thereof.

In one embodiment, the administering comprises administering a pharmaceutical composition comprising said compound and/or its isomer, pharmaceutically acceptable salt, hydrate, N-oxide, or any combination thereof; and a pharmaceutically acceptable carrier.

In one embodiment, the method further increases the physical function of said subject.

In one embodiment, the method further increases the quality of life of said subject.

In one embodiment, this invention is directed to a method of increasing the physical function of a subject suffering from Duchenne muscular dystrophy, comprising the step of administering to said subject a selective androgen receptor modulator (SARM) compound in represented by the structure of formula S-(III):

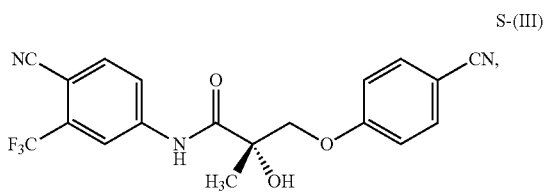 [SMILES: C[C@](O)(COc1ccc(C#N)cc1)C(=O)Nc1ccc(C#N)c(C(F)(F)F)c1]

or its isomer, pharmaceutically acceptable salt, hydrate, N-oxide, or any combination thereof.

In one embodiment, this invention is directed to a method of increasing the quality of life of a subject suffering from Duchenne muscular dystrophy, comprising the step of administering to said subject a selective androgen receptor modulator (SARM) compound represented by the structure of formula S-(III):

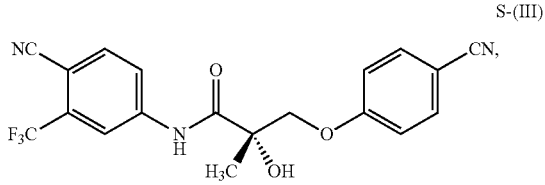 [SMILES: C[C@](O)(COc1ccc(C#N)cc1)C(=O)Nc1ccc(C#N)c(C(F)(F)F)c1]

or its isomer, pharmaceutically acceptable salt, hydrate, N-oxide, or any combination thereof.

In one embodiment, this invention is directed to a method of increasing the survival of a subject suffering from Duchenne muscular Dystrophy, comprising the step of administering to said subject a selective androgen receptor modulator (SARM) compound represented by the structure of formula S-(III):

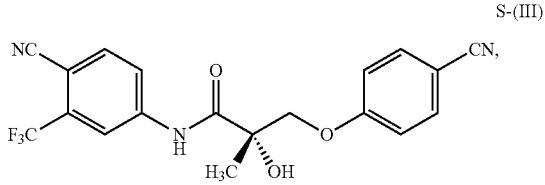 [SMILES: C[C@](O)(COc1ccc(C#N)cc1)C(=O)Nc1ccc(C#N)c(C(F)(F)F)c1]

or its isomer, pharmaceutically acceptable salt, hydrate, N-oxide, or any combination thereof.

In one embodiment, the present invention is directed to a method of treating, reducing the severity, reducing the incidence, delaying the onset, or reducing the pathogenesis of cardiomyopathy in a subject suffering from Duchenne muscular dystrophy, comprising the step of administering to said subject a selective androgen receptor modulator (SARM) compound represented by the structure of formula S-(III):

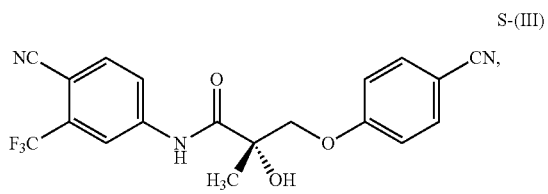

or its isomer, pharmaceutically acceptable salt, hydrate, N-oxide, or any combination thereof.

In one embodiment, the present invention is directed to a method of treating, reducing the severity, reducing the incidence, delaying the onset, or reducing the pathogenesis of respiratory failure in a subject suffering from Duchenne muscular dystrophy, comprising the step of administering to said subject a selective androgen receptor modulator (SARM) compound represented by the structure of formula S-(III):

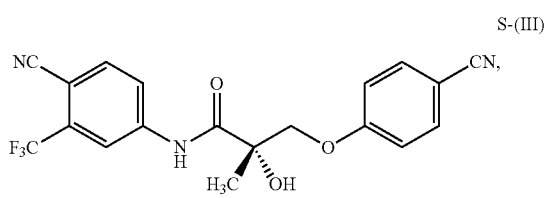

or its isomer, pharmaceutically acceptable salt, hydrate, N-oxide, or any combination thereof.

In one embodiment, this invention is directed to a method of treating, reducing the severity, reducing the incidence, delaying the onset, or reducing the pathogenesis of Becker muscular dystrophy or myotonic dystrophy in a subject in need thereof, comprising the step of administering to said subject a selective androgen receptor modulator (SARM) compound represented by the structure of formula S-(III):

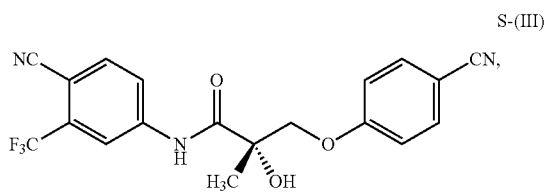

or its isomer, pharmaceutically acceptable salt, hydrate, N-oxide, or any combination thereof.

In one embodiment, this invention provides a method of treating, reducing the severity, reducing the incidence, delaying the onset, or reducing the pathogenesis of cardiovascular disease in a human subject suffering from Duchenne muscular dystrophy comprising the step of administering an effective amount of a compound of formula S-(III) or its isomer, pharmaceutically acceptable salt, pharmaceutical product, crystal, N-oxide, hydrate or any combination thereof to said subject.

In one embodiment, this invention provides a method of treating, reducing the severity, reducing the incidence, delaying the onset, or reducing the pathogenesis of cardiovascular disease in a human subject suffering from Becker muscular dystrophy comprising the step of administering an effective amount of a compound of formula S-(III) or its isomer, pharmaceutically acceptable salt, pharmaceutical product, crystal, N-oxide, hydrate or any combination thereof to said subject.

In one embodiment, this invention provides a method of treating, reducing the severity, reducing the incidence, delaying the onset, or reducing the pathogenesis of cardiovascular disease in a human subject suffering from myotonic dystrophy comprising the step of administering an effective amount of a compound of formula S-(III) or its isomer, pharmaceutically acceptable salt, pharmaceutical product, crystal, N-oxide, hydrate or any combination thereof to said subject.

In one embodiment, the present invention provides a method of reducing a fat mass in a subject suffering from Duchenne muscular dystrophy comprising the step of administering an effective amount of a compound of formula S-(III) or its isomer, pharmaceutically acceptable salt, pharmaceutical product, crystal, N-oxide, hydrate or any combination thereof to the subject.

In one embodiment, the present invention provides a method of reducing a fat mass in a subject suffering from Becker muscular dystrophy comprising the step of administering an effective amount of a compound of formula S-(III) or its isomer, pharmaceutically acceptable salt, pharmaceutical product, crystal, N-oxide, hydrate or any combination thereof to the subject.

In one embodiment, the present invention provides a method of reducing a fat mass in a subject suffering from myotonic dystrophy comprising the step of administering an effective amount of a compound of formula S-(III) or its isomer, pharmaceutically acceptable salt, pharmaceutical product, crystal, N-oxide, hydrate or any combination thereof to the subject.

In one embodiment, the present invention provides a method of increasing a lean mass in a subject suffering from Duchenne muscular dystrophy comprising the step of administering an effective amount of a compound of formula S-(III) or its isomer, pharmaceutically acceptable salt, pharmaceutical product, crystal, N-oxide, hydrate or any combination thereof to the subject.

In one embodiment, the present invention provides a method of increasing a lean mass in a subject suffering from Becker muscular dystrophy comprising the step of administering an effective amount of a compound of formula S-(III) or its isomer, pharmaceutically acceptable salt, pharmaceutical product, crystal, N-oxide, hydrate or any combination thereof to the subject.

In one embodiment, the present invention provides a method of increasing a lean mass in a subject suffering from myotonic dystrophy comprising the step of administering an effective amount of a compound of formula S-(III) or its isomer, pharmaceutically acceptable salt, pharmaceutical product, crystal, N-oxide, hydrate or any combination thereof to the subject.

In one embodiment, the present invention provides a method of treating, reducing the severity, reducing the incidence, delaying the onset, or reducing the pathogenesis of myotonic dystrophy, limb-girdle muscular dystrophy, facioscapulhumeral muscular dystrophy, congenital muscular dystrophy, oculopharyngeal muscular dystrophy, distal muscular dystrophy, or Emery Dreifuss muscular dystrophy in a subject in need thereof, comprising the step of administering to said subject a selective androgen receptor modulator (SARM) compound represented by the structure of formula S-(III):

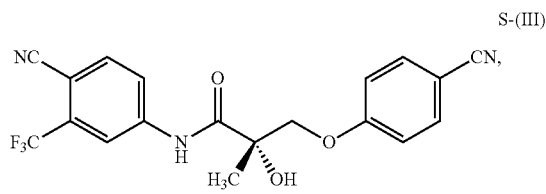

or its isomer, pharmaceutically acceptable salt, hydrate, N-oxide, or any combination thereof.

BRIEF DESCRIPTION OF THE DRAWINGS

FIG. 14A is a Ven diagram showing the number of promoters significantly recruiting AR over vehicle in response to DHT, SARM or DHT and SARM. FIG. 14B illustrates classification of genes assayed with known function (1023) whose promoters were occupied by AR in response to DHT (open bars), SAM (filled bars) or promoters common to DHT SARM (hatched bars). FIG. 14C depicts computational identification of androgen responsive AR direct target gene promoters in response to DHT, SARM or DHT and SARM. Human and orthologous mouse sequences determined from the AR promoter array experiment were searched for the presence of ARE.

FIGS. 15A-15D: depict recruitment of SRC-1 in response to DHT or SARM. FIG. 15A illustrates recruitment to PSA enhancer as measured by realtime quantitative PCR. Values are reported as the ratio of target detected in the immunoprecipitated (IP) DNA pool to target detected in the total input DNA pool. Open bars are vehicle treated, filled bars are DHT treated and hatched bars are SARM treated, FIG. 15B depicts is a Ven diagram showing the number of promoters significantly recruiting SRC-1 over vehicle in response to DHT or SARM or DHT and SARM. FIG. 15C depicts classification of genes assayed with known function (1015) whose promoters were occupied by SRC-1 in response to DHT (open bars), SARM (filled bars) or promoters common to DHT and SARM (hatched bars). FIG. 15D illustrates computational identification of androgen responsive elements in SRC-1 target gene promoters in response to DHT, SARM DHT and SARM. Human and orthologous mouse sequences determined from the SRC-1 promoter array experiment were searched for the presence of ARE.

FIG. 16A. Validation of AR recruitment to various promoters. LNCaP cells were maintained in 1% csFBS for 6 days to reduce the basal transcription factor recruitment and were treated with vehicle (open bars), 100 nM DHT (filled bars) SARM (hatched bars) for 60 min. ChIP assay was performed with AR antibody and recruitment to various promoters showing significance from the array were measured using realtime rtPCR primers and probes (Table 16). Values are reported as the ratio of target DNA detected in the IP DNA pool to target DNA detected in the total input DNA pool. The experiments were performed in triplicate. FIG. 16B. Measurement of gene transcription of promoters to which AR was recruited. Gene transcription was measured by treating LNCaP cells maintained in 1% csFBS (STAT5B, SHC-1, GAS7, APIG1, AXIN1, ATM and MSX-1) or full serum (NFkB1E). The cells were treated with vehicle (open bars), DHT (filled bars) or SARM (hatched bars). RNA was extracted and realtime rtPCR was performed using TaqMan primers and probe and normalized to 18S, The experiments were performed in triplicate. Cells were treated for 24 hrs. * indicate significance at $P<0.05$ from vehicle treated samples. IP-Immunoprecipitation; ChIP-Chromatin Immunoprecipitation.

FIG. 20A: MMRM analysis through Day 84 visit; FIG. 20B: MMRM analysis through Day 147 visit.

FIG. 21A: MMRM analysis through Day 84 visit; FIG. 21B: MMRM analysis through Day 147 visit.

FIG. 22A: MMRM analysis through Day 84 visit; FIG. 22B: MMRM analysis through Day 147 visit.

FIG. 23A: MMRM analysis through Day 84 visit; FIG. 23B: MMRM analysis through Day 147 visit.

FIG. 24A: MMRM analysis through Day 84 visit; FIG. 24B: MMRM analysis through Day 147 visit.

FIG. 25A: MMRM analysis through Day 84 visit; FIG. 25B: MMRM analysis through Day 147 visit.

FIG. 37A shows the effects of S-(III) on body weight in DMD (−/−) UTRN (+/+) mice. FIG. 37B shows the effects of S-(III) on fat mass in DMD (−/−) UTRN (+/+) mice. FIG. 37C shows the effects of S-(III) on lean [muscle] mass in DMD (−/−) UTRN (+/+) mice. FIG. 37D shows the effects of S-(III) on grip strength in DMD (−/−) UTRN (+/+) mice.

FIGS. 38A-38C show that compounds of formulas S-(III), S-(IV), and S-(V) (labeled as 'SARMs' because the data shown is cumulative across groups 2, 3 and 4 (see Example 18)) delayed the deterioration of body weight, lean mass, and grip strength of DMD (−/−) UTRN (−/−) double knockout mice. FIG. 38A shows the effects of 'SARMs' on the body weight of DMD (−/−) UTRN (−/−)) mice. FIG. 38B shows the effects of 'SARMs' on the lean mass of DMD (−/−) UTRN (−/−) mice. FIG. 38C shows the effects of 'SARMs' on the grip strength of DMD (−/−) UTRN (−/−) mice. N=6-9 in each group.

FIG. 39A shows cumulative data whereas FIG. 39B shows data from mice from the same litter (each group of two bars represents one litter). Despite similar characteristics at birth, mice treated with 'SARM' or S-(III), respectively, exhibited increased survival than mice treated with vehicle.

FIG. 40A depicts the effect of S-(III) on body weight of intact DMD (−/−) UTRN (+/+) mice whereas FIG. 40B depicts the effects in castrated mdx mice.

FIG. 41A depicts the effect of S-(III) on lean mass of intact DMD (−/−) UTRN (+/+) mice whereas FIG. 41B depicts the effects in castrated mdx mice.

DETAILED DESCRIPTION OF THE PRESENT INVENTION

Figure 1:
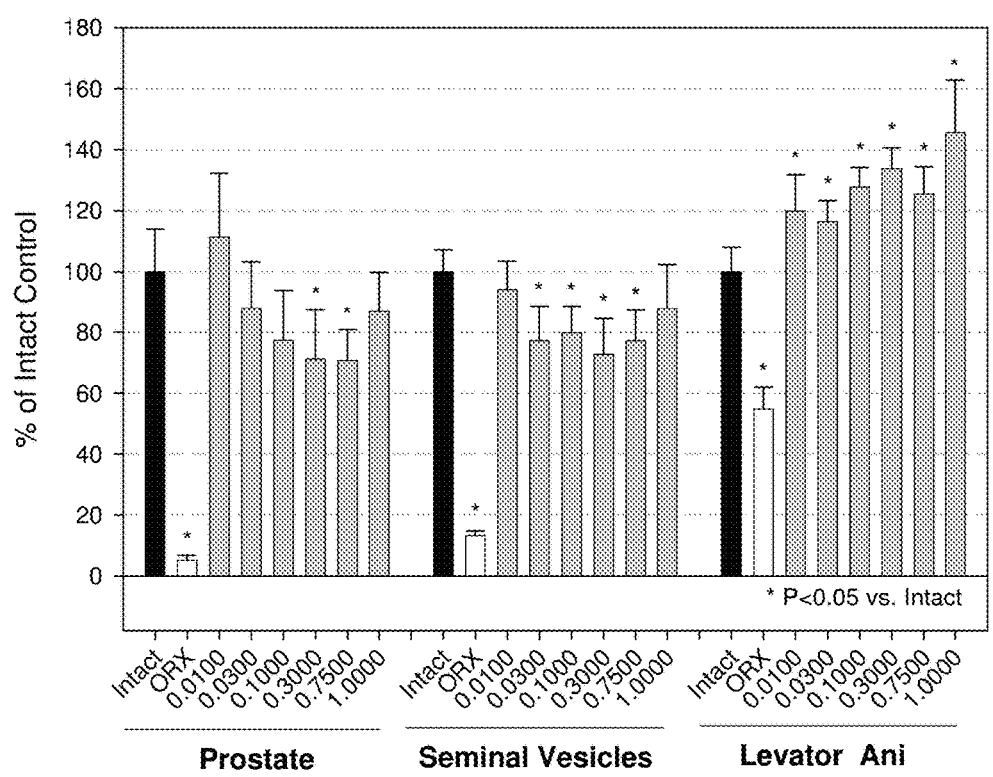
FIG. 1: Organ weights from intact rats treated with a compound of formula S-(III) presented as a percentage of intact control. * P-value <0.05 versus intact controls.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In one embodiment, this invention provides methods of treating, suppressing, inhibiting, reducing the severity of, reducing the incidence of reducing the pathogenesis of or delaying onset of, inter alia: a) muscle wasting in patients with cancer, wherein the patients are subjected to cancer therapy; b) muscle wasting in patients with non-small cell lung cancer (NSCLC), wherein the patients are subjected to cancer therapy; c) muscle wasting in patients with non-small cell lung cancer (NSCLC), wherein the patients are subjected to taxane therapy d) pre-cachexia or early cachexia (preventing muscle wasting in a cancer patient), wherein the patients are subjected to cancer therapy; e) treating loss of physical function due to cancer or cancer therapy (radiation, chemotherapy, surgery); f) increasing physical function of a subject, wherein the subject is subjected to cancer therapy; g) increasing physical function of a cancer patient, wherein the patient is subjected to cancer therapy; h) increasing physical function of a cancer patient, wherein said patient suffers from non-small cell lung cancer, colorectal cancer, non-Hodgkin lymphoma, chronic lymphocytic leukemia or breast cancer, and is subjected to cancer therapy; i) increasing physical function of a cancer patient, wherein said patient suffers from non-small cell lung cancer, and is subjected to taxane therapy treating, suppressing, inhibiting, reducing the severity of, reducing the incidence of reducing the pathogenesis of, or delaying onset of lung cancer in a patient, wherein the patient is subjected to cancer therapy; k) increasing survival, functional independence, and increasing quality of life of a subject suffering from cancer, and is subjected to cancer therapy; l) increasing survival, functional independence, and increasing quality of life of a subject suffering from non-small cell lung cancer, and is subjected to taxane therapy; m) preventing or treating declines in quality of life due to cancer or cancer therapy; and treating diseases, disorders or conditions related thereto; n) increasing lean body mass of a cancer patient that is subjected to cancer therapy; o) increasing lean body mass of a cancer patient, wherein said patient suffers from non-small cell lung cancer, and is subjected to taxane therapy; via the administration of any SARM as herein described and optionally other therapeutic agents, including but not limited to chemotherapeutic agents, or compositions comprising the same.

In another embodiment, the methods of this invention comprise the step of administering to the subject a compound of formula S-(III):

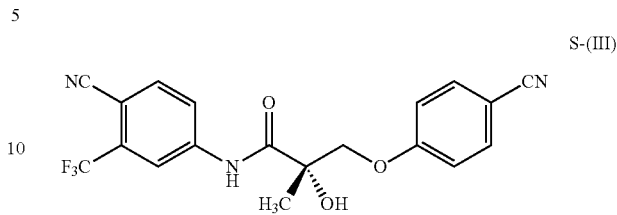

or is isomer, pharmaceutically acceptable salt, pharmaceutical product, hydrate, N-oxide, or any combination thereof.

In another embodiment, the methods of this invention comprise the step of administering to the subject a compound of formula S-(III):

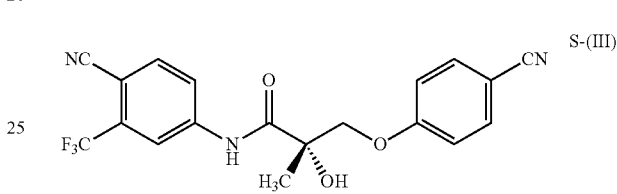

or its isomer, pharmaceutically acceptable salt, pharmaceutical product, hydrate, N-oxide, or any combination thereof and a chemotherapeutic agent.

In another embodiment, the methods of this invention comprise the step of administering to the subject a compound of formula S-(III):

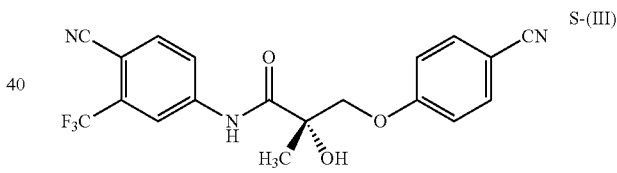

or its isomer, pharmaceutically acceptable salt, pharmaceutical product, hydrate, N-oxide, or any combination thereof and a platinum and a taxane.

In another embodiment, the methods of this invention comprise the step of administering to the subject a compound of formula S-(III):

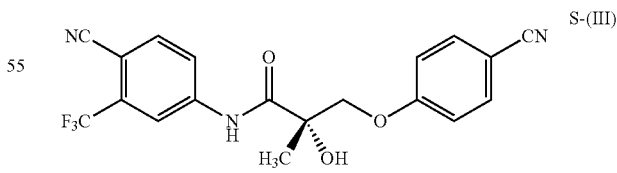

or its isomer, pharmaceutically acceptable salt, pharmaceutical product, hydrate, N-oxide, or any combination thereof, and platinum and non-taxane chemotherapeutic agent.

In some embodiments, the invention provides compositions comprising the compound of formula S-(III) or use of the compound of formula S-(III) for treating muscle wasting in a subject, wherein said subject has non-small cell lung cancer. In another embodiment, the subject is subjected to cancer therapy. In another embodiment, the subject is subjected to radiation therapy. In another embodiment, the compound is administered in combination with chemotherapeutic agent. In another embodiment, the compound is administered in combination with radiation therapy.

In one embodiment, this invention provides methods of treatment using a compound of formula S-(III) or composition comprising the same, as herein described. In some embodiments, the compound of formula S-(III) or composition comprising the same is administered in combination with other therapeutic agents. In some embodiments, the compound of formula S-(III) or composition comprising the same is administered to a subject subjected to cancer therapy. In some embodiments, the compound of formula S-(III) or composition comprising the same is administered to a subject subjected to radiation therapy. In some embodiments, the compound of formula S-(III) or composition comprising the same is administered in combination with a chemotherapeutic agent. In some embodiments, the compound of formula S-(III) or composition comprising the same is administered in combination with radiation therapy. In another embodiment, the compound of formula S-(III) or composition comprising the same is administered in combination with platinum and a taxane chemotherapeutic agents. In another embodiment, the compound of formula S-(III) or composition comprising the same is administered in combination with platinum and a non-taxane chemotherapeutic agents.

In some embodiments, the invention provides methods of treatment, wherein the compound is a selective androgen receptor modulator (SARM). In some embodiments, the invention provides methods of use of a SARM for the treatment of the indicated diseases, disorders or conditions, and includes use of compositions comprising the same.

In one embodiment, the terms "treating" or "treatment" is disorder ruminative treatment. The terms "reducing", "suppressing" and "inhibiting" have their commonly understood meaning of lessening or decreasing, in another embodiment, or delaying, in another embodiment, or reducing, in another embodiment the incidence, severity or pathogenesis of a disease, disorder or condition. In some embodiments, the term "treatment" refers to delayed progression of prolonged remission of, reduced incidence of, or amelioration of symptoms associated with the disease, disorder or condition. In one embodiment, the terms "treating" "reducing", "suppressing" or "inhibiting" refer to a reduction in morbidity, mortality, or a combination thereof, in association with the indicated disease, disorder or condition. In one embodiment, the term "progression" refers to an increasing in scope or severity, advancing, growing or becoming worse. The term "recurrence" means, in another embodiment, the return of a disease after a remission. In one embodiment, the methods of treatment of the invention reduce the severity of the disease, or in another embodiment, symptoms associated with the disease, or in another embodiment, reduces the number of biomarkers expressed during disease.

In one embodiment, the term "treating" and its included aspects, refers to the administration to a subject with the indicated disease, disorder or condition, or in some embodiments, to a subject predisposed to the indicated disease, disorder or condition. The term "predisposed to" is to be considered to refer to, inter alia, a genetic profile or familial relationship which is associated with a trend or statistical increase in incidence, severity, etc. of the indicated disease. In some embodiments, the term "predisposed to" is to be considered to refer to inter alia, a lifestyle which is associated with increased risk of the indicated disease. In some embodiments, the term "predisposed to" is to be considered to refer to inter alia, the presence of biomarkers which are associated with the indicated disease, for example, in cancer, the term "predisposed to" the cancer may comprise the presence of precancerous precursors for the indicated cancer.

In some embodiments, the term "reducing the pathogenesis" is to be understood to encompass reducing tissue damage, or organ damage associated with a particular disease, disorder or condition. In another embodiment, the term "reducing the pathogenesis" is to be understood to encompass reducing the incidence or severity of an associated disease, disorder or condition, with that in question. In another embodiment, the term "reducing the pathogenesis" is to be understood to encompass reducing the number of associated diseases, disorders or conditions with the indicated, or symptoms associated thereto.

The term "administering", in another embodiment, refers to bringing a subject in contact with a compound of the present invention. Administration can be accomplished in vitro, i.e. in a test tube, or in vivo, i.e. in cells or tissues of living organisms, for example humans. In one embodiment, the present invention encompasses administering the compounds of the present invention to a subject.

In one embodiment, this invention provides for the use of a SARM compound or its prodrug, analog, isomer, metabolite, derivative, pharmaceutically acceptable salt, pharmaceutical product, polymorph, crystal, impurity, N-oxide, hydrate or any combination thereof, represented by the structure of formula (I):

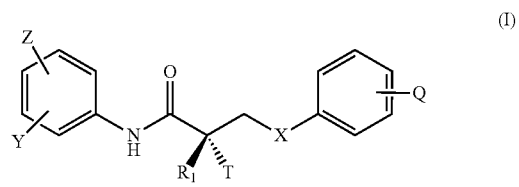

(I)

wherein
X is O;
Z is alkyl $NO_2$, CN, COR, COOH or CONHR;
Y is $CF_3$, $CH_3$, formyl, alkoxy, H, F, I, Br, Cl, or $Sn(R)_3$;
Q is alkyl, halogen, $N(R)_2$, CN, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, acetamido-, trifluoroacetamido-, alkylamines, ether, alkyl, N-sulfonyl, O-sulfonyl, alkylsulfonyl, carbonyl, or a ketone;
$R_1$ is $CH_3$, $CH_2F$, $CHF_2$, $CF_3$, $CH_2CH_3$, or $CF_2CF_3$;
T is OH, OR, —$NHCOCH_3$, NHCOR or OC(O)R;
wherein R is a $C_1$-$C_4$ alkyl, aryl, phenyl, alkenyl, hydroxyl, a $C_1$-$C_4$ haloalkyl, halogen, or haloalkenyl.

In one embodiment, Q is in the para position. In another embodiment, X is O, or in another embodiment, T is OH, or in another embodiment, R is $CH_3$, or in another embodiment, Z is $NO_2$, or in another embodiment, Z is CN, or in another embodiment, Z is in the para position, or in another embodiment, Y is $CF_3$, or in another embodiment, Y is in the meta position, or in another embodiment, Q is in the para position, or in another embodiment, Q is para alkyl, halogen, CN, $N(R)_2$, $NHCOCH_3$, $NHCOCF_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R or SR, or in another embodiment, any combination thereof. In another embodiment Q is F. In another embodiment Q is CN.

In one embodiment the present invention provides for the use of a SARM compound or its prodrug, analog, isomer, metabolite, derivative, pharmaceutically acceptable salt, pharmaceutical product, polymorph, crystal, impurity, N-oxide, hydrate or any combination thereof, represented by a structure of formula (I):

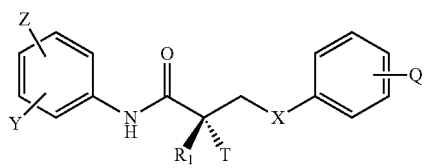

(I)

wherein
X is O;
Z is NO$_2$, CN, COR, or CONHR;
Y is alkyl, CF$_3$, CH$_3$, formyl, alkoxy, H, F, I, Br, Cl, F or Sn(R)$_3$;
Q is CN;
T is OH, OR, —NHCOCH$_3$, NHCOR or OC(O)R;
R is alkyl, haloalkyl, dihaloalkyl, trihaloalkyl, CH$_2$F, CHF$_2$, CF$_3$, CF$_2$CF$_3$, aryl, phenyl, halogen, alkenyl, haloalkenyl or OH; and
R$_1$ is CH$_3$, CH$_2$F, CHF$_2$, CF$_3$, CH$_2$CH$_3$, or CF$_2$CF$_3$.

In one embodiment, Q is in the para position. In another embodiment, X is O, or in another embodiment, T is OH, or in another embodiment, R$_1$ is CH$_3$, or in another embodiment, Z is NO$_2$ or in another embodiment, Z is CN, or in another embodiment, Z is in the para position, or in another embodiment, Y is CF$_3$, or in another embodiment, Y is in the meta position, or in another embodiment, Q is in the para position, or in another embodiment, Q is para alkyl, halogen, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R or SR, or in another embodiment, any combination thereof. In another embodiment Q is F. In another embodiment Q is CN.

In one embodiment, this invention provides for the use of a racemate SARM compound represented by the structure of formula (Ia):

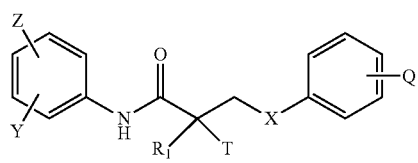

(Ia)

wherein
X is O;
Z is NO$_2$, CN, COR, COOH or CONHR;
Y is alkyl, CF$_3$, CH$_3$, formyl, alkoxy, H, F, I, Br, Cl, or Sn(R)$_3$;

Q is alkyl, halogen, N(R)$_2$, CN, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, acetamido-, trifluoroacetamido-, alkylamines, ether, alkyl, N-sulfonyl, O-sulfonyl, alkylsulfonyl, carbonyl, or a ketone;
R$_1$ is CH$_3$, CH$_2$F, CHF$_2$, CF$_3$, CH$_2$CH$_3$, or CF$_2$CF$_3$;
T is OH, OR, —NHCOCH$_3$, NHCOR or OC(O)R;
wherein R is a C$_1$-C$_4$, alkyl, aryl, phenyl, alkenyl, hydroxyl, C$_1$-C$_4$ haloalkyl, halogen, or haloalkenyl.

In one embodiment, Q is in the para position. In another embodiment, X is O. In another embodiment, Q is in the para position and X is O. In another embodiment, Q is para alkyl, halogen, N(R)$_2$, CN, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R or SR. In another embodiment Q is F. In another embodiment Q is CN. In another embodiment, R is an aryl, phenyl, hydroxyl, C$_1$-C$_4$ alkyl, C$_1$-C$_4$ haloalkyl, halogen, alkenyl or haloalkenyl.

In one embodiment the present invention provides for the use of a SARM compound or its prodrug, analog, isomer, metabolite, derivative, pharmaceutically acceptable salt, pharmaceutical product, polymorph, crystal, impurity, N-oxide, hydrate or any combination thereof, represented by the structure of formula (II):

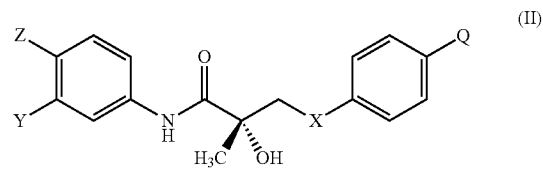

(II)

wherein
X is O;
Z is a NO$_2$, CN, COR, or CONHR;
Y is an alkyl, I, F, CF$_3$, alkyl, formyl, alkoxy, Br, Cl, or Sn(R)$_3$;
R is an alkyl, aryl, phenyl, alkenyl, haloalkyl, haloalkenyl, halogen or OH;
and
Q is alkyl, halogen, N(R)$_2$, CN, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_3$R, OR, COR, OCOR, OSO$_2$R, SO$_2$R, SR, acetamido-, trifluoroacetamido-, alkylamines, ether, alkyl, N-sulfonyl, O-sulfonyl, alkylsulfonyl, carbonyl, or a ketone.

In one embodiment, this invention provides for the use of a SARM compound or its prodrug, analog, isomer, metabolite, derivative, pharmaceutically acceptable salt, pharmaceutical product, polymorph, crystal, impurity, N-oxide, hydrate or any combination thereof, represented by the structure of formula (II):

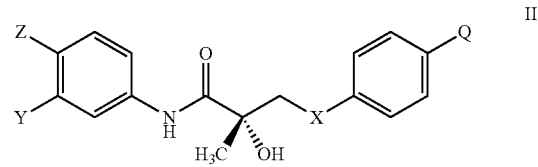

II wherein

X is O;

Z is NO$_2$, CN, COR, or CONHR;

Y is an alkyl, CF$_3$, CH$_3$, formyl, alkoxy, H, F, I, Br, Cl, or Sn(R)$_3$;

R is an alkyl, aryl, phenyl, alkenyl, haloalkyl, haloalkenyl, halogen or OH;

and Q is alkyl, halogen, N(R)$_2$, CN, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_3$R, SO$_2$R, SR, acetamido-, trifluoroacetamido-, alkylamines, ether, alkyl, N-sulfonyl, O-sulfonyl, alkylsulfonyl, carbonyl, or a ketone.

In one embodiment, X is O, or in another embodiment, T is OH, or in another embodiment, R$_1$ is CH$_3$, or in another embodiment, Z is NO$_2$, or in another embodiment, Z is CN, or in another embodiment, Y is CF$_3$, or in another embodiment, Q is alkyl, F, Cl, Br, I, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, acetamido-, trifluoroacetamido-, alkylamines, ether, alkyl, N-sulfonyl, O-sulfonyl, alkylsulfonyl, carbonyl, or a ketone or in another embodiment, any combination thereof. In another embodiment Q is F. In another embodiment Q is CN.

In another embodiment, the present invention provides for the use of a SARM represented by a structure of formula (II):

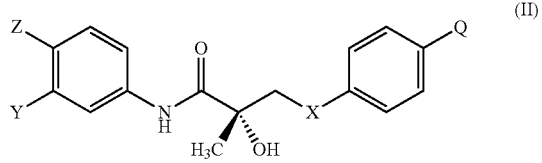

wherein

X is O;

Z is NO$_2$, CN, COR, or CONHR;

Y is CF$_3$, an alkyl, CH$_3$, formyl, alkoxy, H, I, Br, Cl, F or Sn(R)$_3$;

R is an alkyl, aryl, phenyl, alkenyl, haloalkyl, haloalkenyl, halogen or OH; and Q is CN.

In one embodiment, the invention provides for the use of a compound or its prodrug, analog, isomer, metabolite, derivative pharmaceutically acceptable salt, pharmaceutical product, polymorph, crystal, impurity, N-oxide, hydrate or any combination thereof, represented by a structure of formula S-(III):

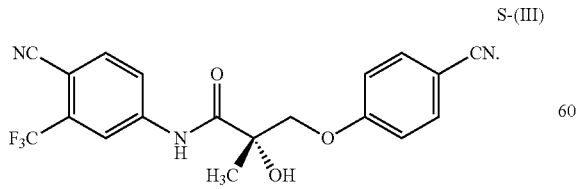

In another embodiment, this invention provides for the use of a SARM compound or its prodrug, analog, isomer, metabolite, derivative, pharmaceutically acceptable salt, pharmaceutical product, polymorph, crystal, impurity, N-oxide, hydrate or any combination thereof, represented by a structure of formula (IV):

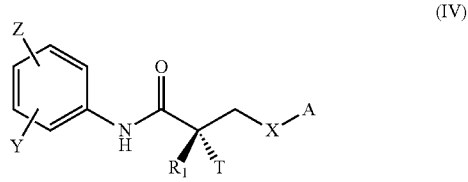

wherein

X is O;

T is OH, OR, NHCOCH$_3$, NHCOR or OC(O)R;

Z is NO$_2$, CN, COOH, COR, NHCOR or CONHR;

Y is hydrogen, alkyl, CF$_3$, formyl alkoxy, halogen, hydroxyalkyl or alkyl aldehyde;

R is alkyl, haloalkyl, dihaloalkyl trihaloalkyl, CH$_2$F, CHF$_2$, CF$_3$, CF$_2$CF$_3$, aryl, phenyl, halogen, haloalkenyl, alkenyl or OH;

R$_1$ is CH$_3$, CH$_2$F, CHF$_2$, CF$_3$, CH$_2$CH$_3$, or CF$_2$CF$_3$; and

A is a group selected from:

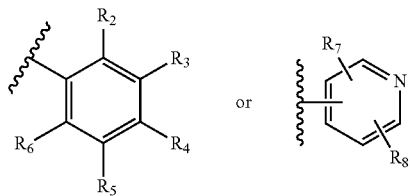

wherein

R$_2$, R$_3$, R$_4$, R$_5$, and R$_6$ are independently is H, halogen, NO$_2$, CN, NHCOR$_9$, N(COR)$_2$, COR$_{10}$, OR$_{11}$, OSO$_2$R$_{12}$, SO$_2$R$_{13}$, NHSO$_2$R$_{12}$, SR$_{14}$, an imide ring, alkyl or substituted alkyl with at least one substituent of halogen, CN, NH$_2$, OH, alkoxy; or R$_2$ and R$_3$, R$_3$ and R$_4$, R$_4$ and R$_5$, or R$_5$ and R$_6$ form, together with any of the ring atom(s) to which they are attached, a condensed 5 to 7 membered aliphatic or aromatic carbocyclic ring or a condensed 5 to 7 membered heterocyclic ring containing 1 to 3 heteroatom(s) selected from N, O, S; or represented by structures A, B or C:

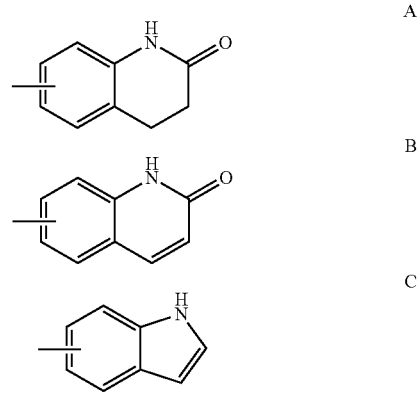

$R_7$ and $R_8$ are independently H, halogen, alkyl or alkenyl;
$R_9$ and $R_{10}$ are independently alkyl, alkenyl, haloalkyl, aminoalkyl, mono- or di-alkylaminoalkyl, aryl, $N(R_{15})_2$ or $-OR_{16}$;
$R_{11}$ and $R_{14}$ independently H, alkyl, alkenyl, haloalkyl, aminoalkyl, mono- or di-alkylaminoalkyl, aryl, $-COR_{17}$;
$R_{12}$ and $R_{13}$ are independently alkyl or alkenyl, haloalkyl or aryl;
$R_{15}$ and $R_{16}$ are independently H, alkyl, alkenyl, haloalkyl, aminoalkyl or aryl; and
$R_{17}$ is alkyl, alkenyl, haloalkyl or aryl.

In one embodiment, according to this aspect of the invention, X is O, or in another embodiment, T is OH, or in another embodiment, $R_1$ is $CH_3$, or in another embodiment, Z is $NO_2$, or in another embodiment, Z is CN, or in another embodiment. $R_2$, $R_3$, $R_5$, and $R_6$ are hydrogens and $R_4$ is $NHCOCF_3$, or in another embodiment, $R_2$, $R_3$, $R_5$, and $R_6$ are hydrogens and $R_4$ is CN, or in another embodiment, $R_2$, $R_3$, $R_5$, and $R_6$ are hydrogens and $R_4$ is F, or in another embodiment, $R_2$, $R_3$, $R_5$, and $R_6$ are hydrogens, or in another embodiment, Z is in the para position, or in another embodiment, Y is in the meta position, or in another embodiment, any combination thereof.

In another embodiment, this invention is directed to the use of a compound represented by the structure of formula (XX):

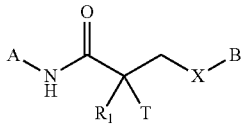

(XX)

wherein
X is O;
$R_1$ is $CH_3$, $CF_3$, $CH_2CH_3$, or $CF_2CF_3$;
T is OH, OR, $NHCOCH_3$, or NHCOR;
wherein R is a $C_1$-$C_4$ alkyl, a $C_1$-$C_4$ haloalkyl, aryl, phenyl, halogen, alkenyl, haloalkenyl, or hydroxyl;
A is a 5 or 6 membered saturated, unsaturated or aromatic carbocyclic or heterocyclic ring represented by the structure:

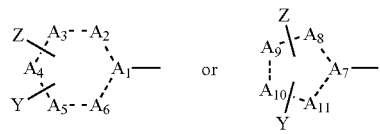

B is a 5 or 6 membered saturated, unsaturated or aromatic carbocyclic or heterocyclic ring represented by the structure:

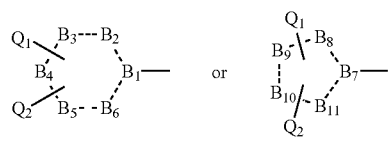

wherein $A_1$-$A_{11}$ are each C, CH, $CH_2$, O, S, N, or NH;
$B_1$-$B_{11}$ are each C, CH, $CH_2$, O, S, N, or NH;
Z is a hydrogen bond acceptor, alkyl. H, $NO_2$, CN, COOH, COR, NHCOR or CONHR;

Y is a lipid soluble group, hydrogen, alkyl, formyl, alkoxy, hydroxylalkyl, alkylaldehyde, $CF_3$, F, I, Br, Cl, CN, $C(R)_3$ or $Sn(R)_3$; and
$Q_1$ and $Q_2$ are independently of each other H, alkyl, halogen, CN, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$ or SR;
wherein R is a $C_1$-$C_4$ alkyl, a $C_1$-$C_4$ haloalkyl, aryl, phenyl, halogen, alkenyl, haloalkenyl, or hydroxyl. In one embodiment, the alkyl group is $CH_3$.

The substitutents Z and Y of the structure of formula XX can be in any position of the five or 6 membered ring carrying these substitutents (hereinafter "A ring"). Similarly, the substituent $Q_1$ and/or $Q_2$ can be in any position of the five or 6 membered ring carrying this substitutent (hereinafter "B ring"). It is understood that when any of the ring members $A_1$-$A_{11}$ or $B_1$-$B_{11}$ are O or S, then these ring members are unsubstituted. It is further understood that when any of the ring members $A_1$-$A_{11}$ or $B_1$-$B_{11}$ are O or S, then the dotted line between O or S atoms and adjacent ring members represents a single bond.

In one embodiment, the A ring of the structure of formula XX includes any type of saturated or unsaturated carbocyclic ring. In one embodiment, the A ring is a 6 membered saturated carbocyclic ring, which may be unsubstituted, monosubstituted or polysubstituted by any of the substitutents described hereinabove. In one embodiment, the A ring is a 5 membered saturated carbocyclic ring, which may be unsubstituted, monosubstituted or polysubstituted by any of the substitutents described hereinabove. In another embodiment, the A ring is a 6 membered carbocyclic ring containing one or more double bonds, which ring may be unsubstituted, monosubstituted or polysubstituted by any of the substitutents described hereinabove. In another embodiment, the A ring is a 5 membered carbocyclic ring containing one or more double bonds, which ring may be unsubstituted, monosubstituted or polysubstituted by any of the substitutents described hereinabove.

In another embodiment, the A ring of the structure of formula XX includes any type of saturated, unsaturated or aromatic heterocyclic ring. In another embodiment, the A ring is a 6 membered saturated heterocyclic ring, which may be unsubstituted, monosubstituted or polysubstituted by any of the substitutents described hereinabove. In another embodiment, the A ring is a 5 membered saturated heterocyclic ring, which may be unsubstituted, monosubstituted or polysubstituted by any of the substituents described hereinabove. In another embodiment, the A ring is a 6 membered heterocyclic ring containing one or more double bonds, which ring may be unsubstituted, monosubstituted or polysubstituted by any of the substitutents described hereinabove. In another embodiment, the A ring is a 5 membered heterocyclic ring containing one or more double bonds, which ring may be unsubstituted, monosubstituted or polysubstituted by any of the substitutents described hereinabove. In another embodiment, the A ring is a 6 membered heteroaromatic ring which may be unsubstituted, monosubstituted or polysubstituted by any of the substitutents described hereinabove. In another embodiment, the A ring is a 5 membered heteroaromatic ring which may be unsubstituted, monosubstituted or polysubstituted by any of the substitutents described hereinabove.

Similarly, the B ring of the structure of formula XX includes any type of saturated or unsaturated carbocyclic ring. In one embodiment, the B ring is a 6 membered saturated carbocyclic ring, which may be unsubstituted, monosubstituted or polysubstituted by any of the substitutents described hereinabove. In one embodiment, the B ring is a 5 membered saturated carbocyclic ring, which may be unsubstituted, monosubstituted or polysubstituted by any of the substitutents described hereinabove. In another embodiment, the B ring is a 6 membered carbocyclic ring containing one or more double bonds, which ring may be unsubstituted, monosubstituted or polysubstituted by any of the substitutents described hereinabove. In another embodiment, the B ring is a 5 membered carbocyclic ring containing one or more double bonds, which ring may be unsubstituted, monosubstituted or polysubstituted by any of the substitutents described hereinabove.

In another embodiment, the B ring of the structure of formula XX includes any type of saturated, unsaturated or aromatic heterocyclic ring. In another embodiment, the B ring is a 6 membered saturated heterocyclic ring, which may be unsubstituted, monosubstituted or polysubstituted by any of the substitutents described hereinabove. In another embodiment, the B ring is a 5 membered saturated heterocyclic ring, which may be unsubstituted, monosubstituted or polysubstituted by any of the substituents described hereinabove. In another embodiment, the B ring is a 6 membered heterocyclic ring containing one or more double bonds, which ring may be unsubstituted, monosubstituted or polysubstituted by any of the substitutents described hereinabove. In another embodiment, the B ring is a 5 membered heterocyclic ring containing one or more double bonds, which ring may be unsubstituted, monosubstituted or polysubstituted by any of the substitutents described hereinabove. In another embodiment, the B ring is a 6 membered heteroaromatic ring which may be unsubstituted, monosubstituted or polysubstituted by any of the substituents described hereinabove. In another embodiment, the B ring is a 5 membered heteroaromatic ring which may be unsubstituted, monosubstituted or polysubstituted by any of the substitutents described hereinabove.

Nonlimiting examples of suitable A rings and/or B rings are carbocyclic rings such as cyclopentane, cyclopentene, cyclohexane, and cyclohexene rings, and heterocyclic rings such as pyran, dihydropyran, tetrahydropyran, pyrrole, dihydropyrrole, tetrahydropyrrole, pyrazine, dihydropyrazine, tetrahydropyrazine, pyrimidine, dihydropyrimidine, tetrahydropyrimidone, pyrazole, dihydropyrazole, tetrahydropyrazole, piperidine, piperazine, pyridine, dihydropyridine, tetrahydropyridine, morpholine, thiomorpholine, furan, dihydrofuran, tetrahydrofuran, thiophene, dihydrothiophene, tetrahydrothiophene, thiazole, imidazole, isoxazole, and the like.

An "alkyl" group refers, in one embodiment, to a saturated aliphatic hydrocarbon, including straight-chain, branched-chain and cyclic alkyl groups. In one embodiment, the alkyl group has 1-12 carbons. In another embodiment, the alkyl group has 1-7 carbons. In another embodiment, the alkyl group has 1-6 carbons. In another embodiment, the alkyl group has 1-4 carbons. The alkyl group may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl. In one embodiment, the alkyl group is $CH_3$.

An "alkenyl" group refers, in another embodiment, to an unsaturated hydrocarbon, including straight chain, branched chain and cyclic groups having one or more double bond. The alkenyl group may have one double bond, two double bonds, three double bonds, etc. Examples of alkenyl groups are ethenyl, propenyl, butenyl, cyclohexenyl, etc. The alkenyl group may be unsubstituted or substituted by one or more groups selected from halogen, hydroxy, alkoxy carbonyl, amido, alkylamido, dialkylamido, nitro, amino, alkylamino, dialkylamino, carboxyl thio and thioalkyl.

A "haloalkyl" group refers to an alkyl group as defined above, which is substituted by one or more halogen atoms, in one embodiment by F, in another embodiment by Cl, in another embodiment by Br, or in another embodiment by 1.

An "aryl" group refers to an aromatic group having at least one carbocyclic aromatic group or heterocyclic aromatic group, which may be unsubstituted or substituted by one or more groups selected from halogen, haloalkyl, hydroxy, alkoxy carbonyl, amido, alkylamido, dialkylamido, nitro, amino, alkylamino, dialkylamino, carboxy or thio or thioalkyl. Nonlimiting examples of aryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like. In one embodiment, the aryl group is a 1-12 membered ring. In another embodiment, the aryl group is a 1-8 membered ring. In another embodiment, the aryl group comprises of 1-4 fused rings.

A "hydroxyl" group refers to an OH group. It is understood by a person skilled in the art that when T is OR, R is not OH.

In one embodiment, the term "halogen" refers to in one embodiment to F, in another embodiment to Cl, in another embodiment to Br, or in another embodiment to 1.

An "arylalkyl" group refers, in another embodiment, to an alkyl bound to an aryl, wherein alkyl and aryl are as defined above. An example of an arylalkyl group is a benzyl group.

In one embodiment, this invention provides for the use of a compound as herein described and/or, its analog, derivative, isomer, metabolite, pharmaceutically acceptable salt, pharmaceutical product, hydrate, N-oxide, prodrug, polymorph, impurity or crystal or combinations thereof.

In one embodiment, the term "isomer" includes, but is not limited to, optical isomers and analogs, structural isomers and analogs, conformational isomers and analogs, and the like.

In one embodiment, the term "isomer" is meant to encompass optical isomers of the SARM compound. It will be appreciated by those skilled in the art that the SARMs of the present invention contain at least one chiral center. Accordingly, the SARMs used in the methods of the present invention may exist in, and be isolated in, optically-active or racemic forms. Some compounds may also exhibit polymorphism. It is to be understood that the present invention encompasses any racemic, optically-active, polymorphic, or stereoisomeric form, or mixtures thereof, which form possesses properties useful in the treatment of androgen-related conditions described herein. In one embodiment, the SARMs are the pure (R)-isomers. In another embodiment, the SARMs are the pure (S)-isomers. In another embodiment, the SARMs are a mixture of the (R) and the (S) isomers. In another embodiment, the SARMs are a racemic mixture comprising an equal amount of the (R) and the (S) isomers. It is well known in the art how to prepare optically-active forms (for example, by resolution of the racemic form by recrystallization techniques, by synthesis from optically-active starting materials, by chiral synthesis, or by chromatographic separation using a chiral stationary phase).

The invention includes "pharmaceutically acceptable salts" of the compounds of this invention, which may be produced, by reaction of a compound of this invention with an acid or base.

Suitable pharmaceutically-acceptable salts of amines of formulas I-XX may be prepared from an inorganic acid or from an organic acid. In one embodiment, examples of inorganic salts of amines are bisulfates, borates, bromides, chlorides, hemisulfates, hydrobromates, hydrochlorates, 2-hydroxyethylsulfonates (hydroxyethanesulfonates), iodates, iodides, isothionates, nitrate, persulfates, phosphates, sulfates, sulfamates, sulfanilates, sulfonic acids (alkylsulfonates, arylsulfonates, halogen substituted alkylsulfonates, halogen substituted arylsulfonates), sulfonates and thiocyanates.

In one embodiment, examples of organic salts of amines may be selected from aliphatic, cycloaliphatic, aromatic, araliphatic, heterocyclic, carboxylic and sulfonic classes of organic acids, examples of which are acetates, arginines, aspartates, ascorbates, adipates, anthranilates, algenates, alkane carboxylates, substituted alkane carboxylates, alginates, benzenesulfonates, benzoates, bisulfates, butyrates, bicarbonates, bitartrates, carboxylates, citrates, camphorates, camphorsulfonates, cyclohexylsulfamates, cyclopentanepropionates, calcium edetates, camsylates, carbonates, clavulanates, cinnamates, dicarboxylates, digluconates, dodecylsulfonates, dihydrochlorides, decanoates, enanthuates, ethanesulfonates, edetates, edisylates, estolates, esylates, fumarates, formates, fluorides, galacturonates, gluconates, glutamates, glycolates, glucorates, glucoheptanoates, glycerophosphates, gluceptates, glycollylarsanilates, glutarates, glutamates, heptanoates, hexanoates, hydroxymaleates, hydroxycarboxylic acids, hexylresorcinates, hydroxybenzoates, hydroxynaphthoates, hydrofluorate, lactates, lactobionates, laurates, malates, maleates, methylenebis(beta-oxynaphthoate), malonates, mandelates, mesylates, methane sulfonates, methylbromides, methylnitrates, methylsulfonates, monopotassium maleates, mucates, monocarboxylates, naphthalenesulfonates, 2-naphthalenesulfonates, nicotinates, napsylates, N-methylglucamines, oxalates, octanoates, oleates, pamoates, phenylacetates, picrates, phenylbenzoates, pivalates, propionates, phthalates, phenylacetate, pectinates, phenylpropionates, palmitates, pantothenates, polygalacturates, pyruvates, quinates, salicylates, succinates, stearates, sulfanilate, subacetates, tartarates, theophyllineacetates, p-toluenesulfonates (tosylates), trifluoroacetates, terephthalates, tannates, teoclates, trihaloacetates, triethiodide, tricarboxylates, undecanoates and valerates.

In one embodiment, examples of inorganic salts of carboxylic acids or phenols may be selected from ammonium, alkali metals to include lithium, sodium, potassium, or cesium; alkaline earth metals to include calcium, magnesium, or aluminium; zinc, barium, cholines, or quaternary ammoniums.

In another embodiment, examples of organic salts of carboxylic acids or phenols may be selected from arginine, organic amines to include aliphatic organic amines, alicyclic organic amines, aromatic organic amines, benzathines, t-butylamines, benethamines (N-benzylphenethylamine), dicyclohexylamines, dimethylamines, diethanolamines, ethanolamines, ethylenediamines, hydrabamines, imidazoles, lysines, methylamines, meglamines, N-methyl-D-glucamines, N,N'-dibenzylethylenediamines, nicotinamides, organic amines, ornithines, pyridines, picolines, piperazines, procaine, tris(hydroxymethyl)methylamines, triethylamines, triethanolamines, trimethylamines, tromethamines and ureas.

In one embodiment, the salts may be formed by conventional means, such as by reacting the free base or free acid form of the product with one more equivalents of the appropriate acid or base in a solvent or medium in which the salt is insoluble or in a solvent such as water, which is removed in vacuo or by freeze drying or by exchanging the ions of a existing salt for another ion or suitable ion-exchange resin.

The invention also includes use of N-oxides of the amino substituents of the compounds described herein.

This invention provides for the use of derivatives of the compounds as herein described. In one embodiment, "derivatives" includes but is not limited to ether derivatives, acid derivatives, amide derivatives, ester derivatives and the like. In another embodiment, this invention further includes use of hydrates of the compounds as described herein. In one embodiment, "hydrate" includes but is not limited to hemihydrate, monohydrate, dihydrate, trihydrate and the like.

This invention provides, in other embodiments, use of metabolites of the compounds as herein described. In one embodiment, "metabolite" means any substance produced from another substance by metabolism or a metabolic process.

This invention provides, in other embodiments, use of pharmaceutical products of the compounds as herein described. The term "pharmaceutical product" refers, in other embodiments, to a composition suitable for pharmaceutical use (pharmaceutical composition), for example, as described herein.

Compounds as herein described may be prepared by any means known in the art, including inter alia, those described in U.S. patent application Ser. No. 11/505,363 and U.S. patent application Ser. No. 11/505,499; fully incorporated by reference herein in their entirety.

In some embodiments, the compounds for use in the methods of this invention are nonsteroidal ligands for the androgen receptor and may demonstrate tissue-selective androgenic and/or anabolic activity. These novel agents are useful in males for the treatment of a variety of hormone-related conditions such as sexual dysfunction, decreased sexual libido, erectile dysfunction, hypogonadism, sarcopenia, osteopenia, osteoporosis, alterations in cognition and mood, depression, anemia, hair loss, obesity, benign prostate hyperplasia and/or prostate cancer. Further, the compounds are useful for oral testosterone replacement therapy, and treating prostate cancer. In other embodiments, the compounds are useful for the treatment of a variety of hormone-related conditions in females including, sexual dysfunction, decreased sexual libido, hypogonadism, sarcopenia, osteopenia, osteoporosis, alterations in cognition and mood, depression, anemia, hair loss, obesity, endometriosis, infertility, breast cancer, uterine cancer and ovarian cancer. In other embodiments, the SARMs are useful for treating, suppressing, inhibiting or reducing the incidence of diabetes type II, diabetes type I, glucose intolerance, hyperinsulinemia, insulin resistance, dyslipidemia, hypercholesterolemia, high blood pressure, obesity, fatty liver conditions, diabetic nephropathy, diabetic neuropathy, diabetic retinopathy, cardiovascular disease, atherosclerosis, cerebrovascular conditions and stroke.

In some embodiments, the compounds as described herein are useful in preventing and treating muscle wasting disorders, bone related disorders, and diabetes related disorders.

In some embodiments, the compounds as described herein are useful in the treatment of a) muscle wasting in patients with cancer, wherein the patients are subjected to cancer therapy; b) muscle wasting in patients with non-small cell lung cancer (NSCLC), wherein the patients are subjected to cancer therapy; c) muscle wasting in patients with non-small cell lung cancer (NSCLC), wherein the patients are subjected to taxane therapy; d) pre-cachexia or early cachexia (preventing muscle wasting in a cancer patient), wherein the patients are subjected to cancer therapy e) treating loss of physical function due to cancer or cancer therapy (radiation, chemotherapy, surgery); f) increasing physical function of a subject, wherein the subject is subjected to cancer therapy; g) increasing physical function of a cancer patient, wherein the patient is subjected to cancer therapy; h) increasing physical function of a cancer patient, wherein said patient suffers from non-small cell lung cancer, colorectal cancer, non-Hodgkin lymphoma, chronic lymphocytic leukemia or breast cancer, and is subjected to cancer therapy; i) increasing physical function of a cancer patient, wherein said patient suffers from non-small cell lung cancer, and is subjected to taxane therapy; j) treating, suppressing, inhibiting, reducing the severity of, reducing the incidence of, reducing the pathogenesis of or delaying onset of, ng cancer in a patient, wherein the patient is subjected to cancer therapy; k) increasing survival, functional independence, and increasing quality of life of a subject suffering from cancer, and is subjected to cancer therapy; l) increasing survival, functional independence, and increasing quality of life of a subject suffering from non-small cell lung cancer, and is subjected to taxane therapy; m) preventing or treating declines in quality of life due to cancer or cancer therapy, and treating diseases, disorders or conditions related thereto; n) increasing lean body mass of a cancer patient, and is subjected to cancer therapy; or o) increasing lean body mass of a cancer patient, wherein said patient suffers from non-small cell lung cancer, and is subjected to taxane therapy; via the administration of any SARM as herein described and optionally other therapeutic agents, including but not limited to chemotherapeutic agents, or compositions comprising the same. In another embodiment, the compounds as described herein are administered to cancer patients that are subjected to cancer therapy. In another embodiment, the compounds as described herein are administered to cancer patients that are subjected to radiation therapy. In another embodiment, the compounds as described herein are administered to cancer patients that are subjected to taxane therapy. In another embodiment, the compounds as described herein are administered to cancer patients that are subjected to taxane therapy in combination with platinum therapy. In another embodiment, the compounds as described herein are administered to cancer patients that are subjected to platinum therapy in combination with non-taxane chemotherapeutic agent(s). In another embodiment, the compounds as described herein are administered in combination with radiation therapy. In another embodiment, the compounds as described herein are administered in combination with other therapeutic agents. In another embodiment, the compounds as described herein are administered in combination with chemotherapeutic agents.

In some embodiments, the compounds as described herein are useful, either alone or as a composition, in males and females for the treatment of a variety of hormone-related conditions, such as hypogonadism, sarcopenia, erectile dysfunction, lack of libido, osteoporosis and fertility. In some embodiments, the compounds as described herein are useful in stimulating or promoting or restoring function to various processes, which in turn result in the treatment of the conditions as herein described, including, inter alia, promoting erythropoiesis, osteogenesis, muscle growth, glucose uptake, insulin secretion, and/or preventing lipidogenesis, clotting, insulin resistance, atherosclerosis, osteoclast activity, and others.

In one embodiment, the methods of this invention make use of the described compound contacting or binding a receptor, and thereby mediating the described effects. In some embodiments, the receptor is a nuclear receptor, which in one embodiment, is an androgen receptor, or in another embodiment, is an estrogen receptor, or in another embodiment, is a progesterone receptor, or in another embodiment, is a glucocorticoid receptor. In some embodiments, the multitude of effects may occur simultaneously, as a function of binding to multiple receptors in the subject. In some embodiments, the tissue selective effects of the compounds as described herein provide for simultaneous action on different target organs.

In some embodiments, tissue selectivity may be a function of specific promoter interaction, as exemplified herein in Example 10.

Pharmaceutical Compositions

In some embodiments, this invention provides methods of use which comprise administering a composition comprising the described compounds. As used herein, "pharmaceutical composition" means a "therapeutically effective amount" of the active ingredient, i.e. the SARM compound, together with a pharmaceutically acceptable carrier or diluent. A "therapeutically effective amount" as used herein refers to that amount which provides a therapeutic effect for a given condition and administration regimen.

As used herein, the term "administering" refers to bringing a subject in contact with a SARM compound of the present invention. As used herein, administration can be accomplished in vitro, i.e. in a test tube, or in vivo, i.e. in cells or tissues of living organisms, for example humans. In one embodiment, the present invention encompasses administering the compounds of the present invention to a subject.

In one embodiment, this invention is directed to a composition comprising a compound of formula S-(III):

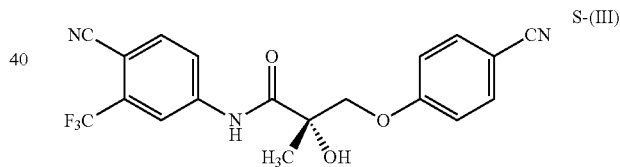

or its isomer, pharmaceutically acceptable salt, pharmaceutical product, hydrate, N-oxide, or any combination thereof, and a chemotherapeutic agent.

In one embodiment, this invention is directed to a composition comprising a compound of formula S-(III):

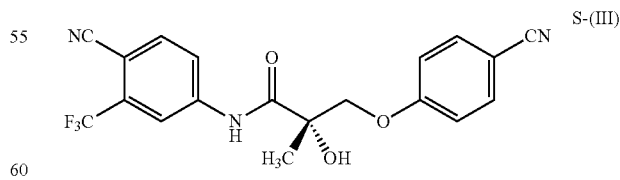

or its isomer, pharmaceutically acceptable salt, pharmaceutical product, hydrate, N-oxide, or any combination thereof; and a platinum and a taxane.

In one embodiment, this invention is directed to a composition comprising a compound of formula S-(III):

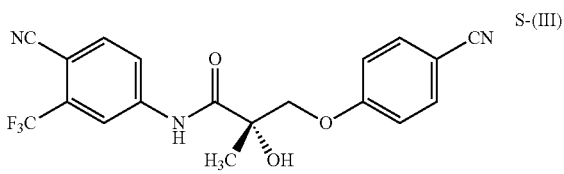 [SMILES: C[C@](O)(COc1ccc(C#N)cc1)C(=O)Nc1ccc(C#N)c(C(F)(F)F)c1]

S-(III)

or its isomer, pharmaceutically acceptable salt, pharmaceutical product, hydrate, N-oxide, or any combination thereof, and a platinum and a non-taxane chemotherapeutic agent.

The pharmaceutical compositions containing a SARM compound of this invention can be administered to a subject by any method known to a person skilled in the art, such as orally, parenterally, intravascularly, paracancerally, transmucosally, transdermally, intramuscularly, intranasally, intravenously, intradermally, subcutaneously, sublingually, intraperitoneally, intraventricularly, intracranially, intravaginally, by inhalation, rectally, intratumorally, or by any means in which the recombinant virus/composition can be delivered to tissue (e.g., needle or catheter). Alternatively, topical administration may be desired for application to mucosal cells, for skin or ocular application. Another method of administration is via aspiration or aerosol formulation.

In one embodiment, the pharmaceutical compositions are administered orally, and are thus formulated in a form suitable for oral administration, i.e. as a solid or a liquid preparation. Suitable solid oral formulations include tablets, capsules, pills, granules, pellets, powders, and the like. Suitable liquid oral formulations include solutions, suspensions, dispersions, emulsions, oils and the like. In one embodiment of the present invention, the SARM compounds are formulated in a capsule. In accordance with this embodiment, the compositions of the present invention comprise in addition to the SARM active compound and the inert carrier or diluent, a hard gelatin capsule.

In one embodiment, the micronized capsules comprise particles containing a SARM of this invention, wherein the term "micronized" used herein refers to particles having a particle size is of less than 100 microns, or in another embodiment, less than 50 microns, or in another embodiment, less than 35 microns, or in another embodiment, less than 15 microns, or in another embodiment, less than 10 microns, or in another embodiment, less than 5 microns.

Further, in another embodiment, the pharmaceutical compositions are administered by intravenous, intraarterial, or intramuscular injection of a liquid preparation. Suitable liquid formulations include solutions, suspensions, dispersions, emulsions, oils and the like. In one embodiment, the pharmaceutical compositions are administered intravenously, and are thus formulated in a form suitable for intravenous administration. In another embodiment, the pharmaceutical compositions are administered intraarterially, and are thus formulated in a form suitable for intraarterial administration. In another embodiment, the pharmaceutical compositions are administered intramuscularly, and are thus formulated in a form suitable for intramuscular administration.

Further, in another embodiment, the pharmaceutical compositions are administered topically to body surfaces, and are thus formulated in a form suitable for topical administration. Suitable topical formulations include gels, ointments, creams, lotions, drops and the like. For topical administration, the SARM agents or their physiologically tolerated derivatives such as salts, esters, N-oxides, and the like are prepared and applied as solutions, suspensions, or emulsions in a physiologically acceptable diluent with or without a pharmaceutical carrier.

Further, in another embodiment, the pharmaceutical compositions are administered as a suppository, for example a rectal suppository or a urethral suppository. Further, in another embodiment, the pharmaceutical compositions are administered by subcutaneous implantation of a pellet. In a further embodiment, the pellet provides for controlled release of SARM agent over a period of time. In a further embodiment, the pharmaceutical compositions are administered intravaginally.

In another embodiment, the active compound can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid).

As used herein "pharmaceutically acceptable carriers or diluents" are well known to those skilled in the art. The carrier or diluent may be a solid carrier or diluent for solid formulations, a liquid carrier or diluent for liquid formulations, or mixtures thereof.

Solid carriers/diluents include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

In one embodiment, the compositions of this invention may include, a SARM of this invention or any combination thereof, together with one or more pharmaceutically acceptable excipients.

Suitable excipients and carriers may be, according to embodiments of the invention, solid or liquid and the type is generally chosen based on the type of administration being used. Liposomes may also be used to deliver the composition. Examples of suitable solid carriers include lactose, sucrose, gelatin and agar. Oral dosage forms may contain suitable binders, lubricants, diluents, disintegrating agents, coloring agents, flavoring agents, flow-inducing agents, and melting agents. Liquid dosage forms may contain, for example, suitable solvents, preservatives, emulsifying agents, suspending agents, diluents, sweeteners, thickeners, and melting agents. Parenteral and intravenous forms should also include minerals and other materials to make them compatible with the type of injection or delivery system chosen. Of course, other excipients may also be used.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, cyclodextrins, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil.

Parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of petroleum, animal, vegetable, or synthetic origin, for example, peanut oil, soybean oil, mineral oil, olive oil, sunflower oil, and fish-liver oil.

In addition, the compositions may further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch alginic acid, silicon dioxide, croscarmellose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween® 20, Tween® 80, Pluronic F68®, bile acid salts), protease inhibitors, surfactants (e.g. sodium lauryl sulfate), permeation enhancers, solubilizing agents (e.g., Cremophor®, glycerol, polyethylene glycerol, benzalkonium chloride, benzyl benzoate, cyclodextrins, sobitan esters, stearic acids), anti-oxidants (e.g., ascorbic acid, sodium metabisulfite, butylated hydroxyanisole), stabilizers (e.g. hydroxypropyl cellulose, hydroxypropylmethyl cellulose), viscosity increasing agents (e.g. carbomer, colloidal silicon dioxide, ethyl cellulose, guar gum), sweetners (e.g. aspartame, citric acid), preservatives (e.g., Thimerosal®, benzyl alcohol, parabens), coloring agents, lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates), and/or adjuvants.

In one embodiment, the pharmaceutical compositions provided herein are controlled release compositions, i.e. compositions in which the SARM compound is released over a period of time after administration. Controlled or sustained release compositions include formulation in lipophilic depots (e.g. fatty acids, waxes, oils). In another embodiment, the composition is an immediate release composition, i.e. a composition in which all of the SARM compound is released immediately after administration.

In another embodiment, the pharmaceutical composition can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88-507 (1980); Saudek et al, N. Engl. J. Med. 321:574 (1989). In another embodiment, polymeric materials can be used. In yet another embodiment, a controlled release system can be placed in proximity to the therapeutic target, i.e., the brain, thus requiring only a fraction of the systemic dose (see, e.g., Goodson, in Medical Applications of Controlled Release, supra, vol. 2, pp. 115-138 (1984). Other controlled release systems are discussed in the review by Langer (Science 249:1527-1533 (1990).

The compositions may also include incorporation of the active material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance.

Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Also comprehended by the invention are compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

The preparation of pharmaceutical compositions, which contain an active component is well understood in the art, for example by mixing, granulating, or tablet-forming processes. The active therapeutic ingredient is often mixed with excipients which are pharmaceutically acceptable and compatible with the active ingredient. For oral administration, the SARM agents or their physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. For parenteral administration, the SARM agents or their physiologically tolerated derivatives such as salts, esters, N-oxides, and the like are converted into a solution, suspension, or emulsion, if desired with the substances customary and suitable for this purpose, for example, solubilizers or other.

An active component can be formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For use in medicine, the salts of the compounds of formula I-XX and S-(III) will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid.

In one embodiment, this invention provides pharmaceutical compositions comprising compound I-XX and S-(III) of this invention. In one embodiment, such compositions are useful for oral testosterone replacement therapy.

In one embodiment, this invention also provides a composition comprising two or more compounds of I-XX and S-(III) of this invention, or polymorphs, isomers, hydrates, salts, N-oxides, etc., thereof. The present invention also relates to compositions and a pharmaceutical compositions which comprises a SARM alone or in combination with another therapeutic agent. Therapeutic agents include but are not limited to: progestin or estrogen, chemotherapeutic compounds, osteogenic or myogenic compounds, or other agents suitable for the applications as herein described. In one embodiment, the compositions of this invention will comprise a suitable carrier, diluent or salt.

In one embodiment, the methods of this invention may comprise administration of a compound of formula I-XX and S-(III) of this invention at various dosages. In one embodiment, the compound of formula I-XX and S-(III) is administered at a dosage of 0.01-1 mg per day. In one embodiment, compound of formula I-XX and S-(III) is administered at a dosage of 0.1-200 mg per day. In one embodiment, compound of formula I-XX and S-(III) is administered at a dose of 0.1-10 mg per day, or in another embodiment, 0.1-25 mg per day, or in another embodiment, 0.1-50 mg per day, or in another embodiment, 0.3-15 mg per day, or in another embodiment, 0.3-30 mg per day, or in another embodiment, 0.5-25 mg per day, or in another embodiment, 0.5-50 mg per day, or in another embodiment, 0.75-15 mg per day, or in another embodiment, 0.75-60 mg per day, or in another embodiment, 1-5 mg per day, or in another embodiment, 1-20 mg per day, or in another embodiment, 3-15 mg per day, or in another embodiment, 30-50 mg, or in another embodiment, 30-75 mg per day, or in another embodiment, 100-2000 mg per day.

In one embodiment, the methods of this invention may comprise administration of a compound of formula and S-(III) at various dosages. In one embodiment, compound of formula S-(III) is administered at a dosage of 1 mg. In one embodiment, compound of formula S-(III) is administered at a dosage of 3 mg. In another embodiment the compound of formula S-(III) is administered at a dosage of 0.01 mg, 0.03 mg, 0.1 mg, 0.3 mg, 0.75 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg or 100 mg.

In one embodiment, the compound of formula and S-(III) of this invention may be administered at various dosages. In one embodiment, compound of formula and S-(III) is administered at a dosage of 0.01-1 mg per day. In one embodiment, compound of formula and S-(III) is administered at a dosage of 0.1-200 mg per day. In one embodiment, compound of formula and S-(III) is administered at a dose of 0.1-10 mg per day, or in another embodiment, 0.1-25 mg per day, or in another embodiment, 0.1-50 mg per day, or in another embodiment, 0.3-15 mg per day, or in another embodiment, 0.3-30 mg per day, or in another embodiment, 0.5-25 mg per day, or in another embodiment, 0.5-50 mg per day, or in another embodiment, 0.75-15 mg per day, or in another embodiment, 0.75-60 mg per day, or in another embodiment, 1-5 mg per day, or in another embodiment, 1-20 mg per day, or in another embodiment, 3-15 mg per day, or in another embodiment, 30-50 mg, or in another embodiment, 30-75 mg per day, or in another embodiment, 100-2000 mg per day.

In one embodiment, the present invention provides methods of use comprising the administration of a pharmaceutical composition of this invention comprising: a) any embodiment of a compound as described herein; and b) a pharmaceutically acceptable carrier or diluent; which is to be understood to include an analog, isomer, metabolite, derivative, pharmaceutically acceptable salt, N-oxide, hydrate or any combination thereof of a compound as herein described, and may comprise compounds of formulas I-XX and S-(III).

In some embodiments, the present invention provides methods of use of a pharmaceutical composition comprising: a) any embodiment of the compounds as described herein, including an analog, isomer, metabolite, derivative, pharmaceutically acceptable salt, pharmaceutical product, N-oxide, hydrate thereof or any combination thereof; b) a pharmaceutically acceptable carrier or diluent; c) a flow-aid; and d) a lubricant.

In another embodiment, the present invention provides methods of use of a pharmaceutical composition comprising: a) any embodiment of the compounds as described herein, including an analog, isomer, metabolite, derivative, pharmaceutically acceptable salt, pharmaceutical product, N-oxide, hydrate thereof or any combination thereof; b) lactose monohydrate; c) microcrystalline cellulose; d) magnesium stearate; e) additives; and f) colloidal silicon dioxide.

In some embodiments, the methods of this invention make use of compositions comprising SARM compounds, which offer the advantage that the compounds are nonsteroidal ligands for the androgen receptor, and exhibit anabolic activity in vivo. According to this aspect, such compounds are unaccompanied by serious side effects, provide convenient modes of administration, and lower production costs and are orally bioavailable, lack significant cross-reactivity with other undesired steroid receptors, and may possess long biological half-lives.

For administration to mammals, and particularly humans, it is expected that the physician will determine the actual dosage and duration of treatment, which will be most suitable for an individual and can vary with the age, weight and response of the particular individual.

In one embodiment, the compositions for administration may be sterile solutions, or in other embodiments, aqueous or non-aqueous, suspensions or emulsions. In one embodiment, the compositions may comprise propylene glycol, polyethylene glycol, injectable organic esters, for example ethyl oleate, or cyclodextrins. In another embodiment, compositions may also comprise wetting, emulsifying and/or dispersing agents. In another embodiment, the compositions may also comprise sterile water or any other sterile injectable medium.

In one embodiment, the invention provides compounds and compositions, including any embodiment described herein, for use in any of the methods of this invention. In one embodiment, use of a SARM or a composition comprising the same, will have utility in inhibiting, suppressing, enhancing or stimulating a desired response in a subject, as will be understood by one skilled in the art. In another embodiment, the compositions may further comprise additional active ingredients, whose activity is useful for the particular application for which the SARM compound is being administered. In another embodiment, the compositions may further comprise chemotherapeutic agents.

In some embodiments, the compositions will further comprise a 5α-reductase inhibitors (5ARI), another SARM, a selective estrogen receptor modulator (SERM), an aromatase inhibitor, such as but not limited to anastrozole, exemestane, or letrozole, a GnRH agonist or antagonist, a steroidal or nonsteroidal GR ligand, a steroidal or nonsterodial PR ligand, a steroidal or nonsteroidal AR antagonist, a 17-aldoketoreductase inhibitor or 17β-hydroxysteroid dehydrogenase inhibitor. Such compositions may be used, in some embodiments, for treating a hormone dependent condition, such as, for example, infertility, neoplasia of a hormone-responsive cancer, for example, a gonadal cancer, or a urogenital cancer.

In some embodiments, the composition will comprise the SARMs as described herein, as well as another therapeutic compound, including inter alia, a 5ARI such as finasteride, dutasteride, izonsteride; other SARMs, such as, RU-58642, RU-56279, WS9761 A and B, RU-59063, RU-58841, bexlosteride, LG-2293, L-245976, LG-121071, LG-121091, LG-121104, LGD-2226, LGD-2941, YM-92088, YM-175735, LGD-1331, BMS-357597, BMS-391197, S-40503, BMS-482404, EM-4283, EM-4977, BMS-564929, BMS-391197, BMS-434588, BMS-487745, BMS-501949, SA-766, YM-92088, YM-580, LG-123303, LG-123129, PMCol, YM-175735, BMS-591305, BMS-591309, BMS-665139, BMS-665539, CE-590, 116BG33, 154BG31, arcarine, ACP-105; SERMs, such as tamoxifen, 4-hydroxytamoxifen, idoxifene, toremifene, ospemifene, droloxifene, raloxifene, arzoxifene, bazedoxifene, PPT (1,3,5-tris(4-hydroxyphenyl)-4-propyl-1H-pyrazole), DPN (diarylpropionitrile), lasofoxifene, pipendoxifene, EM-800, EM-652, nafoxidine, zindoxifene, tesmilifene, miproxifene phosphate, RU 58,688, EM 139, ICI 164,384, ICI 182,780, clomiphene, MER-25, diethylstilbestrol, coumestrol genistein, GW5638, LY353581, zuclomiphene, enclomiphene, delmadinone acetate, DPPE, (N,N-diethyl-2-{4-(phenylmethyl)-phenoxy}ethanamine), TSE-424, WAY-070, WAY-292, WAY-818, cyclocommunol, prinaberel, ERB-041, WAY-397, WAY-244, ERB-196, WAY-169122, MF-101, ERb-002, ERB-037, ERB-017, BE-1060, BE-380, BE-381, WAY-358, [$^{18}$F]FEDNP, LSN-500307, AA-102, CT-101, CT-102, VG-101; GnRH agonists or antagonists, such as, leuprolide, goserelin, triptorelin, alfaprostol, histrelin, detirelix, ganirelix, antide iturelix, cetrorelix, ramorelix, ganirelix, antarelix teverelix, abarelix, ozarelix, sufugolix, prazarelix, degarelix, NBI-56418, TAK-810, acyline; FSH agonist/antagonist, LH agonist/antagonists, aromatase inhibitors, such as, letrozole, anastrazole, atamestane, fadrozole, minamestane, exemestane, plomestane, liarozole, NKS-01, vorozole, YM-511, finrozole, 4-hydroxyandrostenedione, aminogluethimide, rogletimide; steroidal or nonsteroidal glucocorticoid receptor ligands, such as, ZK-216348, ZK-243149, ZK-243185, LGD-5552, mifepristone, RPR-106541, ORG-34517, GW-215864X, sesquicillin, CP-472555, CP-394531, A-222977, AL-438, A-216054, A-276575, CP-394531, CP-409069, UGR-07; steroidal or nonsterodial progesterone receptor ligands; steroidal or nonsteroidal AR antagonists such as flutamide, hydroxyflutamide, bicalutamide, enzalutamide, nilutamide, hydroxysteroid dehydrogenase inhibitors; PPARα ligands such as bezafibrate, fenofibrate, gemfibrozil; PPARγ ligands such as darglitazone, pioglitazone, rosiglitazone, isaglitazone, rivoglitazone, netoglitazone; dual acting PPAR ligands, such as naveglitazar, farglitazar, tesaglitazar, ragaglitazar, oxeglitazar, PN-2034; PPAR δ ligands; 17-ketoreductase inhibitors, 3β-DHΔ4,6-isomerase inhibitors, 3β-DHΔ4,5-isomerase inhibitors, 17,20 desmolase inhibitors, p450c17 inhibitors, p450ssc inhibitors, 17,20-lyase inhibitors, or combinations thereof.

In some embodiments, the compositions will further comprise ghrelin receptor ligand or growth hormone analogues and secretagogues, IGF-1, IGF-1 analogues and secretagogues, myostatin analogues, proteasome inhibitors, androgenic/anabolic steroid, Enbrel®, melanocortin 4 receptor agonist, insulins, or combinations thereof. Such compositions may be used, in some embodiments, for treating sarcopenia or a musculoskeletal condition.

In some embodiments, the composition will comprise the SARMs as described herein, as well as another therapeutic compound, including inter alia, ghrelin receptor ligand or growth hormone analogues and secretagogues, such as, pralmorelin, examorelin, tabimorelin, capimorelin, capromorelin, ipamorelin, EP-01572, EP-1572, JMV-1843, an androgenic/anabolic steroid such as testosterone and oxandrolone; a melanocortin 4 receptor agonist, such as bremelanotide; a ghrelin or analogue thereof, such as human ghrelin, CYT-009-GhrQb, L-692429, GHRP-6, SK&F-110679, U-75799E; leptin (metreleptin, pegylated leptin; a leptin receptor agonist, such as LEP(116-130), OB3, [D-Leu4]-OB3, rAAV-leptin, AAV-hOB, rAAVhOB; an insulin (short-, intermediate-, and long acting formulations; a cortisol or corticosteroid, or a combination thereof.

In some embodiments, the composition comprise the SARMs as described herein, and at least one chemotherapeutic agent, including inter alia, alkylating agents including but not limited to: cyclophosphamide, mechlorethamine, chlorambucil, and melphalan; antimetabolites, Tubulin antagonists such as taxanes, colchicines, and vinca alkaloids; anthracyclines including but not limited to: daunorubicin, doxorubicin, epirubicin, idarubicin, mitoxantrone and valrubicin; cytoskeletal disruptors (taxanes) including but not limited to: paclitaxel and docetaxel; epothilones; histone deacetylase inhibitors including but not limited to: vorinostat and romidepsin; inhibitors of topoisomerase II including but not limited to: etoposide, teniposide and tafluposide; kinase inhibitors including but not limited to: bortezomib, erlotinib, gefitinib, imatinib and vismodegib; monoclonal antibodies including but not limited to: bevacizumab, cetuximab, ipilimumab, ofatumumab, ocrelizumab, panitumab, rituximab and vemrafenib; nucleotide analogs and precursor analogs including but not limited to: azacitidine, azathioprine, capecitabine, cytarabine, doxifluridine, fluorouracil, gemcitabine, hydroxyurea, mercaptopurine, methotrexate and tioguanine (Thioguanine); peptide antibiotics including but not limited to: bleomycin and actinomycin; platinum-based agents including but not limited to: carboplatin, cisplatin and pxaliplatin; retinoids including but not limited to: tretinoin, alitretinoin and bexarotene; vinca alkaloids including but not limited to: vinblastine, vincristine, vindesine and vinorelbine; or any combination thereof. In another embodiment, the SARM is compound of formula II as described hereinabove. In another embodiment, the SARM is compound of formula S-(III) as described hereinabove.

In a preferred embodiment, the composition comprise the SARMs as described herein, and at least one chemotherapeutic agent selected from: an alkylating agent, a monoclonal antibody, an antimetabolite, a kinase inhibitor, a topoisomerase (topo) II inhibitor, a tubulin antagonist or any combination thereof. In another embodiment, the SARM is compound of formula II as described hereinabove. In another embodiment, the SARM is compound of formula S-(III) as described hereinabove.

In some embodiments, the composition comprises the SARMs as described herein, and at least one chemotherapeutic agent, including inter alia, bendamustine, bevacizumab, bleomycin, calcium folinate, capecitabine, carboplatin, cetuximab, chlorambucil, cisplatin, cyclophosphamide, cytarabine, dasatinib, docetaxel, doxorubicin, erlotinib, etoposide, fludarabine, fluorouracil, gemcitabine hydrochloride, irinotecan hydrochloride, lapatinib, methotrexate, methylprednisolone acetate, mitoxantrone, mitoxantrone hydrochloride, oxaliplatin, paclitaxel, pamidronate disodium, panitumumab, pemetrexed, prednisone, rituximab, trastuzumab, vincristine, vinorelbine or any combination thereof. In another embodiment, the SARM is compound of formula II as described hereinabove. In another embodiment, the SARM is compound of formula or S-(III) as described hereinabove.

In some embodiments, the composition comprises the SARMs as described herein, and a taxane.

In some embodiments, the composition comprises the SARMs as described herein a taxane agent and platinum agent(s).

In some embodiments, the composition comprises the SARMs as described herein platinum agent(s) and a non-taxane chemotherapeutic agent.

In another embodiment, a taxane (or taxane therapy) include non-limiting examples such as paclitaxel, docetaxel or combination thereof.

In another embodiment, platinum (or platinum therapy) include non-limiting examples such as cisplatin, carboplatin, oxaliplatin or combination thereof.

In another embodiment, non-taxane chemotherapeutic agent include non-limiting examples such as gemcitabine, pemetrexed, or vinorelbine or combination thereof.

The invention contemplates, in some embodiments, administration of compositions comprising the individual agents, administered separately and by similar or alternative routes, formulated as appropriately for the route of administration. The invention contemplates, in some embodiments, administration of compositions comprising the individual agents, administered in the same formulation. The invention contemplates, in some embodiments, staggered administration, concurrent administration, of administration of the various agents over a course of time, however, their effects are synergistic in the subject.

It is to be understood that any of the above means, timings, routes, or combinations thereof, of administration of two or more agents is to be considered as being encompassed by the phrase "administered in combination", as described herein.

In one embodiment, the SARM compound of this invention is administered in combination with an anti-cancer agent. In one embodiment, the anti-cancer agent is a monoclonal antibody. In some embodiments, the monoclonal antibodies are used for diagnosis, monitoring, or treatment of cancer. In one embodiment, monoclonal antibodies react against specific antigens on cancer cells. In one embodiment, the monoclonal antibody acts as a cancer cell receptor antagonist. In one embodiment, monoclonal antibodies enhance the patient's immune response. In one embodiment, monoclonal antibodies act against cell growth factors, thus blocking cancer cell growth. In one embodiment, anti-cancer monoclonal antibodies are conjugated or linked to anti-cancer or chemotherapeutic drugs, radioisotopes, other biologic response modifiers, other toxins, or a combination thereof. In one embodiment, anti-cancer monoclonal antibodies are conjugated or linked to a SARM compound as described hereinabove.

In another embodiment, the present invention includes SARM compounds of this invention and compositions in which a compound of the invention is either combined with, or covalently bound to, an agent bound to a targeting agent, such as a monoclonal antibody (e.g., a murine or humanized monoclonal antibody). In one embodiment, the agent bound to a targeting agent is a cytotoxic agent. It will be appreciated that the latter combination may allow the introduction of cytotoxic agents into for example cancer cells with greater specificity. Thus, the active form of the cytotoxic agent (i.e., the free form) will be present only in cells targeted by the antibody. Of course, the compounds of the invention may also be combined with monoclonal antibodies that have therapeutic activity against cancer.

In one embodiment, the SARM compound of this invention is administered in combination with a selective tyrosine kinase inhibitor. In some embodiments, the selective tyrosine kinase inhibitor inhibits catalytic sites of cancer promoting receptors thereby inhibiting tumor growth. In one embodiment, a selective tyrosine kinase inhibitor modulates growth factor signaling. In some embodiments, the selective tyrosine kinase inhibitor targets EGFR (ERB B/HER) family members. In one embodiment, the selective tyrosine kinase inhibitor is a BCR-ABL tyrosine kinase inhibitor. In one embodiment, the selective tyrosine kinase inhibitor is an epidermal growth factor receptor tyrosine kinase inhibitor. In one embodiment, the selective tyrosine kinase inhibitor is a vascular endothelial growth factor tyrosine kinase inhibitor. In one embodiment, the selective tyrosine kinase inhibitor is a platelet derived growth factor (PDGF) inhibitor.

In one embodiment, the SARM compound of this invention is administered in combination with a topoisomerase (topo) II inhibitor. Topo II inhibitors include but are not limited to: etoposide, teniposide and tafluposide.

In one embodiment, the SARM compound of this invention is administered in combination with a tubulin antagonist. Tubulin antagonists include but are not limited to: vinca alkaloids such as vinblastine, vincristine, vindesine, vinorelbine, vinflunine, or vinca site binders such as cryptophycin 52, halichondrins, dolastatins, and hemiasterlins; taxanes such as paclitaxel and docetaxel, or taxane site binders such as epothilones and discodermolide; and colchicine site binders such as colchicine, combrestatin, 2-methoxy estradiol, methoxy benzenesulfonamides (E7010), and ABT-751.

In one embodiment, the SARM compound of this invention is administered in combination with a cancer vaccine. In one embodiment, the cancer vaccine is a therapeutic vaccine thus, treating an existing cancer. In some embodiments, the cancer vaccine is a prophylactic vaccine thus, preventing the development of cancer. In one embodiment, both types of vaccines have the potential to reduce the burden of cancer. In one embodiment, treatment or therapeutic vaccines are administered to cancer patients and are designed to strengthen the body's natural defenses against cancers that have already developed. In one embodiment, therapeutic vaccines may prevent additional growth of existing cancers, prevent the recurrence of treated cancers, or eliminate cancer cells not killed by prior treatments. In some embodiments, prevention or prophylactic vaccines are administered to healthy individuals and are designed to target cancer in individuals who present high risk for the disease. In one embodiment, the cancer vaccine is an antigen/adjuvant vaccine. In one embodiment, the cancer vaccine is a whole cell tumor vaccine. In one embodiment, the cancer vaccine is a dendritic cell vaccine. In one embodiment, the cancer vaccine comprises viral vectors and/or DNA vaccines. In one embodiment, the cancer vaccine is an idiotype vaccine.

In one embodiment, the SARM compound of this invention is administered in combination with an chemotherapeutic agent. In one embodiment, the chemotherapeutic agent is an alkylating agent, such as but not limited to cyclophosphamide. In one embodiment, the chemotherapeutic agent is a cytotoxic antibiotic such as but not limited to doxorubicin. In one embodiment, the chemotherapeutic agent is an antimetabolite, such as but not limited to methotrexate. In one embodiment, the chemotherapeutic agent is a vinca alkaloid, such as but not limited to vindesine. In some embodiments, the chemotherapeutic agents include platinum compounds such as but not limited to carboplatin, and taxanes such as docetaxel. In one embodiment, the chemotherapeutic agent is an aromatase inhibitor such as but not limited to anastrazole, exemestane, or letrozole. In one embodiment, the chemotherapeutic agent is a tubulin antagonist, such as but not limited to vinca alkaloids such as vinblastine, vincristine, vindesine, vinorelbine, vinflunine, or vinca site binders such as cryptophycin 52, halichondrins, dolastatins, and hemiasterlins; taxanes such as paclitaxel and docetaxel, or taxane site binders such as epothilones, and discodermolide; and colchicine site binders such as colchicine, combrestatin, 2-methoxy estradiol, methoxy benzenesulfonamides (E7010), and ABT-751. In one embodiment, the chemotherapeutic agent is a topoisomerase (topo) II inhibitor, such as but not limited to etoposide, teniposide and tafluposide.

In one embodiment, the SARM compound of this invention is administered in combination with a Bax activity modulator such as alisol B acetate. In one embodiment, the SARM compound is administered in combination with an angiotensin II receptor blocker such as losartan. In one embodiment, the SARM compound is administered in combination with selenium, green tea cachecins, saw palmetto, lycopene, vitamin D, dietary soy, genistein or isoflavone.

In one embodiment, the SARM compound of this invention is administered in combination with antineoplastic agents, such as alkylating agents, antibiotics, hormonal antineoplastics and antimetabolites. Examples of useful alkylating agents include alkyl sulfonates such as busulfan, improsulfan and piposulfan; aziridines, such as a benzodizepa, carboquone, meturedepa and uredepa; ethylenimines and methylmelamines such as altretamine, triethylenemelamine, triethylenephosphoramide, triethylenethiophosphoramide and trimethylolmelamine; nitrogen mustards such as chlorambucil, chlomaphazine, cyclophosphamide, estramustine, iphosphamide, mechlorethamine, mechlorethamine oxide hydrochloride, melphalan, novembichine, phenesterine, prednimustine, trofosfamide, and uracil mustard; nitroso ureas, such as carmustine, chlorozotocin, fotemustine, lomustine, nimustine, ranimustine, dacarbazine, mannomustine, mitobronitol, mitolactol and pipobroman. More such agents will be known to those having skill in the medicinal chemistry and oncology arts.

In some embodiments, other agents suitable for combination with SARMs include protein synthesis inhibitors such as abrin, aurintricarboxylic acid, chloramphenicol, colicin E3, cycloheximide, diphtheria toxin, edeine A, emetine, erythromycin, ethionine, fluoride, 5-fluorotryptophan, fusidic acid, guanylyl methylene diphosphonate and guanylyl imidodiphosphate, kanamycin, kasugamycin, kirromycin, and O-methyl threonine, modeccin, neomycin, norvaline, pactamycin, paromomycine, puromycin, ricin, α-sarcin, shiga toxin, showdomycin, sparsomycin, spectinomycin, streptomycin, tetracycline, thiostrepton and trimethoprim. Inhibitors of DNA synthesis, including alkylating agents such as dimethyl sulfate, mitomycin C, nitrogen and sulfur mustards, MNNG and NMS; intercalating agents such as acridine dyes, actinomycins, adriamycin, anthracenes, benzopyrene, ethidium bromide, propidium diiodide-intertwining, and agents such as distamycin and netropsin, can also be combined with compounds of the present invention in pharmaceutical compositions. DNA base analogs such as acyclovir, adenine, β-1-D-arabinoside, amethopterin, aminopterin, 2-aminopurine, aphidicolin, 8-azaguanine, azaserine, 6-azauracil, 2'-azido-2'-deoxynucliosides, 5-bromodeoxycytidine, cytosine, β-1-D-arabinoside, diazooxynorleucine, dideoxynucleosides, 5-fluorodeoxycytidine, 5-fluorodeoxyuridine, 5-fluorouracil, hydroxyurea and 6-mercaptopurine also can be used in combination therapies with the compounds of the invention. Topoisomerase inhibitors, such as coumermycin, nalidixic acid, novobiocin and oxolinic acid, inhibitors of cell division, including colcemide, colchicine, vinblastine and vincristine; and RNA synthesis inhibitors including actinomycin D, α-amanitine and other fungal amatoxins, cordycepin (3'-deoxyadenosine), dichororibofuranosyl benzimidazole, rifampicine, streptovaricin and streptolydigin also can be combined with the compounds of the invention to provide pharmaceutical compositions.

In one embodiment, the SARM compound of this invention is administered in combination with a vaccine for prostate cancer, alisol B acetate, angiotensin II receptor blocker, or others known in the art. In one embodiment, the SARM compound is administered in combination with an agent to decrease prostate (benign or malignant) hypertrophy, such as, for example, selenium, green tea cachecins, saw palmetto, lycopene, vitamin D, dietary soy, genistein and isoflavone food product and others.

In one embodiment, the SARM compound of this invention is administered in combination with an immunomodulating agent. In one embodiment, the immunomodulating agent is an immunosuppressive agent. In one embodiment, immunosuppressive agents comprise corticosteroids, cyclosporine, azathioprine, methotrexate, cyclophosphamide, tacrolimus or FK-506, anti-thymocyte globulin, mycophenylate moeftil, or a combination thereof. In one embodiment, the corticosteroid is a glucocorticoid.

In one embodiment, the immunomodulating agent is an immunostimulatory agent. In one embodiment, the immunostimulatory agent is a specific immunostimulator thus, provides antigenic specificity during an immune response, such as a vaccine or any antigen. In one embodiment, the immunostimulatory agent is a non-specific immunostimulator thus, acting irrespective of antigenic specificity to augment immune response of other antigen or stimulate components of the immune system without antigenic specificity. In one embodiment, the non-specific immunostimulator is Freund's® complete adjuvant. In one embodiment, the non-specific immunostimulator is Freund's® incomplete adjuvant. In one embodiment, the non-specific immunostimulator is a montanide ISA adjuvant. In one embodiment, the non-specific immunostimulator is a Ribi's® adjuvant. In one embodiment, the non-specific immunostimulator is a Hunter's TiterMax®. In one embodiment, the non-specific immunostimulator is an aluminum salt adjuvant. In one embodiment, the non-specific immunostimulator is a nitrocellulose-adsorbed protein. In one embodiment, the non-specific immunostimulator is a Gerbu Adjuvant®.

In one embodiment, the SARM compound of this invention is administered in combination with an agent, which treats bone diseases, disorders or conditions, such as osteoporosis, bone fractures, etc., and this invention comprises methods of treating the same, by administering the SARMs as herein described, alone or in combination with other agents.

In one embodiment, the methods provided herein and/or utilizing the compositions provided herein, are effective in reducing metastases to the bone, such as in terms of number of foci, the size of foci, or a combination thereof. According to this aspect of the invention and in one embodiment, provided herein is a method of preventing or inhibiting cancer metastasis to bone in a subject, comprising the step of administering to the subject a composition comprising a compound of this invention in combination with toremifene, raloxifene, tamoxifen or an analogue, functional derivative, metabolite or a combination thereof, or a pharmaceutically acceptable salt thereof. In one embodiment, such metabolites may comprise ospemifene, fispemifene or their combination. In one embodiment, the cancer is is prostate cancer.

A person skilled in the art would readily recognize that changes in the antineoplastic therapy according to the methods provided herein, utilizing the compositions provided herein may be conducted as a function of, or adjusted or varied as a function of, inter-alia, the severity of the underlying disease, the source of the underlying disease, the extent of the patients' pain and source of the patients' pain, as well as the stage of the disease. The therapeutic changes may include in certain embodiments, changes in the route of administration (e.g. intracavitarily, intraartiarly, intratumorally etc.), forms of the compositions administered (e.g. tablets, elixirs, suspensions etc.), changes in dosage and the like. Each of these changes are well recognized in the art and are encompassed by the embodiments provided herein.

In males, while the natural decline in sex-hormones at maturity (direct decline in androgens as well as lower levels of estrogens derived from peripheral aromatization of androgens) is associated with the frailty of bones, this effect is more pronounced in males who have undergone androgen deprivation therapy.

Such agents for combined use may comprise a SERM, as herein described, a bisphosphonate, for example, alendronate, tiludroate, clodroniate, pamidronate, etidronate, alendronate, zolendronate, cimadronate, neridronate, minodronic acid, ibandronate, risedronate, homoresidronate; a calcitonin, for example, salmon, Elcatonin®, SUN-8577, TJN-135; a vitamin D or derivative (ZK-156979); a vitamin D receptor ligand or analogues thereof, such as calcitriol, topitriol ZK-150123, TEI-9647, BXL-628, Ro-26-9228, BAL-2299, Ro-65-2299, DP-035; an estrogen, estrogen derivative, or conjugated estrogen; an antiestrogen, progestin, synthetic estrogen/progestin; a RANK ligand mAb, for example, denosumab or AMG162 (Amgen); an αvβ3 integrin receptor antagonist; an osteoclast vacuolar ATPase inhibitor, an antagonist of VEGF binding to osteoclast receptors, a calcium receptor antagonist, PTh (parathyroid hormone) or analogues thereof, PTHrP analogues (parathyroid hormone-related peptide), cathepsin K inhibitors (AAE581), strontium ranelate, tibolone; HCT-1026, PSK3471, gallium maltolate, Nutropin AQ®, prostaglandins, p38 protein kinase inhibitor, a bone morphogenetic protein, an inhibitor of BMP antagonism, an HMG-CoA reductase inhibitor, a vitamin K or derivative, an antiresorptive, an ipriflavone, a fluoride salt, dietary calcium supplement, osteoprotegerin, or any combination thereof. In one embodiment, the combined administration of a SARM as herein described, osteoprotegerin and parathyroid hormone is contemplated for treating any disease, disorder or condition of the bone.

In one embodiment, the immunomodulating agent is an anti-inflammatory agent. In one embodiment, the anti-inflammatory agent is a non-steroidal anti-inflammatory agent. In one embodiment, the non-steroidal anti-inflammatory agent is a Cox-1 inhibitor. In one embodiment, the non-steroidal anti-inflammatory agent is a Cox-2 inhibitor. In one embodiment, the non-steroidal anti-inflammatory agent is a Cox-1 and Cox-2 inhibitor. In some embodiments, non-steroidal anti-inflammatory agents include but are not limited to aspirin, salsalate, diflunisal, ibuprofen, fenoprofen, flurbiprofen, fenamate, ketoprofen, nabumetone, piroxicam, naproxen, diclofenac, indomethacin, sulindac, tolmetin, etodolac, ketorolac, oxaprozin, or celecoxib. In one embodiment, the anti-inflammatory agent is a steroidal anti-inflammatory agent. In one embodiment, the steroidal anti-inflammatory agent is a corticosteroid.

In one embodiment, the immunomodulating agent is an anti-rheumatic agent. In one embodiment, the anti-rheumatic agent is a non-steroidal anti-inflammatory agent. In one embodiment, the anti-rheumatic agent is a corticosteroid. In one embodiment, the corticosteroid is prednisone or dexamethasone. In one embodiment, the anti-rheumatic agent is a disease modifying anti-rheumatic drug. In one embodiment, the disease modifying anti-rheumatic drug is a slow-acting anti-rheumatic drug. In one embodiment, the disease modifying anti-rheumatic drug is an antimalarial agent. In one embodiment, disease modifying anti-rheumatic drugs include but are not limited to chloroquine, hydroxychloroquine, methotrexate, sulfasalazine, cyclosporine, azathioprine, cyclophosphamide, azathioprine, sulfasalazine, penicillamine, aurothioglucose, gold sodium thiomalate, or auranofin. In one embodiment, the anti-rheumatic agent is an immunosuppressive cytotoxic drug. In one embodiment, immunosuppressive cytotoxic drugs include but are not limited to methotrexate, mechlorethamine, cyclophosphamide, chlorambucil, or azathioprine.

In one embodiment, the SARM compound of this invention is administered in combination with an antidiabetic agent. In one embodiment, the antidiabetic agent is a sulfonylurea. In one embodiment, sulfonylureas include but are not limited to tolbutamide, acetohexamide, tolazamide, chlorpropamide, glipizide, glyburide, glimepiride, or gliclazide. In one embodiment, the antidiabetic agent is a meglitinide. In one embodiment, meglitinides include but are not limited to prandin or nateglinide. In one embodiment, the antidiabetic agent is a biguanide. In one embodiment, biguanides include but are not limited to metformin. In one embodiment, the antidiabetic agent is a thiazolidinedione. In one embodiment, thiazolidinediones include but are not limited to rosiglitazone, pioglitazone, or troglitazone. In one embodiment, the antidiabetic agent is an alpha glucosidase inhibitor. In one embodiment, alpha glucosidase inhibitors include but are not limited to miglitol or acarbose. In one embodiment, the antidiabetic agent is PPARα/γ ligand, dipeptidylpeptidase 4 (DPP-4) inhibitor, SGLT (sodium-dependent glucose transporter 1) inhibitor, or FBPase (fructose 1,6-bisphosphatase) inhibitor. In one embodiment, the antidiabetic agent is insulin. In one embodiment, the insulin is rapid-acting insulin. In one embodiment, the insulin is short-acting insulin. In one embodiment, the insulin is intermediate-acting insulin. In one embodiment, the insulin is intermediate- and short-acting insulin mixtures. In one embodiment, the insulin is long-acting insulin. In one embodiment, the antidiabetic agents are inhibitors of fatty acid binding protein (aP2) such as those disclosed in U.S. Ser. No. 09/519,079 filed Mar. 6, 2000, glucagon-like peptide-1 (GLP-1), and dipeptidyl peptidase IV (DPP4) inhibitors such as those disclosed in WO 0168603, which are incorporated by reference.

In one embodiment, the SARM compound of this invention is administered in combination with an agent treating the nervous system. In one embodiment, the agent treating the nervous system is an agent treating the autonomic nervous system. In one embodiment, the agent treating the autonomic nervous system is an adrenomimetic drug. In one embodiment, the adrenomimetic drug is a beta-adrenoceptor agonist, alpha-adrenoceptor agonist, or a combination thereof. In one embodiment, the adrenomimetic drug is a catecholamine. In one embodiment, adrenomimetic drugs include but are not limited to isoproterenol, norepinephrine, epinephrine, amphetamine, ephedrine, or dopamine. In one embodiment, the adrenomimetic drug is a directly acting adrenomimetic drug. In some embodiments, directly acting adrenomimetic drugs include but are not limited to phenylephrine, metaraminol, or methoxamine.

In one embodiment, the agent treating the autonomic nervous system is an adrenoceptor antagonist. In one embodiment, the adrenoceptor antagonist is a haloalkylamine, imidazoline, or quinazoline. In one embodiment, haloalkylamines include but are not limited to phenoxybenzamine. In one embodiment, imidazolines include but are not limited to phentolamine or tolazoline. In one embodiment, quinazolines include but are not limited to prazosin, terazosin, doxazosin, or trimazosin. In one embodiment, the adrenoceptor antagonist has a combined alpha and beta blocking activity. In one embodiment, the combined alpha and beta blocking agent is labetalol, bucindolol, carvedilol, or medroxalol.

In one embodiment, the agent treating the autonomic nervous system is a cholinomimetic agent. In one embodiment, the cholinomimetic agent is a direct-acting parasympathomimetic drug. In one embodiment, direct-acting parasympathomimetic drugs include but are not limited to methacholine, pilocarpine, carbachol, or bethanechol.

In one embodiment, the agent treating the autonomic nervous system is a cholinesterase inhibitor. In one embodiment, the cholinesterase inhibitor is a quaternary ammonium agent. In one embodiment, quaternary ammonium agents include but are not limited to edrophonium or ambenonium. In one embodiment, the cholinesterase inhibitor is a carbamate such as physostigmine, pyridostigmine, neostigmine, or rivastigmine. In one embodiment, the cholinesterase inhibitor is an organophosphate agent. In one embodiment, the inhibitor targets acetylcholine in the central nervous system such as tacrine, donepezil, or galanthamine.

In one embodiment, the agent treating the autonomic nervous system is a muscarinic blocking agent. In one embodiment, the muscarinic blocking agent is a belladonna alkaloid such as atropine or scopolamine.

In one embodiment, the agent treating the autonomic nervous system is a ganglionic blocking agent. In one embodiment, ganglionic blocking agents include but are not limited to nicotine, trimethaphan, or mecamylamine.

In one embodiment, the agent treating the nervous system is an agent treating the central nervous system. In one embodiment, the agent treating the central nervous system is a local anesthetic agent. In one embodiment, local anesthetic agents include but are not limited to benzocaine, chloroprocaine, cocaine, procaine, bupivacaine, levobupivacaine, lidocaine, mepivacaine, prilocaine, or ropivacaine. In one embodiment, the agent treating the central nervous system is a general anaesthetic agent. In one embodiment, general anesthetic agents include but are not limited to esflurane, sevoflurane, isoflurane, halothane, enflurane, methoxyflurane, xenon, propofol, etomidate, methohexital, midazolam, diazepamor, ketamine, thiopentone/thiopental, or lidocaine/prilocaine.

In one embodiment, the agent treating the central nervous system is an analgesic agent. In some embodiments, analgesic agents include but are not limited to paracetamol or non-steroidal anti-inflammatory agent. In some embodiments, analgesic agents include opiates or morphinomimetics such as morphine, pethidine, oxycodone, hydrocodone, diamorphine, tramadol, or buprenorphine. In some embodiments, a combination of two or more analgesics is desired.

In one embodiment, the agent treating the central nervous system is a muscle relaxant or vasoconstrictor agent. In one embodiment, muscle relaxants include but are not limited to methocarbamol, baclofen, carisoprodol, chlorzoxazone, cyclobenzaprine, dantrolene, metaxalone, orphenadrine, amyl nitrite, pancuronium, tizanidine, clonidine, or gabapentin. In one embodiment, vasoconstrictor agents include but are not limited to antihistamines, adrenalin dimethylarginine, caffeine, cannabis, catecholamines, decongestants, pseudoephedrinse, norepinephrines, tetrahydrozoline, or thromboxane.

In one embodiment, the agent treating the central nervous system is an antiemetic drug. In one embodiment, the antiemetic drug is a 5-$HT_3$ receptor antagonist such as dolasetron, granisetron, ondansetron, or tropisetron. In one embodiment, the antiemetic drug is a dopamine antagonist such as domperidone droperidol, haloperidol, chlorpromazine, promethazine, or metoclopramide. In one embodiment, the antiemetic drug is an antihistamine such as cyclizine, diphenhydramine, dimenhydrinate, or meclizine. In one embodiment, the antiemetic drug is a cannabinoid such as cannabis or marinol.

In one embodiment, the agent treating the central nervous system is a sedative agent. In one embodiment, the sedative agent is an antidepressant agent such as mirtazapine or trazodone. In one embodiment, the sedative agent is a barbiturate such as secobarbital, pentoberbital, or amobarbital. In one embodiment, the sedative agent is a benzodiazepine such as diazepam, clonazepam, alprazolam, temazepam, chlordiazepoxide, flunitrazepam, lorazepam, or clorazepate. In one embodiment, the sedative agent is an imidazopyridines such as zolpidem or alpidem. In one embodiment, the sedative agent is a pyrazolopyrimidine such as zaleplon. In one embodiment, the sedative agent is an antihistamine such as diphenhydramine, dimenhydrinate, or doxylamine. In one embodiment, the sedative agent is an antipsychotic agent such as ziprasidone, risperidone, quetiapine, clozapine, prochlorperazine, perphenazine, loxapine, trifluoperazine, thiothixene, haloperidol, or fluphenazine. In one embodiment, the sedative agent is an herbal sedative such as valerian plant mandrake, or kava. In some embodiments, the sedative agent is eszopiclone, ramelteon, methaqualone, ethchlorvynol, chloral hydrate, meprobamate, glutethimide, methyprylon, gamma-hydroxybutyrate, ethyl alcohol, methyl trichloride, zopiclone, or diethyl ether.

In one embodiment, the agent treating the central nervous system is a neurodegenerative disorder medication. In one embodiment, the neurodegenerative disorder medication is an acetylcholinesterase inhibitor such as tacrine, donepezil, galanthamine, or rivastigmine. In one embodiment, the neurodegenerative disorder medication is an N-methyl-D-aspartate (NMDA) antagonist such as memantine. In one embodiment, the neurodegenerative disorder medication reduces damage to motor neurons such as riluzole. In one embodiment, the neurodegenerative disorder medication silences the gene that causes the progression of the disease. In one embodiment, the agent treating the central nervous system is an antiepileptic drug (AED). In some embodiments, antiepileptic agents include sodium channel blockers, GABA receptor agonists, GABA reuptake inhibitors, GABA transaminase inhibitor, AEDs with a potential GABA mechanism of action, glutamate blockers, or AEDs with other mechanisms of action. In some embodiments, antiepileptic agents include but are not limited to carbamazepine, fosphenytoin, oxcarbazepine, lamotrigine, zonisamide, clobazam, clonazepam, phenobarbital, primidone, tiagabine, vigabatrin, gabapentin, valproate, felbamate, topiramate, levetiracetam, or pregabalin.

In one embodiment, the agent treating the central nervous system is an anti-addiction drug. In one embodiment, the anti-addiction is an anti-alcoholism drug such as disulfiram. In one embodiment, the anti-addiction drug is a serotonin uptake inhibitor, dopaminergic agonist, or opioid antagonist.

In one embodiment, the agent treating the central nervous system is an agent treating Alzheimer's disease. In some embodiments, agents treating Alzheimer's disease include but are not limited to a cholinesterase inhibitor, gamma secretase inhibitor, or an A-beta lowering drug.

In one embodiment, the agent treating the central nervous system is an agent treating mild cognitive impairment. In some embodiments, agents treating mild cognitive impairment include but are not limited to an AMPA regulator.

In one embodiment, the agent treating the central nervous system is an agent treating Parkinson's disease. In some embodiments, agents treating Parkinson's disease include but are not limited to a dopaminergic drugs, amantadine, benztropine, biperiden, bromocriptine, entacapone, carbidopa/levodopa, selegiline/deprenyl, diphenhydramine, pergolide, procyclidine, selegiline, or trihexyphenidyl.

In one embodiment, the SARM compound of this invention is administered with an agent, which treats Alzheimer's disease, such as cholinesterase inhibitors, gamma secretase inhibitors, or A-beta lowering drugs; or an agent, which treats mild cognitive impairment (MCI)—such as AMPA regulators, or an agent, which treats Parkinson's disease, such as dopaminergic drugs, or an agent, which treats major depression, such as SSRI's, SNRI's, for example, duloxetine, or an agent, which treats sexual dysfunction, such as PDE5 inhibitors.

In one embodiment, the SARM compound of this invention is administered in combination with an agent treating the cardiovascular system. In one embodiment, the agent treating the cardiovascular system is treating a congestive heart failure. In one embodiment, the agent treating congestive heart failure is an angiotensin converting enzyme (ACE) inhibitor such as benazepril, captopril, cilazapril, enalapril, fosinopril, lisinopril, moexipril, perindopril, quinapril, ramipril, trandolapril, or enalaprilat. In one embodiment, the agent treating congestive heart failure is a beta-blocker such as acebutolol, atenolol betaxolol hydrochloride, bisoprolol fumarate, carteolol hydrochloride, carvedilol, celiprolol hydrochloride, esmolol hydrochloride, labetalol hydrochloride, levobunolol, metoprolol tartrate, metipranolol, nadolol, nebivolol, oxprenolol hydrochloride, pindolol propranolol hydrochloride, sotalol hydrochloride, or timolol maleate. In one embodiment, the agent treating congestive heart failure is digoxin. In one embodiment, the agent treating congestive heart failure is a diuretic such as thiazide diuretic, loop diuretic, potassium-sparing diuretic, or a combination thereof. In some embodiments, thiazide diuretics include but are not limited to bendrofluazide, bendroflumethiazide, benzthiazide, chlorothiazide, chlorthalidone, cyclopenthiazide, Diucardin®, Diuril®, Enduron®, Esidrix®, Exna®, HCTZ, hydrochlorothiazide, Hydrodiuril®, hydroflumethiazide, Hydromox®, Hygroton®, indapamide, Lozol®, methylclothiazide, metolazone, Mykrox®, Naqua®, Naturetin®, Oretic®, polythiazide, quinethazone, Renese®, trichloromethiazide, xipamide, or Zaroxolyn®. In some embodiments, loop diuretics include but are not limited to furosemide, bumetanide, or torsemide. In some embodiments, potassium-sparing diuretics include but are not limited to amiloride, triamterene, aldosterone antagonists, or spironolactone.

In one embodiment, the agent treating the cardiovascular system is an anti-arrhythmic agent. In one embodiment, the anti-arrhythmic agent is a sodium channel blocker, beta-adrenergic blocker, calcium channel blocker, or an agent that prolongs repolarization. In one embodiment, sodium channel blockers include but are not limited to quinidine, procainamide, disopyramide, lidocaine, tocainide, mexiletine, encainide, or flecainide. In one embodiment, beta-adrenergic blockers include but are not limited to propranolol, acebutolol esmolol, or sotalol. In one embodiment, agents that prolong repolarization include but are not limited to sotalol or amiodarone. In one embodiment, calcium channel blockers include but are not limited to verapamil, diltiazem, nifedipine, or mebefradil. In one embodiment, the anti-arrhythmic agent is adenosine or digoxin.

In one embodiment, the agent treating the cardiovascular system is an anti-anginal agent. In one embodiment, the anti-anginal agent is an antiplatelet agent, adrenoceptor antagonist, calcium channel blocker, or a vasodilator. In some embodiments, the adrenoceptor antagonists and calcium channel blockers comprise agents as described hereinabove. In one embodiment, the antiplatelet agent is a cyclooxygenase inhibitor, ADP inhibitor, phosphodiesterase III inhibitor, glycoprotein IIb/IIIa inhibitor, or an adenosine reuptake inhibitor. In one embodiment, cyclooxygenase inhibitors include but are not limited to acetylsalicylic acid or an acetylsalicylic acid in combination with dipyridimole. In one embodiment, ADP inhibitors include but are not limited to clopidogrel, CS-747, or ticlopdipine. In one embodiment, phosphodiesterase III inhibitors include but are not limited to cilostazol. In one embodiment, glycoprotein IIb/IIIa inhibitors include but are not limited to abciximab, Rheopro®, eptifibatide, integrilin, tirofiban, or Aggrastat®. In one embodiment, adenosine reuptake inhibitors include but are not limited to dipyridimole. In one embodiment, vasodilator agents include but are not limited to isosorbide dinitrate, isosorbide mononitrate, or nitroglycerin. In one embodiment, cardiac glycosides such as digitalis or ouabain may be used in combination with a SARM compound.

In one embodiment, the agent treating the cardiovascular system is a vasoactive agent or an inotrope. In one embodiment, vasoactive agents or inotropes include but are not limited to digoxin, dopamine, dobutamine, hydralazine, prazosin, carvedilol, nitroprusside, nitroglycerin, captopril, lisinopril, nifedipine, diltiazem, hydrochlorothiazide, furosemide, spironolactone, AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), or nitrates.

In one embodiment, the agent treating the cardiovascular system is an anticoagulant agent. In one embodiment, the anticoagulant agent is a coumarin derivative or an unfractionated heparin. In one embodiment, coumarin derivatives include but are not limited to warfarin.

In one embodiment, the agent treating the cardiovascular system is a fibrinolytic agent such as streptokinase, urokinase, alteplase, anistreplase, prourokinase, reteplase, tenecteplase, lanoteplase, staphylokinase, vampire, or alfimeprase.

In one embodiment, the agent treating the cardiovascular system is a hypercholesterolemic agent such as niacin-lovastatin, colestipol HCl, fluvastatin sodium, atorvastatin calcium, simvastatin, gemfibrozil, lovastatin, pravastatin sodium, cholestyramine, cholestyramine light, fenofibrate, colesevelam HCl, or ezetimibe.

In one embodiment, the SARM compound of this invention is administered in combination with an agent treating the gastrointestinal system. In one embodiment, the agent treating the gastrointestinal (GI) system is enhancing GI motility. In one embodiment, the agent enhancing GI motility is a prokinetic agent such as metoclopramide, cisapride, tegaserod, or erythromycin. In one embodiment, the agent treating the GI system is decreasing GI motility. In one embodiment, the agent decreasing GI motility is an opioid such as morphine, diphenoxylate, loperamide hydrochloride, or opium.

In one embodiment, the agent treating the GI system is an adsorbent or a bulking agent. In one embodiment, the adsorbent is kaolin or other hydrated aluminum silicate clays. In one embodiment, the hydrated aluminum silicate clay is further combined with pectin. In one embodiment, adsorbents or bulking agents comprise bismuth subsalicylate, methylcellulose, psyllium derivative, or calcium polycarbophil.

In one embodiment, the agent treating the GI system is a stool softener. In one embodiment, stool softeners include but are not limited to mineral oil, docusate dioctyl sodium sulfosuccinate, dioctyl calcium sulfosuccinate, or dioctyl potassium sulfosuccinate.

In one embodiment, the agent treating the GI system is a laxative. In one embodiment, the agent treating the GI system is a bulk forming laxative as described hereinabove. In one embodiment, the laxative is an osmotic laxative such as lactulose, sorbitol, or polyethylene glycol. In one embodiment, the laxative is a saline laxative such as milk of magnesia, magnesium citrate, sodium phosphate, docusate potassium, sorbitol, sodium phosphate-biphosphate, or visicol.

In one embodiment, the agent treating the GI system is a cathartic stimulant. In one embodiment, the cathartic stimulant is an anthraquinone derivative such as cascara, aloe, senna, or rhubarb. In one embodiment, the cathartic stimulant is phenolphthalein, castor oil, or bisacodyl.

In one embodiment, the agent treating the GI system is an emetic agent. In one embodiment, the emetic agent is ipecac or apomorphine. In one embodiment, the agent treating the GI system is an anti-emetic agent such as antihistamine, anti-cholinergic agent, benzodiazepine, cannabinoid, dopamine antagonist, phenothiazine derivative, or 5-HT$_3$ antagonist such as ondansetron or granisetron.

In one embodiment, the agent treating the GI system is an antacid. In one embodiment the antacid pharmaceutical preparation comprises buffering agents such as sodium bicarbonate, calcium carbonate, magnesium hydroxide, or aluminum hydroxide.

In one embodiment, the agent treating the GI system is an H$_2$-receptor antagonist. In some embodiments, the H$_2$-receptor antagonist is cimetidine, ranitidine, famotidine, or nizatidine.

In one embodiment, the agent treating the GI system is a proton pump inhibitor. In some embodiments, the proton pump inhibitor is omeprazole, lansoprazole, pantoprazole, rebeprazole, or esomeprazole In one embodiment, the agent treating the GI system is an agent treating inflammation. In one embodiment, the agent treating inflammation is 5-amino-salicylate, corticosteroid, metronidazole, ciprofloxacin, infliximab, budesonide, or anti-TNF alpha antibody.

In one embodiment, the SARM compound of this invention is administered in combination with an agent treating a metabolic disease, disorder or condition, which in some embodiments refers to metabolic syndrome. In some embodiments, such agents comprise, inter alia, pancreatic lipase inhibitors, such as for example, orlistat, cetilistat; serotonin and norepinephrine reuptake inhibitors, such as sibutramine; insulin-sensitizers such as biguanides (metformin) or PPAR agonists, dual-acting PPAR agonists (muraglitazar, tesaglitazar, naveglitazar), PPAR-delta agonists (GW-501516), DPP-IV inhibitors (vildagliptin, sitagliptin), alpha glucosidase inhibitors (acarbose), anti-diabetic combinations (ActoPlusMet®, AvandaMet®, metformin/pioglitazone, metformin/rosiglitazone, Glucovance®, etc.), glucagon-like peptide-1 analogues (exenatide, liraglutide), amylin analogues (pramlintide), statins (atorvastatin, simvastatin, rosuvastatin, pravastatin, fluvastatin, lovastatin, pitavastatin), cholesterol absorption inhibitors (ezetimibe), nicotinic acid derivatives (immediate release and controlled release niacins, Niaslo®, etc.), antidyslipidemic fixed combinations (simvastatin/ezetimibe, lovastatin/nicotinic acid, atorvastatin/amlodipine, atorvastatin/torcetrapib, simvastatin/nicotinic acid (ER)), ACE inhibitors (ramipril, captopril, lisinopril), AT-II receptor antagonists (valsartan, telmisartan), cannabinoid receptor antagonists (rimonabant), cholesteryl ester transfer protein or CETP inhibitors (anacetrapib, JTT-705, CETi-1), beta3 adrenergic agonists, PPARα ligands, or combinations thereof.

In one embodiment, the SARM compound of this invention is administered in combination with an agent treating a dermatological disorder. In one embodiment, the agent treating a dermatological disorder is a corticosteroid or glucocorticosteroid such as betamethasone dipropionate, clobetasol, diflorasone, amcinonide, desoximetasone, fluocinonide, aclometasone, desonide triamcinolone, fluticasone, halobetasol, mometasone, or hydrocortisone. In one embodiment, the agent treating a dermatological disorder is a retinoid such as isotretinoin, acitretin, tretinoin, adapalene, tazarotene, bexarotene, alitretinoin, or beta-carotene.

In one embodiment, the agent treating a dermatological disorder is photochemotherapy agent. In one embodiment, the photochemotherapy agent is PUVA or psoralen such as oxsoralen. In one embodiment, the agent treating a dermatological disorder is a photodynamic agent such as porphyrin.

In one embodiment, the agent treating a dermatological disorder is dapsone, thalidomide, anti-malarial agent, anti-microbial agent, or antifungal agent. In one embodiment, the anti-malarial agent is chloroquine or hydroxychloroquine.

In one embodiment, the agent treating a dermatological disorder is an antibiotic. In one embodiment, the antibiotic is a systemic antibiotic such as griseofulvin, ketoconazole, fluconazole, itraconazole, terbinafine, or potassium iodide. In one embodiment, the antibiotic is a topical antifungal agent. In some embodiment, topical antifungal agents include but are not limited to ciclopirox, clotrimazole, econazole, ketoconazole, miconazole, naftifine, oxiconazole, terbinafine, or tolnaftate.

In one embodiment, the agent treating a dermatological disorder is an antiviral agent such as interferon alpha. In one embodiment, the agent treating a dermatological disorder is an antiscabies agent such as pyrethrin or pyrethroid. In one embodiment, the agent treating a dermatological disorder is an immunosuppressive agent such as mycophenolate motefil or 6-thioguanine. In one embodiment, the agent treating a dermatological disorder is a topical immunosuppressive agent such as tacrolimus, pimecrolimus, imiquimod, 5-fluorouracil, or mechlorethamine. In one embodiment, the agent treating a dermatological disorder is an antihistamine such as doxepin. In one embodiment, the agent treating a dermatological disorder is treating pigmentation such as hydroquinone or monobenzone. In one embodiment, the agent treating a dermatological disorder is a protein or a recombinant protein such as becaplermin, etanercept, denileukin diftitox, or botulinum toxin. In one embodiment, the agent treating a dermatological disorder is capsaicin, anthralin, benzoyl peroxide, or calcipotriene.

In one embodiment, the agent treating a dermatological disorder is a keratolytic agent. In one embodiment, the agent treating a dermatological disorder is selenium sulfide. In one embodiment, the agent treating or preventing a dermatological disorder is a sunscreen. In one embodiment, the sunscreen absorbs UVB, UVA, or a combination thereof.

In one embodiment, the agent treating a dermatological disorder may be a growth factor such as epidermal growth factor (EGF), transforming growth factor-α (TGF-α), platelet derived growth factor (PDGF), fibroblast growth factors (FGFs) including acidic fibroblast growth factor (α-FGF) and basic fibroblast growth factor (β-FGF), transforming growth factor-β (TGF-β) and insulin like growth factors (IGF-1 and IGF-2), or any combination thereof.

In one embodiment, the SARM compound of this invention is administered in combination with an anti-infective agent. In one embodiment, the anti-infective agent is an antibiotic agent. In one embodiment the antibiotic is a beta-lactam antibiotic. In one embodiment beta-lactam antibiotics include but are not limited to penicillin, benzathine penicillin, benzylpenicillin, amoxicillin, procaine penicillin, dicloxacillin, amoxicillin, flucloxacillin, ampicillin, methicillin, azlocillin, carbenicillin, ticarcillin, mezocillin, piperacillin, phenoxymethylpenicillin, Co-Amoxiclav®, cephalosporin, cefalexin, cephalothin, cefazolin, cefaclor, cefuroxime, cefamandole, cefotetan, cefoxitin, ceftriaxone, cefotaxime, ceftazidime, cefepime, cefpirome, imipenem, meropenem, ertapenem, faropenem, monobactam, aztreonam, or carbapenem.

In one embodiment the antibiotic is a tetracycline antibiotic. In one embodiment tetracycline antibiotics include but are not limited to tetracycline, chlortetracycline, demeclocycline, doxycycline, lymecycline, minocycline, or oxytetracycline.

In one embodiment the antibiotic is a macrolide antibiotic. In one embodiment macrolide antibiotics include but are not limited to erythromycin, azithromycin, oxithromycin, dirithromycin, clarithromycin, josamycin, oleandomycin, kitasamycin, spiramycin, tylosin/tylocine, troleandomycin, carbomycin, cethromycin, or telithromycin.

In one embodiment the antibiotic is an aminoglycoside antibiotic. In one embodiment, aminoglycoside antibiotics include but are not limited to gentamicin, tobramycin, faropenem, imipenem, kanamycin, neomycin, ertapenem, apramycin, paromomycin sulfate, streptomycin, or amikacin.

In one embodiment the antibiotic is a quinolone antibiotic. In one embodiment quinolone antibiotics include but are not limited to ciprofloxacin, norfloxacin, lomefloxacin, enoxacin, ofloxacin, ciprofloxacin, levofloxacin, sparfloxacin, gatifloxacin, moxifloxacin, trovafloxacin, or alatrofloxacin.

In one embodiment the antibiotic is a cyclic peptide antibiotic. In one embodiment cyclic peptide antibiotics include but are not limited to vancomycin, streptogramins, Microcin J25®, Bacteriocin AS-48®, RTD-1, or polymyxins.

In one embodiment the antibiotic is a lincosamide antibiotic. In one embodiment lincosamide antibiotics include but are not limited to clindamycin.

In one embodiment, the antibiotic is an oxazolidinone antibiotic. In one embodiment oxazolidinone antibiotics include but are not limited to linezolid, U-100592, DA-7867, AZD2563, or U-100766.

In one embodiment, the antibiotic is a sulfa antibiotic. In one embodiment, sulfa antibiotics include but are not limited to sulfisoxazole.

In one embodiment, the antibiotic is an antiseptic agent. In one embodiment, antiseptic agents include but are not limited to alcohols, chlorhexidine, chlorine, hexachlorophene, iodophors, chloroxylenol (PCMX), quaternary ammonium compounds, or triclosan.

In one embodiment, the antibiotic is an anti-tuberculosis agent. In one embodiment an anti-tuberculosis agents include but are not limited to ethambutol, rifabutin, isoniazid, rifampicin, pyrazinamide, or rifampin In one embodiment, the antibiotic is an antifungal agent. In one embodiment, antifungal agents include but are not limited to terbinafine, flucytosine, fluconazole, itraconazole, ketoconazole, ravuconazole, posaconazole, voriconazole, caspofungin, micafungin, v-echinocandin, amphotericin B, amphotericin B lipid complex (ABLC), amphotericin B colloidal dispersion (ABCD), liposomal amphotericin b (1-Amb), liposomal nystatin, or griseofulvin.

In one embodiment, the antibiotic is an antiprotozoal agent. In one embodiment the antiprotozoal agent is an antimalarial agent. In one embodiment, antimalarial agents include but are not limited to chloroquine, mefloquine, proguanil, pyrimethamine with dapsone, pyrimethamine with sulfadoxine, quinine, or primaquine. In one embodiment, the antiprotozoal agent is an amoebicide. In one embodiment, amoebicides include but are not limited to metronidazole, tinidazole, or diloxanide furoate. In one embodiment, the antiprotozoal agent is an antigiardial agent. In one embodiment, antigiardial agents include but are not limited to metronidazole, tinidazole, or mepacrine. In one embodiment, the antiprotozoal agent is a leishmanicide. In one embodiment, leishmanicides include but are not limited to sodium stibogluconate. In one embodiment, the antibiotic is an anthelmintic agent.

In one embodiment, the antibiotic is an antiviral agent. In one embodiment, antiviral agents include but are not limited to abacavir, acyclovir, amantadine, didanosine, entricitabine, enfuvirtide, entecavir, lamivudine, nevirapine, oseltamivir, ribavirin, rimantadine, stavudine, valaciclovir, vidarabine, zalcitabine, or zidovudine. In one embodiment, the antiviral agent is a nucleotide analog reverse transcriptase inhibitor. In one embodiment, nucleotide analog reverse transcriptase inhibitors include but are not limited totenofovir or adefovir. In one embodiment, the antiviral agent is a protease inhibitor. In one embodiment, protease inhibitors include but are not limited to saquinavir, ritonavir, indinavir, nelfinavir, amprenavir, lopinavir, fosamprenavir, or tipranavir. In one embodiment, the antiviral agent is a fusion inhibitor such as enfuvirtide. In one embodiment, a combination of antiviral or antiretroviral agents is desired. In one embodiment, antiviral or antiretroviral agents or a combination thereof, further comprise hydroxyurea, resveratrol, grapefruit, ritonavir, leflunomide, or a combination thereof.

In one embodiment, the SARM compound of this invention is administered in combination with an agent treating the liver. In one embodiment, the SARM compound is administered in combination with a statin. In some embodiment, statins include but are not limited to atorvastatin, fluvastatin, lovastatin, pravastatin, simvastatin, or rosuvastatin.

In one embodiment, the SARM compound of this invention is administered in combination with a bile acid sequestrant. In some embodiment, bile acid sequestrants include but are not limited to cholestyramine, colestipol, or colesevelam.

In one embodiment, the SARM compound of this invention is administered in combination with a cholesterol absorption inhibitor. In some embodiment, cholesterol absorption inhibitors include but are not limited to ezetimibe.

In one embodiment, the SARM compound of this invention is administered in combination with a nicotinic acid agent. In some embodiments, nicotinic acid agents include but are not limited to niacin, niacor, or Slo-Niacin®.

In one embodiment, the SARM compound of this invention is administered in combination with a fibrate. In some embodiments, fibrates include but are not limited to gemfibrozil, or fenofibrate.

In one embodiment, the agent treating the liver is cortisone, cortisol or corticosterone. In some embodiments, the agent treating the liver is colchicine, methotrexate, ursodeoxycholic acid, or penicillamine.

In one embodiment, the SARM compound of this invention is administered in with an agent treating the kidney. In one embodiment, the agent treating the kidney is a diuretic. In some embodiments, diuretics include but are not limited to organomercurial, ethacrynic acid, furosemide, bumetanide, piretanide, muzolimine, chlorothiazide and thiazide, phthalimidine, chlorthalidone, clorexolone, quinazolinone, quinethazone, metolazone ilenzenesulphonamide, mefruside, chlorobenzamide, copamidesalicylamide, xipamide, xanthine, aminophylline, carbonic anhydrase inhibitor, acetazolamide mannitol, potassium-sparing compound, aldosterone antagonist, spironolactone and canrenoate, pteridines, pyrazine, carboxamide-triamterene, or amiloride. In one embodiment, the agent treating the kidney is a steroid.

In one embodiment, the agent treating the kidney is erythropoietin. In one embodiment, erythropoietin is obtained by natural sources (e.g., urinary erythropoietin; See U.S. Pat. No. 3,865,801), or is a recombinantly produced protein and analogs thereof, for example, as described in U.S. Pat. Nos. 5,441,868, 5,547,933, 5,618,698 and 5,621,080 as well as human erythropoietin analogs with increased glycosylation and/or changes in the amino acid sequence as those described in European Patent Publication No. EP 668351 and the hyperglycosylated analogs having 1-14 sialic acid groups and changes in the amino acid sequence described in PCT Publication No. WO 91/05867. In one embodiment, erythropoietin-like polypeptides are administered in combination with SARM compounds. In some embodiments, erythropoietin-like polypeptides comprise darbepoietin (from Amgen, also known as Aranesp® and novel erthyropoiesis stimulating protein (NESP)).

In one embodiment, the SARM compound of this invention is administered in with an agent treating a metabolic disease. In some embodiments, agents treating a metabolic disease include but are not limited to a vitamin, coenzyme Q10, glucosidase alfa, sodium bicarbonate, bisphosphonate, biotin, allopurinol, levodopa, diazepam, phenobarbital, haloperidol, folic acid, antioxidants, activators of cation channels haptoglobin, or carnitine.

In one embodiment, the agent treating a metabolic disease is a pancreatic lipase inhibitor such as orlistat or cetilistat, serotonin or norepinephrine reuptake inhibitor such as sibutramine, insulin-sensitizers such as biguanide, PPAR agonist, dual-acting PPAR agonist such as muraglitazar, tesaglitazar, or naveglitazar, PPAR-delta agonist such as GW-501516, DPP-IV inhibitor such as vildagliptin or sitagliptin, alpha glucosidase inhibitor such as acarbose, antidiabetic combination such as ActoPlusMet®, AvandaMet®, metformin/pioglitazone, metformin/rosiglitazone, or Glucovance®, glucagon-like peptide-1 analogue such as exenatide or liraglutide, amylin analogue such as pramlintide, statin such as atorvastatin, simvastatin, rosuvastatin, pravastatin, fluvastatin, lovastatin, or pitavastatin, cholesterol absorption inhibitor such as ezetimibe, nicotinic acid derivative such as niacin or Niaslo®, antidyslipidemic fixed combination such as simvastatin/ezetimibe, lovastatin/nicotinic acid, atorvastatin/amlodipine, or atorvastatin/torcetrapib, simvastatin/nicotinic acid. ACE inhibitor such as ramipril, captopril, or lisinopril, AT-II receptor antagonist such as valsartan or telmisartan, cannabinoid receptor antagonist such as rimonabant, cholesteryl ester transfer protein (CETP) inhibitor such as anacetripib, JTT-705, CETi-1, or beta-3 adrenergic agonist.

In one embodiment, the SARM compound of this invention is administered with an agent treating a wasting disease. In some embodiments, agents treating a wasting disease include but are not limited to corticosteroids, anabolic steroids, cannabinoids, metoclopramide, cisapride, medroxyprogesterone acetate, megestrol acetate, cyproheptadine, hydrazine sulfate, pentoxifylline, thalidomide, anti-cytokine antibodies, cytokine inhibitors, eicosapentaenoic acid, indomethacin, ibuprofen, melatonin, insulin, growth hormone, clenbuterol, porcine pancreas extract, IGF-1, IGF-1 analogue and secretagogue, myostatin analogue, proteasome inhibitor, testosterone, oxandrolone, etanercept (Enbrel®), melanocortin 4 receptor agonist, or a combination thereof.

In one embodiment, the agent treating a wasting disease is a ghrelin receptor ligand, growth hormone analogue, or a secretagogue. In some embodiments, ghrelin receptor ligands, growth hormone analogues, or secretagogues include but are not limited to pralmorelin, examorelin, tabimorelin, capimorelin, capromorelin, ipamorelin, EP-01572, EP-1572, or JMV-1843.

In one embodiment, growth promoting agents such as but not limited to TRH, diethylstilbestrol, theophylline, enkephalins, E series prostaglandins, compounds disclosed in U.S. Pat. No. 3,239,345, e.g., zeranol, and compounds disclosed in U.S. Pat. No. 4,036,979, e.g., sulbenox or peptides disclosed in U.S. Pat. No. 4,411,890 are utilized as agents treating a wasting disease.

In other embodiments, agents treating a wasting disease may comprise growth hormone secretagogues such as GHRP-6, GHRP-1 (as described in U.S. Pat. No. 4,411,890 and publications WO 89/07110 and WO 89/07111), GHRP-2 (as described in WO 93/04081), NN703 (Novo Nordisk), LY444711 (Lilly), MK-677 (Merck), CP424391 (Pfizer) and B-HT920, or, in other embodiments, with growth hormone releasing factor and its analogs or growth hormone and its analogs, or with alpha-adrenergic agonists, such as clonidine or serotinin 5-$HT_D$ agonists, such as sumatriptan, or agents which inhibit somatostatin or its release, such as physostigmine and pyridostigmine. In some embodiments, agents treating a wasting disease may comprise parathyroid hormone, PTH(1-34) or bisphosphonates, such as MK-217 (alendronate). In other embodiments, agents treating wasting disease may further comprise estrogen, a selective estrogen receptor modulator, such as tamoxifen or raloxifene, or other androgen receptor modulators, such as those disclosed in Edwards, J. P. et al., Bio. Med. Chem. Let., 9, 1003-1008 (1999) and Hamann, L. G. et al., J. Med. Chem., 42, 210-212 (1999). In some embodiments, agents treating a wasting disease may further comprise a progesterone receptor agonists ("PRA"), such as levonorgestrel, medroxyprogesterone acetate (MPA). In some embodiments, agents treating a wasting disease may include nutritional supplements, such as those described in U.S. Pat. No. 5,179,080, which, in other embodiments are in combination with whey protein or casein, amino acids (such as leucine, branched amino acids and hydroxymethylbutyrate), triglycerides, vitamins (e.g., A, B6, B 12, folate, C, D and E), minerals (e.g., selenium, magnesium, zinc, chromium, calcium and potassium), carnitine, lipoic acid, creatinine, β-hyroxy-β-methylbutyrate (Juven®) and coenzyme Q. In one embodiment, agents treating a wasting disease may further comprise antiresorptive agents, vitamin D analogues, elemental calcium and calcium supplements, cathepsin K inhibitors, MMP inhibitors, vitronectin receptor antagonists. Src SH2 antagonists, vacuolar-$H^+$-ATPase inhibitors, ipriflavone, fluoride, tibolone, prostanoids, 17-beta hydroxysteroid dehydrogenase inhibitors and Src kinase inhibitors.

In one embodiment, the SARM compound of this invention is administered in with an agent treating the endocrine system. In some embodiments, agents treating the endocrine system include but are not limited to radioactive iodine, antithyroid agent, thyroid hormone supplement, growth hormone, cabergoline, bromocriptine, thyroxine, gonadotropin, glucocorticoid, glucocorticoid analogue, corticotrophin, metyrapone, aminoglutethimide, mitotane, ketoconazole, mifepristone, dexamethasone somatostatin analogue, gonadotropin-releasing hormone analogue, leuprolide, goserelin, antidiuretic hormone, antidiuretic hormone analogue, oxytocin, calcium supplement, vitamin D, or a combination thereof.

In one embodiment, the agent treating the endocrine system is a 5-alpha-reductase inhibitor. In some embodiments, 5-alpha-reductase inhibitors include but are not limited to finasteride, dutasteride, or izonsteride.

In one embodiment, the agent treating the endocrine system is a SARM compound. In some embodiments, SARMs include but are not limited to RU-58642, RU-56279, WS9761 A and B, RU-59063, RU-58841, bexlosteride, LG-2293, L-245976, LG-121071. LG-121091, LG-121104, LGD-2226, LGD-2941, YM-92088., YM-175735, LGD-1331, BMS-357597, BMS-391197, S-40503, BMS-482404, EM-4283, EM-4977, BMS-564929, BMS-391197, BMS-434588, BMS-487745, BMS-501949, SA-766, YM-92088, YM-580, LG-123303, LG-123129, PMCol, YM-175735, BMS-591305, BMS-591309, BMS-665139, BMS-665539, CE-590, 116BG33, 154BG31, arcarine, or ACP-105.

In one embodiment, the additional agent treating the endocrine system is a SERM compound. In some embodiments, SERMs include but are not limited to tamoxifene, 4-hydroxytamoxifene, idoxifene, toremifene, ospemifene, droloxifene, raloxifene, arzoxifene, bazedoxifene, PPT (1,3, 5-tris(4-hydroxyphenyl)-4-propyl-1H-pyrazole), DPN, lasofoxifene, pipendoxifene, EM-800, EM-652, nafoxidine, zindoxifene, tesmilifene, miproxifene phosphate, RU 58,688, EM 139, ICI 164,384, ICI 182,780, clomiphene, MER-25, diethylstilbestrol coumestrol, genistein, GW5638, LY353581, zuclomiphene, enclomiphene, delmadinone acetate, DPPE, (N,N-diethyl-2-[4-(phenylmethyl)-phenoxy] ethanamine), TSE-424, WAY-070, WAY-292, WAY-818, cyclocommunol, prinaberel, ERB-041, WAY-397, WAY-244, ERB-196, WAY-169122, MF-101, ERb-002, ERB-037, ERB-017. BE-1060, BE-380, BE-381, WAY-358, [$^{18}$F] FEDNP, LSN-500307, AA-102, CT-101, CT-102, or VG-101.

In one embodiment, the agent treating the endocrine system is a gonadotropin-releasing hormone agonist or antagonist. In some embodiments, gonadotropin-releasing hormone agonists or antagonists include but are not limited to leuprolide, goserelin, triptorelin, alfaprostol, histrelin, detirelix, ganirelix, antide iturelix, cetrorelix, ramorelix, ganirelix, antarelix, teverelix, abarelix, ozarelix, sufugolix, prazarelix, degarelix, NBI-56418, TAK-810, or acyline.

In one embodiment, the agent treating the endocrine system is a luteinizing hormone agonist or antagonist. In some embodiments, luteinizing hormone agonists or antagonists include but are not limited to letrozole, anastrazole, atamestane, fadrozole, minamestane, exemestane, plomestane, liarozole, NKS-01, vorozole, YM-511, finrozole, 4-hydroxyandrostenedione, aminogluethimide, or rogletimide. In one embodiment, the agent treating the endocrine system is a follicle stimulating hormone agonist or antagonist. In one embodiment, the agent treating the endocrine system is a luteinizing hormone releasing hormone (LHRH) or a LHRH analog.

In one embodiment, the agent treating the endocrine system is a steroidal or to nonsteroidal glucocorticoid receptor ligand. In some embodiments, nonsteroidal glucocorticoid receptor ligands include but are not limited to ZK-216348, ZK-243149, ZK-243185, LGD-5552, mifepristone, RPR-106541, ORG-34517, GW-215864X, sesquicillin, CP-472555, CP-394531, A-222977, AL-438, A-216054, A-276575, CP-394531, CP-409069, or UGR-07.

In one embodiment, the agent treating the endocrine system is a steroidal or non-steroidal progesterone receptor ligand. In one embodiment, the agent treating the endocrine system is a steroidal or nonsteroidal androgen receptor antagonist. In some embodiments, steroidal or nonsteroidal androgen receptor antagonists include but are not limited to flutamide, hydroxyflutamide, bicalutamide, enzalutamide, nilutamide, or hydroxysteroid dehydrogenase inhibitor.

In one embodiment, the agent treating the endocrine system is a peroxisome proliferator-activated receptor ligand. In some embodiments, peroxisome proliferator-activated receptor ligands include but are not limited to bezafibrate, fenofibrate, gemfibrozil, darglitazone, pioglitazone, rosiglitazone, isaglitazone, rivoglitazone, netoglitazone, naveglitazar, farglitazar, tesaglitazar, ragaglitazar, oxeglitazar, or PN-2034.

In one embodiment, an agent treating the endocrine system is a human growth hormone. In some embodiments, human growth hormones include but are not limited to somatotropin or analogues.

In one embodiment, the agent treating the endocrine system is a ghrelin. In some embodiments, ghrelins include but are not limited to human ghrelin, CYT-009-GhrQb, L-692429, GHRP-6, SK&F-110679, or U-75799E.

In one embodiment, the agent treating the endocrine system is a leptin. In some embodiments, leptins include but are not limited to metreleptin or pegylated leptin. In one embodiment, an agent treating the endocrine system is a leptin receptor agonist. In some embodiments, leptin receptor agonists include but are not limited to LEP(116-130), OB3, [D-Leu4]-OB3, rAAV-leptin, AAV-hOB, or rAAVhOB.

In one embodiment, the SARM compound of this invention is administered with an inhibitor of an enzyme involved in the androgen biosynthetic pathway. In some embodiments, inhibitors of enzymes involved in the androgen biosynthetic pathway include but are not limited to 17-ketoreductase inhibitor, 3-ΔH4,6-isomerase inhibitor, 3-ΔH4,5-isomerase inhibitor, 17,20 desmolase inhibitor, p450c17 inhibitor, p450ssc inhibitor, or 17,20-lyase inhibitor.

In one embodiment, the SARM compound is administered with an agent treating osteoporosis. In some embodiments, osteoporosis is induced by alcohol and/or smoking. In some embodiments, agents treating osteoporosis include but are not limited to SERMs, calcitonin, vitamin D, vitamin D derivatives, vitamin D receptor ligand, vitamin D receptor ligand analogue, estrogen, estrogen derivative, conjugated estrogen, antiestrogen, progestin, synthetic estrogen, synthetic progestin, RANK ligand monoclonal antibody, integrin receptor antagonist, osteoclast vacuolar ATPase inhibitor, antagonist of VEGF binding to osteoclast receptors, calcium receptor antagonist, parathyroid hormone, parathyroid hormone analogue, parathyroid hormone-related peptide, cathepsin K inhibitor, strontium ranelate, tibolone, HCT-1026, PSK3471, gallium maltolate, Nutropin AQ®, prostaglandin, p38 protein kinase inhibitor, bone morphogenetic protein (BMP), inhibitor of BMP antagonism, HMG-CoA reductase inhibitor, vitamin K, vitamin K derivative, ipriflavone, fluoride salts, dietary calcium supplement, or osteoprotegerin.

In one embodiment, the agent treating osteoporosis is a calcitonin. In some embodiments, calcitonins include but are not limited to salmon, elcatonin, SUN-8577, or TJN-135.

In one embodiment, the agent treating osteoporosis is a vitamin D receptor ligand or analogue. In some embodiments, vitamin D receptor ligands or analogues include but are not limited to calcitriol, topitriol, ZK-150123, TEI-9647, BXL-628, Ro-26-9228, BAL-2299, Ro-65-2299, or DP-035.

In one embodiment, the SARM compound is administered with an agent treating pharmacotherapy induced hypogonadal and/or osteopenic and/or sarcopenic state. In some embodiments, agents treating pharmacotherapy induced hypogonadal and/or osteopenic and/or sarcopenic states include but are not limited to opioids, narcotics, opiates, opioids, methadone, Kadian®, 12 dopamine receptor antagonist, zotepine, haloperidol, amisulpride, risperidone, anti-epileptic agent, valproic acid, carbamazepine, oxcarbamazepine, chemotherapeutic agent, methotrexate, cyclophosphamide, ifosfamide, adriamycin, doxorubicin, glucocorticoids, cyclosporine, L-thyroxine, SERMs, aromatase inhibitors (AT), fulvestrant, gonadotropin-releasing hormone agent, androgen depravation agent, prolactinemia-inducing agent, serotonergic antidepressant, selective serotonin reuptake inhibitor, monoamine oxidase inhibitor, tricyclic antidepressant, antihypertensive agents, methyldopa, reserpine, clonidine, verapamil, antidopaminergic agent, anti-emetic agent, metoclopramide, $H_2$ receptor antagonist, cimetidine, ranitidine, estrogen, or amphetamine.

In one embodiment, the SARM compound is administered with a vitamin. In some embodiments, vitamins include but are not limited to vitamin D, vitamin E, vitamin K, vitamin B, vitamin C, or a combination thereof.

In one embodiment, the SARM compound is administered with a behavior-modulating agent. In some embodiments, behavior-modulating agents include but are not limited to an anti-anxiety agent, anti-psychotic agent, antidepressant, beta-blocker, beta-2 agonist, anticholinergic bronchodilator, theophylline, aminophylline, nedocromil sodium, sodium chromoglycate, leukotriene receptor antagonist, corticosteroid, expectorant, mucolytic agent, antihistamine, pseudoephedrine, methylphenidate, amphetamine, buspirone, benzodiazepine, dextroamphetamine, tricyclic antidepressant, serotonin reuptake inhibitor, phenothiazines, benztropine, bupropion, propranolol lithium, venlafaxine, haloperidol, buspirone, or a neuraminidase inhibitor.

In one embodiment, the behavior-modulating agent is a benzodiazepine. In one embodiment, benzodiazepines comprise alprazolam, chlordiazepoxide, diazepam, flurazepam, lorazepam, oxazepam, temazepam, or triazolam.

In one embodiment, the behavior-modulating agent is a phenothiazine. In one embodiment, phenothiazines comprise fluphenazine, perphenazine, thioridazine, or trifluoperazine.

In one embodiment, the behavior-modulating agent is a tricyclic antidepressant or a serotonin reuptake inhibitor. In one embodiment, tricyclic antidepressants or serotonin reuptake inhibitors comprise phenothiazine, protriptyline, fluoxetine, paroxetine, or sertraline.

In one embodiment, the SARM compound of this invention is administered with an agent treating a connective tissue. In some embodiments, agents treating a connective tissue include but are not limited to an anti-malaria agent, a cytotoxic agent, a steroid, corticosteroid, lupus medication, azathioprine, cyclophosphamide, anti-rheumatic agent, corticosteroid, nifedipine, aspirin, colchicine, captopril, penicillamine, azathioprine, methotrexate, prednisone, nicardipine, or a non-steroidal anti-inflammatory agent.

In one embodiment, the compound of this invention is administered with an agent treating an ophthalmic disease. In some embodiments, agents treating an ophthalmic disease include but are not limited to Betagan®, Betimol®, Timoptic®, Betoptic®, Ocupress®, Optipranolol®, Xalatan®, Alphagan®, Azopt®, Trusopt®, Cosopt®, Pilocar®, Pilagan®, Propine®, Opticrom®, Acular®, Livostin®, Alomide®, Emadine®, Patanol®, Akrex®, Poly-Pred®, Pred-G®, Dexacidin®, erythromycin, Maxitrol®, Tobradex®, Blephamide®, FML®, Ocufen®, Voltaren®, Profenal®, Pred Porte®, Econpred Plus®, Eflone®, Flarex®, Inflamase Forte®, betadine, gramicidin, prednisolone, betaxolol, Humorsol®, proparacaine, Hylartin®, Inflamase Mild®, Lotemax®, flurbiprofen, chloramphenicol, methazolamide, timolol Ciloxan®, terramycin, ciprofloxacin, Miostat®, triamcinolone, miconazole, tobramycin, physostigmine, gentamicin, pilocarpine, bacitracin, goniosol, polymyxin, oxytetracycline, Viroptic®, Vexol®, Suprofen®, Celluvisc®, Polytrim®, Illotycin®, Ocuflox®, brinzolamide, cefazolin, Tobrex®, latanoprost, indocycanine, trifluridine, phenylephrine, demecarium, neomycin, tropicamide, dexamethasone, neptazane, dipivefrin, vidarabine, dorzolamide, ofloxacin, epinephrine, acyclovir, carbonic anhydrase inhibitor, antihistamine vitamin A, vitamin C, vitamin E, zinc, copper, atropine, or garamycin.

In one embodiment, the SARM compound of this invention is administered in with a gene therapy agent. In some embodiments, gene therapy agents include but are not limited to an antisense agent, or a replacement gene.

In one embodiment, the SARM compound of this invention is administered in combination with an agent treating the lung. In one embodiment, the SARM compound is administered in combination with a temozolomide, paclitaxel, cisplatin, docetaxel or combination thereof.

In some embodiments, any of the compositions of this invention will comprise a compound of formula I-XX or S-(III), in any form or embodiment as described herein. In some embodiments, any of the compositions of this invention will consist of a compound of formula I-XX or S-(III), in any form or embodiment as described herein. In some embodiments, of the compositions of this invention will consist essentially of a compound of I-XX or S-(III), in any form or embodiment as described herein. In some embodiments, the term "comprise" refers to the inclusion of the indicated active agent, such as the compound of formula I-XX or S-(III), as well as inclusion of other active agents, and pharmaceutically acceptable carriers, excipients, emollients, stabilizers, etc., as are known in the pharmaceutical industry. In some embodiments, the term "consisting essentially of" refers to a composition, whose only active ingredient is the indicated active ingredient, however, other compounds may be included which are for stabilizing, preserving, etc. the formulation, but are not involved directly in the therapeutic effect of the indicated active ingredient. In some embodiments, the term "consisting essentially of" may refer to components which facilitate the release of the active ingredient. In some embodiments, the term "consisting" refers to a composition, which contains the active ingredient and a pharmaceutically acceptable carrier or excipient.

In one embodiment, the present invention provides combined preparations. In one embodiment, the term "a combined preparation" defines especially a "kit of parts" in the sense that the combination partners as defined above can be dosed independently or by use of different fixed combinations with distinguished amounts of the combination partners i.e., simultaneously, concurrently, separately or sequentially. In some embodiments, the parts of the kit of parts can then, e.g., be administered simultaneously or chronologically staggered, that is at different time points and with equal or different time intervals for any part of the kit of parts. The ratio of the total amounts of the combination partners, in some embodiments, can be administered in the combined preparation. In one embodiment, the combined preparation can be varied, e.g., in order to cope with the needs of a patient subpopulation to be treated or the needs of the single patient which different needs can be due to a particular disease, severity of a disease, age, sex, or body weight as can be readily made by a person skilled in the art.

It is to be understood that this invention is directed to compositions and combined therapies as described herein, for any disease, disorder or condition, as appropriate, as will be appreciated by one skilled in the art. Certain applications of such compositions and combined therapies have been described hereinabove, for specific diseases, disorders and conditions, representing embodiments of this invention, and methods of treating such diseases, disorders and conditions in a subject by administering a SARM as herein described, alone or as part of the combined therapy or using the compositions of this invention represent additional embodiments of this invention.

Biological Activity of Selective Androgen Modulator Compounds

The SARM compounds of this invention may be useful, in some embodiments for treating, suppressing, inhibiting, reducing the severity of, reducing the incidence of, reducing the pathogenesis of or delaying onset of, inter alia: a) muscle wasting in patients with cancer, wherein the patients are subjected to cancer therapy; b) muscle wasting in patients with non-small cell lung cancer (NSCLC), wherein the patients are subjected to cancer therapy; c) muscle wasting in patients with non-small cell lung cancer (NSCLC), wherein the patients are subjected to taxane therapy; d) pre-cachexia or early cachexia (preventing muscle wasting in a cancer patient), wherein the patients are subjected to cancer therapy; e) treating loss of physical function due to cancer or cancer therapy (radiation, chemotherapy, surgery); f) increasing physical function of a subject, wherein the subject is subjected to cancer therapy; g) increasing physical function of a cancer patient, wherein the patient is subjected to cancer therapy; h) increasing physical function of a cancer patient, wherein said patient suffers from non-small cell lung cancer, colorectal cancer, non-Hodgkin lymphoma, chronic lymphocytic leukemia or breast cancer, and is subjected to cancer therapy; i) increasing physical function of a cancer patient, wherein said patient suffers from non-small cell lung cancer, and is subjected to taxane therapy; j) treating, suppressing, inhibiting, reducing the severity of reducing the incidence of, reducing the pathogenesis of or delaying onset of lung cancer in a patient, wherein the patient is subjected to cancer therapy; k) increasing survival, functional independence, and increasing quality of life of a subject suffering from cancer, and is subjected to cancer therapy; l) increasing survival, functional independence, and increasing quality of life of a subject suffering from non-small cell lung cancer, and is subjected to taxane therapy; m) preventing or treating declines in quality of life due to cancer or cancer therapy; and n) treating diseases, disorders or conditions related thereto; via the administration of any SARM as herein described and optionally other therapeutic agents, including but not limited to chemotherapeutic agents, or compositions comprising the same.

The SARMs of this invention may be useful, in some embodiments, for oral testosterone replacement therapy. In other embodiments, appropriately substituted compounds are useful for: a) male contraception; b) treatment of a variety of hormone-related conditions, for example conditions associated with androgen deficiency in an aging male (ADAM), such as fatigue, depression, decreased libido, sexual dysfunction, erectile dysfunction, hypogonadism, osteoporosis, hair loss, obesity, sarcopenia, osteopenia, benign prostate hyperplasia, and alterations in mood and cognition; c) treatment of conditions associated with androgen deficiency in a female (ADIF), such as sexual dysfunction, decreased sexual libido, hypogonadism, sarcopenia, osteopenia, osteoporosis, alterations in cognition and mood, depression, anemia, hair loss, obesity, endometriosis, breast cancer, uterine cancer and ovarian cancer; d) treatment and/or prevention of chronic muscular wasting; e) treatment of prostate cancer, imaging of prostate cancer, or decreasing the incidence of, halting or causing a regression of prostate cancer; f) treatment of diabetes type I; g) treatment of diabetes type II; h) suppressing or inhibiting or reducing the incidence of diabetes; i) treatment of glucose intolerance; j) treatment of hyperinsulinemia; k) treatment of insulin resistance; l) treatment of diabetic nephropathy; m) treatment of diabetic neuropathy; n) treatment of diabetic retinopathy; o) treatment of fatty liver conditions; p) treatment of cachexia; q) oral androgen replacement and/or other clinical therapeutic and/or diagnostic areas, including any embodiment of what is encompassed by the term "treating" as described herein.

In some embodiments, the SARM compounds possess in vivo tissue selective androgenic and anabolic activity, which is accordingly utilized for particular applications, as will be appreciated by one skilled in the art.

In one embodiment, this invention provides: a) a method of treating a subject having a muscle wasting disorder; b) a method of treating a subject suffering from malnutrition; c) a method of treating a bone-related disorder in a subject; d) a method of increasing a bone mass in a subject; e) a method of improving the lipid profile in a subject; f) a method of treating atherosclerosis and its associated diseases; g) a method of improving dexterity and movement in a subject; h) a method of treating a subject suffering from dwarfism; i) a method of treating a subject having dysmenorrhea; j) a method of treating a subject having dysparuia; and k) a method of treating a subject having dysspermtogenic sterility; comprising the step of administering to said subject a selective androgen receptor modulator (SARM) compound of formula I-XX or S-(III) and/or an analog, derivative, isomer, metabolite, pharmaceutically acceptable salt, pharmaceutical product, hydrate, N-oxide, prodrug, polymorph, impurity or crystal of said SARM compound, or any combination thereof.

In some embodiments, the SARMs as described herein and/or compositions comprising the same may be used for applications and treating diseases in which the improvement of cognition, reduction or treatment of depression, or other neuroprotective effects are desired.

In one embodiment, the methods of this invention are useful a subject, which is a human. In another embodiment, the subject is a mammal. In another embodiment the subject is an animal. In another embodiment the subject is an invertebrate. In another embodiment the subject is a vertebrate.

In one embodiment, the subject is male. In another embodiment, the subject is female. In some embodiments, while the methods as described herein may be useful for treating either males or females, females may respond more advantageously to administration of certain compounds, for certain methods, as described and exemplified herein.

In some embodiments, while the methods as described herein may be useful for treating either males or females, males may respond more advantageously to administration of certain compounds, for certain methods, as described herein.

In some embodiments, the SARMs as described herein and/or compositions may be used for applications in or treating hair loss, alopecia, androgenic alopecia, alopecia areata, alopecia secondary to chemotherapy, alopecia secondary to radiation therapy, alopecia induced by scarring or alopecia induced by stress. In one embodiment, "hair loss", or "alopecia", refers to baldness as in the very common type of male-pattern baldness. Baldness typically begins with patch hair loss on the scalp and sometimes progresses to complete baldness and even loss of body hair. Hair loss affects both males and females.

In some embodiments, the SARMs as described herein and/or compositions comprising the same may be used for applications in, or treating diseases or conditions associated with a subject having anemia. In one embodiment, "anemia" refers to the condition of having less than the normal number of red blood cells or less than the normal quantity of hemoglobin in the blood, reduced hematocrit or reduced mean corpuscular volume, or reduced corpuscular size. The oxygen-carrying to capacity of the blood is decreased in anemia. In some embodiments, treating anemia may also refer herein to treating underlying factors resulting in anemia, such as for example a) hemorrhage (bleeding); b) hemolysis (excessive destruction of red blood cells); c) underproduction of red blood cells; and d) not enough normal hemoglobin. In some embodiments, treating anemia in this invention refers to treating any form thereof, including aplastic anemia, benzene poisoning. Fanconi anemia, hemolytic disease of the newborn, hereditary spherocytosis, iron deficiency anemia, osteoporosis, pernicious anemia, sickle cell disease, aplastic anemia, hemolytic anemia, sickle cell anemia, renal anemia, thalassemia, myelodysplastic syndrome, and a variety of bone marrow diseases.

In some embodiments, the SARMs as described herein and/or compositions comprising the same may be used for applications in and/or treating diseases and/or conditions associated with problems with a subject's libido, or erectile dysfunction in a subject. In one embodiment, "libido", may refer to sexual desire.

In one embodiment, the term "erectile" refers to the ability to be erect or upright. An erectile tissue is a tissue, which is capable of being greatly dilated and made rigid by the distension of the numerous blood vessels, which it contains.

In another embodiment of the present invention, a method is provided for hormonal therapy in a patient (i.e., one suffering from an androgen-dependent condition) which includes contacting an androgen receptor of a patient with a SARM compound and/or a non steroidal agonist of the present invention and/or its analog, derivative, isomer, metabolite, pharmaceutically acceptable salt, pharmaceutical product, polymorph, crystal, impurity, hydrate, N-oxide or any combination thereof, in an amount effective to bind the SARM compound to the androgen receptor and effect a change in an androgen-dependent condition.

In one embodiment of this invention, a method is provided for hormone replacement therapy in a patient (i.e., one suffering from an androgen-dependent condition) which includes administering a SARM compound as herein described and/or its analog, derivative, isomer, metabolite, pharmaceutically acceptable salt, pharmaceutical product, polymorph, crystal, impurity, hydrate, N-oxide or any combination thereof, to a subject, in an amount sufficient to effect a change in a hormone-dependent condition in the subject.

Androgen-dependent conditions which may be treated with the compounds and/or compositions as herein described, comprising the methods of the present invention include those conditions which are associated with aging, hypogonadism, sarcopenia, diminished erythropoiesis, osteoporosis, and any other conditions dependent upon low androgen (e.g., testosterone) or estrogen levels.

Androgen-dependent conditions which may be treated with the compounds and/or compositions as herein described, and comprising a method of the invention, may comprise conditions characterized by elevated androgen or estrogen levels, including hirsutism, infertility, polycystic ovarian syndrome, endometrial carcinoma, breast cancer, male pattern baldness, prostate cancer, testicular cancer, and others, as will be known to one skilled in the art. For such conditions, the subject may be administered a SARM as herein described, alone or in combination with another therapeutic agent, as will be appreciated by one skilled in the art.

In one embodiment this invention provides methods for the treatment of a cancer in a subject, reduction of incidence or severity or pathogenesis of a cancer in a subject, delaying progression, prolonging remission or delaying onset of cancer in a subject, comprising the step of administering to the subject a SARM compound as herein described and/or its analog, derivative, isomer, metabolite, pharmaceutically acceptable salt, pharmaceutical product, polymorph, crystal, impurity, hydrate, N-oxide or any combination thereof. In some embodiments, such cancers are hormone-dependent or associated with reproductive tissue in males or females, such as cancer of the prostate, ovary, breast, uterus, testicle, or others.

In some embodiments, this invention provides methods for the treatment of a precancerous precursor or lesion in a subject, reduction of incidence of precancerous precursors or lesions in a subject, comprising the step of administering to the subject a SARM compound as herein described and/or its analog, derivative, isomer, metabolite, pharmaceutically acceptable salt, pharmaceutical product, polymorph, crystal, impurity, hydrate, N-oxide or any combination thereof. In some embodiments, such precancerous precursors are found in hormone-responsive tissue or are associated with reproductive tissue in males or females, such as in the prostate, ovary, breast, uterus, testicle, or others. In some embodiments, such precancerous precursors comprise any local intraepithelial neoplasia, for example, of the prostate, the cervix, etc. In some embodiments, such methods are useful in treating neoplasia or pre-neoplasia, dysplasia or hyperplasia in a tissue, such as in reproductive tissue in males or females.

In one embodiment, this invention provides compounds, compositions and/or methods of use thereof in treating benign prostate hyperplasia (BPH). "BPH (benign prostate hyperplasia)" is a nonmalignant enlargement of the prostate gland, and is the most common non-malignant proliferative abnormality found in any internal organ and the major cause of morbidity in the adult male. BPH occurs in over 75% of men over 50 years of age, reaching 88% prevalence by the ninth decade. BPH frequently results in a gradual squeezing of the portion of the urethra which traverses the prostate (prostatic urethra). This causes patients to experience a frequent urge to urinate because of incomplete emptying of the bladder and urgency of urination. The obstruction of urinary flow can also lead to a general lack of control over urination, including difficulty initiating urination when desired, as well as difficulty in preventing urinary flow because of the inability to empty urine from the bladder, a condition known as overflow urinary incontinence, which can lead to urinary obstruction and to urinary failure.

In another embodiment of the present invention, the method for treating benign prostate hyperplasia (BPH) in a subject, comprises the step of administering to the subject a SARM compound as herein described and/or its analog, derivative, isomer, metabolite, pharmaceutically acceptable salt, pharmaceutical product, polymorph, crystal, impurity, hydrate, N-oxide or any combination thereof, in an amount effective to treat BPH in the subject.

In another embodiment of the present invention, this invention provides a method for treating, including all embodiments encompassed by such term, prostatitis in a subject, comprises the step of administering to the subject a SARM compound as herein described and/or its analog, derivative, isomer, metabolite, pharmaceutically acceptable salt, pharmaceutical product, polymorph, crystal, impurity, hydrate, N-oxide or any combination thereof, in an amount effective to treat prostatitis in the subject.

In some embodiments, this invention provides for the use of a SARM compound as herein described, or its prodrug, analog, isomer, metabolite, derivative, pharmaceutically acceptable salt, pharmaceutical product, polymorph, crystal, impurity, N-oxide, hydrate or any combination thereof, for treating, reducing the severity of, reducing the incidence of, or reducing the pathogenesis of cachexia and/or cachexia associated with cancer in a subject. In another embodiment, the cancer comprises adrenocortical carcinoma, anal cancer, bladder cancer, brain tumor, brain stem glioma, brain tumor, cerebellar astrocytoma, cerebral astrocytoma, colorectal cancer, chronic lymphocytic leukemia, ependymoma, medulloblastoma, supratentorial primitive neuroectodermal, pineal tumors, hypothalamic glioma, breast cancer, carcinoid tumor, carcinoma, cervical cancer, colon cancer, endometrial cancer, esophageal cancer, extrahepatic bile duct cancer, Ewings family of tumors (Pnet), extracranial germ cell tumor, eye cancer, intraocular melanoma, gallbladder cancer, gastric cancer, germ cell tumor, extragonadal, gestational trophoblastic tumor, head and neck cancer, hypopharyngeal cancer, islet cell carcinoma laryngeal cancer, leukemia, acute lymphoblastic leukemia, oral cavity cancer, liver cancer, lung can, small cell kung cancer, non-small cell kung cancer (NSCLC), lymphoma, AIDS-related lymphoma, central nervous system (primary), lymphoma, cutaneous T-cell, lymphoma, Hodgkin's disease, on-Hodgkin's disease, malignant mesothelioma, melanoma, Markel cell carcinoma, metastatic squamous carcinoma, multiple myeloma, plasma cell neoplasms, mycosis fungoides, myelodysplastic syndrome, myeloproliferative disorders, nasopharyngeal cancer, neuroblastoma, oropharyngeal cancer, osteosarcoma, ovarian epithelial cancer, ovarian germ cell tumor, ovarian low malignant potential tumor, pancreatic cancer, exocrine, pancreatic cancer, islet cell carcinoma, paranasal sinus and nasal cavity cancer, parathyroid cancer, penile cancer, pheochromocytoma cancer, pituitary cancer, plasma cell neoplasm, prostate cancer, rhabdomyosarcoma, rectal cancer, renal cell cancer, salivary gland cancer, Sezary syndrome, skin cancer, cutaneous T-cell lymphoma, skin cancer, Kaposi's sarcoma, skin cancer, melanoma, small intestine cancer, soft tissue sarcoma, soft tissue sarcoma, testicular cancer, thymoma, malignant, thyroid cancer, urethral cancer, uterine cancer, sarcoma, unusual cancer of childhood, vaginal cancer, vulvar cancer. Wilms' tumor, or any combination thereof. In another embodiment, the SARM is compound of formula II as described hereinabove. In another embodiment, the SARM is compound of formula S-(III) as described hereinabove. In another embodiment, the cancer patient is subjected to a cancer therapy. In another embodiment, the cancer patient is subjected to radiation therapy. In another embodiment, the compound is administered in combination with radiation therapy. In another embodiment, the compound is administered in combination with a chemotherapeutic agent. In another embodiment, the chemotherapeutic agent comprises bendamustine, bevacizumab, bleomycin, calcium folinate, capecitabine, carboplatin, cetuximab, chlorambucil, cisplatin, cyclophosphamide, cytarabine, dasatinib, docetaxel, doxorubicin, erlotinib, etoposide, fludarabine, fluorouracil, gemcitabine hydrochloride, irinotecan hydrochloride, lapatinib methotrexate, methylprednisolone acetate, mitoxantrone, mitoxantrone hydrochloride, oxaliplatin, paclitaxel, pamidronate disodium, panitumumab, pemetrexed, prednisone, rituximab, trastuzumab, vincristine, vinorelbine or any combination thereof.

In another embodiment, this invention provides the use of a SARM compound as herein described including comprising an analog, derivative, isomer, metabolite, pharmaceutically acceptable salt, pharmaceutical product, polymorph, crystal, impurity, hydrate, N-oxide or any combination thereof, of a compound of formula S-(III) for treating, reducing the severity of, reducing the incidence of, or delaying the onset of lung cancer, which in one embodiment is non-small cell lung cancer. In another embodiment, the lung cancer patient is subjected to a cancer therapy. In another embodiment, the lung cancer patient is subjected to radiation therapy. In another embodiment, the compound is administered in combination with radiation therapy. In another embodiment, the compound is administered in combination with a chemotherapeutic agent. In another embodiment, the chemotherapeutic agent comprises: bendamustine, bevacizumab, bleomycin, calcium folinate, capecitabine, carboplatin, cetuximab, chlorambucil, cisplatin, cyclophosphamide, cytarabine, dasatinib docetaxel, doxorubicin, erlotinib, etoposide, fludarabine, fluorouracil, gemcitabine hydrochloride, irinotecan hydrochloride, lapatinib, methotrexate, methylprednisolone acetate, mitoxantrone, mitoxantrone hydrochloride, oxaliplatin, paclitaxel, pamidronate disodium, panitumumab pemetrexed, prednisone, rituximab, trastuzumab, vincristine, vinorelbine or any combination thereof.

In another embodiment, this invention provides the use of a SARM compound as herein described including comprising an analog, derivative, isomer, metabolite, pharmaceutically acceptable salt, pharmaceutical product, polymorph, crystal, impurity, hydrate, N-oxide or any combination thereof, of a compound of formula S-(III) for treating reducing the severity of, reducing the incidence of, or delaying the onset of cachexia or other conditions arising as a result of lung cancer in the subject, which in one embodiment is non-small cell lung cancer.

In another embodiment, the lung cancer patient is subjected to a cancer therapy. In another embodiment, the lung cancer patient is subjected to radiation therapy. In another embodiment the compound is administered in combination with radiation therapy. In another embodiment, the compound is administered in combination with a chemotherapeutic agent. In another embodiment, the chemotherapeutic agent comprises: bendamustine, bevacizumab, bleomycin, calcium folinate, capecitabine, carboplatin, cetuximab, chorambucil, cisplatin, cyclophosphamide, cytarabine, dasatinib, docetaxel, doxorubicin, erlotinib, etoposide, fludarabine, fluorouracil, gemcitabine hydrochloride, irinotecan hydrochloride, lapatinib, methotrexate, methylprednisone acetate, mitoxantrone, mitoxantrone hydrochloride, oxaliplatin, paclitaxel, pamidronate disodium, panitumumab, pemetrexed, prednisone, rituximab, trastuzumab, vincristine, vinorelbine or any combination thereof.

In one embodiment, this invention provides a method of treating, reducing the severity, reducing the incidence, delaying the onset, or reducing the pathogenesis of muscle wasting in a human subject with cancer, comprising administering a compound of this invention. In another embodiment, the compound is compound of formula II as described hereinabove. In another embodiment, the compound is compound of formula S-(III) as described hereinabove. In another embodiment, said subject suffers from non-small cell lung cancer. In another embodiment the subject suffers from colon cancer. In another embodiment the subject suffers from breast cancer. In another embodiment the subject suffers from non-Hodgkin's lymphoma. In another embodiment the subject suffers chronic lymphocytic leukemia. In another embodiment the subject suffers from lung cancer. In another embodiment, the cancer patient is subjected to a cancer therapy. In another embodiment, the cancer patient is subjected to radiation therapy. In another embodiment, the compound is administered in combination with radiation therapy. In another embodiment, the compound is administered in combination with a chemotherapeutic agent. In another embodiment, the chemotherapeutic agent comprises: bendamustin, bevacizumab, bleomycin, calcium folinate, capecitabine, carboplatin, cetuximab, chlorambucil, cisplatin, cyclophosphamide, cytarabine, dasatinib, docetaxel, doxorubicin, erlotinib, etoposide, fludarabine, fluorouracil, gemcitabine hydrochloride, irinotecan hydrochloride, lapatinib, methotrexate, methylprednisolone acetate, mitoxantrone, mitoxantrone, hydrochloride, oxaliplatin, paclitaxel, pamidronate disodium, panitumumab, pemetrexed, prednisone, rituximab, trastuzumab, vincristine, vinorelbine or any combination thereof.

In one embodiment, this invention provides a method of treating, reducing the severity, reducing the incidence, delaying the onset, or reducing the pathogenesis of muscle wasting in a human subject with non-small cell lung cancer, comprising the step of administering to said subject a compound of this invention. In another embodiment, the compound is compound of formula II as described hereinabove. In another embodiment, the compound is compound of formula S-(III) as described hereinabove. In another embodiment, the non-small cell lung cancer patient is subjected to a cancer therapy. In another embodiment, the non-small cell lung cancer patient is subjected to radiation therapy. In another embodiment, the non-small cell lung cancer patient is subjected to taxane therapy. In another embodiment, the non-small cell lung cancer patient is subjected to taxane and platinum therapy. In another embodiment, the non-small cell lung cancer patient is subjected to platinum and non-taxane chemotherapy. In another embodiment, the compound is administered in combination with radiation therapy. In another embodiment, the compound is administered in combination with a chemotherapeutic agent. In another embodiment, the chemotherapeutic agent comprises: bendamustine, bevacizumab, bleomycin, calcium folinate, capecitabine, carboplatin, cetuximab, chlorambucil, cisplatin, cyclophosphamide, cytarabine, dasatinib, docetaxel, doxorubicin, erlotinib, etoposide, fludarabine, fluorouracil, gemcitabine hydrochloride, irinotecan hydrochloride, lapatinib, methotrexate, methylprednisolone acetate, mitoxantrone, mitoxantrone hydrochloride, oxaliplatin, paclitaxel, pamidronate disodium, panitumumab, pemetrexed, prednisone, rituximab, trastuzumab, vincristine, vinorelbine or any combination thereof.

In another embodiment, this invention is directed to a method of treating, reducing the severity, reducing the incidence, delaying the onset, or reducing the pathogenesis of muscle wasting in a human subject with non-small cell lung cancer, said method comprises administering a selective androgen receptor modulator (SARM) compound of formula II:

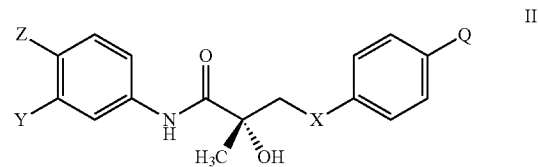

wherein
X is O;
Z is NO$_2$, CN, COR, or CONHR;
Y is an alkyl, CF$_3$, CH$_3$, formyl, alkoxy, H, F, I, Br, Cl, or Sn(R)$_3$;
R is an alkyl, aryl, phenyl, alkenyl, haloalkyl, haloalkenyl, halogen or OH;
and
Q is alkyl, halogen, N(R)$_2$, CN, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$. NHSO$_2$R, OR, COR, OCOR, OSO$_2$R, SO₂R, SR, acetamido-, trifluoroacetamido, alkylamines, ether, alkyl, N-sulfonyl, O-sulfonyl, alkylsulfonyl, carbonyl, or a ketone;

wherein said subject is subjected to cancer therapy.

In another embodiment, Q is CN.

In another embodiment, said method comprises administering a selective androgen receptor modulator (SARM) compound of formula or S-(III):

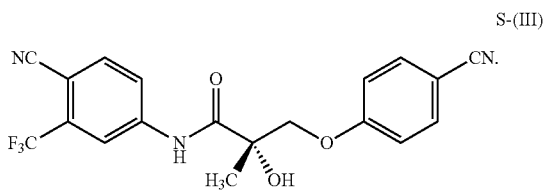 [SMILES: C[C@](O)(COc1ccc(C#N)cc1)C(=O)Nc1ccc(C#N)c(C(F)(F)F)c1]

S-(III)

In another embodiment, this invention provides a method of treating, reducing the severity, reducing the incidence, delaying the onset, or reducing the pathogenesis of muscle wasting in a human subject with non-small cell lung cancer, wherein said subject is subjected to a cancer therapy. In another embodiment, the subject is subjected to taxane therapy. In another embodiment, subject is subjected to taxane and platinum therapy. In another embodiment, the subject is subjected to platinum and non-taxanechemotherapy. In another embodiment, the cancer therapy is radiation therapy. In another embodiment, the cancer therapy is chemotherapy. In another embodiment, the compound is compound of formula II as described hereinabove. In another embodiment, the compound is compound of formula S-(III) as described hereinabove. In another embodiment, the compound is administered in combination with radiation therapy. In another embodiment, the compound is administered in combination with a chemotherapeutic agent. In another embodiment, the chemotherapeutic agent comprises bendamustine, bevacizumab, bleomycin, calcium folinate, capecitabine, carboplatin, cetuximab, chorambucil, cisplatin, cyclophosphamide, cytarabine, dasatinib docetaxel, doxorubicin, erlotinib etoposide, fludarabine, fluorouracil, gemcitabine hydrochloride, irinotecan hydrochloride, lapatinib, methotrexate, methylprednisolone acetate, mitoxantrone, mitoxantrone hydrochloride, oxaliplatin, paclitaxel, pamidronate disodium, panitumumab, pemetrexed, prednisone, rituximab, trastuzumab, vincristine, vinorelbine or any combination thereof. In another embodiment, the chemotherapeutic agent comprises platinum and taxane. In another embodiment, the chemotherapeutic agent comprises platinum and non-taxane chemotherapeutic agent. In another embodiment, said method further increases the physical function of said subject. In another embodiment, said method further increases the quality of life of said subject. In another embodiment, said method further increases the lean body mass of said subject.

In another embodiment, this invention provides a method of treating, reducing the severity, reducing the incidence, delaying the onset, or reducing the pathogenesis of muscle wasting in a human subject with cancer, wherein said subject is subjected to a cancer therapy. In another embodiment, the cancer therapy is radiation therapy. In another embodiment, the cancer therapy is chemotherapy. In another embodiment, the compound is administered in combination with radiation therapy. In another embodiment, the compound is administered in combination with a chemotherapeutic agent. In another embodiment, the chemotherapeutic agent comprises: bendamustine, bevacizumab, bleomycin, calcium folinate, capecitabine, carboplatin, cetuximab, chorambucil cisplatin, cyclophosphamide, cytarabine, dasatinib, docetaxel, doxorubicin, erlotinib, etoposide, fludarabine, fluorouracil, gemcitabine hydrochloride, irinotecan hydrochloride, lapatinib, methotrexate, methylprednisolone acetate, mitoxantrone, mitoxantrone hydrochloride, oxaliplatin, paclitaxel, pamidronate disodium, panitumumab, pemetrexed, prednisone, rituximab, trastuzumab, vincristine, vinorelbine or any combination thereof. In another embodiment, the chemotherapeutic agent comprises platinum and taxane. In another embodiment, the chemotherapeutic agent comprises platinum and non-taxane chemotherapeutic agent. In another embodiment, said method further increases the physical function of said subject. In another embodiment, said method further increases the quality of life of said subject. In another embodiment, said method further increases lean body mass of a subject. In another embodiment, the cancer is non-small cell lung cancer. In another embodiment the cancer is colon cancer. In another embodiment the cancer is breast cancer. In another embodiment the cancer is non-Hodgkin's lymphoma. In another embodiment the cancer is chronic lymphocytic leukemia. In another embodiment the cancer is lung cancer.

In one embodiment, this invention provides a method of treating, reducing the severity, reducing the incidence, delaying the onset, or reducing the pathogenesis of cachexia, pre-cachexia or early cachexia in a subject with cancer, comprising the step of administering a compound of this invention. In another embodiment, said method comprises administering a selective androgen receptor modulator (SARM) compound of formula II:

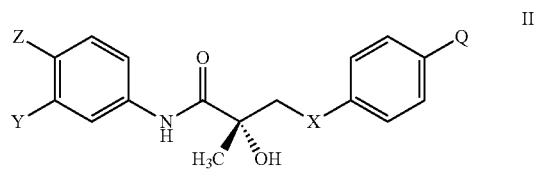

II wherein

X is O;

Z is NO₂, CN, COR, or CONHR;

Y is an alkyl, CF₃, CH₃, formyl, alkoxy, H, F, I, Br, Cl, or Sn(R)₃;

R is an alkyl, aryl, phenyl, alkenyl, haloalkyl, haloalkenyl, halogen or OH;

and

Q is alkyl, halogen, N(R), CN, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, acetamido-, trifluoroacetamido-, alkylamines, ether, alkyl, N-sulfonyl, O-sulfonyl, alkylsulfonyl, carbonyl, or a ketone;

wherein said subject is subjected to cancer therapy.

In another embodiment, Q is CN.

In another embodiment, said method comprises administering a selective androgen receptor modulator (SARM) compound of formula S-(III):

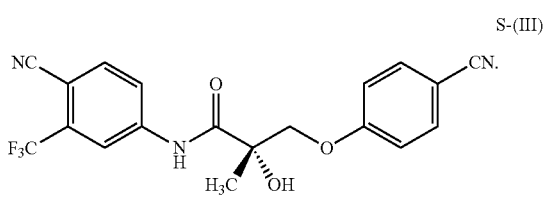 [SMILES: C[C@](O)(COc1ccc(C#N)cc1)C(=O)Nc1ccc(C#N)c(C(F)(F)F)c1]

In another embodiment, this invention provides a method of treating, reducing the severity, reducing the incidence, delaying the onset, or reducing the pathogenesis of cachexia, pre-cachexia or early cachexia in a subject with cancer, wherein said subject is subjected to a cancer therapy. In another embodiment, the cancer therapy is radiation therapy. In another embodiment, the cancer therapy is chemotherapy. In another embodiment, the compound is administered in combination with radiation therapy. In another embodiment, the compound is administered in combination with a chemotherapeutic agent. In another embodiment, the chemotherapeutic agent comprises: bendamustine, bevacizumab, bleomycin, calcium folinate, capecitabine, carboplatin, cetuximab, chlorambucil, cisplatin, cyclophosphamide, cytarabine, dasatinib, docetaxel, doxorubicin, erlotinib, etoposide, fludarabine, fluorouracil, gemcitabine hydrochloride, irinotecan hydrochloride, lapatinib, methotrexate, methylprednisolone acetate, mitoxantrone, mitoxantrone hydrochloride, oxaliplatin, paclitaxel, pamidronate disodium, panitumumab, pemetrexed, prednisone, rituximab, trastuzumab, vincristine, vinorelbine or any combination thereof. In another embodiment, the chemotherapeutic agent comprises platinum and taxane. In another embodiment, the chemotherapeutic agent comprises platinum and non-taxane chemotherapeutic agent. In another embodiment, said method further increases the physical function of said subject. In another embodiment, said method further increases the quality of life of said subject. In another embodiment, said method further increases lean body mass of a subject. In another embodiment, said method further increases the survival of said subject. In another embodiment, said subject suffers from non-small cell lung cancer. In another embodiment the subject suffers from colon cancer. In another embodiment the subject suffers from breast cancer. In another embodiment the subject suffers from non-Hodgkin's lymphoma. In another embodiment the subject suffers chronic lymphocytic leukemia. In another embodiment the subject suffers from lung cancer.

In one embodiment, this invention provides a method of treating, reducing the severity, reducing the incidence, delaying the onset, or reducing the pathogenesis of pre-cachexia or early cachexia in a subject suffering from cancer, comprising the step of administering a compound of this invention. In another embodiment, said method comprising administering a selective androgen receptor modulator (SARM) compound of formula II:

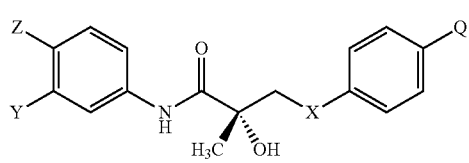

wherein
X is O;
Z is $NO_2$, CN, COR, or CONHR;
Y is an alkyl, $CF_3$, $CH_3$, formyl, alkoxy, H, F, I, Br, Cl, or $Sn(R)_3$;
R is an alkyl, aryl, phenyl, alkenyl, haloalkyl, haloalkenyl, halogen or OH;
and
Q is alkyl, halogen, N(R), CN, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR $OSO_2R$, $SO_2R$, SR, acetamido-, trifluoroacetamido-, alkylamines ether, alkyl, N-sulfonyl, O-sulfonyl, alkysulfonyl, carbonyl, or a ketone;
wherein said subject is subjected to cancer therapy.
In another embodiment Q is CN.

In another embodiment, said method comprising administering a selective androgen receptor modulator (SARM) compound of formula S-(III):

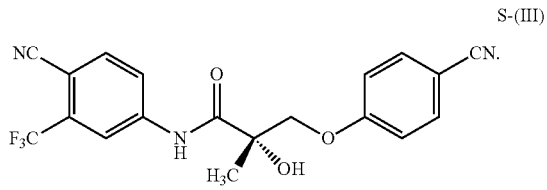 [SMILES: C[C@](O)(COc1ccc(C#N)cc1)C(=O)Nc1ccc(C#N)c(C(F)(F)F)c1]

In another embodiment, this invention provides a method of treating, reducing the severity, reducing the incidence, delaying the onset, or reducing the pathogenesis of pre-cachexia or early cachexia in a subject suffering from cancer, wherein said subject is subjected to a cancer therapy. In another embodiment, the cancer therapy is radiation therapy. In another embodiment, the cancer therapy is chemotherapy. In another embodiment, the compound is administered in combination with radiation therapy. In another embodiment, the compound is administered in combination with a chemotherapeutic agent. In another embodiment, the chemotherapeutic agent comprises: bendamustine, bevacizumab, bleomycin, calcium folinate, capecitabine, carboplatin, cetuximab, chlorambucil, cisplatin, cyclophosphamide, cytarabine, dasatinib, docetaxel, doxorubicin, erlotinib, etoposide, fludarabine, fluorouracil, gemcitabine hydrochloride, irinotecan hydrochloride, lapatinib, methotrexate, methylprednisolone acetate, mitoxantrone, mitoxantrone hydrochloride, oxaliplatin, paclitaxel, pamidronate disodium, panitumumab, pemetrexed, prednisone, rituximab, trastuzumab, vincristine, vinorelbine or any combination thereof. In another embodiment, the chemotherapeutic agent comprises platinum and taxane. In another embodiment, the chemotherapeutic agent comprises platinum and non-taxane chemotherapeutic agent. In another embodiment, said method further increases the physical function of said subject. In another embodiment, said method further increases the quality of life of said subject. In another embodiment, said method increases the survival of said subject. In another embodiment, said method further increases lean body mass of a subject In another embodiment, the cancer is non-small cell lung cancer.

In one embodiment, this invention provides a method of treating, reducing the severity, reducing the incidence, delaying the onset, or reducing the pathogenesis of lung cancer in a subject, comprising the step of administering a compound of this invention. In another embodiment, said method comprises administering a selective androgen receptor modulator (SARM) compound of formula II:

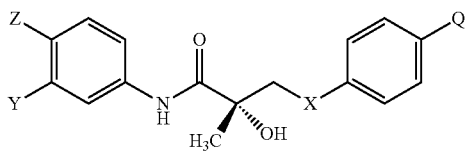

wherein
X is O;
Z is NO$_2$, CN, COR, or CONHR;
Y is an alkyl, CF$_3$, CH$_3$, formyl, alkoxy, H, F, I, Br, Cl, or Sn(R)$_3$;
R is an alkyl, aryl, phenyl, alkenyl, haloalkyl, haloalkenyl, halogen or OH;
and
Q is alkyl halogen, N(R)$_2$, CN, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, acetamido-, trifluoroacetamido-, alkylamines, ether, alkyl, N-sulfonyl, O-sulfonyl, alkylsulfonyl, carbonyl, or a ketone;
wherein said subject is subjected to cancer therapy.
In another embodiment, Q is CN.
In another embodiment, said method comprises administering a selective androgen receptor modulator (SARM) compound of formula S-(III):

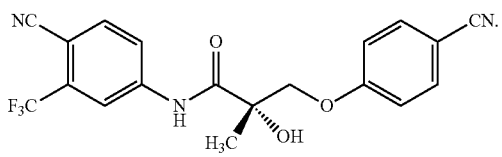

In another embodiment, this invention provides a method of treating, reducing the severity, reducing the incidence, delaying the onset, or reducing the pathogenesis of lung cancer in a subject, wherein said subject is subjected to a cancer therapy. In another embodiment, the cancer therapy is radiation therapy. In another embodiment, the cancer therapy is chemotherapy. In another embodiment, the compound is administered in combination with radiation therapy. In another embodiment, the compound is administered in combination with a chemotherapeutic agent. In another embodiment, the chemotherapeutic agent comprises: bendamustine, bevacizumab, bleomycin, calcium folinate, capecitabine, carboplatin, cetuximab, chlorambucil, cisplatin, cyclophosphamide, cytarabine, dasatinib, docetaxel, doxorubicin, erlotinib, etoposide, fludarabine, fluorouracil, gemcitabine hydrochloride, irinotecan hydrochloride, lapatinib, methotrexate, methylprednisolone acetate, mitoxantrone, mitoxantrone hydrochloride, oxaliplatin, paclitaxel, pamidronate disodium, panitumumab, pemetrexed, prednisone, rituximab, trastuzumab, vincristine, vinorelbine or any combination thereof. In another embodiment, the chemotherapeutic agent comprises platinum and taxane. In another embodiment, the chemotherapeutic agent comprises platinum and non-taxane chemotherapeutic agent. In another embodiment, said method further increases the physical function of said subject. In another embodiment, said method further increases the quality of life of said subject. In another embodiment, said method further increases the survival of said subject. In another embodiment, said method further increases lean body mass of a subject In another embodiment, said subject suffers from non-small cell lung cancer. In another embodiment the subject suffers from colon cancer. In another embodiment the subject suffers from breast cancer. In another embodiment the subject suffers from non-Hodgkin's lymphoma. In another embodiment the subject suffers chronic lymphocytic leukemia. In another embodiment the subject suffers from lung cancer.

In one embodiment, this invention provides a method of treating, reducing the severity, reducing the incidence, delaying the onset, or reducing the pathogenesis of non-small cell lung cancer in a subject, comprising the step of administering a compound of this invention. In another embodiment, said method comprises administering a selective androgen receptor modulator (SARM) compound of formula II:

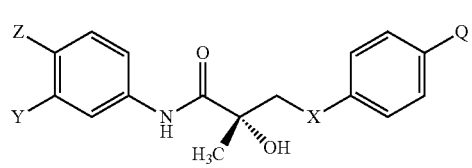

wherein
X is O;
Z is NO$_2$, CN, COR, or CONHR;
Y is an alkyl, CF$_3$, CH$_3$, formyl, alkoxy, H, F, I, Br, Cl, or Sn(R)$_3$;
R is an alkyl, aryl, phenyl, alkenyl, haloalkyl, haloalkenyl, halogen or OH;
and
Q is alkyl, halogen, N(R)$_2$, CN, NHCOCH$_3$, NHCOCF$_3$, NHCOR NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, acetamido-, trifluoroacetamido-, alkylamines, ether, alkyl, N-sulfonyl, O-sulfonyl, alkylsufonyl, carbonyl or a ketone;
wherein said subject is subjected to cancer therapy.
In another embodiment, Q is CN.
In another embodiment, said method comprises administering a selective androgen receptor modulator (SARM) compound of formula S-(III):

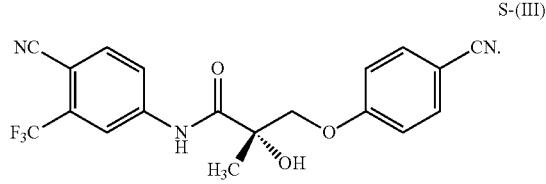 [SMILES: C[C@](O)(COc1ccc(C#N)cc1)C(=O)Nc1ccc(C#N)c(C(F)(F)F)c1]

In another embodiment, this invention provides a method of treating, reducing the severity, reducing the incidence, delaying the onset, or reducing the pathogenesis of non-small cell lung cancer in a subject, wherein said subject is subjected to a cancer therapy. In another embodiment, the cancer therapy is radiation therapy. In another embodiment, the cancer therapy is chemotherapy. In another embodiment, the compound is administered in combination with radiation therapy. In another embodiment, the compound is administered in combination with a chemotherapeutic agent. In another embodiment, the chemotherapeutic agent comprises: bendamustine, bevacizumab, bleomycin, calcium folinate, capecitabine, carboplatin, cetuximab, chlorambucil, cisplatin, cyclophosphamide, cytarabine, dasatinib, docetaxel, doxorubicin, erlotinib, etoposide, fludarabine, fluorouracil, gemcitabine hydrochloride, irinotecan hydrochloride, lapatinib, methotrexate, methylprednisolone acetate, mitoxantrone, mitoxantrone hydrochloride, oxaliplatin, paclitaxel, pamidronate disodium, panitumumab, pemetrexed, prednisone, rituximab trastuzumab, vincristine, vinorelbine or any combination thereof. In another embodiment, the chemotherapeutic agent comprises platinum and taxane. In another embodiment, the chemotherapeutic agent comprises platinum and non-taxane chemotherapeutic agent. In another embodiment, said method further increases the physical function of said subject. In another embodiment, said method further increases the quality of life of said subject. In another embodiment, said method further increases the survival of said subject. In another embodiment, said method further increases lean body mass of a subject. In another embodiment, said subject suffers from non-small cell lung cancer. In another embodiment the subject suffers from colon cancer. In another embodiment the subject suffers from breast cancer. In another embodiment the subject suffers from non-Hodgkin's lymphoma. In another embodiment the subject suffers chronic lymphocytic leukemia. In another embodiment the subject suffers from lung cancer.

In some embodiments, this invention provides the use of a SARM compound as herein described including comprising an analog, derivative, isomer, metabolite, pharmaceutically acceptable salt, pharmaceutical product, polymorph, crystal, impurity, hydrate, N-oxide or any combination thereof, of a compound of formula S-(III) for treating, reducing the severity, reducing the incidence, or reducing the pathogenesis of cancer. In another embodiment, the cancer comprises androgen AR dependent tumors (malignant or benign) such as prostate cancer, or breast cancer (male or female, operable or inoperable). In another embodiment the SARM compounds adjunct to ADT for treating prostate cancer, bladder cancers, brain cancers, bone tumors, colon cancer, endometrial cancer, liver cancer, lung cancer, non-small cell lung cancer, lymphatic cancer, kidney cancer, osteosarcoma cancer, ovarian cancer, pancreas cancer, penis cancer, skin cancer, thyroid cancer, and/or hormone-dependent cancers.

In one embodiment, this invention provides for the use of a SARM compound as herein described, or its prodrug, analog, isomer, metabolite, derivative, pharmaceutically acceptable salt, pharmaceutical product, polymorph, crystal, impurity, N-oxide, hydrate or any combination thereof, for: a) treating a bone related disorder; b) preventing a bone related disorder; c) suppressing a bone related disorder; d) inhibiting a bone related disorder; e) increasing a strength of a bone of a subject; f) increasing a bone mass in a subject; or g) use for osteoclastogenesis inhibition.

In one embodiment, this invention provides for the use of a SARM compound as herein described including comprising an analog, derivative, isomer, metabolite, pharmaceutically acceptable salt, pharmaceutical product, polymorph, crystal, impurity, hydrate, N-oxide or any combination thereof, of a compound of formula I for a) accelerating bone repair; b) treating bone disorders; c) treating bone density loss; d) treating low bone mineral density (BMD); e) treating reduced bone mass; f) treating metabolic bone disease; g) promoting bone growth or regrowth; h) promoting bone restoration; i) promoting bone fracture repair; j) promoting bone remodeling k) treating bone damage following reconstructive surgery including of the face, hip, or joints; l) enhancing of bone strength and function; m) increasing cortical bone mass; or n) increasing trabecular connectivity.

In one embodiment, the bone related disorder is a genetic disorder, or in another embodiment, is induced as a result of a treatment regimen for a given disease. For example, and in one embodiment, the SARMs as herein described are useful in treating a bone-related disorder that arises as a result of cancer metastasis to bone, or in another embodiment, as a result of androgen-deprivation therapy, for example, given in response to prostate carcinogenesis in the subject.

In one embodiment, the bone-related disorder is osteoporosis. In another embodiment the bone-related disorder is osteopenia. In another embodiment, the bone-related disorder is to increased bone resorption. In another embodiment, the bone-related disorder is bone fracture. In another embodiment, the bone-related disorder is bone frailty.

In another embodiment, the bone-related disorder is a loss of bone mineral density (BMD). In another embodiment, the bone-related disorder is any combination of osteoporosis, osteopenia, increased bone resorption, bone fracture, bone frailty and loss of BMD. Each disorder represents a separate embodiment of the present invention.

"Osteoporosis" refers, in one embodiment, to a thinning of the bones with reduction in bone mass due to depletion of calcium and bone protein. In another embodiment, osteoporosis is a systemic skeletal disease, characterized by low bone mass and deterioration of bone tissue, with a consequent increase in bone fragility and susceptibility to fracture. In osteoporotic patients, bone strength is abnormal, in one embodiment, with a resulting increase in the risk of fracture. In another embodiment, osteoporosis depletes both the calcium and the protein collagen normally found in the bone, in one embodiment, resulting in either abnormal bone quality or decreased bone density. In another embodiment, bones that are affected by osteoporosis can fracture with only a minor fall or injury that normally would not cause a bone fracture. The fracture can be, in one embodiment, either in the form of cracking (as in a hip fracture) or collapsing (as in a compression fracture of the spine). The spine, hips, and wrists are common areas of osteoporosis-induced bone fractures, although fractures can also occur in other skeletal areas. Unchecked osteoporosis can lead, in another embodiment, to changes in posture, physical abnormality, and decreased mobility.

In one embodiment, the osteoporosis results from androgen deprivation. In another embodiment, the osteoporosis follows androgen deprivation. In another embodiment, the osteoporosis is primary osteoporosis. In another embodiment, the osteoporosis is secondary osteoporosis. In another embodiment, the osteoporosis is postmenopausal osteoporosis. In another embodiment, the osteoporosis is juvenile osteoporosis. In another embodiment, the osteoporosis is idiopathic osteoporosis. In another embodiment, the osteoporosis is senile osteoporosis.

In another embodiment, the primary osteoporosis is type I primary osteoporosis. In another embodiment, the primary osteoporosis is type II primary osteoporosis. Each type of osteoporosis represents a separate embodiment of the present invention.

According to this aspect of the invention and in one embodiment, the bone-related disorder is treated with a SARM compound as herein described, or a combination thereof. In another embodiment, other bone-stimulating compounds can be provided to the subject, prior to, concurrent with or following administration of a SARM or SARMs as herein described. In one embodiment, such a bone stimulating compound may comprise natural or synthetic materials.

In one embodiment, the bone stimulating compound may comprise a bone morphogenetic protein (BMP), a growth factor, such as epidermal growth factor (EOF), a fibroblast growth factor (FGF), a transforming growth factor (TGF), an insulin growth factor (IGF), a platelet-derived growth factor (PDGF), hedgehog proteins such as sonic, indian and desert hedgehog, a hormone such as follicle stimulating hormone, parathyroid hormone, parathyroid hormone related peptide, activins, inhibins, follistatin, fizzled, frzb or frazzled proteins, BMP binding proteins such as chordin and fetuin, a cytokine such as IL-3, IL-7, GM-CSF, a chemokine, such as eotaxin, a collagen, osteocalcin, osteonectin and others, as will be appreciated by one skilled in the at.

In another embodiment, the compositions for use in treating a bone disorder of this invention may comprise a SARM or SARMs as herein described, an additional bone stimulating compound, or compounds, and osteogenic cells. In one embodiment, an osteogenic cell may be a stem cell or progenitor cell, which may be induced to differentiate into an osteoblast. In another embodiment, the cell may be an osteoblast. In another embodiment, nucleic acids which encode bone-stimulating compounds may be administered to the subject, which is to be considered as part of this invention.

In one embodiment, the methods of the present invention comprise administering the SARM compound for treating osteoporosis. In another embodiment, the methods of this invention comprise administering a SARM compound in combination with SERMs for treating osteoporosis. In another embodiment, the SERMs are tamoxifen, 4-hydroxytamoxifen, idoxifene, toremifene, ospemifene, droloxifene, raloxifene, arzoxifene, bazedoxifene, PPT (1,3,5-tris (4-hydroxyphenyl)-4-propy-1H-pyrazol), DPN, lasofoxifene, pipendoxifene, EM-800, EM-652, nafoxidine, zindoxifene, tesmilifene, miproxifene phosphate, RU 58,688, EM 139, ICI 164.384, IC 182,780, clomiphene, MER-25, diethylstilbestrol, coumestrol, genistein, GW5638, LY353581, zuclomiphene, enclomiphene, delmadinone acetate, DPPE (N,N-diethyl-2-(4-(phenylmethyl)-phenoxy) ethanamine), TSE-424, WAY-070, WAY-292, WAY-818, cyclocommunol, prinaberel, ERB-041, WAY-397, WAY-244, ERB-196, WAY-169122, MF-101, ERb-002, ERB-037, ERB-017, BE-1060, BE-380, BE-381, WAY-358, [$^{18}$F] FEDNP, LSN-500307, AA-102, CT-101, CT-102, or VG-101.

In one embodiment, this invention provides for the treatment, prevention, suppression or inhibition of, or the reduction of the risk of developing a skeletal-related event (SRE), such as bone fractures, surgery of the bone, radiation of the bone, spinal cord compression, new bone metastasis, bone loss, or a combination thereof in a subject with cancer, comprising administering to the a selective androgen receptor modulator (SARM) as herein described and/or its analog, derivative, isomer, metabolite, pharmaceutically acceptable salt, pharmaceutical product, hydrate, N-oxide, or any combination thereof. The invention relates, inter alia to treatment of an SRE with the compound of formula S-(III) in a subject with prostate cancer undergoing or having undergone androgen deprivation therapy (ADT).

In one embodiment, the skeletal-related events treated using the methods provided herein and/or utilizing the compositions provided herein, are fractures, which in one embodiment, are pathological fractures, non-traumatic fractures, vertebral fracture, non-vertebral fractures, morphometric fractures, or a combination thereof. In some embodiments, fractures may be simple, compound, transverse, greenstick, or comminuted fractures. In one embodiment, fractures may be to any bone in the body, which in one embodiment, is a fracture in any one or more bones of the arm, wrist, hand, finger, leg, ankle, foot, toe, hip, collar bone, or a combination thereof.

In another embodiment, the methods and/or compositions provided herein, are effective in treatment, prevention, suppression, inhibition or reduction of the risk of skeletal-related events such as pathologic fractures, spinal cord compression, hypercalcemia, bone-related pain, or their combination.

In another embodiment, the skeletal-related events sought to be treated using the methods provided herein and/or utilizing the compositions provided herein, comprise the necessity for bone surgery and/or bone radiation, which in some embodiments, is for the treatment of pain resulting in one embodiment from bone damage, or nerve compression. In another embodiment, the skeletal-related events sought to be treated using the methods provided herein and/or utilizing the compositions provided herein, comprise spinal cord compression, or the necessity for changes in antineoplastic therapy, including changes in hormonal therapy, in a subject. In some embodiments, skeletal-related events sought to be treated using the methods provided herein and/or utilizing the compositions provided herein, comprise treating, suppressing, preventing, reducing the incidence of, or delaying progression or severity of bone metastases, or bone loss. In one embodiment, bone loss may comprise osteoporosis, osteopenia, or a combination thereof. In one embodiment, skeletal-related events may comprise any combination of the embodiments listed herein.

In one embodiment, the skeletal-related events are a result of cancer therapy. In one embodiment, the skeletal-related events are a result of hormone deprivation therapy, while in another embodiment, they are a product of androgen deprivation therapy (ADT).

In another embodiment, the methods of the present invention comprise administering the SARM compound, in combination with bisphosphonates such as alendronate, tiludroate, clodroniate, pamidronate, etidronate, alendronate, zolendronate, cimadronate, neridronate, minodronic acid, ibandronate, risedronate, or homoresidronate for treating osteoporosis.

In another embodiment, the methods of the present invention comprise administering the SARM compound, in combination with calcitonin such as salmon, Elcatonin®, SUN-8577 or TJN-135 for treating osteoporosis.

In another embodiment, the methods of treating osteoporosis of the present invention comprise administering the SARM compound, in combination with: a) vitamin D or derivative such as ZK-156979; b) vitamin D receptor ligand and analogues such as calcitriol, topitriol, ZK-150123, TEI-9647, BXL-628, Ro-26-9228, BAL-2299, Ro-65-2299 or DP-035; c) estrogen, estrogen derivative, or conjugated estrogens; d) antiestrogen, progestins, or synthetic estrogen/progestins; e) RANK ligand mAb such as denosumab formerly AMG162 (Amgen); f) αvβ3 integrin receptor antagonist; g) osteoclast vacuolar ATPase inhibitor; h) antagonist of VEGF binding to osteoclast receptors; i) calcium receptor antagonist; j) PTh (parathyroid hormone) and analogues, PTHrP analogues (parathyroid hormone-related peptide); k) cathepsin K inhibitors (AAE581, etc.); l) strontium ranelate; m) tibolone; n) HCT-1026, PSK3471; o) gallium maltolate; p) Nutropin AQ®; q) prostaglandins (for osteo); r) p38 protein kinase inhibitor; s) bone morphogenetic protein; t) inhibitor of BMP antagonism; u) HMG-CoA reductase inhibitor; v) vitamin K or derivative; w) ipriflavone x) fluoride salts; y) dietary calcium supplement, or z) osteoprotegerin.

In one embodiment, the methods of this invention are useful in treating diseases or disorders caused by, or associated with a hormonal disorder, disruption or imbalance.

In one embodiment, the hormonal disorder, disruption or imbalance comprises an excess of a hormone. In another embodiment, the hormonal disorder, disruption or imbalance comprises a deficiency of a hormone. In one embodiment, the hormone is a steroid hormone. In another embodiment, the hormone is an estrogen. In another embodiment, the hormone is an androgen. In another embodiment, the hormone is a glucocorticoid. In another embodiment, the hormone is a cortico-steroid. In another embodiment, the hormone is luteinizing hormone (LH). In another embodiment, the hormone is follicle stimulating hormone (FSH). In another embodiment, the hormone is any other hormone known in the art. In another embodiment, the hormonal disorder, disruption or imbalance is associated with menopause. In another embodiment, the hormonal disorder, disruption or imbalance is associated with andropause, andropausal vasomotor symptoms, andropausal gynecomastia, muscle strength and/or function, bone strength and/or function and anger. In another embodiment, hormone deficiency is a result of specific manipulation, as a byproduct of treating a disease or disorder in the subject. For example, the hormone deficiency may be a result of androgen depletion in a subject, as a therapy for prostate cancer in the subject. Each possibility represents a separate embodiment of the present invention.

In another embodiment the invention is directed to treating sarcopenia or cachexia, and associated conditions related thereto, for example diseases or disorders of the bone.

In one embodiment, this invention provides for the use of a SARM compound as herein described, or its prodrug, analog, isomer, metabolite, derivative, acceptable salt, pharmaceutical product, polymorph, crystal, impurity, N-oxide, hydrate or any combination thereof, for: 1) treating a muscle wasting disorder; 2) preventing a muscle wasting disorder; 3) treating, preventing, suppressing, inhibiting or reducing muscle loss due to a muscle wasting disorder; 4) treating, preventing, inhibiting, reducing or suppressing muscle wasting due to a muscle wasting disorder; 5) treating, preventing, inhibiting, reducing or suppressing muscle protein catabolism due to a muscle wasting disorder, 6) treating, preventing, inhibiting, reducing or suppressing end stage renal disease; and/or 7) treating, preventing, inhibiting, reducing or suppressing frailty.

In some embodiments, the invention provides compositions comprising the compound of formula S-(III) or use of the compound of formula S-(III) for treating bone disease and/or resorption, muscle wasting or diseases associated with muscle wasting, prostate cancer, and/or providing hormonal therapy for androgen-dependent conditions, and/or end stage renal disease, frailty, and/or osteoporosis.

In another embodiment, the use of a SARM compound for treating a subject having a muscle wasting disorder, or any of the disorders described herein, includes administering a pharmaceutical composition including a SARM compound as herein described. In another embodiment, the administering step includes intravenously, intraarterially, or intramuscularly injecting to said subject said pharmaceutical composition in liquid form; subcutaneously implanting in said subject a pellet containing said pharmaceutical composition; orally administering to said subject said pharmaceutical composition in a liquid or solid form; or topically applying to the skin surface of said subject said pharmaceutical composition.

A muscle is a tissue of the body that primarily functions as a source of power. There are three types of muscles in the body: a) skeletal muscle—the muscle responsible for moving extremities and external areas of the bodies; b) cardiac muscle—the heart muscle; and c) smooth muscle—the muscle that is in the walls of arteries and bowel.

A wasting condition or disorder is defined herein as a condition or disorder that is characterized, at least in part, by an abnormal, progressive loss of body, organ or tissue mass. A wasting condition can occur as a result of a pathology such as, for example, cancer, or an infection, or it can be due to a physiologic or metabolic state, such as disuse deconditioning that can occur, for example, due to prolonged bed rest or when a limb is immobilized, such as in a cast. A wasting condition can also be age associated. The loss of body mass that occurs during a wasting condition can be characterized by a loss of total body weight, or a loss of organ weight such as a loss of bone or muscle mass due to a decrease in tissue protein.

In one embodiment, the terms "muscle wasting" or "muscular wasting", used herein interchangeably, refer to the progressive loss of muscle mass and/or to the progressive weakening and degeneration of muscles, including the skeletal or voluntary muscles which control movement, cardiac muscles which control the heart, and smooth muscles. In one embodiment, the muscle wasting condition or disorder is a chronic muscle wasting condition or disorder. "Chronic muscle wasting" is defined herein as the chronic (i.e. persisting over a long period of time) progressive loss of muscle mass and/or to the chronic progressive weakening and degeneration of muscle.

The term cachexia may be defined as a multifactoral syndrome characterized by severe body weight, fat and muscle loss and increased protein catabolism due to underlying disease(s). Cachexia is clinically relevant since it increases patients' morbidity and mortality. Contributory factors to the onset of cachexia are anorexia and metabolic alterations, i.e. increased inflammatory status, increased muscle proteolysis, impaired carbohydrate, protein and lipid metabolism "Pre-cachexia" or "early cachexia" are defined based on the presence of some or all of the following criteria: (a) underlying chronic disease; (b) unintentional weight loss <5% of usual body weight during the last 6 months; (c) chronic or recurrent systemic inflammatory response; and (d) anorexia or anorexia-related symptoms. Pre-cachexia or early cachexia may include therefore patients with a chronic disease, small weight loss, and a chronic or recurrent systemic inflammatory disease and/or anorexia Muscle wasting can occur as a result of pathology, disease, condition or disorders, including disorders for treatment via the methods of this invention, such as, for example, end stage renal failure.

The loss of muscle mass that occurs during muscle wasting can be characterized by a muscle protein breakdown or degradation, or by muscle protein catabolism. Protein catabolism occurs because of an unusually high rate of protein degradation, an unusually low rate of protein synthesis, or a combination of both. Protein catabolism or depletion, whether caused by a high degree of protein degradation or a low degree of protein synthesis, leads to a decrease in muscle mass and to muscle wasting. The term "catabolism" has its commonly known meaning in the art, specifically an energy burning form of metabolism.

Muscle wasting can occur as a result of a pathology, disease, condition or disorder. In one embodiment, the pathology, illness, disease or condition is chronic. In another embodiment, the pathology, illness, disease or condition is genetic. In another embodiment, the pathology, illness, disease or condition is neurological. In another embodiment, the pathology, illness, disease or condition is infectious. As described herein, the pathologies, diseases, conditions or disorders for which the compounds and compositions of the present invention are administered are those that directly or indirectly produce a wasting (i.e. loss) of muscle mass, that is a muscle wasting disorder.

In one embodiment, muscle wasting in a subject is a result of the subject having a muscular dystrophy, muscle atrophy, or X-linked spinal-bulbar muscular atrophy (SBMA).

In some embodiments, muscle loss or muscle wasting or cachexia in a subject results in reduced protein reserves, decreased strength and functional capacity, frailty, falls, reduced aerobic capacity, reduced energy requirements or increased mortality in patients and the methods of this invention serve to treat these conditions, as well, in the subject, via the administration of any embodiment of a SARM and/or composition as described herein.

In some embodiments, muscle loss or muscle wasting or cachexia in a subject results in increased dietary protein needs, inflammation (accelerated muscle protein breakdown), loss of motor units (aging CNS), reduced rate of muscle protein synthesis (post-prandial), and/or changing endocrine function (testosterone, estrogen, growth hormone, insulin resistance) and the methods of this invention serve to treat these conditions, as well in the subject, via the administration of any embodiment of a SARM and/or composition as described herein.

In some embodiments, this invention provides methods for the treating of sarcopenia and/or cachexia, via the administration of any embodiment of a compound and/or composition as described herein.

In some embodiments, treatment with a compound and/or composition as described herein may provide for the increased rate of muscle protein synthesis, increased muscle size and strength, improved functional status in elderly people, increased independence for older, frail people, increased insulin sensitivity, which in some embodiments is whereby such administration results in the treatment of cachexia and/or sarcopenia or other disorders as described herein. Muscle is the primary site for glucose metabolism, insulin resistance is largely a problem of resistance of muscle to insulin, resulting from increased lipid in muscle cells, increased total fat, increased visceral fat, with the compounds and/or compositions of this invention being useful to reduce total fat, thereby increasing insulin sensitivity and/or reducing the risk of or treating, etc., diabetes, as described herein.

The muscular dystrophies are genetic diseases characterized by progressive weakness and degeneration of the skeletal or voluntary muscles that control movement. The muscles of the heart and some other involuntary muscles are also affected in some form of muscular dystrophy. The nine forms of muscular dystrophy (MD) are: myotonic dystrophy, Duchenne muscular dystrophy, Becker muscular dystrophy, lib-girdle muscular dystrophy, facioscapulhumeral muscular dystrophy, congenital muscular dystrophy, oculopharyngeal muscular dystrophy, distal muscular dystrophy and Emery-Dreifuss muscular dystrophy.

Muscular dystrophy can affect people of all ages. Although some forms first become apparent in infancy or childhood, others may not appear until middle age or later. Myotonic dystrophy is the most common of these diseases in adults. Myotonic dystrophy is an autosomal dominant genetic disease that occurs in ⅛₀₀₀ people and is characterized by 2 types. Type I has a genetic defect in the DMPK gene whereas type II has a genetic defect in the CNBP gene. The mutation is an abnormal repeat of a DNA segment which presents a disease phenotype of variable severity in the $2^{nd}$ or $3^{rd}$ decade of life. Symptoms of the disease may include inter alia prolonged contractions (myotonia) of certain muscles, cataracts, cardiac conduction defects, balding, or male infertility.

Duchenne MD is the most common form, typically affecting children. Duchenne muscular dystrophy includes weakness and degeneration of skeletal and voluntary muscle which is exacerbated by high impact exercise, muscle contractures that worsen mobility if not corrected, and scoliosis. Although braces and walkers provide some protection, declines in physical function result in loss of ambulation during childhood leading to wheelchair confinement, and eventually impaired cardiac (cardiomyopathy) or respiratory (diaphragm fibrosis) function leads to death. Average life expectancy has improved (and rare cases of men living into their $4^{th}$ or $5^{th}$ decade) as a result of better respiratory (glucocorticoids) and cardiac (ACE inhibitors, angiotensin receptor blockers, and beta-blockers) supportive care but no disease-modifying therapeutics exist.

Becker muscular dystrophy is a rarer and milder variation of Duchenne muscular dystrophy caused by DMD mutants that do not completely abrogate dystrophin glycoprotein complex function in males or more commonly is observed in some female carriers (Duchenne muscular dystrophy is often asymptomatic in females).

In one embodiment, this invention provides therapeutic effects on dystrophic skeletal, cardiac, and diaphragm muscles, or may delay onset or improve symptoms of loss of mobility/autonomy, cardiomyopathy, or respiratory insufficiency in Duchenne muscular dystrophy or Becker muscular dystrophy and other muscular dystrophy patients; by administering the compound of this invention.

Muscle atrophy (MA) is characterized by wasting away or diminution of muscle and a decrease in muscle mess. For example, post-polio MA is a muscle wasting that occurs as part of the post-polio syndrome (PPS). The atrophy includes weakness, muscle fatigue, and pain.

Another type of MA is X-linked spinal-bulbar muscular atrophy (SBMA—also known as Kennedy's Disease). This disease arises from a defect in the androgen receptor gee on the X chromosome, affects only males, and its onset is in adulthood. Because the primary disease cause is an androgen receptor mutation, androgen replacement is not a current therapeutic strategy. There are some investigational studies where exogenous testosterone propionate is being given to boost the levels of androgen with hopes of overcoming androgen insensitivity and perhaps provide an anabolic effect. Still, use of supraphysiological levels of testosterone for supplementation will have limitations and other potentially serious complications.

In one embodiment, this invention is directed to a method of treating, reducing the severity, reducing the incidence, delaying the onset, or reducing the pathogenesis of Duchenne muscular dystrophy in a subject in need thereof, comprising the step of administering to said subject a selective androgen receptor modulator (SARM) compound represented by the structure of formula S-(III):

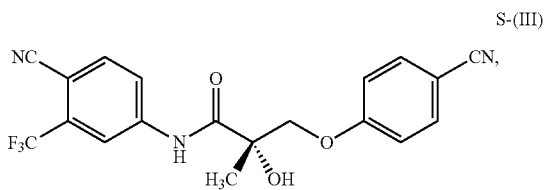 [SMILES: C[C@](O)(COc1ccc(C#N)cc1)C(=O)Nc1ccc(C#N)c(C(F)(F)F)c1]

or its isomer, pharmaceutically acceptable salt, hydrate, N-oxide, or any combination thereof.

In one embodiment, this invention is directed to a method of treating, reducing the severity, reducing the incidence, delaying the onset, or reducing the pathogenesis of Duchenne muscular dystrophy in a subject in need thereof, comprising the step of administering a pharmaceutical composition comprising a selective androgen receptor modulator (SARM) compound represented by the structure of formula S-(III):

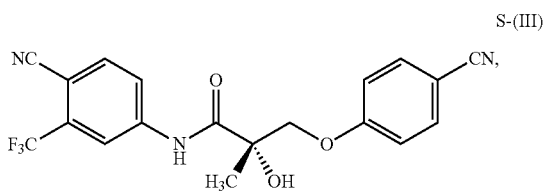 [SMILES: C[C@](O)(COc1ccc(C#N)cc1)C(=O)Nc1ccc(C#N)c(C(F)(F)F)c1]

or its isomer, pharmaceutically acceptable salt, hydrate, N-oxide, or any combination thereof, and a pharmaceutically acceptable carrier.

In another embodiment, the method of this invention for treating, reducing the severity, reducing the incidence, delaying the onset, or reducing the pathogenesis of Duchenne muscular dystrophy in a subject in need thereof, further increases the quality of life of said subject. In another embodiment, the method of this invention for treating, reducing the severity, reducing the incidence, delaying the onset, or reducing the pathogenesis of Duchenne muscular dystrophy in a subject in need thereof, further increases the survival of said subject. In another embodiment, the method of this invention for treating, reducing the severity, reducing the incidence, delaying the onset, or reducing the pathogenesis of Duchenne muscular dystrophy in a subject in need thereof, further increases the physical function of said subject. In another embodiment, the method of this invention for treating, reducing the severity, reducing the incidence, delaying the onset, or reducing the pathogenesis of Duchenne muscular dystrophy in a subject in need thereof, further delays the loss of body weight of said subject. In another embodiment, the method of this invention for treating, reducing the severity, reducing the incidence, delaying the onset, or reducing the pathogenesis of Duchenne muscular dystrophy in a subject in need thereof, further delays loss of ambulation of said subject. In another embodiment, the method of this invention for treating, reducing the severity, reducing the incidence, delaying the onset, or reducing the pathogenesis of Duchenne muscular dystrophy in a subject in need thereof, further delays loss of lean body mass of said subject. In another embodiment, the method of this invention for treating, reducing the severity, reducing the incidence, delaying the onset, or reducing the pathogenesis of Duchenne muscular dystrophy in a subject in need thereof, further delays the gain of fat body mass of said subject. In another embodiment, the method of this invention for treating, reducing the severity, reducing the incidence, delaying the onset, or reducing the pathogenesis of Duchenne muscular dystrophy in a subject in need thereof, further delays muscle fibrosis of said subject. In another embodiment, the method of this invention for treating, reducing the severity, reducing the incidence, delaying the onset, or reducing the pathogenesis of Duchenne muscular dystrophy in a subject in need thereof, further delays cardiomyopathy of said subject. In another embodiment, the method of this invention for treating, reducing the severity, reducing the incidence, delaying the onset, or reducing the pathogenesis of Duchenne muscular dystrophy in a subject in need thereof, further delays respiratory failure or insufficiency of said subject. In another embodiment, the method of this invention for treating, reducing the severity, reducing the incidence, delaying the onset, or reducing the pathogenesis of Duchenne muscular dystrophy in a subject in need thereof, further increases the exercise tolerance of said subject. In another embodiment, the method of this invention for treating, reducing the severity, reducing the incidence, delaying the onset, or reducing the pathogenesis of Duchenne muscular dystrophy in a subject in need thereof, further decreases the extent and severity of muscle contractures of said subject. In another embodiment, the method of this invention for treating, reducing the severity, reducing the incidence, delaying the onset, or reducing the pathogenesis of Duchenne muscular dystrophy in a subject in need thereof, further prevents or delays scoliosis of said subject.

In another embodiment, the method of this invention for treating, reducing the severity, reducing the incidence, delaying the onset, or reducing the pathogenesis of Duchenne muscular dystrophy in a subject in need thereof, further delays onset or improves symptoms of cardiomyopathy and/or respiratory function.

In one embodiment, this invention is directed to a method of increasing the physical function of a subject suffering from Duchenne muscular dystrophy, comprising the step of administering to said subject a selective androgen receptor modulator (SARM) compound represented by the structure of formula S-(III):

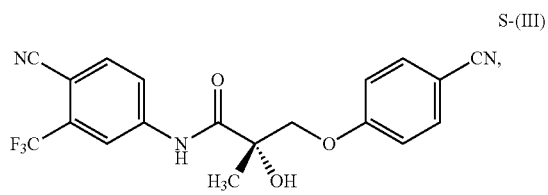 [SMILES: C[C@](O)(COc1ccc(C#N)cc1)C(=O)Nc1ccc(C#N)c(C(F)(F)F)c1]

or its isomer, pharmaceutically acceptable salt, hydrate, N-oxide, or any combination thereof.

In one embodiment, this invention is directed to a method of increasing the quality of life of a subject suffering from Duchenne muscular dystrophy, comprising the step of administering to said subject a selective androgen receptor modulator (SARM) compound represented by the structure of formula S-(III):

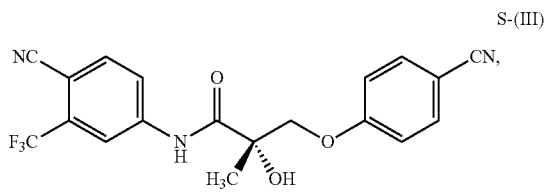 [SMILES: C[C@](O)(COc1ccc(C#N)cc1)C(=O)Nc1ccc(C#N)c(C(F)(F)F)c1]

or its isomer, pharmaceutically acceptable salt, hydrate, N-oxide, or any combination thereof.

The term "quality of life" refers herein to improvement of one or more of the following: motor skills such as ambulation and limb strength, less fatigue, delaying onset, treating, or preventing cardiopathies; delaying onset, treating, or preventing respiratory symptoms and respiratory insufficiency or failure, or improved cognition.

In one embodiment, this invention is directed to a method of increasing the survival of a subject suffering from Duchenne muscular dystrophy, comprising the step of administering to said subject a selective androgen receptor modulator (SARM) compound represented by the structure of formula S-(III):

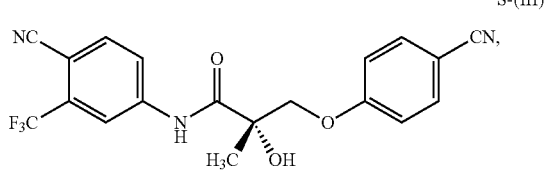

or its isomer, pharmaceutically acceptable salt, hydrate, N-oxide, or any combination thereof.

In one embodiment, this invention provides a method of treating, reducing the severity, reducing the incidence, delaying the onset, or reducing the pathogenesis of cardiomyopathy in a subject suffering from Duchenne muscular dystrophy, comprising the step of administering to said subject a selective androgen receptor modulator (SARM) compound represented by the structure of formula S-(III):

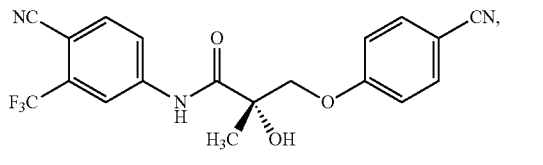

or its isomer, pharmaceutically acceptable salt, hydrate, N-oxide, or any combination thereof.

In one embodiment, the method of this invention for treating, reducing the severity, reducing the incidence, delaying the onset, or reducing the pathogenesis of cardiomyopathy in a subject suffering from Duchenne muscular dystrophy, further increases the quality of life of said subject. In another embodiment, the method of this invention for treating, reducing the severity, reducing the incidence, delaying the onset, or reducing the pathogenesis of cardiomyopathy in a subject suffering from Duchenne muscular dystrophy, further increases the survival of said subject. In another embodiment, the method of this invention for treating, reducing the severity, reducing the incidence, delaying the onset, or reducing the pathogenesis of cardiomyopathy a subject suffering from Duchenne muscular dystrophy, further increases the physical function of said subject.

In one embodiment, this invention provides a method of treating, reducing the severity, reducing the incidence, delaying the onset, or reducing the pathogenesis of respiratory failure in a subject suffering from Duchenne muscular dystrophy, comprising the step of administering to said subject a selective androgen receptor modulator (SARM) compound represented by the structure of formula S-(III):

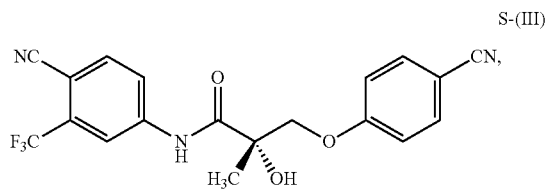 [SMILES: C[C@](O)(COc1ccc(C#N)cc1)C(=O)Nc1ccc(C#N)c(C(F)(F)F)c1]

or its isomer, pharmaceutically acceptable salt, hydrate, N-oxide, or any combination thereof.

In one embodiment, the method of this invention for treating, reducing the severity, reducing the incidence, delaying the onset, or reducing the pathogenesis of respiratory failure in a subject suffering from Duchenne muscular dystrophy, further increases the quality of life of said subject. In another embodiment, the method of this invention for treating, reducing the severity, reducing the incidence, delaying the onset, or reducing the pathogenesis of respiratory failure in a subject suffering from Duchenne muscular dystrophy, further increases the survival of said subject. In another embodiment, the method of this invention for treating, reducing the severity, reducing the incidence, delaying the onset, or reducing the pathogenesis of respiratory failure in a subject suffering from Duchenne muscular dystrophy, further increases the physical function of said subject.

In one embodiment, this invention provides a method of treating, reducing the severity, reducing the incidence, delaying the onset, or reducing the pathogenesis of Becker muscular dystrophy or myotonic dystrophy in a subject in need thereof, comprising the step of administering to said subject a selective androgen receptor modulator (SARM) compound represented by the structure of formula S-(III):

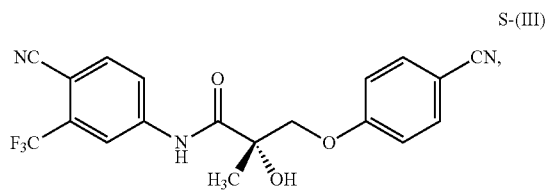

or its isomer, pharmaceutically acceptable salt, hydrate, N-oxide, or any combination thereof.

In one embodiment, the method of this invention for treating, reducing the severity, reducing the incidence, delaying the onset, or reducing the pathogenesis of Becker muscular dystrophy or myotonic dystrophy in a subject in need thereof, further increases the quality of life of said subject. In another embodiment, the method of this invention for treating, reducing the severity, reducing the incidence, delaying the onset, or reducing the pathogenesis of Becker muscular dystrophy or myotonic dystrophy in a subject in need thereof, further increases the survival of said subject. In another embodiment, the method of this invention for treating, reducing the severity, reducing the incidence, delaying the onset, or reducing the pathogenesis of Becker muscular dystrophy or myotonic dystrophy in a subject in need thereof, further increases the physical function of said subject.

In another embodiment, the method of this invention for treating, reducing the severity, reducing the incidence, delaying the onset, or reducing the pathogenesis of Becker muscular dystrophy or myotonic dystrophy in a subject in need thereof, further delays onset or improves symptoms of cardiomyopathy and/or respiratory function.

In one embodiment, this invention is directed to a method of treating, reducing the severity, reducing the incidence, delaying the onset, or reducing the pathogenesis of myotonic dystrophy, limb-girdle muscular dystrophy, facioscapulhumeral muscular dystrophy, congenital muscular dystrophy, oculopharyngeal muscular dystrophy, distal muscular dystrophy, or Emery-Dreifuss muscular dystrophy in a subject in need thereof, comprising the step of administering to said subject a selective androgen receptor modulator (SARM) compound represented by the structure of formula S-(III):

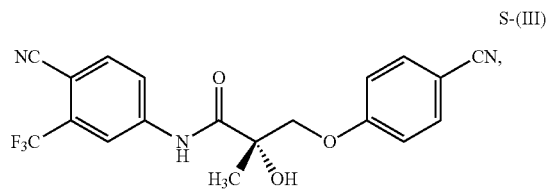 [SMILES: C[C@](O)(COc1ccc(C#N)cc1)C(=O)Nc1ccc(C#N)c(C(F)(F)F)c1]

or its isomer, pharmaceutically acceptable salt, hydrate, N-oxide, or any combination thereof.

In one embodiment, this invention is directed to a method of treating, reducing the severity, reducing the incidence, delaying the onset, or reducing the pathogenesis of myotonic dystrophy in a subject in need thereof, comprising the step of administering to said subject a selective androgen receptor modulator (SARM) compound represented by the structure of formula S-(III):

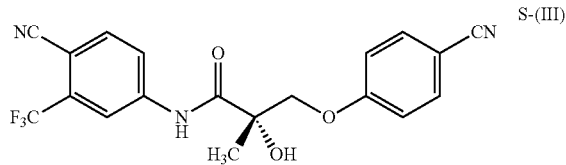 [SMILES: C[C@](O)(COc1ccc(C#N)cc1)C(=O)Nc1ccc(C#N)c(C(F)(F)F)c1]

or its isomer, pharmaceutically acceptable salt, hydrate, N-oxide, or any combination thereof.

In one embodiment, this invention is directed to a method of treating, reducing the severity, reducing the incidence, delaying the onset, or reducing the pathogenesis of limb-girdle muscular dystrophy in a subject in need thereof, comprising the step of administering to said subject a selective androgen receptor modulator (SARM) compound represented by the structure of formula S-(III):

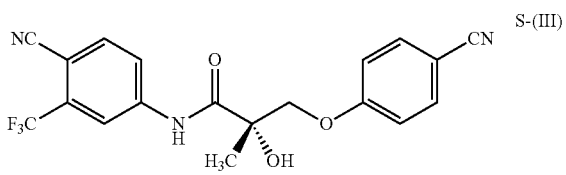 [SMILES: C[C@](O)(COc1ccc(C#N)cc1)C(=O)Nc1ccc(C#N)c(C(F)(F)F)c1]

or its isomer, pharmaceutically acceptable salt, hydrate, N-oxide, or any combination thereof.

In one embodiment, this invention is directed to a method of treating, reducing the severity, reducing the incidence, delaying the onset, or reducing the pathogenesis of facioscapulhumeral muscular dystrophy in a subject in need thereof, comprising the step of administering to said subject a selective androgen receptor modulator (SARM) compound represented by the structure of formula S-(III):

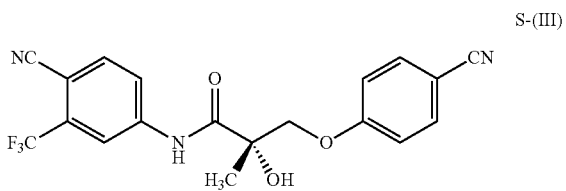 [SMILES: C[C@](O)(COc1ccc(C#N)cc1)C(=O)Nc1ccc(C#N)c(C(F)(F)F)c1]

or its isomer, pharmaceutically acceptable salt, hydrate, N-oxide, or any combination thereof.

In one embodiment, this invention is directed to a method of treating, reducing the severity, reducing the incidence, delaying the onset, or reducing the pathogenesis of congenital muscular dystrophy in a subject in need thereof, comprising the step of administering to said subject a selective androgen receptor modulator (SARM) compound represented by the structure of formula S-(III):

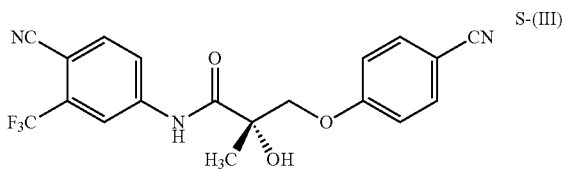 [SMILES: C[C@](O)(COc1ccc(C#N)cc1)C(=O)Nc1ccc(C#N)c(C(F)(F)F)c1]

or its isomer, pharmaceutically acceptable salt, hydrate, N-oxide, or any combination thereof.

In one embodiment, this invention is directed to a method of treating, reducing the severity, reducing the incidence, delaying the onset, or reducing the pathogenesis of oculopharyngeal muscular dystrophy in a subject in need thereof, comprising the step of administering to said subject a selective androgen receptor modulator (SARM) compound represented by the structure of formula S-(III):

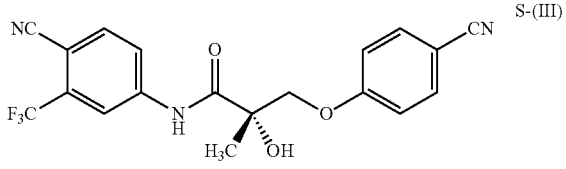 [SMILES: C[C@](O)(COc1ccc(C#N)cc1)C(=O)Nc1ccc(C#N)c(C(F)(F)F)c1]

or its isomer, pharmaceutically acceptable salt, hydrate, N-oxide, or any combination thereof.

In one embodiment, this invention is directed to a method of treating, reducing the severity, reducing the incidence, delaying the onset, or reducing the pathogenesis of distal muscular dystrophy in a subject in need thereof, comprising the step of administering to said subject a selective androgen receptor modulator (SARM) compound represented by the structure of formula S-(III):

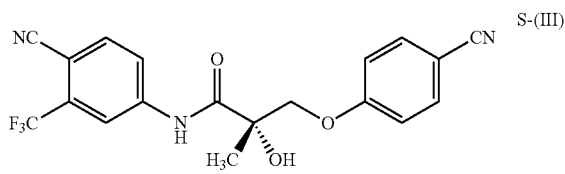 [SMILES: C[C@](O)(COc1ccc(C#N)cc1)C(=O)Nc1ccc(C#N)c(C(F)(F)F)c1]

S-(III)

or its isomer, pharmaceutically acceptable salt, hydrate, N-oxide, or any combination thereof.

In one embodiment, this invention is directed to a method of treating, reducing the severity, reducing the incidence, delaying the onset, or reducing the pathogenesis of Emery-Dreifuss muscular dystrophy in a subject in need thereof, comprising the step of administering to said subject a selective androgen receptor modulator (SARM) compound represented by the structure of formula S-(III):

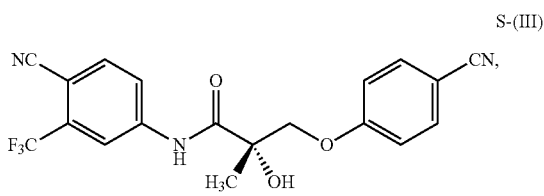 [SMILES: C[C@](O)(COc1ccc(C#N)cc1)C(=O)Nc1ccc(C#N)c(C(F)(F)F)c1]

S-(III)

or its isomer, pharmaceutically acceptable salt, hydrate, N-oxide, or any combination thereof.

In another embodiment, the method of this invention for treating, reducing the severity, reducing the incidence, delaying the onset, or reducing the pathogenesis of myotonic dystrophy, limb-girdle muscular dystrophy, facioscapulhumeral muscular dystrophy, congenital muscular dystrophy, oculopharyngeal muscular dystrophy, distal muscular dystrophy, or Emery-Dreifuss muscular dystrophy in a subject in need thereof, further increases the quality of life of said subject. In another embodiment, the method of this invention for treating, reducing the severity, reducing the incidence, delaying the onset, or reducing the pathogenesis of myotonic dystrophy, limb-girdle muscular dystrophy, facioscapulhumeral muscular dystrophy, congenital muscular dystrophy, oculopharyngeal muscular dystrophy, distal muscular dystrophy, or Emery-Dreifuss muscular dystrophy in a subject in need thereof, further increases the survival of said subject. In another embodiment, the method of this invention for treating, reducing the severity, reducing the incidence, delaying the onset, or reducing the pathogenesis of myotonic dystrophy, limb-girdle muscular dystrophy, facioscapulhumeral muscular dystrophy, congenital muscular dystrophy, oculopharyngeal muscular dystrophy, distal muscular dystrophy, or Emery-Dreifuss muscular dystrophy in a subject in need thereof, further increases the physical function of said subject.

In another embodiment, the method of this invention for treating, reducing the severity, reducing the incidence, delaying the onset, or reducing the pathogenesis of myotonic dystrophy, limb-girdle muscular dystrophy, facioscapulhumeral muscular dystrophy, congenital muscular dystrophy, oculopharyngeal muscular dystrophy, distal muscular dystrophy, or Emery-Dreifuss muscular dystrophy in a subject in need thereof, further delays onset or improves symptoms of cardiomyopathy and/or respiratory function.

In one embodiment, this invention provides a method of treating, reducing the incidence of, delaying progression of, reducing the severity of, or alleviating symptoms associated with a muscle wasting disorder in a subject, comprising the step of administering to said subject the selective androgen receptor modulator compound of this invention or its isomer, pharmaceutically acceptable salt, pharmaceutical product, crystal, hydrate, N-oxide or any combination thereof, or a composition comprising the same, in an amount effective to treat the muscle wasting disorder in said subject. In another embodiment, the compound is a compound of formula S-(III).

According to this aspect, and in one embodiment, the muscle wasting disorder is due to a pathology, illness, disease or condition. In one embodiment, the pathology, illness, disease or condition is neurological, infectious, chronic or genetic. In one embodiment, the pathology, illness, disease or condition is a muscular dystrophy, a muscular atrophy, X-linked spinal-bulbar muscular atrophy (SBMA), a cachexia, malnutrition, leprosy, diabetes, renal disease, chronic obstructive pulmonary disease (COPD), cancer, end stage renal failure, sarcopenia, emphysema, osteomalacia, HIV infection, AIDS, or cardiomyopathy. In one embodiment, the compound is a compound of this invention. In another embodiment, the compound is a compound of formula S-(III).

In one embodiment, the muscle wasting disorder is an age-associated muscle wasting disorder, a disuse deconditioning-associated muscle wasting disorder; or the muscle wasting disorder is due to chronic lower back pain, burns, central nervous system (CNS) injury or damage, peripheral nerve injury or damage, spinal cord injury or damage, chemical injury or damage, or alcoholism.

In one embodiment, this invention provides a method of treating, reducing the severity, reducing the incidence, delaying the onset, or reducing the pathogenesis of cardiovascular disease in a human subject, comprising the step of administering an effective amount of a compound of this invention or its isomer, pharmaceutically acceptable salt, pharmaceutical product, crystal, N-oxide, hydrate or any combination thereof to said subject. In another embodiment, the compound is a compound of formula S-(III).

In one embodiment, this invention provides a method of treating, reducing the severity, reducing the incidence, delaying the onset, or reducing the pathogenesis of cardiovascular disease in a human subject suffering from Duchenne muscular dystrophy comprising the step of administering an effective amount of a compound of this invention or its isomer, pharmaceutically acceptable salt, pharmaceutical product, crystal, N-oxide, hydrate or any combination thereof to said subject. In another embodiment, the compound is a compound of formula S-(III).

In one embodiment, this invention provides a method of treating, reducing the severity, reducing the incidence, delaying the onset, or reducing the pathogenesis of cardiovascular disease in a human subject suffering from Becker muscular dystrophy comprising the step of administering an effective amount of a compound of this invention or its isomer, pharmaceutically acceptable salt, pharmaceutical product, crystal, N-oxide, hydrate or any combination thereof to said subject. In another embodiment, the compound is a compound of formula S-(III).

In one embodiment, this invention provides a method of treating, reducing the severity, reducing the incidence, delaying the onset, or reducing the pathogenesis of cardiovascular disease in a human subject suffering from myotonic dystrophy comprising the step of administering an effective amount of a compound of this invention or its isomer, pharmaceutically acceptable salt, pharmaceutical product, crystal, N-oxide, hydrate or any combination thereof to said subject. In another embodiment, the compound is a compound of formula S-(III).

In one embodiment, this invention provides a method of treating, reducing the severity, reducing the incidence, delaying the onset, or reducing the pathogenesis of cachexia in a subject, comprising the step of administering an effective amount of a compound of this invention or its isomer, pharmaceutically acceptable salt, pharmaceutical product, crystal, N-oxide, hydrate or any combination thereof to said subject. In one embodiment, the compound is of formula S-(III).

In one embodiment, the present invention provides a method of reducing a fat mass in a subject comprising the step of administering an effective amount of a compound of this invention or its isomer, pharmaceutically acceptable salt, pharmaceutical product, crystal, N-oxide, hydrate or any combination thereof to the subject. In another embodiment, the compound is a compound of formula S-(III).

In one embodiment, the present invention provides a method of reducing a fat mass in a subject suffering from Duchenne muscular dystrophy comprising the step of administering an effective amount of a compound of this invention or its isomer, pharmaceutically acceptable salt, pharmaceutical product, crystal, N-oxide, hydrate or any combination thereof to the subject. In another embodiment, the compound is a compound of formula S-(III). In one embodiment, the present invention provides a method of reducing or preventing fibrosis in a subject suffering from Duchenne muscular dystrophy comprising the step of administering an effective amount of a compound of formula (I) or its isomer, pharmaceutically acceptable salt, pharmaceutical product, crystal, N-oxide, hydrate or any combination thereof to the subject.

In one embodiment, the present invention provides a method of reducing a fat mass in a subject suffering from Becker muscular dystrophy comprising the step of administering an effective amount of a compound of this invention or its isomer, pharmaceutically acceptable salt, pharmaceutical product, crystal, N-oxide, hydrate or any combination thereof to the subject. In another embodiment, the compound is a compound of formula S-(III). In one embodiment, the present invention provides a method of reducing or preventing fibrosis in a subject suffering from Becker muscular dystrophy comprising the step of administering an effective amount of a compound of formula (I) or its isomer, pharmaceutically acceptable salt, pharmaceutical product, crystal, N-oxide, hydrate or any combination thereof to the subject.

In one embodiment, the present invention provides a method of reducing a fat mass in a subject suffering from myotonic dystrophy comprising the step of administering an effective amount of a compound of this invention or its isomer, pharmaceutically acceptable salt, pharmaceutical product, crystal, N-oxide, hydrate or any combination thereof to the subject. In another embodiment, the compound is a compound of formula S-(III). In one embodiment, the present invention provides a method of reducing or preventing fibrosis in a subject suffering from myotonic dystrophy comprising the step of administering an effective amount of a compound of formula (I) or its isomer, pharmaceutically acceptable salt, pharmaceutical product, crystal, N-oxide, hydrate or any combination thereof to the subject.

In one embodiment, the present invention provides a method of increasing a lean mass in a subject comprising the step of administering an effective amount of a compound of this invention or its isomer, pharmaceutically acceptable salt, pharmaceutical product, crystal, N-oxide, hydrate or any combination thereof to the subject. In another embodiment, the compound is a compound of formula S-(III).

In one embodiment, the present invention provides a method of increasing a lean mass in a subject suffering from Duchenne muscular dystrophy comprising the step of administering an effective amount of a compound of this invention or its isomer, pharmaceutically acceptable salt, pharmaceutical product, crystal, N-oxide, hydrate or any combination thereof to the subject. In another embodiment, the compound is a compound of formula S-(III).

In one embodiment, the present invention provides a method of increasing a lean mass in a subject suffering from Becker muscular dystrophy comprising the step of administering an effective amount of a compound of this invention or its isomer, pharmaceutically acceptable salt, pharmaceutical product, crystal, N-oxide, hydrate or any combination thereof to the subject. In another embodiment, the compound is a compound of formula S-(III).

In one embodiment, the present invention provides a method of increasing a lean mass in a subject suffering from myotonic dystrophy comprising the step of administering an effective amount of a compound of this invention or its isomer, pharmaceutically acceptable salt, pharmaceutical product, crystal, N-oxide, hydrate or any combination thereof to the subject. In another embodiment, the compound is a compound of formula S-(III).

In another embodiment, this invention provides a method of treating, reducing the incidence of, delaying progression of, reducing the severity of, or alleviating symptoms associated with a muscle wasting disorder; reducing a fat mass; or increasing a lean mass in a subject, comprising the step of administering an effective amount of a compound of this invention or its isomer, pharmaceutically acceptable salt, pharmaceutical product, crystal, N-oxide, hydrate or any combination thereof to the subject as herein described. In another embodiment, the compound is a compound of formula S-(III).

Sarcopenia is a debilitating disease that afflicts the elderly and chronically ill patients and is characterized by loss of muscle mass and function. Further, increased lean body mass is associated with decreased morbidity and mortality for certain muscle-wasting disorders. In addition, other circumstances and conditions are linked to, and can cause muscle wasting disorders. For example, studies have shown that in severe cases of chronic lower back pain, there is paraspinal muscle wasting.

Muscle wasting and other tissue wasting is also associated with advanced age. It is believed that general weakness in old age is due to muscle wasting. As the body ages, an increasing proportion of skeletal muscle is replaced by fibrous tissue. The result is a significant reduction in muscle power, performance and endurance.

Long term hospitalization due to illness or injury, or disuse deconditioning that occurs, for example, when a limb is immobilized, can also lead to muscle wasting, or wasting of other tissue. Studies have shown that in patients suffering injuries, chronic illnesses, burns, trauma or cancer, who are hospitalized for long periods of time, there is a long-lasting unilateral muscle wasting, and a decrease in body mass.

Injuries or damage to the central nervous system (CNS) are also associated with muscle wasting and other wasting disorders. Injuries or damage to the CNS can be, for example, caused by diseases, trauma or chemicals. Examples are central nerve injury or damage, peripheral nerve injury or damage and spinal cord injury or damage. In one embodiment CNS damage or injury comprise Alzheimer's diseases (AD), anger (mood), anorexia, anorexia nervosa, anorexia associated with aging and/or assertiveness (mood).

In another embodiment, muscle wasting or other tissue wasting may be a result of alcoholism, and may be treated with the compounds and compositions of the invention, representing embodiments thereof.

In one embodiment, the invention provides a use of SARM compound as described herein or its prodrug, analog, isomer, metabolite, derivative, pharmaceutically acceptable salt, pharmaceutical product, polymorph, crystal, impurity, N-oxide, hydrate or any combination thereof for the treatment of a wasting disease, disorder or condition in a subject.

In one embodiment, the wasting disease, disorder or condition being treated is associated with chronic illness This invention is directed to treating, in some embodiments, any wasting disorder, which may be reflected in muscle wasting, weight loss, malnutrition, starvation, or any wasting or loss of functioning due to a loss of tissue mass.

In some embodiments, wasting diseases or disorders, such as cachexia, malnutrition, tuberculosis, leprosy, diabetes, renal disease, chronic obstructive pulmonary disease (COPD), cancer, end stage renal failure, sarcopenia, emphysema, osteomalacia, or cardiomyopathy, may be treated by the methods of this invention, via the administration of a SARM compound as herein described, compositions comprising the same, with or without additional drugs, compounds, or agents, which provide a therapeutic effect for the condition being treated.

In some embodiments, wasting is due to infection with enterovirus, Epstein-Barr virus, herpes zoster, HIV, trypanosomes, influenza, coxsackie, rickettsia, trichinella, schistosoma or mycobacteria, and this invention, in some embodiments, provides methods of treatment thereof.

Cachexia is weakness and a loss of weight caused by a disease or as a side effect of illness. Cardiac cachexia, i.e. a muscle protein wasting of both the cardiac and skeletal muscle, is a characteristic of congestive heart failure. Cancer cachexia is a syndrome that occurs in patients with solid tumors and hematological malignancies and is manifested by weight loss with massive depletion of both adipose tissue and lean muscle mass.

Cachexia is also seen in acquired immunodeficiency syndrome (AIDS), human immunodeficiency virus (HIV)-associated myopathy and/or muscle weakness/wasting is a relatively common clinical manifestation of AIDS. Individuals with HIV-associated myopathy or muscle weakness or wasting typically experience significant weight loss, generalized or proximal muscle weakness, tenderness, and muscle atrophy.

In some embodiments, the present invention provides a method for treating, reducing the incidence, delaying the onset or progression, or reducing and/or abrogating the symptoms associated with an infection in a subject. In one embodiment, the method comprises administering to a subject a composition comprising a SARM compound and an immunomodulating agent, an anti-infective agent, a gene therapy agent, or a combination thereof. In some embodiments, infections comprise actinomycosis, anaplasmosis, anthrax, aspergillosis, bacteremia, bacterial mycoses, bartonella infections, botulism, brucellosis, burkholderia infections, campylobacter infections, candidiasis, cat-scratch disease, chlamydia infections, cholera, clostridium infections, coccidioidomycosis, cross infection, cryptococcosis, dermatomycoses, diphtheria, ehrlichiosis, *Escherichia coli* infections, fasciitis, necrotizing, Fusobacterium infections, gas gangrene, gram-negative bacterial infections, gram-positive bacterial infections, histoplasmosis, impetigo, *Klebsiella* infections, legionellosis, leprosy, leptospirosis, *Listeria* infections, lyme disease, maduromycosis, melioidosis, mycobacterium infections, mycoplasma infections, mycoses, nocardia infections, onychomycosis, plague, pneumococcal infections, *pseudomonas* infections, psittacosis, q fever, rat-bite fever, relapsing fever, rheumatic fever, Rickettsia infections, rocky mountain spotted fever, salmonella infections, scarlet fever, scrub typhus, sepsis, sexually transmitted diseases, Staphylococcal infections, Streptococcal infections, tetanus, tick-borne diseases, tuberculosis, tularemia, typhoid fever, typhus, louse-borne, vibrio infections, yaws, *yersinia* infections, zoonoses, zygomycosis, acquired immunodeficiency syndrome, adenoviridae infections, alphavirus infections, arbovirus infections, borna disease, bunyaviridae infections, caliciviridae infections, chickenpox, coronaviridae infections, coxsackievirus infections, cytomegalovirus infections, dengue, DNA virus infections, ecthyma, contagious, encephalitis, arbovirus, Epstein-berr virus infections, erythema infectiosum, hantavirus infections, hemorrhagic fevers, viral hepatitis, viral human herpes simplex, herpes zoster, herpes zoster oticus, herpesviridae infection, infectious mononucleosis, human-lassa fever, measles, molluscum, contagiosum, mumps, paramyxoviridae infections, phlebotomus fever, polyomavirus infections, rabies, respiratory syncytial virus infections, rift valley fever, RNA virus infections, rubella, slow virus diseases, smallpox, subacute sclerosing panencephalitis, tumor virus infections, warts, west nile fever, virus diseases, yellow fever, amebiasis, anisakiasis, ascariasis, babesiosis, blastocystis hominis infections, bug bite, cestode infections, chagas disease, cryptosporidiosis, cyclosporiasis, cysticercosis, dientamoebiasis, diphyllobothriasis, dracunculiasis, echinococcosis, ectoparasitic infestations, filariasis, giardiasis, helminthiasis, hookworm infections, larva migrans, leishmaniasis, lice infestations, loiasis, malaria, mite infestations, myiasis, onchocerciasis, protozoan infections, scabies, schistosomiasis, skin diseases, parasitic, strongyloidiasis, taeniasis, toxocariasis, toxoplasmosis, trichinosis, trichomonas infections, trypanosomiasis, trypanosomiasis, african, or whipworm infections.

In some embodiments, the present invention provides a method for treating, reducing the incidence, delaying the onset or progression, or reducing and/or abrogating the symptoms associated with a musculoskeletal disease in a subject. In some embodiments, musculoskeletal diseases comprise achondroplasia, acquired hyperostosis syndrome, acrocephalosyndactylia, arthritis, arthrogryposis, arthropathy, neurogenic bursitis, cartilage diseases, cleidocranial dysplasia, clubfoot, compartment syndromes, craniofacial dysostosis, craniosynostoses, dermatomyositis, Dupuytren's contracture, dwarfism, Ellis Van Creveld syndrome, enchondromatosis, eosinophilia-myalgia syndrome, exostoses, fasciitis, fatigue syndrome, fibromyalgia, fibrous dysplasia of bone, fibrous dysplasia, polyostotic, flatfoot, foot deformities, Freiberg's disease, funnel chest, Goldenhar syndrome, gout, hallux valgus, hip dislocation, hyperostosis, intervertebral disk displacement, kabuki make-up syndrome, Klippel-Feil syndrome, Langer-Giedion syndrome, Legg-Perthes disease, lordosis, mandibulofacial dysostosis, melorheostosis, mitochondrial myopathies, muscle cramp, muscle spasticity, muscular dystrophies, musculoskeletal abnormalities, musculoskeletal diseases, myositis, myositis ossificans, myotubular myopathy, osteitis deformans, osteoarthritis, osteochondritis, osteogenesis imperfecta, osteomyelitis, osteonecrosis, osteopetrosis, osteoporosis, poland syndrome, polychondritis, relapsing, polymyalgia rheumatica, polymyositis, rhabdomyolysis, rheumatic diseases, Russel silver syndrome, Scheuermannn's disease, scoliosis, Sever's disease/calceneal apophysitis, spinal diseases, spinal osteophytosis, spinal stenosis, spondylitis, ankylosing, spondylolisthesis, sprengel's deformity, synovitis, tendinopathy, tennis elbow, tenosynovitis, thanatophoric dysplasia, or Tietze's syndrome.

In some embodiments, the present invention provides a method for treating, reducing the incidence, delaying the onset or progression, or reducing and/or abrogating the symptoms associated with a digestive system disease in a subject. In some embodiments, gastrointestinal diseases comprise adenomatous polyposis coli, Alagille syndrome, anus diseases, appendicitis, Barrett esophagus, biliary atresia, biliary tract diseases, Caroli disease, celiac disease, cholangias, cholecystitis, cholelithiasis, colitis, ulcerative, Crohn's disease, deglutition disorders, duodenal ulcer, dysentery, enterocolitis, pseudomembranous, esophageal achalasia esophageal atresia, esophagitis, exocrine pancreatic insufficiency, fatty liver, fecal incontinence, gastritis, gastritis, hypertrophic, gastroenteritis, gastroesophageal reflux, gastroparesis, hemorrhoids, hepatic vein thrombosis, hepatitis, hepatitis, chronic, hernia, diaphragmatic, hernia, hiatal, Hirschsprung disease, hypertension, portal, inflammatory bowel diseases, intestinal diseases, intestinal neoplasms, intestinal neuronal dysplasia, intestinal obstruction, irritable bowel syndrome, lactose intolerance, liver cirrhosis, liver diseases, meckel diverticulum, pancreatic diseases, pancreatic neoplasms, pancreatitis, peptic ulcer, Peutz-Jeghers syndrome, proctitis, rectal diseases, rectal prolapse, short bowel syndrome, tracheoesophageal fistula, whipple disease, or Zollinger-Ellison syndrome.

In some embodiments, the present invention provides a method for treating, reducing the incidence, delaying the onset or progression, or reducing and/or abrogating the symptoms associated with a stomatognathic disease in a subject. In some embodiments, stomatognathic diseases comprise ankylogossia, bruxism, burning mouth syndrome, cheilitis, cherubism, cleft lip, dentigerous cyst, gingivitis, glossitis, benign migratory, herpes labials, Ludwig's angina, macroglossia, Melkersson-Rosenthal syndrome, periodontal diseases, Pierre Robin syndrome, prognathism, salivary gland diseases, sialorrhea, stomatitis, aphthous, temporomandibular joint disorders, temporomandibular joint dysfunction syndrome, or xerostomia.

In some embodiments, the present invention provides a method for treating, reducing the incidence, delaying the onset or progression, or reducing and/or abrogating the symptoms associated with a respiratory tract disease in a subject. In some embodiments, respiratory tract diseases comprise airway obstruction, apnea, asbestosis, asthma, atelectasis, berylliosis, bronchial diseases, bronchiectasis, bronchiolitis, bronchiolitis obliterans organizing pneumonia, bronchitis, bronchopulmonary dysplasia, common cold, cough, respiratory failure secondary to Duchenne muscular dystrophy, empyema, pleural, epiglottitis, hemoptysis, hypertension, pulmonary, hyperventilation, Kartagener syndrome, lung abscess, lung diseases, meconium aspiration syndrome, pleural effusion, pleurisy, pneumonia, pneumothorax, pulmonary alveolar proteinosis, pulmonary disease, chronic obstructive, pulmonary edema, pulmonary embolism, pulmonary emphysema, pulmonary fibrosis, respiratory distress syndrome, newborn-respiratory hypersensitivity, respiratory tract infections, rhinoscleroma, scimitar syndrome, severe acute respiratory syndrome, silicosis, sleep apnea, central stridor, tracheal stenosis, Wegener's granulomatosis, or whooping cough.

In some embodiments, the present invention provides a method for treating, reducing the incidence, delaying the onset or progression, or reducing and/or abrogating the symptoms associated with an otorhinolaryngologic disease in a subject. In some embodiments, otorhinolaryngologic diseases comprise cholesteatoma, middle ear, croup, deafness, epistaxis, hearing loss, hyperacusis, labyrinthitis, laryngitis, laryngomalacia, laryngostenosis, mastoiditis, Meniere's disease, nasal obstruction, nasal polyps, otitis, otorhinolayngologic diseases, otosclerosis, pharyngitis, presbycusis, retropharyngeal abscess, rhinitis, sinusitis, tinnitus, tonsillitis, tympanic membrane perforation, vestibular neuronitis, vocal cord paralysis, or voice disorders.

In some embodiments, the preset invention provides a method for treating, reducing the incidence, delaying the onset or progression, or reducing and/or abrogating the symptoms associated with a nervous system disease in a subject. In some embodiments, nervous system diseases comprise autonomic nervous system diseases, central nervous system diseases, cranial nerve diseases, demyelinating diseases, nervous system malformations, neurologic manifestations, or neuromuscular diseases.

In some embodiments, autonomic nervous system diseases comprise causalgia, or reflex sympathetic dystrophy.

In some embodiments, central nervous system diseases comprise Alzheimer's disease, arachnoiditis, train abscess, brain ischemia, central nervous system infections, cerebral palsy, cerebrovascular disorders, corticobasal ganglionic degeneration (CBGD), Creutzfeldt-Jakob syndrome, Dandy-Walker syndrome, dementia, encephalitis, encephalomyelitis, epilepsy, epilepsy induced hypogonadal and/or hypermetabolic state, essential tremor, Friedreich ataxia, Gerstmann-Straussler-Sheinker disease, Hallervorden-Spatz syndrome, Huntington disease, hydrocephalus, hypoxia, insomnia, ischemic attack, kuru, Landau-Kleffner syndrome, Lewy Body disease, Machado-Joseph disease, meige syndrome, meningitis, bacterial meningitis, viral, migraine disorders, movement disorders, multiple system atrophy, myelitis, olivopontocerebellar atrophies, Parkinson's disease, parkinsonian disorders, poliomyelitis, postpoliomyelitis syndrome, prion diseases, pseudotumor cerebri, Shy-Drager syndrome, spasms, infantile, spinal cord diseases, supranuclear palsy, syringomyelia, thalamic diseases, tic disorders, tourette syndrome, or uveomeningoencephalitic syndrome. In some embodiments, the central nervous system disease is cystic fibrosis induced hypogonadal state.

In some embodiments, cranial nerve diseases comprise bell palsy, cranial nerve diseases, facial hemiatrophy, facial neuralgia, glossopharyngeal nerve diseases, Moebius syndrome, or trigeminal neuraglia.

In some embodiments, central nervous system diseases comprise injuries or damage to the central nervous system (CNS). In some embodiments, injuries or damage to the CNS may be associated with muscle wasting disorders. Injuries or damage to the CNS can be, for example, caused by diseases, trauma or chemicals. Examples are central nerve injury or damage, peripheral nerve injury or damage and spinal cord injury or damage.

Studies involving patients with spinal cord injuries (SCI) have shown that central neurotransmitters may be altered after SQ causing hypothalamus-pituitary-adrenal axis dysfunction, whose disruption led to a significant decrease in testosterone and other hormone levels. SC or other acute illness or trauma characteristically includes heightened catabolism in conjunction with the lowered anabolic activity resulting in a condition that is prone to loss of lean body tissue, which is often accompanied by disturbed nutrient utilization. The effects of the loss of lean body mass include the development of wounds and impaired healing mechanisms, further compounding the problem. Because of poor nutrition and protein combined with immobilization, patients with spinal cord injury are at high risk for bed sores.

In one embodiment, a wide variety of injuries of the CNS may be treated by the methods of the present invention. CNS injury may refer, in one embodiment, to a breakdown of the membrane of a nerve cell, or, in another embodiment, to the inability of the nerve to produce and propagate nerve impulses, or in another embodiment, to the death of the cell. An injury includes damage that directly or indirectly affects the normal functioning of the CNS. The injury may be a structural, physical, or mechanical impairment and may be caused by physical impact, as in the case of a crushing, compression, or stretching of nerve fibers. Alternatively, the cell membrane may be destroyed by or degraded by an illness, a chemical imbalance, or a physiological malfunction such as anoxia (e.g., stroke), aneurysm, or reperfusion. A CNS injury includes, for example and without limitation, damage to retinal ganglion cells, a traumatic brain injury, a stroke-related injury, a cerebral aneurism-related injury, a spinal cord injury, including monoplegia, diplegia, paraplegia, hemiplegia and quadriplegia, a neuroproliferative disorder, or neuropathic pain syndrome.

With injury to the spinal cord of a mammal, connections between nerves in the spinal cord are broken. Such injuries block the flow of nerve impulses for the nerve tracts affected by the injury, with a resulting impairment to both sensory and motor function. Injuries to the spinal cord may arise from compression or other contusion of the spinal cord, or a crushing or severing of the spinal cord. A severing of the spinal cord, also referred to herein as a "transection." may be a complete severing or, may be an incomplete severing of the spinal cord.

In some embodiments, the methods of treating a subject suffering from a CNS injury or, in other embodiments, spinal cord injury, may be accompanied by treatment of the subject with electrical stimulation of the injured site and the administration of a purine nucleoside, or analog thereof, for example as described in United States Patent Application Publication Number 20040214790A1.

In some embodiments, demyelinating diseases comprise adrenoleukodystrophy, alexander disease, canavan disease, demyelinating disease, diffuse cerebral sclerosis of schilder, leukodystrophy-globoid cell, leukodystrophy-metachromatic, multiple sclerosis, or neuromyelitis optica.

In some embodiments, nervous system malformations comprise Arnold-Chiari malformation, Charcot-Marie-Tooth disease, encephalocele, hereditary motor and sensory neuropathies, septo-optic dysplasia, spina bifida occulta, or spinal dysraphism.

In some embodiments, neurologic manifestations comprise agnosia, amnesia, anomia, aphasia, apraxias, back pain, Brown-Sequard syndrome, cerebellar ataxia, chorea, communication disorders, confusion, dizziness, dyslexia, dystonia, facial paralysis, fasciculation, gait disorders, neurologic-headache, herniplegia, memory disorders, mental retardation, mutism, myoclonus, neck pain, nonverbal learning disorder, olfaction disorders, pain, paralysis, phantom limb, prosopagnosia, quadriplegia, seizures, spasm, speech disorders, synesthesia tardive dyskinesia, taste disorders, torticollis, tremor, trismus, unconsciousness, or vertigo.

In some embodiments, neuromuscular diseases comprise amyotrophic lateral sclerosis, brachial plexus neuritis, brachial plexus neuropathies, bulber palsy, carpal tunnel syndrome, cubital tunnel syndrome, diabetic neuropathies, dysautonomia, Guillain, Bare syndrome, hereditary sensory and autonomic neuropathies, Miller Fisher syndrome, motor neuron disease, muscular atrophy, spinal, myasthenia gravis, myopathies structural, congenital, nerve compression syndromes, neuralgia, neuromuscular diseases, paralyses, familial periodic, peripheral nervous system diseases, poems syndrome, polyneuropathies, polyradiculopathy, refsum disease, sciatica, spinal muscular atrophies of childhood, stiff-person syndrome, thoracic outlet syndrome, or ulnar nerve compression syndromes.

In one embodiment, methods of treating a subject with a nervous system disease encompass treating any secondary conditions in the subject, which arise due to the subject having a nervous system disease, some of which are described herein.

In some embodiments, the present invention provides a method for treating, reducing the incidence, delaying the onset or progression, or reducing and/or abrogating the symptoms associated with an ophthalmic disease in a subject. In some embodiments ophthalmic disease comprise acute zonal occult outer retinopathy, Adie syndrome, albinism, ocular-amaurosis, fugax, amblyopia, aniridia, anisocoria, anopithalmos, aphakia, astigmatism, blepharitis, blepharoptosis, blepharospasm, blindness, cataract, chalazion, chorioretinitis, choroideremia, coloboma, color vision defects, conjunctivitis, corneal diseases, corneal dystrophies, corneal edema, corneal ulcer, diabetic retinopathy, diplopia, distichiasis, dry eye syndromes, Duane retraction syndrome, ectropion, entropion, esotropia, exfoliation syndrome, exotropia, eye hemorrhage, eye neoplasms, eyelid diseases, floaters, general fibrosis syndrome, glaucoma, gyrate atrophy, hemianopsia, Hermanski-Pudlak syndrome, hordeolum, Homer syndrome, hyperopia, hyphema, iritis, Kearns-Sayer syndrome, keratitis, keratoconus, lachrymal apparatus diseases, lacrimal duct obstruction, lens diseases, macular degeneration, microphthalmos, myopia, nystagmus, pathologic, ocular motility disorders, oculomotor nerve diseases, ophthalmoplegia, optic atrophies, optic nerve diseases, optic neuritis, optic neuropathy, orbital cellulitis papilledema, Peter's anomaly, presbyopia, pterygium, pupil disorders, refractive errors, retinal detachment, retinal diseases, retinal vein occlusion, retinitis pigmentosa, retinopathy of prematurity, retnoschisis, scleritis, scotoma, strabismns, Thygeson's superficial punctuate keratitis, trachoma, uveitis, white dot syndrome, vision disorders, or vitreous disorders In some embodiments, the present invention provides a method for treating, reducing the incidence, delaying the onset or progression or reducing and/or abrogating the symptoms associated with an urologic and/or male genital disease in a subject. In some embodiments, an urologic and/or male genital diseases comprise anti-glomerular basement membrane disease, balanitis, bladder exstrophy, bladder neoplasms, cryptorchidism, cystitis, interstitial, diabetes insipidus, nephrogenic, epididymitis, fournier gangrene, glomerulonephritis, Goodpasture syndrome, hematospermia, hematuria, hemolytic-uremic syndrome, hydronephrosis, hypospadias, impotence, infertility, kidney calculi, kidney failure, acute, kidney failure, chronic, kidney tubular necrosis, acute, medullary sponge kidney, multicystic dysplastic kidney, nephritis, hereditary, nephrosis, nephrotic syndrome, nocturia, oliguria, penile diseases, penile induration, penile neoplasms, phimosis, priapism, prostatic diseases, benign prostate hyperplasia, prostatic neoplasms, proteinuria pyelonephritis, Reiter disease, renal artery obstruction, spermatic cord torsion, testicular diseases, urethral stricture, urethritis, urinary retention, urinary tract infections, urination disorders, urologic and male genital diseases, urologic diseases, varicocele, vesico, or urethral reflux.

In some embodiments, the present invention provides a method for treating, reducing the incidence, delaying the onset or progression, or reducing and/or abrogating the symptoms associated with a dermatological disorder in a subject. In some embodiments, dermatological disorders comprise acne, actinic keratosis, alopecia, androgenic alopecia, alopecia areata, alopecia secondary to chemotherapy, alopecia secondary to radiation therapy, alopecia induced by scarring, alopecia induced by stress, angioma, athlete's foot, aquagenic pruritus, atopic dermatitis, baldness, basal cell carcinoma, bed sore, Behcet's disease, blepharitis, boil, Bowen's disease, bullous pemphigoid, canker sore, carbuncles, cellulitis, chloracne, chronic dermatitis of the hands and feet, dyshidrosis, cold sores, contact dermatitis, creeping eruption, dandruff, dermatitis, dermatitis herpetiformis, dermatofixbroma, diaper rash, eczema, epidermolysis bullosa, erysipelas, erythroderma, friction blister, genital wart, hidradenitis, suppurativa, hives, hyperhidrosis, ichthyosis, impetigo, jock itch, Kaposi's sarcoma, keloid, keratoacanthoma, keratois pilaris, lice infection, lichen planus, lichen simplex chronicus, lipoma, lymphadenitis, malignant melanoma, melasma, miliaria, molluscum contagiosum, nummular dermatitis, Paget's disease of the nipple, pediculosis, pemphigus, perioral dermatitis, photoallergy, photosensitivity, pityriasis rosea, pityriasis rubra pilaris, psoriasis, raynaud's disease, ring worm rosacea, scabies, scleroderma, sebaceous cyst, seborrheic keratosis, seborrhoeic dermatitis, shingles, skin cancer, skin tags, spider veins, squamous cell carcinoma, stasis dermatitis, tick bite, tinea barbae, tinea capitis, tinea corporis, tinea cruris, tinea pedis, tinea unguium, tinea versicolor, tinea, tungiasis, vitiligo, or warts.

In one embodiment, the dermatological disorder is a wound or a burn. In some embodiments, wounds and/or ulcers are found protruding from the skin or on a mucosal surface or as a result of an infarction in an organ. A wound may be a result of a sot tissue defect or a lesion or of an underlying condition. In one embodiment, the term "wound" denotes a bodily injury with disruption of the normal integrity of tissue structures. The term is also intended to encompass the terms "sore", "lesion", "necrosis" and "ulcer". In one embodiment, the term "sore" refers to any lesion of the skin or mucous membranes and the term "ulcer" refers to a local defect, or excavation, of the surface of an organ or tissue, which is produced by the sloughing of necrotic tissue. Lesion generally relates to any tissue defect. Necrosis is related to dead tissue resulting from infection, injury, inflammation or infarctions. All of these are encompassed by the term "wound", which denotes any wound at any particular stage in the healing process including the stage before any healing has initiated or even before a specific wound like a surgical incision is made (prophylactic treatment).

Examples of wounds which can be prevented and/or treated in accordance with the present invention are, e.g., aseptic wounds, contused wounds, incised wounds, lacerated wounds, non-penetrating wounds (i.e. wounds in which there is no disruption of the skin but there is injury to underlying structures), open wounds, penetrating wounds, perforating wounds, puncture wounds, septic wounds, subcutaneous wounds, etc. Examples of sores are bed sores, canker sores, chrome sores, cold sores, pressure sores etc. Examples of ulcers are, e.g., peptic ulcer, duodenal ulcer, gastric ulcer, gouty ulcer, diabetic ulcer, hypertensive ischemic ulcer, stasis ulcer, ulcus cruris (venous ulcer), sublingual ulcer, submucous ulcer, symptomatic ulcer, trophic ulcer, tropical ulcer, veneral ulcer, e.g. caused by gonorrhoea (including urethritis, endocervicitis and proctitis). Conditions related to wounds or sores which may be successfully treated according to the invention are burns, anthrax, tetanus, gas gangrene, scalatina, erysipelas, sycosis barbae, folliculitis, impetigo contagiosa, or impetigo bullosa, etc. There is often a certain overlap between the use of the terms "wound" and "ulcer" and "wound" and "sore" and, furthermore, the terms are often used at random. Therefore as mentioned above, in the present context the term "wounds" encompasses the term "ulcer", "lesion", "sore" and "infarction", and the terms are indiscriminately used unless otherwise indicated.

The kinds of wounds to be treated according to the invention include also: i) general wounds such as, e.g., surgical, traumatic, infectious, ischemic, thermal, chemical and bullous wounds; ii) wounds specific for the oral cavity such as, e.g., post-extraction wounds, endodontic wounds especially in connection with treatment of cysts and abscesses, ulcers and lesions of bacterial, vial or autoimmunological origin mechanical, chemical, thermal infectious and lichenoid wounds; herpes ulcers, stomatitis aphthosa, acute necrotising ulcerative gingivitis and burning mouth syndrome are specific examples: and iii) wounds on the skin such as, e.g., neoplasm, burns (e.g. chemical, thermal), lesions (bacterial, viral, autoimmunological), bites and surgical incisions. Another way of classifying wounds is as: i) small tissue loss due to surgical incisions, minor abrasions and minor bites, or as ii) significant tissue loss. The latter group includes ischemic ulcers, pressure sores, fistulae, lacerations, severe bites, thermal burns and donor site wounds (in soft and hard tissues) and infarctions.

In other aspects of the invention, the wound to be prevented and/or treated is selected from the group consisting of aseptic wounds, infarctions, contused wounds, incised wounds, lacerated wounds, non-penetrating wounds, open wounds, penetrating wounds, perforating wounds, puncture wounds, septic wounds and subcutaneous wounds.

Other wounds which are of importance in connection with the present invention are wounds like ischemic ulcers, pressure sores, fistulae, severe bites, thermal burns and donor site wounds.

In one embodiment, the use of the SARM compounds as described herein and/or compositions are useful in wound healing as an adjunct to physical therapy/rehabilitation, as an anabolic agent. In another embodiment, the compositions as described herein are useful in promoting healing of anterior cruciate ligament (ACL) or medial cruciate ligament (MCL) injuries, or accelerating recovery after ACL or MCL surgery. In another embodiment, the compositions as described herein are useful in enhancing athletic performance. In another embodiment, the compositions as described herein are useful in treating burns. In another embodiment, the compositions as described herein are useful in stimulating cartilage regrowth. In another embodiment, the compositions as described herein are useful in preventing, treating, or reversing of catabolism associated with prolonged critical illness, pulmonary dysfunction, ventilator dependency, aging, AIDS, trauma, surgery, congestive heart failure, cardiac myopathy, burns, cancer, COPD). In another embodiment, the compositions as described herein are useful in preventing or revering protein catabolism due to trauma. In another embodiment, the compositions as described herein are useful as: a) adjunct to cauterization therapy (laser or radio) as is used in surgery to promote wound healing, b) adjunct to cryotherapy to promote wound healing, or c) adjunct to chemotherapy to prevent side effects such as alopecia, hypogonadism, muscle wasting, osteopenia, osteoporosis, sarcopenia, increased LDL, TG or total cholesterol, decreased HDL. In another embodiment, the compositions as described herein are useful in chronic catabolic states (coma, wasting conditions, starvation, eating disorders), concomitant bone fracture and muscle damage, critical illness in which muscle or bone wasting are apparent, and/or connective tissue diseases and disorders.

Ischemic ulcers and pressure sores are wounds, which normally only heal very slowly and especially in such cases an improved and more rapid healing is of course of great importance for the patient. Furthermore, the costs involved in the treatment of patients suffering from such wounds are markedly reduced when the healing is improved and takes place more rapidly.

Donor site wounds are wounds which e.g. occur in connection with removal of hard tissue from one part of the body to another part of the body e.g. in connection with transplantation. The wounds resulting from such operations are very painful and an improved healing is therefore most valuable.

The term "skin" is used in a very broad sense embracing the epidermal layer of the skin and in those cases where the skin surface is more or less injured also the dermal layer of the skin. Apart from the stratum corneum, the epidermal layer of the skin is the outer (epithelial) layer and the deeper connective tissue layer of the skin is called the dermis.

In some embodiments, the present invention provides a method for promoting healing of anterior cruciate ligament (ACL) or medial cruciate ligament (MCL) injuries, or accelerating recovery after ACL or MCL surgery.

In some embodiments, burns are associated with reduced testosterone levels, and hypogonadism is associated with delayed wound healing. In one embodiment, the methods of this invention, provide for treating a subject suffering from a wound or a burn.

In some embodiments, the present invention provides a method for treating, reducing the incidence, delaying the onset or progression, or reducing and/or abrogating the symptoms associated with an endocrine disorder in a subject. In some embodiments, endocrine disorders comprise acromegaly, Addison disease, adrenal gland diseases, adrenal hyperplasia, congenital, androgen-insensitivity syndrome, congenital hypothyroidism, Cushing's syndrome, diabetes insipidus, diabetes mellitus, diabetes mellitus-type 1, diabetes mellitus-type 2, diabetic, ketoacidosis, empty sella syndrome, endocrine gland neoplasms, endocrine system diseases, gigantism, gonadal disorders, graves disease, hermaphroditism, hyperaldosteronism, hyperglycemic hyperosmolar nonketotic coma, hyperpituitarism, hyperprolactinemia, hyperthyroidism, hypogonadism, hypopituitarism, hypothyroidism, Kallnmnn syndrome, Nelson syndrome, parathyroid diseases, pituitary diseases, polyendocrinopathies, autoimmune, puberty, delayed, puberty, precocious, renal osteodystrophy, thyroid diseases, thyroid hormone resistance syndrome, thyroid neoplasms, thyroid nodule, thyroiditis, thyroiditis, autoimmune, thyroiditis, subacute, or Wolfram syndrome.

In one embodiment, "hypogonadism" is a condition resulting from or characterised by abnormally decreased functional activity of the gonads, with retardation of growth and sexual development.

In some embodiments, the present invention provides a method for treating, reducing the incidence, delaying the onset or progression, or reducing and/or abrogating the symptoms associated with urogenital disease and/or fertility in a subject. In some embodiments, urogenital diseases and/or fertility diseases comprise abortion, spontaneous-adhesions-pelvic, candidiasis, vulvovaginal, depression-postpartum, diabetes, gestational, dyspareunia, dystocia, eclampsia, endometriosis, fetal death, fetal growth retardation, fetal membranes, premature rupture, genital diseases, female, genital neoplasms, female, hydatidiform mole, hyperemesis gravidarum, infertility, ovarian cysts, ovarian torsion, pelvic inflammatory disease, placenta diseases, placental insufficiency, polycystic ovary syndrome, polyhydramnios, postpartum hemorrhage, pregnancy complications, pregnancy, ectopic, pruritus vulva, puerperal disorders, puerperal infection, salpingitis, trophoblastic neoplasms, uterine cervix incompetence, uterine inversion, uterine prolapse, vaginal diseases, vulvar diseases, or vulvar lichen sclerosis.

In some embodiments the present invention provides a method for treating, reducing the incidence, delaying the onset or progression, or reducing and/or abrogating the symptoms associated with hemic and/or lymphatic disease in a subject. In some embodiments, hemic and/or lymphatic diseases comprise afibriogeneuia, anemia, aplastic anemia, hemolytic anemia, congenital nonspherocytic anemia, megaloblastic anemia, pernicious anemia, sickle cell anemia, angiolymphoid hyperplasia with eosinophilia, antithrombin III deficiency, Bernard-Soulier syndrome, blood coagulation disorders, blood platelet disorders, blue rubber bleb nevus syndrome, Chediak-Higashi syndrome, cryoglobulinemic, disseminated intravascular coagulation, eosinophilia, Erdheim-Chester disease, erythroblastosis, fetal, Evans syndrome, factor V deficiency, factor VII deficiency, factor X deficiency, factor XI deficiency, factor XII deficiency, fanconi anemia, giant lymph node hyperplasia, hematologic diseases, hemoglobinopathies, hemoglobinuria, paroxysmal, hemophilia A, hemophilia B, hemorrhagic disease of newborn, histiocytosis, histiocytosis, Langerhans-cell, histiocytosis, non-Langerhans-cell, Job's syndrome, leukopenia, lymphadenitis, lymphangioleiomyomatosis, lymphedema, methemoglobinemia, myelodysplastic syndromes, myelofibrosis, myeloid metaplasia, myeloproliferative disorders, neutropenia, paraproteinemias, platelet storage pool deficiency, polycythemia vera, protein C deficiency, protein deficiency, purpura, thrombocytopenic, purpura, thrombotic thrombocytopenic, RH-isoimmunization, sarcoidosis, sarcoidosis, spherocytosis, splenic rupture, thalassemia thrombasthenia, thrombocytopenia, Waldenstrom macroglobulinemia, or Von Willebrand disease.

In some embodiments, the present invention provides a method for treating, reducing the incidence, delaying the onset or progression, or reducing and/or abrogating the symptoms associated with a congenital, hereditary, or neonatal disease in a subject. In some embodiments, congenital, hereditary, and neonatal diseases comprise Aicardi syndrome, amniotic band syndrome, anencephaly, Angelman syndrome, ataxia telangiectasia, Bannayan-Zonana syndrome, Barth syndrome, basal cell nevus syndrome, Beckwith-Wiedemann syndrome, bloom syndrome, branchio-oto-renal syndrome, cat eye syndrome, cerebral gigantism-charge syndrome, chromosome 16 abnormalities, chromosome 18 abnormalities, chromosome 20 abnormalities, chromosome 22 abnormalities, Costello syndrome, cri-du-chat syndrome, Currarino syndrome, cystic fibrosis, de-Lange syndrome, distal trisomy 10q, Down's syndrome, ectodermal dysplasia, fetal alcohol syndrome, fetal diseases, fetofetal transfusion, fragile X syndrome, Freeman-Sheldon syndrome, gastroschisis, genetic diseases, inborn, hernia, umbilical, holoprosencephaly, incontinentia pigmenti, Ivemark syndrome, Jacobsen syndrome, jaundice, Klinefelter syndrome, Larsen syndrome, Laurence-moon syndrome, lissencephaly, microcephaly, monosomy 9p, nail-patella syndrome, neurofibromatoses, neuronal ceroid-lipofuscinosis, Noonan syndrome, ochoa syndrome (urofacial syndrome, hydronephrosis with peculiar facial expression), oculocereborenal syndrome, Pallister-Killian syndrome, Prader-Willi syndrome, proteus syndrome, prune belly syndrome, Rett syndrome, Robinow syndrome, Rubinstein-Taybi syndrome, schizencephaly, situs inversus, Smith-Lemli-Opitz syndrome, Smith-Magenis syndrome, Sturge-Weber syndrome, syphilis, congenital, trichothiodystrophy, triple-X females, trisomy 13 (Patau syndrome), trisomy 9, Turner syndrome, twins, conjoined, Usher syndrome, Waardenburg's syndrome, Werner syndrome, or Wolf-Hirschhorn syndrome.

In some embodiments, the present invention provides a method for treating, reducing the incidence, delaying the onset or progression, or reducing and/or abrogating the symptoms associated with a connective tissue disease in a subject. In some embodiments, connective tissue diseases comprise ankylosing spondylitis, Ehlers-Danlos syndrome, Henoch-Schonlein purpura, Kawasaki disease, Marfan syndrome, polyarteritis nodosa, polymyositis, psoriatic arthritis, reactive arthritis, rheumatoid arthritis, scleroderma, Sjögren's syndrome, Still's disease, systemic lupus erythematosus, Takayasu disease, or Wegener's granulomatosis.

In some embodiments, the present invention provides a method for treating, reducing the incidence, delaying the onset or progression, or reducing and/or abrogating the symptoms associated with a metabolic disease in a subject. In some embodiments, metabolic diseases comprise acid-base imbalance, acidosis, alkalosis, alkaptonuria, alpha-mannosidosis, amino acid metabolism inborn errors, amyloidosis, iron-deficiency anemia, ascorbic acid deficiency, avitaminosis, beriberi, biotinidase deficiency, carbohydrate-deficient glycoprotein syndrome, carnitine disorders, cystinosis, cystinuria, dehydration, Fabry disease, fatty acid oxidation disorders, fucosidosis, galactosemias. Gaudier disease, Gilbert disease, glucosephosphate dehydrogenase deficiency, glutaric acidemia, glycogen storage disease, Hartnup disease, hemochromatosis, hemosiderosis, hepatolenticular degeneration, histidinemia, homocystinuria, hyperbilirubinemia, hypercalcemia, hyperinsulinism, hyperkalemia, hyperlipidemia, hyperoxaluria, hypervitaminosis A, hypocalcemia, hypoglycemia, hypokalemia, hyponatremia, hypophosphotasia, insulin resistance, iodine deficiency, iron overload, jaundice, chronic idiopathic, Leigh disease, Lesch-Nyhan syndrome, leucine metabolism disorders, lysosomal storage diseases, magnesium deficiency, maple syrup urine disease, Melas syndrome, Menkes kinky hair syndrome, metabolic diseases, metabolic syndrome X, metabolism, inborn errors, mitochondrial diseases, mucolipidosis, mucopolysaccharidoses, Niemann-Pick diseases, obesity, ornithine carbamoyltransferase deficiency disease, osteomalacia, pellagra, peroxisomal disorders, phenylketonurias, porphyria, erythropoietic, porphyrias, progeria, pseudo, gaucher disease, refsum disease, Reye syndrome, rickets, Sandhoff disease, starvation, tangier disease, Tay-Sachs disease, tetrahydrobiopterin deficiency, trimethylaminuria, tyrosinemias urea cycle disorders, water-electrolyte imbalance, Wernicke encephalopathy, vitamin A deficiency, vitamin B12 deficiency, vitamin B deficiency, Wolman disease, or Zellweger syndrome.

In some embodiments, the present invention provides a method for treating, reducing the incidence, delaying the onset or progression, or reducing and/or abrogating the symptoms associated with a disorder of environmental origin in a subject. In some embodiments, disorders of environmental origin comprise barotrauma, bites and stings, brain concussion, burns, central cord syndrome, craniocerebral trauma, electric injuries, fractures, bone, frostbite, heat stress disorders, motion sickness, occupational diseases, poisoning, shaken baby syndrome, shoulder injuries, space motion sickness, spinal cord injuries, tick paralysis, or wounds (penetrating and non-penetrating).

In some embodiments, the present invention provides a method for treating, reducing the incidence, delaying the onset or progression, or reducing and/or abrogating the symptoms associated with a behavior mechanism in a subject. In some embodiments, behavior mechanisms comprise aggression, attitude to death, codependency, self-injurious behavior, sexual behavior, or social behavior.

In some embodiments, the present invention provides a method for treating, reducing the incidence, delaying the onset or progression, or reducing and/or abrogating the symptoms associated with a mental disorder in a subject. In some embodiments, mental disorders comprise Asperger syndrome, attention deficit disorder with hyperactivity, autistic disorder, bipolar disorder, borderline personality disorder, capgras syndrome, child behavior disorders, combat disorders, cyclothymic disorder, dependent personality disorder, depressive disorder, dissociative disorders, dysthymic disorder, eating disorders, firesetting behavior, hypochondriasis, impulse control disorders, Kleine-Levin syndrome, mental disorders, mental disorders diagnosed in childhood, multiple personality disorder, Munchhausen syndrome, narcissistic personality disorder, narcolepsy, obsessive-compulsive disorder, paraphilias, phobic disorders, psychotic disorders, restless legs syndrome, schizophrenia, seasonal affective disorder, sexual and gender disorders, sexual dysfunctions, psychological, sleep disorders, somatoform disorders, stress disorders, post-traumatic, substance-related disorders, suicidal behavior, or trichotillomania.

In one embodiment, "depression" refers to an illness that involves the body, mood and thoughts that affect the way a person eats, sleeps and the way one feels about oneself and thinks about things. The signs and symptoms of depression include loss of interest in activities, loss of appetite or overeating, loss of emotional expression, an empty mood, feelings of hopelessness, pessimism, guilt or helplessness, social withdrawal fatigue, sleep disturbances, trouble concentrating, remembering, or making decisions, restlessness, irritability, headaches, digestive disorders or chronic pain.

In one embodiment, "cognition" refers to the process of knowing, specifically the process of being aware, knowing, thinking, learning and judging. Cognition is related to the fields of psychology, linguistics computer science, neuroscience, mathematics, ethology and philosophy. In one embodiment, "mood" refers to a temper or state of the mind.

As contemplated herein, alterations mean any change for the positive or negative, in cognition and/or mood.

In some embodiments, the present invention provides a method for treating, reducing the incidence, delaying the onset or progression, or reducing and/or abrogating the symptoms associated with a liver disease in a subject. In some embodiments, liver diseases comprise liver cancer, primary biliary cirrhosis, autoimmune hepatitis, chronic liver disease, cirrhosis of the liver, hepatitis, viral hepatitis (hepatitis A, hepatitis B, chronic hepatitis B, hepatitis C, chronic hepatitis C, hepatitis D, hepatitis E, hepatitis X), liver failure, jaundice, neonatal jaundice, hepatoma, liver cancer, liver abscess, alcoholic liver disease, hemochromatosis, Wilson's disease, portal hypertension, primary sclerosing cholangitis, sarcoidosis, tapeworms, alveolar hydatid disease, fascioliasis, schistosomiasis, Gaucher disease, Zellweger syndrome, alcoholism, food poisoning, pneumococcal pneumonia' or vibrio vulnifius.

In some embodiments, the present invention provides a method for treating, reducing the incidence, delaying the onset or progression, or reducing and/or abrogating the symptoms associated with a kidney disease in a subject. In some embodiments, kidney diseases comprise acromegaly, acute renal failure (ARF) amyloidosis, autosomal dominant polycystic kidney disease, kidney stones, kidney cysts, autosomal recessive polycystic kidney disease, chronic renal failure (CRF), chronic renal disease, chronic kidney disease (CKD), Coffin-Lowry syndrome, cor pulmonale, cryoglobulinemia, diabetic nephropathy, dyslipidemia, Gaucher disease, glomerulonephritis, Goodpasture syndrome, hemolytic uremic syndrome, hepatitis, kidney cancer, kidney stones, leukemia, lipoproteinemia, lupus, multiple myeloma, nephritis, polyarteritis nodosa, kidney cysts, post streptococcal glomerulonephritis, glomerulonephritis, kidney pain, preeclampsia, renal tuberculosis, pyelonephritis, renal tubular acidosis kidney disease, streptococcal toxic shock syndrome, thromboembolism, toxoplasmosis, urinary tract infections, uremia, vesicoureteral reflux, or Williams syndrome. In some embodiments, the kidney disease being treatment comprises kidney metabolic syndrome.

In one embodiment the kidney disease or disorder is acute, or in another embodiment, chronic. In one embodiment clinical indications of a kidney disease or disorder, wherein the methods of treatment may be useful include urinary casts, measured GFR, or other markers of renal function.

In one embodiment, the kidney disease or disorder is a chronic kidney disease (CKD). In some embodiments treating CKD patients includes treating those with advanced disease (uremia), and may comprise treating muscle wasting, repetitive catabolic stimuli (chronic infections, dialysis), anorexia, or other associated conditions, which will comprise what is meant by treating the disease.

In one embodiment, the SARM compounds of this invention are useful in increasing muscle and physical performance in a subject, in some embodiments, improving the patients' quality of life, diminishing morbidity and/or mortality, improving insulin resistance, and other associated conditions, thereby treating the subject afflicted with a disorder as described herein. In same embodiments, use of the compounds/compositions of this invention treats or improves a functional impairment in the subject, including, inter alia, one that results in a decrease in physical performance, inability to perform daily activity, decrease in muscle strength, decrease in exercise capacity, increase in frailty and/or decrease in quality of life.

In one embodiment CKD predisposes the subject to functional impairment, which in turn may result in the presence of a chronic inflammatory state, local and systemic inflammatory effects, increased adiposity (e.g. visceral adipose tissue), decreased LBM and/or any adverse effects of adipose tissue. In some embodiments, conventional therapies such as the administration of anabolic hormones lose efficacy in such subjects, as a result of resistance to the anabolic hormones resulting in decreased levels and resistance to actions (for example due to uremic toxins), however, the compounds/compositions of this invention may in some embodiments be effective in such a scenario.

In one embodiment, S-(III) of this invention and compositions comprising the same is useful in improving Stage 3 and 4 CKD, by, inter alia, and in some embodiments, increasing lean body mass (LBM), improving physical performance, increasing quality of life, decreasing adiposity, improving physical performance, decreasing muscle catabolism, improving or treating renal metabolic syndrome, decreasing risk for development of insulin resistance and/or decreasing the risk for heart disease.

In one embodiment, the SARM compounds of this invention improve muscle wasting and physical performance in end-stage renal disease (dialysis) patients or patients with chronic kidney disease. In some embodiments, the treatment methods of this invention are useful in treating uremic cachexia and/or complications, diseases and/or conditions associated thereto.

In some embodiments, administration of the SARM compound for the above indications is at a dose of 1 or 3 mg daily.

In one embodiment, the methods of this invention are useful in subjects predisposed to kidney diseases or disorders. In one embodiment, the phrase "predisposed to a kidney disease or disorder" with respect to a subject is synonymous with the phrase "subject at risk", and includes a subject at risk of acute or chronic renal failure, or at risk of the need for renal replacement therapy, if the subject is reasonably expected to suffer a progressive loss of renal function associated with progressive loss of functioning nephron units. Whether a particular subject is at risk is a determination which may routinely be made by one of ordinary skill in the relevant medical or veterinary art.

In one embodiment, subjects with kidney disease, in particular male subjects with end-stage renal disease (ESRD) suffer from hypogonadism, with some having concomitant moderate to severe protein-energy malnutrition (PEM), which leads to higher required doses of EPO, lower QoL scores, and higher mortality. Many have other symptoms associated with hypogonadism, including fatigue, lack of appetite, muscle weakness, etc. In some embodiments, the treatment methods of this invention are useful in treating symptom associated with hypogonadism, brought about in the subject by the kidney disease or disorder. In another embodiment, brought about in the subject by androgen deficiency in a female (ADIF); androgen deficiency in aging male (ADAM) to include fatigue, depression, decreased libido, erectile dysfunction, decreased cognition, decreased mood; androgen insufficiency (male or female), or androgen deficiency (male or female).

Hypertension is another comorbid factor for renal disease. In some embodiments, treatment of renal disease according to the present invention may comprise concomitant treatment with a SARM and an agent which treats hypertension.

In some embodiments, the present invention provides a method for treating, reducing the incidence, delaying the onset or progression, or reducing and/or abrogating the symptoms associated with a wasting disease in a subject. In some embodiments, wasting diseases comprise muscle injury, bed rest, immobility, nerve injury, neuropathy, diabetic neuropathy, alcoholic neuropathy, anorexia, anorexia nervosa, anorexia associated with cachexia, anorexia associated with aging, subacute combined degeneration of the spinal cord, diabetes, rheumatoid arthritis, motor neurone diseases, Duchenne muscular dystrophy, carpal tunnel syndrome, chronic infection, tuberculosis, Addison's disease, adult SMA, limb muscle atrophy, back tumour, dermatomyositis, hip cancer, inclusion body myositis, incontinentia pigmenti, intercostal neuralgia, juvenile rheumatoid arthritis, Legg-Calve-Perthes disease, muscle atrophy, multifocal motor neuropathy, nephrotic syndrome, osteogenesis imperfecta, post-polio syndrome, rib tumor, spinal muscular atrophy, reflex sympathetic dystrophy syndrome, or Tay-Sachs.

In some embodiments, the present invention provides a method for prevention of statin induced rhabdomyolysis. In some embodiments, the present invention provides a method for prevention of statin induced rhabdomyolysis, organ failure or insufficiency. In some embodiments, the present invention provides a method for prevention of statin induced kidney or liver failure or insufficiency. In one embodiment, the method comprises administering to a subject a composition comprising a SARM compound and a statin.

In one embodiment, the wasting disease is cachexia or involuntary weight loss in a subject. In another embodiment, the present invention provides a method of treating, preventing, inhibiting, reducing or suppressing muscle wasting in a subject suffering from a kidney disease. In one embodiment, the present invention provides a method of treating, preventing, inhibiting, reducing or suppressing protein catabolism in a subject suffering from a kidney disease or disorder, Cachexia is weakness and a loss of weight caused by a disease or as a side effect of illness. Long term hospitalization due to illness or injury, or disuse deconditioning that occurs, for example, when a limb is immobilized, can also lead to muscle wasting. Studies have shown that in patients suffering injuries, chronic illnesses, burns, trauma or cancer, who are hospitalized for long periods of time, there is a long-lasting unilateral muscle wasting, with a consequent decrease in body mass. Nervous system injury, for example, spinal cord injury, as described further herein, may be a contributory factor, as well.

In some embodiments, the present invention provides a method for treating, reducing the incidence, delaying the onset or progression, or reducing and/or abrogating the symptoms associated with a wasting diseases or disorders in a subject. In another embodiment, the wasting diseases and disorders include inter-alia: a) acquired immunodeficiency syndrome (AIDS) wasting; b) wasting associated with bed rest; c) bulimia, and/or wasting associated with bulimia; d) cachexia; e) cancer cachexia; f) HIV wasting; or g) reduce cachexia and protein loss due to prolonged critical illness, pulmonary dysfunction, ventilator dependency, aging, AIDS, trauma, surgery, congestive heart failure, cardiac myopathy, burns, cancer, chronic obstructive pulmonary disease (COPD), eating disorders such as bulimia, anorexia nervosa, loss of appetite, starvation, and/or depression.

In some embodiments, the present invention provides a method for treating, reducing the incidence, delaying the onset or progression, or reducing and/or abrogating the symptoms associated with invalid or debilitated states in a subject.

In some embodiments, the present invention provides a method for treating, reducing the incidence, delaying the onset or progression, or reducing and/or abrogating the symptoms associated with a hypogonadal state in a subject. In one embodiment, the present invention provides a method for treating, reducing the incidence, delaying the onset or progression, or reducing and/or abrogating the symptoms associated with a pharmacotherapy induced hypogonadal state in a subject. In some embodiments, hypogonadism is caused by treatments which alter the secretion of hormones from the sex glands in both women and men. In some embodiments, hypogonadism may be "primary" or "central." In primary hypogonadism, the ovaries or testes themselves do not function properly. In some embodiments, hypogonadism may be induced by surgery, radiation, genetic and developmental disorders, liver and kidney disease, infection, or certain autoimmune disorders. In some embodiments, menopause is a form of hypogonadism. Menopause may cause, in some embodiments, amenorrhea, hot flashes, vaginal dryness, or irritability due to woman's estrogen levels fall.

In some embodiments, the present invention provides a method for treating, reducing the incidence, delaying the onset or progression, or reducing and/or abrogating the symptoms associated with osteopenic state in a subject. In one embodiment, the present invention provides a method for treating, reducing the incidence, delaying the onset or progression, or reducing and/or abrogating the symptoms associated with a pharmacotherapy induced osteopenic state in a subject. In some embodiments, osteopenia is a mild thinning of the bone mass. In some embodiments, osteopenia is a precursor to osteoporosis. In some embodiments osteopenia is defined as a bone density between one standard deviation (SD) and 2.5 SD below the bone density of a normal young adult.

In some embodiments, the present invention provides a method for treating, reducing the incidence, delaying the onset or progression, or reducing and/or abrogating the symptoms associated with a sarcopenic state in a subject. In one embodiment, the present invention provides a method for treating, reducing the incidence, delaying the onset or progression, or reducing and/or abrogating the symptoms associated with a pharmacotherapy induced sarcopenic state in a subject. In some embodiments, sarcopenia is a significant loss of muscle mass. In one embodiment, sarcopenia definition is having a lean body mass less than two standard deviation below the mean for normal young adults. In some embodiments, sarcopenia is caused by genetic factors, altered circulation, decrease in the capillary:muscle fiber ratio, altered motor neurons, denervation, deterioration of motor end plates, selective reinnervation of type I fibers, inflammatory responses causing muscle damage, reduced exercise, malnutrition, low dietary protein intake, vitamin D deficiency, age-related decline in vitamin D, oxidative stress, muscle mitochondrial mutations, changes in specific types of muscle fibers, decline in muscle protein, disabling disease, strokes, Alzheimer's disease, Parkinson's disease, osteoporosis, atherosclerosis, diabetes mellitus, hyperinsulinemia, renal failure, or hypogonadism.

In some embodiments, the present invention provides a method for treating, reducing the incidence, delaying the onset or progression, or reducing and/or abrogating the symptoms associated with a combination of diseases and/or disorders in a subject as described hereinabove. It is to be understood that any method of this invention, as herein described, encompasses the administration of a SARM compound as herein described, or a composition comprising the same, to the subject, in order to treat the indicated disease, disorder or condition. The methods as herein described each and/or all may further comprise administration of an additional therapeutic agent as herein described, and as will be appreciated by one skilled in the art.

In some embodiments, the present invention provides a method for enhanced production such as milk, sperm, or egg. In some embodiments, the present invention provides a method for enhanced production of lean meats or eggs. In some embodiments, the present invention provides a method for increased productivity of feeds or stud livestock, for example, increased sperm count, improved morphology of sperm, etc. In some embodiments, the present invention provides a method for expanding the productive life of farm animals, for example, egg-laying hens, milk-producing cows, etc., and/or enhanced herd health, for example, improved immune clearance, stronger animals.

In one embodiment, the method comprises administering to a subject a composition comprising a SARM compound and an anti-cancer agent, an immunomodulating agent, an antidiabetic agent, an agent treating the cardiovascular system, an agent treating the gastrointestinal system, an agent treating the central nervous system, an agent treating a metabolic disease, an agent treating a wasting disease, a gene therapy agent, an agent treating the endocrine system, an agent treating a dermatological disorder, an anti-infective agent, an agent treating the liver, an agent treating the kidney, vitamins, nutritional additives, hormones, each and/or all as herein described, or any other therapeutic agent as herein described, or a combination thereof. In another embodiment, the anti-cancer agent is a chemotherapeutic agent as described hereinabove. In another embodiment, the chemotherapeutic agent comprises: bendamustine, bevacizumab, bleomycin, calcium folinate, capecitabine, carboplatin, cetuximab chlorambucil, cisplatin, cyclophosphamide, cytarabine, dasatinib, docetaxel, doxorubicin, erlotinib, etoposide, fludarabine, fluorouracil, gemcitabine hydrochloride, irinotecan hydrochloride, lapatinib, methotrexate, methylprednisolone acetate, mitoxantrone, mitoxantrone hydrochloride, oxaliplatin, paclitaxel, pamidronate disodium, panitumumab, pemetrexed, prednisone, rituximab, trastuzumab, vincristine, vinorelbine or any combination thereof.

In another embodiment, this invention provides methods of treatment of cystic fibrosis and induced hypogonadal states as a result of the same, epilepsy and induced hypogonadal and/or hypermetabolic states as a result of the same, hereditary angioedema, lupus erythematosus and decreased bone mineral density as a result of the same, alcohol and smoking induced osteoporosis, in a subject the methods comprising administering a SARM as herein described to the subject.

In another embodiment, this invention provides methods of treatment of polio and post-polio syndrome and other invalid states, statin induced rhabdomyolysis, statin-induced muscle weakness, statin-induced organ failure or insufficiency, in a subject, the methods comprising the administration of a SARM as herein described, optionally with a statin, as appropriate, as will be appreciated by one skilled in the art, and/or with any therapeutic agent.

In another embodiment, this invention provides a method of treating opioid induced androgen deficiency (OPIAD), the method comprising administering to the subject a SARM as herein described, and optionally opiates, opioids, narcotics, etc. methadone, long-acting opiates/opioids such as Kadian®, extended release morphines, all opiates/opioids/narcotics agents approved by FDA, opiates/opioids used in treatment of heroin addiction, opiates/opioids used in the treatment of chronic pain of malignancy, opiates/opioids used in the treatment non-malignant of chronic pain syndromes.

In another embodiment, this invention provides a method of treating a nervous system disease, disorder or condition, the method comprising administering to the subject a SARM as herein described, and optionally anti-psychotics, such as, for example, zotepine, haloperidol, amisulpride, risperidone, other $D_2$ dopamine receptor antagonists; anti-epileptics, such as valproic acid, carbamazepine, oxcarbamazepine, etc. or combinations thereof.

In another embodiment, this invention provides a method of treating a hormone dependent disease, disorder or condition, the method comprising administering to the subject a SARM as herein described, and optionally chemotherapeutics agents and anti-cancer therapies (methotrexate, cyclophosphamide, ifosfamide, adriamycin, doxorubicin, glucocorticoids, cyclosporine, L-thyroxine, SERMs, aromatase inhibitors, fulvestrant, GnRH agents, ADT, discontinuation of hormone replacement therapy, cranial irradiation, peripheral irradiation, etc.; prolactinemia-inducing pharmcotherapeutics (serotonergic antidepressants acting through $5HT_2$ receptors, selective serotonin reuptake inhibitors, monoamine oxidase inhibitors, tricyclic antidepressants, antihypertensives such as methyldopa, reserpine, clonidine, and verapamil; antidopaminergic anti-emetics such as metoclopramide, $H_2$ receptor antagonists such as cimetidine and ranitidine, estrogens, amphetamines, AR partial antagonists (ketoconazole, spironolactone, eplerenone).

In another embodiment, the SARMs and compositions as described herein are useful in promoting or speeding recovery following a surgical procedure.

In one embodiment, the present invention provides a use of a SARM compound as described herein for reducing a fat mass in a subject. In another embodiment the invention provides such methods for use of the SARM compound as described herein or its prodrug, analog, isomer, metabolite, derivative, pharmaceutically acceptable salt, pharmaceutical product, polymorph, crystal, impurity, N-oxide, hydrate or any combination thereof, or a composition comprising the same.

In another embodiment, this invention provides for the use of the SARM compounds as described herein or its analog, derivative, isomer, metabolite, pharmaceutically acceptable salt, pharmaceutical product, polymorph, crystal, impurity, hydrate, N-oxide or any combination thereof, for treating abdominal fat accumulation improving body composition; lowering body fat content; lowering fat mass; improving blood lipid profile, increasing muscle mass/strength/function; increasing bone mass/bone mineral density/strength/function; lowering body fat; congenital hyperinsulinemia; Cushing's disease (hypercortisolemia); or obesity or diabetes associated with a metabolic syndrome in a subject.

In another embodiment, the subject has a hormonal imbalance, disorder, or disease. In another embodiment the subject has menopause.

In one embodiment, the present invention provides a use of a SARM compound as described herein for increasing a lean mass in a subject. In another embodiment such use comprises administration of a SARM compound as described herein or its prodrug, analog, isomer, metabolite, derivative, pharmaceutically acceptable salt, pharmaceutical product, polymorph, crystal, impurity, N-oxide, hydrate or any combination thereof.

Example 2 demonstrates that a compound of formula S-(III) is anabolic yet minimally androgenic, this such compounds may be useful in treating patient groups in which androgens were contraindicated in the past. Compound of formula S-(III) was shown to stimulate muscle growth, whether in the presence or absence of testosterone while exerting anti-proliferative effects on the prostate, thus, in one embodiment, the methods of this invention provide for restring lost muscle mess in patients with sarcopenia or cachexia.

In one embodiment, the SARM compounds as herein described alter the levels of leptin in a subject. In another embodiment, the SARM compounds as herein described decrease the levels of leptin. In another embodiment, the SARM compounds as herein described increase the levels of leptin in a subject. Leptin is known to have an effect on appetite on weight loss in obese nice, and thus has been implicated in obesity.

The SARM compounds as herein described, in one embodiment, affect circulating, or in another embodiment, tissue levels of leptin. In one embodiment, the term 'level/s of leptin' refers to the serum level of leptin. As contemplated herein, the SARM compounds of the present invention have an effect on leptin in vitro and in vivo. Leptin levels can be measured by methods known to one skilled in the art, for example by commercially available ELISA kits. In addition, leptin levels may be determined in in vitro assays, or in in vivo assays, by any method known to a person skilled in the art.

Since leptin is implicated in controlling appetite, weight loss, food intake, and energy expenditure, modulating and/or controlling the levels of leptin is a useful therapeutic approach in treating, preventing, inhibiting or reducing the incidence of obesity in subjects suffering from obesity. Modulating the level of leptin can result in a loss of appetite, a reduction of food intake, and an increase in energy expenditure in the subject, and thus may contribute to the control and treatment of obesity.

The term "obesity" is defined, in one embodiment, as an increase in body weight beyond the limitation of skeletal and physical requirement, as the result of excessive accumulation of fat in the body.

The term "obesity-associated metabolic disorder" refers, in one embodiment, to a disorder which results from, is a consequence of, is exacerbated by or is secondary to obesity. Non-limiting examples of such a disorder are osteoarthritis, type II diabetes mellitus, increased blood pressure, stroke, and heart disease.

Cholesterol, triacylglycerol and other lipids are transported in body fluids by lipoproteins which may be classified according to their density, for example, the very low density lipoproteins (VLDL), intermediate density lipoproteins (IDL), low density lipoproteins (LDL) and high density lipoproteins (HDL).

It has been shown that high levels of LDL-cholesterol in the blood correlate with atherosclerosis which is a progressive disease characterized in pert by sedimentation of lipids in inner walls of arteries, particularly of coronary arteries. It has also been shown that a high blood level of LDL-cholesterol correlates with coronary heart disease. Also, a negative correlation exists between blood levels of HDL cholesterol and coronary heart disease.

The level of total cholesterol in blood, which is the sum of HDL-cholesterol, LDL-cholesterol, VLDL-cholesterol and chylomicron-cholesterol, is not necessarily predictive of the risk of coronary heart disease and atherosclerosis.

The correlation between atherosclerosis and LDL cholesterol levels, however, is much higher than a similar correlation between atherosclerosis and total serum cholesterol levels.

In one embodiment, this invention provides methods of use of the SARM compounds as herein described for improving the lipid profile and/or reducing the circulating lipid levels in a subject. In some embodiments, according to this aspect of the invention, the subject suffers from one or more conditions comprising atherosclerosis and its associated diseases, premature aging, Alzheimer's disease, stroke, toxic hepatitis, viral hepatitis, peripheral vascular insufficiency, renal disease, and/or hyperglycemia, and the invention provides for the administration of a SARM compound or composition comprising the same, as herein described, which in some embodiments positively affects a lipid profile in the subject, which is one means by which the method is useful in treating the indicated diseases, disorders and conditions.

In one embodiment the invention provides for the treatment of atherosclerosis and its associated diseases, such as for example, cardiovascular disorders, cerebrovascular disorders, peripheral vascular disorders, intestinal vascular disorders, or combinations thereof.

In one embodiment, cardiovascular disorders comprise hypertension (HTN), coronary artery disease (CAD) or myocardial perfusion. In another embodiment this invention provides methods of use of the compositions as herein described for promoting aortic smooth muscle cell proliferation. In another embodiment this invention provides methods of use of the compositions as herein described for treating arteriosclerosis. In another embodiment this invention provides methods of use of the compositions as herein described for lowering blood pressure. In another embodiment this invention provides methods of use of the compositions as herein described for treating cardiac diseases and disorders comprising cardiomyopathy, cardiac dysfunctions such as, myocardial infarction, cardiac hypertrophy and congestive heart failure. In another embodiment this invention provides methods of use of the compositions as herein described for cardioprotection comprising cardioprotection in insulin resistance; treating diabetes type I and II, metabolic syndrome, syndrome X and/or high blood pressure.

In one embodiment, the invention provides a method of treating, preventing, reducing the risk of mortality from cardiovascular and/or cerebrovascular disease in a subject, comprising administering a compound of formula (I-XX or S-(III)) or its prodrug, ester, analog, isomer, metabolite, derivative, pharmaceutically acceptable salt, pharmaceutical product, polymorph, crystal, impurity, N-oxide, hydrate or any combination thereof, or a pharmaceutical composition comprising the same. In one embodiment, the SARM compound is characterized by the structure of formula S-(III).

In one embodiment, compounds of formulae I-XX reduce LDL and total cholesterol levels, and in one embodiment the SARM compound of formula S-(III) reduces LDL and total cholesterol levels in a subject.

In another embodiment, compounds of formulae I-XX are co-administered with HDL-elevating agents. In another embodiment, a compound of formula S-(III) is co-administered with HDL-elevating agents. In another embodiment, HDL-elevating agents include niacin. In another embodiment the HDL-elevating agents include fibrates including gemfibrozil (Lopid®), thiourea based gemfibrozil analogues, and fenofibrate (TriCor®). In another embodiment, HDL-elevating agents include statins. In another embodiment, HDL-elevating agents include cholesteryl ester transferase protein (CETP) inhibitors including anacetripib. In another embodiment, HDL-elevating agents include 1-hydroxyalkyl-3-phenylthiourea, and analogs thereof.

In one embodiment, this invention provides a method of reducing circulating lipid levels in a subject, said method comprising administering a selective androgen receptor modulator (SARM) compound of formula I-XX or S-(III) or its pharmaceutically acceptable salt, hydrate, N-oxide, or any combination thereof, or a composition comprising the same. In one embodiment, the subject suffers from atherosclerosis and its associated diseases, premature aging. Alzheimer's disease, stroke, toxic hepatitis, viral hepatitis, peripheral vascular insufficiency, renal disease, hyperglycemia, or any combination thereof.

In one embodiment, this invention provides a method of treating atherosclerosis and its associated diseases, such as, for example, cardiovascular disorders, cerebrovascular disorders, peripheral vascular disorders, or intestinal vascular disorders in a subject, the method comprising the step of administering to the subject a selective androgen receptor modulator (SARM) compound of formula I-XX or S-(III) or its pharmaceutically acceptable salt, hydrate, N-oxide, or any combination thereof, or a composition comprising the same. The method may further comprise co-administration, subsequent or prior administration with an agent or agents, which are known to be useful in treating cardiovascular disorders, cerebrovascular disorders, peripheral vascular disorders, or intestinal vascular disorders.

In one embodiment, this invention provides a method of improving the dexterity and movement in a subject, for example, by treating arthritis in the subject.

The term "arthritis" refers, in another embodiment, to a non-inflammatory degenerative joint disease occurring chiefly in older people, characterized by degeneration of the articular cartilage, hypertrophy of bones and the margins, changes in the synovial membrane, etc. It is accompanied, in other embodiments, by pain and stiffness, particularly after prolonged activity.

The term "diabetes", in one embodiment, refers to a relative or absolute lack of insulin leading to uncontrolled carbohydrate metabolism. Most patients can be clinically classified as having either insulin-dependent diabetes mellitus (IDDM or type-I diabetes) or non-insulin-dependent diabetes mellitus (NIDDM or type-II diabetes).

The term "increased blood pressure" or "hypertension" refers, in other embodiments, to a repeatedly high blood pressure above 140 over 90 mmHg. Chronically-elevated blood pressure can cause blood vessel changes in the back of the eye, thickening of the heart muscle, kidney failure, and brain damage.

The term "stroke" refers, in other embodiments, to damage to nerve cells in the brain due to insufficient blood supply often caused by a bursting blood vessel or a blood clot. The term "heart disease", in other embodiments, refers to a malfunction in the heart normal function and activity, including heart failure.

In addition, androgens have recently been shown to be involved in commitment of mesenchymal pluripotent cells into myogenic lineage and to block differentiation into adipogenic lineage (Singh et al., Endocrinology, 2003 Jul. 24). Accordingly, SARM compounds can be useful in methods of blocking adipogenesis, and/or alerting stem cell differentiation, as described herein.

In another embodiment, this invention relates to a method of promoting, increasing or facilitating weight loss in a subject, comprising the step of administering to the subject a SARM as herein described and/or its analog, derivative, isomer, metabolite, pharmaceutically acceptable salt, pharmaceutical product, hydrate, N-oxide, prodrug, polymorph, crystal, or any combination thereof, in an amount effective to promote, increase or facilitate weigh loss in the subject.

In another embodiment, this invention relates to a method of decreasing, suppressing, inhibiting or reducing appetite of a subject, comprising the step of administering to the subject a SARM as herein described and/or its analog, derivative, isomer, metabolite, pharmaceutically acceptable salt, pharmaceutical product, hydrate, N-oxide, prodrug, polymorph, crystal, or any combination thereof, in an amount effective to decrease, suppress, inhibit or reduce the appetite of the subject.

In another embodiment, this invention relates to a method of altering the body composition of a subject, comprising the step of administering to the subject a SARM as herein described and/or its analog, derivative, isomer, metabolite, pharmaceutically acceptable salt, pharmaceutical product, hydrate, N-oxide, prodrug, polymorph, crystal, or any combination thereof, in an amount effective to alter the body composition of the subject. In one embodiment, altering the body composition comprises altering the lean body mass, the fat free body mass of the subject, or a combination thereof.

In another embodiment, this invention relates to a method of altering lean body mass or fat free body mass of a subject, comprising the step of administering to the subject a SARM as herein described and/or its analog, derivative, isomer, metabolite, pharmaceutically acceptable salt, pharmaceutical product, hydrate, N-oxide, prodrug, polymorph, crystal, or any combination thereof, in an amount effective to alter the lean body mass or fat free body mass of the subject.

In another embodiment, this invention relates to a method of converting fat to lean muscle in a subject, comprising the step of administering to the subject a SARM as herein described and/or its analog, derivative, isomer, metabolite, pharmaceutically acceptable salt, pharmaceutical product, hydrate, N-oxide, prodrug, polymorph, crystal, or any combination thereof, in an amount effective to convert fat to lean muscle in the subject. In another embodiment, this invention relates to a method of converting fat to lean muscle in a subject suffering from a wasting disorder. In another embodiment, this invention relates to a method of converting fat to lean muscle in a subject suffering from a wasting disorder wherein the wasting disorder is a muscular dystrophy. In another embodiment, this invention relates to a method of converting fat to lean muscle in a subject suffering from a wasting disorder wherein the wasting disorder is Duchenne muscular dystrophy.

In another embodiment, this invention relates to a method of treating an obesity-associated metabolic disorder in a subject, comprising the step of administering to the subject a SARM as herein described and/or its analog, derivative, isomer, metabolite, pharmaceutically acceptable salt, pharmaceutical product, hydrate, N-oxide, prodrug, polymorph, crystal, or any combination thereof, in an amount effective to treat the obesity-associated metabolic disorder in the subject.

In another embodiment, this invention relates to a method of preventing, suppressing, inhibiting or reducing an obesity-associated metabolic disorder in a subject, comprising the step of administering to the subject a SARM as herein described and/or its analog, derivative, isomer, metabolite, pharmaceutically acceptable salt, pharmaceutical product, hydrate, N-oxide, prodrug, polymorph, crystal, or any combination thereof, in an amount effective to prevent, suppress, inhibit or reduce the obesity-associated metabolic disorder in the subject.

In one embodiment, the obesity-associated metabolic disorder is hypertension. In another embodiment, the disorder is osteoarthritis. In another embodiment, the disorder is type II diabetes mellitus. In another embodiment, the disorder is increased blood pressure. In another embodiment, the disorder is stroke. In another embodiment, the disorder is heart disease.

In another embodiment, this invention relates to a method of decreasing, suppressing, inhibiting or reducing adipogenesis in a subject, comprising the step of administering to the subject a SARM as herein described and/or its analog, derivative, isomer, metabolite, pharmaceutically acceptable salt, pharmaceutical product, hydrate, N-oxide, prodrug, polymorph, crystal, or any combination thereof.

In another embodiment, this invention relates to a method of altering stem cell differentiation in a subject, comprising the step of administering to the subject a SARM as herein described and/or its analog, derivative, isomer, metabolite, pharmaceutically acceptable salt, pharmaceutical product, hydrate, N-oxide, prodrug, polymorph, crystal, or any combination thereof, in an amount effective to alter stem cell differentiation in the subject.

In one embodiment, the SARM that's as herein described are useful in: a) treating, preventing, suppressing, inhibiting, or reducing obesity; b) promoting, increasing or facilitating weight loss; c) decreasing, suppressing, inhibiting or reducing appetite; d) altering the body composition; e) altering lean body mass or fat free body mass; f) converting fat to lean muscle; g) treating, preventing, suppressing, inhibiting, or reducing an obesity-associated metabolic disorder, for example hypertension, osteoarthritis, diabetes mellitus, maturity onset diabetes of the young (MODY), increased blood pressure, stroke, or heart disease; h) decreasing, suppressing, inhibiting or reducing adipogenesis; i) altering stem cell differentiation; and/or j) altering the level of leptin.

In one embodiment, the SARMs as herein described find utility in treating or halting the progression of or treating symptoms of diabetes. In another embodiment, the SARMs as herein described are useful in treating co-morbidities related to diabetes. These conditions include: hypertension, cerebrovascular disease, atherosclerotic coronary artery disease, macular degeneration, diabetic retinopathy (eye disease) and blindness, cataracts-systemic inflammation (characterized by elevation of inflammatory markers such as erythrocyte sedimentation rate or C-reactive protein), birth defects, pregnancy related diabetes, pre-eclampsia and hypertension in pregnancy, kidney disease (renal insufficiency, renal failure etc.), nerve disease (diabetic neuropathy), superficial and systemic fungal infections, congestive heart failure, gout/hyperuricemia, obesity, hypertriglyceridemia, hypercholesterolemia, fatty liver disease (non-alcoholic steatohepatitis, or NASH), and diabetes-related skin diseases such as necrobiosis lipoidica diabeticorum (NLD), blisters of diabetes (bullosis diabeticorum), eruptive xanthomatosis, digital sclerosis, disseminated granuloma annulare, and acanthosis nigricans.

In one embodiment this invention provides a method of treating, suppressing, inhibiting or reducing the incidence of (a) diabetes type I; (b) diabetes type II; (c) glucose intolerance; (d) hyperinsulinemia; (e) insulin resistance; (f) nephropathy; (g) diabetic neuropathy; (h) diabetic retinopathy; (i) fatty liver conditions; (j) MODY; and (k) cardiovascular disease in a human subject, comprising the step of administering to said subject a selective androgen receptor modulator compound of formula I-XX or S-(III).

In some embodiments, the SARMs as herein described and/or compositions comprising the same may be used for applications in, or treating diseases or conditions associated with a subject having diabetes. In one embodiment, the subject for whom treatment is sought via the methods of this invention is one with diabetic I. Type I diabetes is characterized by autoimmune destruction of pancreatic beta-cells. Markers of immune destruction of the beta-cell are present at the time of diagnosis in 90% of individuals and include antibodies to the islet cell (ICAs), to glutamic acid decarboxylase (GAD), and to insulin (IAAs). While this form of diabetes usually occurs in children and adolescents, it can occur at any age. Younger individuals typically have a rapid rate of beta-cell destruction and present with ketoacidosis, while adults often maintain sufficient insulin secretion to prevent ketoacidosis for many years. Eventually, all type I diabetic patients require insulin therapy to maintain normglycemia.

In one embodiment, this invention provides a method of treating diabetes type II. Type II diabetes is characterized by insulin resistance and at some stage in pathogenesis of the disease, a relative deficiency of insulin secretion. In absolute terms, the plasma insulin concentration (both fasting and meal-stimulated) usually is increased, although "relative" to the severity of insulin resistance, the plasma insulin concentration is insufficient to maintain normal glucose homeostasis. With time, however, there is progressive beta cell failure and absolute insulin deficiency ensues. Most individuals with type II diabetes exhibit intra abdominal (visceral) obesity, fatty liver, which is closely related to the presence of insulin resistance. The patient's liver becomes insulin resistant and glycogen breakdown is uncontrolled and the result is increased and unphysiological glucose delivery to the bloodstream. The liver generation of cholesterol and VLDL particles is also uncontrolled. In addition, hypertension, dyslipidemia (high triglyceride and low HDL-cholesterol levels; postprandial hyperlipemia), and elevated PAI-1 levels often are present in these individuals. This clustering of abnormalities is referred to as the "insulin resistance syndrome", or the "metabolic syndrome" or obesity related disorders. Because of these abnormalities, patients with type U diabetes are at increased risk of developing macrovascular complications such as myocardial infarction and stroke.

In one embodiment, this invention provides a method of treating diabetic nephropathy. Diabetic nephropathy is a complication of diabetes that evolves early, typically before clinical diagnosis of diabetes is made. The earliest clinical evidence of nephropathy is the appearance of low but abnormal levels (>30 mg/day or 20 µg/min) of albumin in the urine (microalbuminuria), followed by albuminuria (>300 mg/24 h or 200 µg/min) that develops over a period of 10-15 years. In patients with type 1 diabetes, diabetic hypertension typically becomes manifest early on, by the time that patients develop microalbuminuria. Once overt nephropathy occurs, the glomerular filtration rate (GFR) falls over a course of times, which may be several years, resulting in end stage renal disease (ESRD) in diabetic individuals.

In one embodiment, this invention provides a method of treating diabetic neuropathy. Diabetic neuropathy is a family of nerve disorders caused by diabetes. Diabetic neuropathies cause numbness and sometimes pain and weakness in the hands, arms, feet, and legs. Neurologic problems in diabetes may occur in every organ system, including the digestive tract, heart, and genitalia. Diabetic neuropathies are classified as peripheral, autonomic, proximal, and focal. Peripheral neuropathy causes pain or loss of feeling in the toes, feet, legs, bands, and arms. Autonomic neuropathy causes changes in digestion, bowel and bladder function, sexual response, and perspiration and can also affect the nerves that serve the heart and control blood pressure. Proximal neuropathy causes pain in the thighs, hips, or buttocks and leads to weakness in the legs. Focal neuropathy results in the sudden weakness of one nerve, or a group of nerves, causing muscle weakness or pain. Any nerve in the body may be affected.

In one embodiment, this invention provides a method of treating diabetic retinopathy. The effect of diabetes on the eye is called diabetic retinopathy. Patients with diabetes are more likely to develop eye problems such as cataracts and glaucoma. The affect of diabetic retinopathy on vision varies widely, depending on the stage of the disease. Some common symptoms of diabetic retinopathy are blurred vision (this is often linked to blood sugar levels), floaters and flashes and sudden loss of vision.

In one embodiment, the subject for whom treatment is sought via the methods of this invention is one with glucose intolerance. Glucose intolerance is a pre-diabetic state in which the blood glucose is higher than normal but not high enough to warrant the diagnosis of diabetes.

In one embodiment, the subject for whom treatment is sought via the methods of this invention is one with hyperinsulinemia. Hyperinsulinemia is a sign of an underlying problem that is causing the pancreas to secrete excessive amounts of insulin. The most common cause of hyperinsulinemia is insulin resistance, a condition in which your body is resistant to the effects of insulin and the pancreas tries to compensate by making more insulin, hyperinsulinemia is associated with type II diabetes In one embodiment, the subject for whom treatment is sought via the methods of this invention is one with insulin resistance. Insulin resistance is a condition in which normal amounts of insulin are inadequate to produce a normal insulin response from fat, muscle and liver cells. Insulin resistance in fat cells results in hydrolysis of stored triglycerides, which elevates free fatty acids in the blood plasma. Insulin resistance in muscle reduces glucose uptake whereas insulin resistance in liver reduces glucose storage, with both effects serving to elevate blood glucose. High plasma levels of insulin and glucose due to insulin resistance often leads to the metabolic syndrome and type II diabetes.

In one embodiment, this invention provides methods of treating, suppressing, inhibiting, reducing the severity, reducing the incidence, reducing the pathogenesis, or delaying onset of, inter alia: (a) diabetes; (b) glucose intolerance; (c) hyperinsulinemia; (d) insulin resistance; (e) diabetic nephropathy, (f) diabetic neuropathy (g) fatty liver conditions; (h) cardiovascular disease; or (i) cachexia; via the administration of any SARM as herein described and optionally other therapeutic agents, or compositions comprising the same.

Diabetes and the liver obesity is typically associated with elevated levels of free fatty acid (FFAs) that promote lipid accumulation and insulin resistance in target tissues, i.e. reduced action of insulin primarily in skeletal muscle and liver. A prominent role of insulin is to reduce glucose output from the liver. FFAs stimulate hepatic gluconeogenesis which per se does not lead to increased hepatic glucose output as long as it is paralleled by a decrease in hepatic glycogenolysis, a compensatory process referred to as "hepatic autoregulation". FFAs stimulate insulin secretion and insulin blocks glycogenolysis in part by inhibiting secretion of glucagon, an inducer of glycogenolysis. However, long-term elevated levels of FFAs leads to hepatic insulin resistance and thus breakdown of hepatic autoregulation, resulting in increased hepatic glucose production and development of type II diabetes. Fatty liver and hepatic insulin resistance is a major driving force behind hyperglycemia and type II diabetes.

In one embodiment, this invention provides methods that inhibit (improve) the fatty liver, resulting in that the insulin resistance in the liver is inhibited (improved) and thereby solving the basic problem in type II diabetes. In one embodiment, this invention provides a method of treating a human subject having diabetes. In another embodiment, the diabetes is a type I diabetes. In another embodiment, the diabetes is type II diabetes. In one embodiment, this invention provides a method of treating a human subject having glucose intolerance. In one embodiment, this invention provides a method of treating a hyperinsulinemia in a human subject. In one embodiment, this invention provides a method of treating insulin resistance in a human subject. In another embodiment, treatment of insulin resistance is exemplified in Example 6. In one embodiment, this invention provides a method of treating diabetic nephropathy in a human subject. In one embodiment, this invention provides a method of treating diabetic neuropathy in a human subject. In one embodiment, this invention provides a method of treating diabetic retinopathy in a human subject. In one embodiment, this invention provides a method of treating cardiovascular disease in a human subject.

In another embodiment, the methods of this invention comprising the step of administering to said subject a selective androgen receptor modulator compound of formula S-(III):

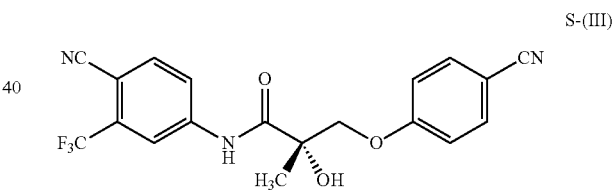

S-(III)

or its isomer, pharmaceutically acceptable salt, pharmaceutical product, hydrate, N-oxide, or any combination thereof.

In one embodiment this invention provides a method for a) treating, preventing, suppressing or inhibiting atherosclerosis; or b) treating, preventing, suppressing, or inhibiting liver damage due to fat deposits; comprising the step of administering to the subject a SARM as described herein and/or its analog, derivative, isomer, metabolite, pharmaceutically acceptable salt, pharmaceutical product, hydrate, N-oxide, prodrug, polymorph, crystal, or any combination thereof or a composition comprising the same, in an amount effective to treat, prevent or inhibit atherosclerosis and liver damage due to fat deposit.

In one embodiment atherosclerosis refers to a slow, complex disease that may begin with damage to the innermost layer of the artery. In another embodiment the causes of damage to the arterial wall may include; a) elevated levels of cholesterol and in the blood; b) high blood pressure; c) tobacco smoke; or d) diabetes. In another embodiment, the condition is treatable in a smoker, despite the fact that tobacco smoke may greatly worsen atherosclerosis and speed its growth in the coronary arteries, the aorta and arteries in the legs. Similarly, in another embodiment, the methods of this invention may be useful in treating subjects with a family history of premature cardiovascular disease who have an increased risk of atherosclerosis.

In one embodiment liver damage due to fat deposits refer to the build-up of fat in the liver cells forming a fatty liver which may be associated with or may lead to inflammation of the liver. This can cause scarring and hardening of the liver. When scarring becomes extensive, it is called cirrhosis.

In another embodiment the fat accumulates in the liver as obesity. In another embodiment fatty liver is also associated with diabetes mellitus, high blood triglycerides, and the heavy use of alcohol. In another embodiment fatty liver may occur with certain illnesses such as tuberculosis and malnutrition, intestinal bypass surgery for obesity, excess vitamin A in the body, or the use of certain drugs such as valproic acid (trade names: Depakene®/Depakote®) and corticosteroids (cortisone, prednisone). Sometimes fatty liver occurs as a complication of pregnancy.

Androgen-dependent conditions which may be treated with the compounds and/or compositions as herein described, comprising the methods of the present invention include those conditions which are associated with aging. In one embodiment, the SARM as described herein is useful in: a) age-related functional decline (ARFD); b) reversal or prevention of ARFD; c) reversal or prevention of ARFD in elderly; d) reversal or prevention of ARFD-induced sarcopenia or osteopenia; e) andropause or andropausal vasomotor symptoms; f) andropausal gynecomastia, muscle strength/function; g) bone strength/function; h) anger; i) asthenia; j) chronic fatigue syndrome; k) cognitive impairment; and/or l) improving cognitive function.

In one embodiment, the SARM compounds as described herein are useful in treating inflammation and related disorders such as: a) prevention, treatment, or reversal of arthritis; b) prevention, treatment, or reveral of an arthritic condition such as Behcet's disease (autoimmune vasculitis), bursitis, calcium pyrophosphate dihydrate crystal (CPPD), deposition disease (or pseudogout), carpal tunnel syndrome, connective tissue disorders, Crohn's diseases, Ehlers-Danlos syndrome (EDS), fibromyalgia, gout, infectious arthritis, inflammatory bowel disease (IBD), juvenile arthritis, systemic lupus erythematosus (SLE), Lyme's disease, Marfan syndrome, myositis, osteoarthritis, polyarteritis nodosa, polymyalgia rheumatica, psoriasis, psoriatic arthritis, Raynaud's phenomenon, reflex sympathetic dystrophy syndrome, Reiter's syndrome, rheumatoid arthritis, scleroderma, Sjögrens' syndrome, tendonitis or ulcerative colitis; or c) preventing, treatment, or reversing an autoimmune disease.

In one embodiment, the compositions as described herein are useful in prevention of iatrogenic effects comprising acute fatigue syndrome (post-surgical) or androgen-deprivation therapy (ADT) induced side effects such as reduced muscle mass, reduced muscle strength, frailty, hypogonadism, osteoporosis, osteopenia, decreased bone mineral density and/or decreased bone mass.

In one embodiment, the methods of the present invention comprise administering a SARM compound as the sole active ingredient. However, also encompassed within the scope of the present invention are methods for diabetes and related disorders, hormone therapy, dry eye, obesity, treating prostate cancer, delaying the progression of prostate cancer, and for preventing and/or treating the recurrence of prostate cancer, male contraception; treatment of osteoporosis, treatment of conditions associated with ADIF and for treatment and/or prevention of chronic muscular wasting which comprise administering the SARM compounds in combination with one or to more therapeutic agents. These agents include, but are not limited to: LHRH analogs, reversible antiandrogens, antiestrogens, anticancer drugs, 5-alpha reductase inhibitors, aromatase inhibitors, progestins, agents acting through other nuclear hormone receptors, selective estrogen receptor modulators (SERM), progesterone, estrogen, PDE5 inhibitors, apomorphine, bisphosphonate, and one or more additional SARMS.

Thus, in one embodiment, the methods of the present invention comprise administering the SARM compound, comprise administering a SARM compound in combination with diabetes drug such as troglitazone, rosiglitazone, and pioglitazone. In another embodiment, the methods of the present invention comprise administering a SARM compound in combination with an LHRH analog. In another embodiment, the methods of the present invention comprise administering a SARM compound, in combination with a reversible antiandrogen. In another embodiment, the methods of the present invention comprise administering a SARM compound, in combination with an antiestrogen. In another embodiment, the methods of the present invention comprise administering a SARM compound, in combination with an anticancer drug. In another embodiment, the methods of the present invention comprise administering a SARM compound, in combination with a chemotherapeutic agent. In another embodiment, the chemotherapeutic agent comprises: bendamustine, bevacizumab, bleomycin, calcium folinate, capecitabine, carboplatin, cetuximab, chlorambucil, cisplatin, cyclophosphamide, cytarabine, dasatinib, docetaxel, doxorubicin, erlotinib, etoposide, fludarabine, fluorouracil, gemcitabine hydrochloride, irinotecan hydrochloride, lapatinib, methotrexate, methylprednisolone acetate, mitoxantrone, mitoxantrone hydrochloride, oxaliplatin, paclitaxel, pamidronate disodium, panitumumab, pemetrexed, prednisone, rituximab, trastuzumab, vincristine, vinorelbine or any combination thereof. In another embodiment, the methods of the present invention comprise administering a SARM compound, in combination with a 5-alpha reductase inhibitor. In another embodiment, the methods of the present invention comprise administering a SARM compound, in combination with an aromatase inhibitor. In another embodiment, the methods of the present invention comprise administering a SARM compound, in combination with a progestin. In another embodiment, the methods of the present invention comprise administering a SARM compound, in combination with an agent acting through other nuclear hormone receptors. In another embodiment, the methods of the present invention comprise administering a SARM compound, in combination with a selective estrogen receptor modulator (SERM). In another embodiment, the methods of the present invention comprise administering a SARM compound, in combination with a progesterone. In another embodiment, the methods of the present invention comprise administering a SARM compound, in combination with an estrogen. In another embodiment, the methods of the present invention comprise administering a SARM compound, in combination with a PDE5 inhibitor. In another embodiment, the methods of the present invention comprise administering a SARM compound, in combination with apomorphine. In another embodiment, the methods of the present invention comprise administering a SARM compound, in combination with a bisphosphonate. In another embodiment, the methods of the present invention comprise administering a SARM compound, in combination with one or more additional SARMS. In some embodiments, the methods of the present invention comprise combined preparations comprising a SARM compound and an agent as described hereinabove. In some embodiments, the combined preparations can be varied, e.g., in order to cope with the needs of a patient subpopulation to be treated or the needs of the single patient which different needs can be due to the particular disease, severity of the disease, age, sex, or body weight as can be readily determined by a person skilled in the art. In some embodiments, the methods of the present invention comprise personalized medicine methods which treat the needs of a single patient. In one embodiment, different needs can be due to the particular disease, severity of the disease, the overall medical state of a patient, or the age of the patient. In some embodiments, personalized medicine is the application of genomic data to better target the delivery of medical interventions. Methods of personalized medicine, in some embodiments, serve as a tool in the discovery and clinical testing of new products of the present invention. In one embodiment, personalized medicine involves the application of clinically useful diagnostic tools that may help determine a patient's predisposition to a particular disease or condition. In some embodiments, personalized medicine is a comprehensive approach utilizing molecular analysis of both patients and healthy individuals to guide decisions throughout all stages of the discovery and development of pharmaceuticals and diagnostics; and applying this knowledge in clinical practice for a more efficient delivery of accurate and quality healthcare through improved prevention, diagnosis, treatment, and monitoring methods.

Age and health related conditions are associated with deterioration in physical function and health-related quality of life. Physical functional decline may impact on the quality of life. Physical function is associated with quality of life.

In one embodiment, the term "physical function" refers to the physical performance, and the physiological capacity, which refers to "the basic cellular & anatomic function such as cardiac ejection fraction, nerve conduction velocity, or muscle strength per cross-sectional area. Physical performance is the ability to integrate these physiological systems into coordinated, efficient movements to achieve optimum physical function. In another embodiment, physical function can also be defined as the ability to perform mobility tasks, activities of daily living, and instrumental activities of daily living that are important for achieving & maintaining an independent living status. In anther embodiment, the physical function of a subject can be analyzed by the time (speed) the activity (function) is performed, and/or by the power (energy) or work the subject used in order to perform the activity. Different physical functions include: walking, running, stair climb, weight lifting, grip strength, etc. In another embodiment, the physical function is as described in Example 4.

In one embodiment, this invention provides a method of treating, reducing the severity of, reducing the incidence of, or delaying the onset of loss of physical function in a subject, comprising the step of administering to said subject a compound of this invention. In another embodiment, said method comprising administering a selective androgen receptor modulator (SARM) compound of formula II:

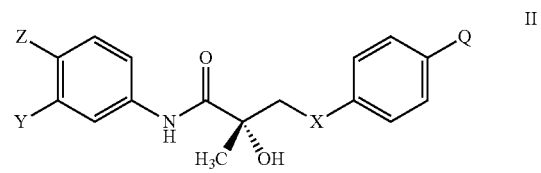

wherein

X is O;

Z is $NO_2$, CN, COR, or CONHR;

Y is an alkyl, $CF_3$, $CH_3$, formyl, alkoxy, H, F, I, Br, Cl, or $Sn(R)_3$;

R is an alkyl, aryl, phenyl, alkenyl, haloalkyl, haloalkenyl, halogen or OH;

and

Q is allyl, halogen, $N(R)_2$, CN, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, acetamido-, trifluoroacetamido-, alkylamines, ether, alkyl, N-sulfonyl, O-sulfonyl, alkylsulfonyl, carbonyl, or a ketone;

wherein said subject is subjected to cancer therapy.

In another embodiment, Q is CN.

In another embodiment, said method comprising administering a selective androgen receptor modulator (SARM) compound of formula S-(III):

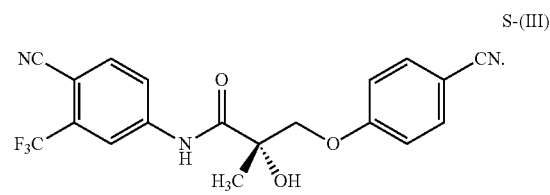

In one embodiment, this invention provides a method of treating, reducing the severity of reducing the incidence of, or delaying the onset of loss of physical function in a subject suffering from cancer, comprising the step of administering to said subject a compound of this invention. In another embodiment, said method comprising administering a selective androgen receptor modulator (SARM) compound of formula II:

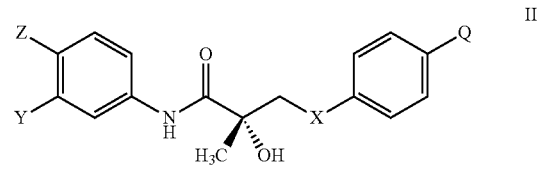

wherein

X is O;

Z is a hydrogen bond acceptor, $NO_2$, CN, COR, or CONHR;

Y is a lipid soluble group, an alkyl, $CF_3$, $CH_3$, formyl, alkoxy, H, F, I, Br, Cl, or $Sn(R)_3$;

R is an alkyl, aryl, phenyl, alkenyl, haloalkyl, haloalkenyl, halogen or OH;
and
Q is alkyl, halogen, N(R)₂, CN, NHCOCH₃, NHCOCF₃, NHCOR, NHCONHR, NHCOOR, OCONHR. CONHR, NHCSCH₃, NHCSCF₃, NHCSR, NHSO₂CH₃, NHSO₂R, OR, COR, OCOR, OSO₂R, SO₂R, SR, acetamido-, trifluoroacetamido-, alkylamines, ether, alkyl N-sulfonyl, O-sulfonyl, alkylsulfonyl, carbonyl, or a ketone;
wherein said subject is subjected to cancer therapy.

In another embodiment, Q is CN.

In another embodiment, said method comprising a selective androgen receptor modulator (SARM) compound of formula S-(III):

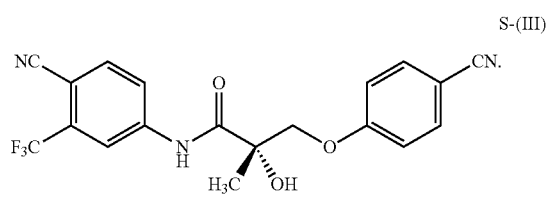 [SMILES: C[C@](O)(COc1ccc(C#N)cc1)C(=O)Nc1ccc(C#N)c(C(F)(F)F)c1]

S-(III)

In another embodiment, said subject suffers from non-small cell lung cancer. In another embodiment the subject suffers from colon cancer. In another embodiment the subject suffers from breast cancer. In another embodiment the subject suffers from non-Hodgkin's lymphoma. In another embodiment the subject suffers chronic lymphocytic leukemia. In another embodiment the subject suffers from lung cancer. In another embodiment, the lung cancer patient is subjected to a cancer therapy. In another embodiment, the lung cancer patient is subjected to radiation therapy. In another embodiment, the compound is administered in combination with radiation therapy. In another embodiment, the compound is administered in combination with a chemotherapeutic agent. In another embodiment, the chemotherapeutic agent comprises: bendamustine, bevacizumab, bleomycin, calcium folinate, capecitabine, carboplatin, cetuximab, chlorambucil, cisplatin, cyclophosphamide, cytarabine, dasatinib, docetaxel, doxorubicin, erlotinib, etoposide, fludarabine, fluorouracil, gemcitabine hydrochloride, irinotecan hydrochloride, lapatinib, methotrexate, methylprednisolone acetate, mitoxantrone, mitoxantrone hydrochloride, oxaliplatin, paclitaxel, pamidronate disodium, panitumumab, pemetrexed, prednisone, rituximab, trastuzumab, vincristine, vinorelbine or any combination thereof. In another embodiment, the chemotherapeutic agent comprises platinum and taxane. In another embodiment, the chemotherapeutic agent comprises platinum and non-taxane chemotherapeutic agent.

In another embodiment, said method further increases the survival of said subject. In another embodiment, said method further increases lean body mass of a subject.

In another embodiment, the loss of physical function is due to cancer or cancer therapy (radiation, chemotherapy, surgery).

In one embodiment, this invention provides a method of increasing the physical function of a subject suffering from cancer, comprising the step of administering to said subject a compound of this invention. In another embodiment, said method comprises administering a selective androgen receptor modulator (SARM) compound of formula II:

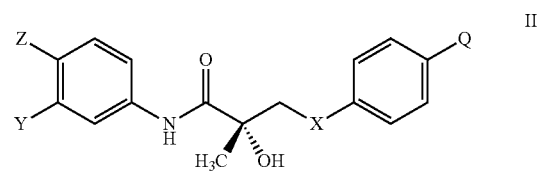

II wherein
X is O;
Z is NO₂, CN, COR, or CONHR;
Y is an alkyl, CF₃, CH₃, formyl, alkoxy, H, F, I, Br, Cl, or Sn(R)₃;
R is an alkyl, aryl, phenyl, alkenyl, haloalkyl, haloalkenyl, halogen or OH;
and
Q is alkyl, halogen, N(R)₂, CN, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, acetamido-, trifluoroacetamido-, alkylamines, ether, alkyl, N-sulfonyl, O-sulfonyl, alkylsulfonyl, carbonyl, or a ketone;
wherein said subject is subjected to cancer therapy.

In another embodiment, Q is CN.

In another embodiment, said method comprising administering a selective androgen receptor modulator (SARM) compound of formula S-(III):

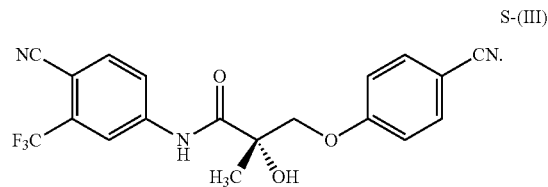

S-(III)

In another embodiment, said subject suffers from non-small cell lung cancer. In another embodiment the subject suffers from colon cancer. In another embodiment the subject suffers from breast cancer. In another embodiment the subject suffers from non-Hodgkin's lymphoma. In another embodiment the subject suffers chronic lymphocytic leukemia. In another embodiment the subject suffers from lung cancer. In another embodiment, the lung cancer patient is subjected to a cancer therapy. In another embodiment, the lung cancer patient is subjected to radiation therapy. In another embodiment, the compound is administered in combination with radiation therapy. In another embodiment, the compound is administered in combination with a chemotherapeutic agent. In another embodiment, the chemotherapeutic agent comprises: bendamustine, bevacizumab, bleomycin, calcium folinate, capecitabine, carboplatin, cetuximab, chlorambucil, cisplatin, cyclophosphamide, cytarabine, dasatinib, docetaxel, doxorubicin, erlotinib, etoposide, fludarabine, fluorouracil, gemcitabine hydrochloride, irinotecan hydrochloride, lapatinib, methotrexate, methylprednisolone acetate, mitoxantrone, mitoxantrone hydrochloride, oxaliplatin, paclitaxel, pamidronate disodium, panitumumab, pemetrexed, prednisone, rituximab, trastuzumab, vincristine, vinorelbine or any combination thereof. In another embodiment, the chemotherapeutic agent comprises platinum and taxane. In another embodiment, the chemotherapeutic agent comprises platinum and non-taxane chemotherapeutic agent. In another embodiment, said method further improves the quality of life of said subject. In another embodiment, said method further increases the survival of said subject. In another embodiment, said method further increases lean body mass of a subject.

In one embodiment, this invention provides a method of improving the quality of life of a subject suffering from cancer, comprising the step of administering to said subject a compound of this invention. In another embodiment, said method comprising administering a compound of this invention. In another embodiment, said method comprises administering a selective androgen receptor modulator (SARM) compound of formula II:

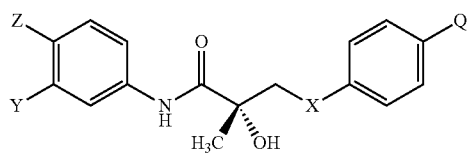

wherein
X is O;
Z is $NO_2$, CN, COR, or CONHR;
Y is an alkyl, $CF_3$, $CH_3$, formyl, alkoxy, H, F, 1, Br, Cl, or $Sn(R)_3$;
R is an alkyl, aryl, phenyl, alkenyl, haloalkyl, haloalkenyl, halogen or OH;
and
Q is alkyl, halogen, $N(R)_2$, CN, $NHCOCH_3$, $NHCOCF_3$, NHCOR, NHCONHR, NHCOOR, OCONHR. CONHR, $NHCSCH_3$, $NHCSCF_3$, NHCSR, $NHSO_2CH_3$, $NHSO_2R$, OR, COR, OCOR, $OSO_2R$, $SO_2R$, SR, acetamido-, trifluoroacetamido-, alkylamines, ether, alkyl, N-sulfonyl, O-sulfonyl, alkylsulfonyl, carbonyl, or a ketone;
wherein said subject is subjected to cancer therapy.
In another embodiment, Q is CN.
In another embodiment, said method comprising administering a selective androgen receptor modulator (SARM) compound of formula S-(III):

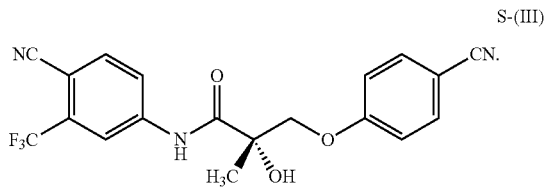 [SMILES: C[C@](O)(COc1ccc(C#N)cc1)C(=O)Nc1ccc(C#N)c(C(F)(F)F)c1]

In another embodiment, said subject suffers from non-small cell lung cancer. In another embodiment the subject suffers from colon cancer. In another embodiment the subject suffers from breast cancer. In another embodiment the subject suffers from non-Hodgkin's lymphoma. In another embodiment the subject suffers chronic lymphocytic leukemia. In another embodiment the subject suffers from lung cancer. In another embodiment, the lung cancer patient is subjected to a cancer therapy. In another embodiment, the lung cancer patient is subjected to radiation therapy. In another embodiment, the compound is administered in combination with radiation therapy. In another embodiment, the compound is administered in combination with a chemotherapeutic agent. In another embodiment, the chemotherapeutic agent comprises: bendamustine, bevacizumab, bleomycin, calcium folinate, capecitabine, carboplatin, cetuximab, chlorambucil, cisplatin, cyclophosphamide, cytarabine, dasatinib, docetaxel, doxorubicin, erlotinib etoposide, fludarabine, fluorouracil, gemcitabine hydrochloride, irinotecan hydrochloride, lapatinib, methotrexate, methylprednisolone acetate, mitoxantrone, mitoxantrone hydrochloride, oxaliplatin, paclitaxel, pamidronate disodium, panitumumab, pemetrexed, prednisone, rituximab, trastuzumab, vincristine, vinorelbine or any combination thereof. In another embodiment, the chemotherapeutic agent comprises platinum and taxane. In another embodiment, the chemotherapeutic agent comprises platinum and non-taxane chemotherapeutic agent. In another embodiment, said method further increases the survival of said subject. In another embodiment, said method further increases lean body mass of a subject.

Figure 19:
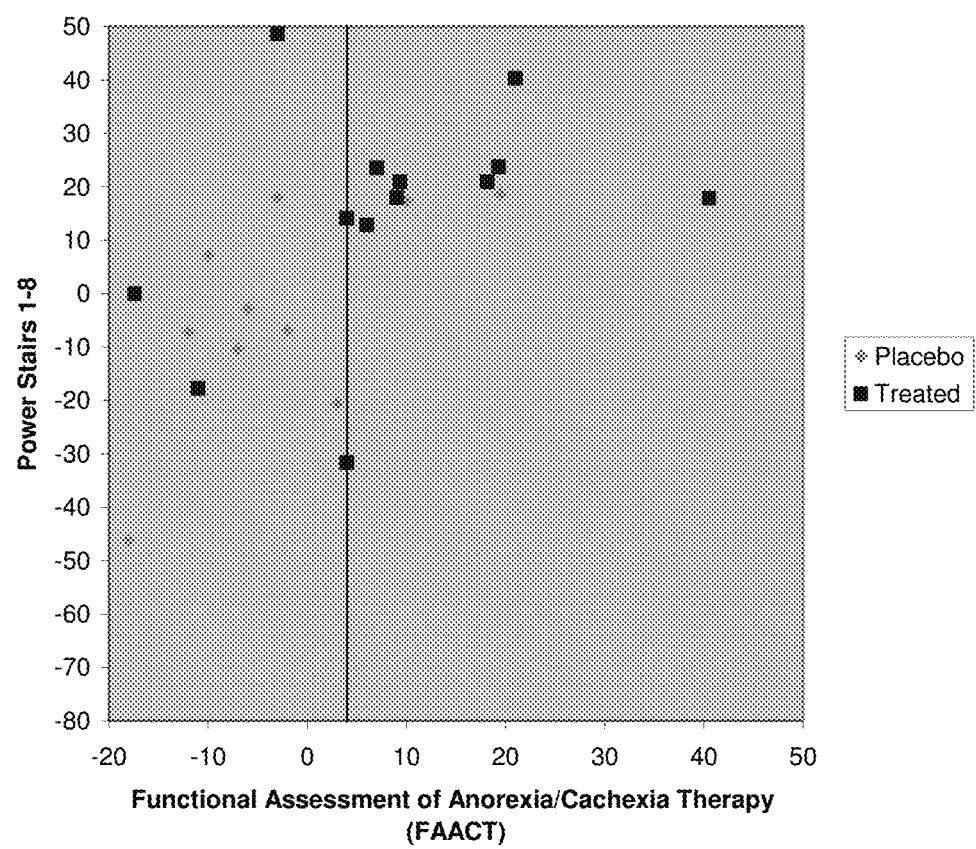
FIG. 19: Correlation between stair climb power and QoL per FAACT questionnaire in NSCLC patients.
Figure 35:
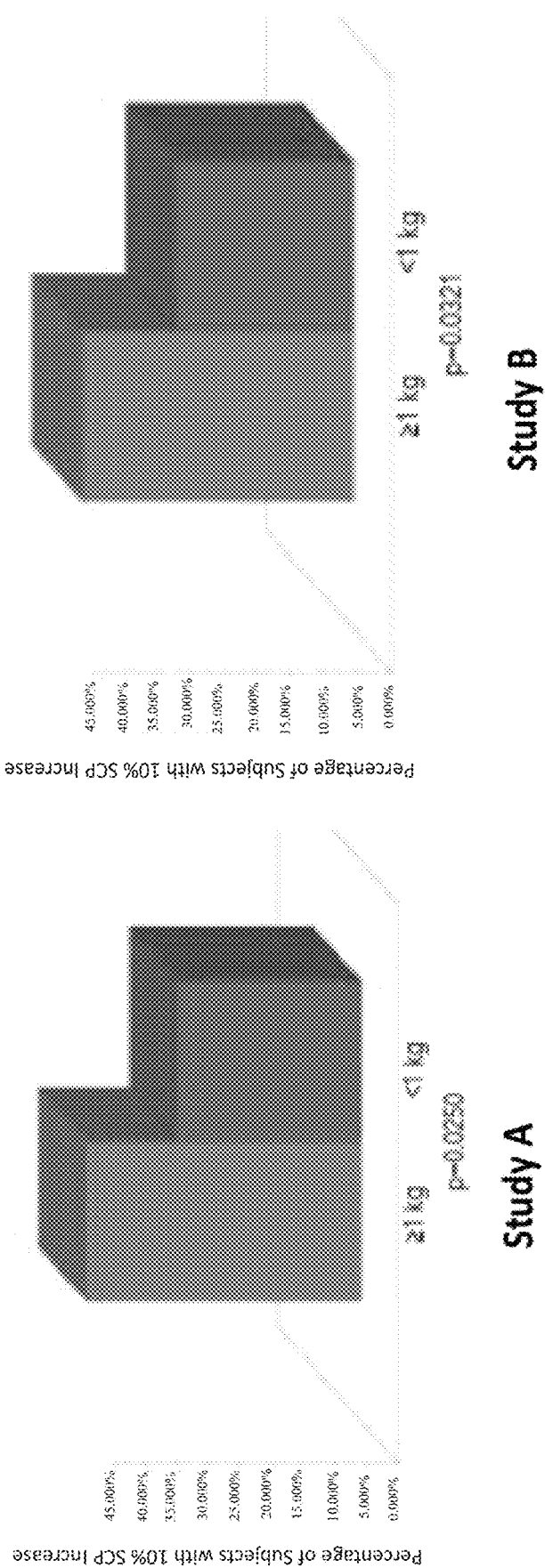
FIG. 35 depicts 10% SCP response by ≥1 kg LBM response in post-hoc analyses.
Figure 36:
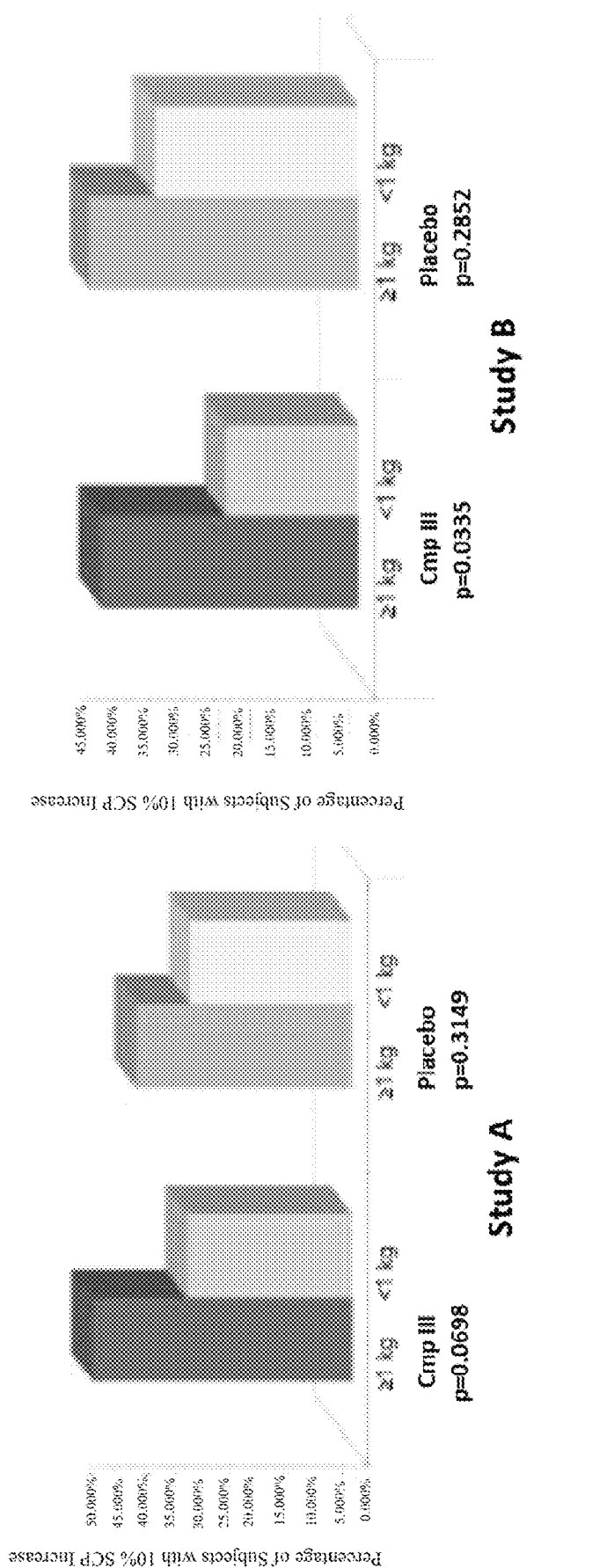
FIG. 36 depicts 10% SCP response by ARM by ≥1 kg LBM response in post-hoc analyses.

In one embodiment, this invention provide increase in the physical function of a subject suffering from cancer and increasing the quality of life of said subject as disclosed in Examples 11, 12, and 15 and in FIGS. 19, 35 and 36.

In one embodiment, this invention provides a method of increasing of the physical function of a subject. In another embodiment, said method further comprising an increase of the quality of life of said subject. In another embodiment, said subject suffers from non-small cell lung cancer. In another embodiment the subject suffers from colon cancer. In another embodiment the subject suffers from breast cancer. In another embodiment the subject suffers from non-Hodgkin's lymphoma. In another embodiment the subject suffers chronic lymphocytic leukemia. In another embodiment the subject suffers from lung cancer. In another embodiment, the lung cancer patient is subjected to a cancer therapy. In another embodiment, the lung cancer patient is subjected to radiation therapy. In another embodiment, said method further increases the survival of said subject with cancer.

In one embodiment, this invention is directed to increasing the survival of a subject that suffers from cancer.

The term "increase survival" refers to increase in the timespan or duration of time that a patient is alive following diagnosis or therapy for a disease, which may include a longer duration without disease progression or mortality.

In another embodiment, said subject suffers from non-small cell lung cancer. In another embodiment the subject suffers from colon cancer. In another embodiment the subject suffers from breast cancer. In another embodiment the subject suffers from non-Hodgkin's lymphoma. In another embodiment the subject suffers chronic lymphocytic leukemia. In another embodiment the subject suffers from lung cancer. In another embodiment, said method comprises using a compound of this invention. In another embodiment, said method comprises administering a compound of formula II. In another embodiment, said method comprises administering a compound of formula II in combination with a chemotherapeutic agent. In another embodiment, said method comprises administering a compound of formula II in combination with radiation therapy. In another embodiment, said method comprises administering a compound of formula S-(III). In another embodiment, said method comprises administering a compound of formula S-(III) in combination with a chemotherapeutic agent. In another embodiment, said method comprises administering a compound of formula S-(III) in combination with taxane and platinum. In another embodiment, said method comprises administering a compound of forma S-(III) in combination with platinum and non-taxane chemotherapeutic agents. In another embodiment, said method comprises administering a compound of formula S-(III) in combination with radiation therapy.

In one embodiment, the methods of this invention comprise administering a compound of this invention and/or its isomer, pharmaceutically acceptable salt, pharmaceutical product, hydrate, N-oxide, or any combination thereof; and a pharmaceutically acceptable carrier.

In one embodiment, the methods of this invention comprise administering a compound of this invention and/or its isomer, pharmaceutically acceptable salt, pharmaceutical product, hydrate, N-oxide, or any combination thereof, at least one chemotherapeutic agent, and a pharmaceutically acceptable carrier.

It is to be understood that any use of any of the SARMs as herein described can be used in the treatment of any disease, disorder or condition as described herein, and represents an embodiment of this invention.

The following examples are presented in order to more fully illustrate the preferred embodiments of the invention. They should in no way, however, be construed as limiting the broad scope of the invention.

EXAMPLE

Example 1

Synthesis of (S) Enantiomer of Compound of Formula S-(III)

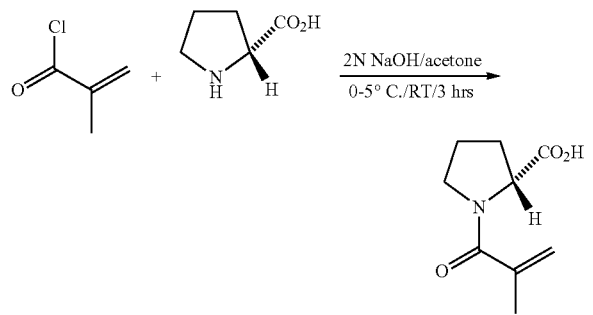

(2R)-1-Methacryloylpyrrolidin-2-carboxylic Acid

D-Proline, 14.93 g, 0.13 mol) was dissolved in 71 mL of 2 N NaOH and cooled in an ice bath; the resulting alkaline solution was diluted with acetone (71 mL). An acetone solution (71 mL) of methacryloyl chloride (13.56 g, 0.13 mol) and 2 N NaOH solution (71 mL) were simultaneously added over 40 min to the aqueous solution of D-proline in an ice bath. The pH of the mixture was kept at 10-11° C. during the addition of the methacryloyl chloride. After stirring (3 h, room temperature), the mixture was evaporated in vacuo at a temperature at 35-45° C. to remove acetone. The resulting solution was washed with ethyl ether and was acidified to pH 2 with concentrated HCl. The acidic mixture was saturated with NaCl and was extracted with EtOAc (100 mL×3). The combined extracts were dried over $Na_2SO_4$, filtered through Celite®, and evaporated in vacuo to give the crude product as a colorless oil. Recrystallization of the oil from ethyl ether and hexanes afforded 16.2 g (68%) of the desired compound as colorless crystals: mp 102-103° C. (lit. mp 102.5-103.5° C.); the NMR spectrum of this compound demonstrated the existence of two rotamers of the title compound. $^1$H NMR (300 MHz, DMSO-$d_6$) δ 5.28 (s) and 5.15 (s) for the first rotamer, 5.15 (s) and 5.03 (s) for the second rotamer (totally 2H for both rotamers, vinyl $CH_2$), 4.48-4.44 for the first rotamer, 4.24-4.20 (m) for the second rotamer (totally 1H for both rotamers, CH at the chiral canter), 3.57-3.38 (m, 2H, $CH_2$), 2.27-2.12 (1H, CH), 1.97-1.72 (m, 6H, $CH_2$, CH, Me); $^{13}$C NMR (75 MHz, DMSO-$d_6$) δ for major rotamer 173.3, 169.1, 140.9, 116.4, 58.3, 48.7, 28.9, 24.7, 19.5: for minor rotamer 174.0, 170.0, 141.6, 115.2, 60.3, 45.9, 31.0, 22.3, 19.7; IR (KBr) 3437 (OH), 1737 (C=O), 1647 (CO, COOH), 1584, 1508, 1459, 1369, 1348, 1178 cm$^{-1}$; $[\alpha]_D^{26}$ +80.8° (c=1, MeOH); Anal. Calcd. for $C_9H_{13}NO_3$: C, 59.00, H, 7.15, N, 7.65. Found: C, 59.13, H, 7.19, N, 7.61.

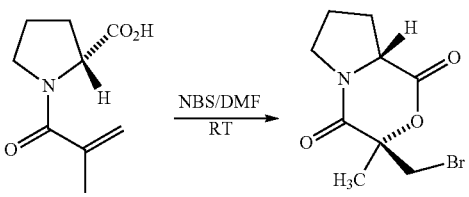

(3R,8aR)-3-Bromomethyl-3-methyl-tetrahydro-pyrrolo[2,1-c][1,4]oxazine-1,4-dione

A solution of NBS (23.5 g, 0.132 mol) in 100 mL of DMF was added dropwise to a stirred solution of the (methylacryloyl)-pyrrolidine (16.1 g, 88 mmol) in 70 mL of DMF under argon at room temperature, and the resulting mixture was stirred 3 days. The solvent was removed in vacuo, and a yellow solid was precipitated. The solid was suspended in water, stirred overnight at room temperature, filtered, and dried to give 18.6 g (81%) (smaller weight when dried ~34%) of the title compound as a yellow solid: mp 152-154° C.; $^1$H NMR (300 MHz, DMSO-$d_6$) δ 4.69 (dd, J=9.6 Hz, J=6.7 Hz, 1H, CH at the chiral center), 4.02 (d, J=11.4 Hz, 1H, CHH$_a$), 3.86 (d, J=11.4 Hz, 1H, CHH$_b$), 3.53-3.24 (m, 4H, $CH_2$), 2.30-2.20 (m, 1H, CH), 2.04-1.72 (m, 3H, $CH_2$ and CH), 1.56 (s, 2H, Me); $^{13}$C NMR (75 MHz, DMSO-$d_6$) δ 167.3, 163.1, 83.9, 57.2, 45.4, 37.8, 29.0, 22.9, 21.6; IR (KBr) 3474, 1745 (C=O), 1687 (C=O), 1448, 1377, 1360, 1308, 1227, 1159, 1062 cm$^{-1}$; $[\alpha]_D^{26}$ +124.5° (c=1.3, chloroform); Anal. Calcd. for $C_9H_{12}BrNO_3$: C, 41.24, H, 4.61, N, 5.34. Found: C, 41.46, H, 4.64, N, 5.32.

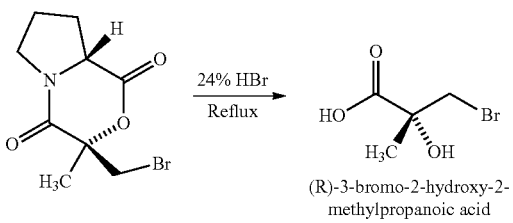

(2R)-3-Bromo-2-hydroxy-2-methylpropanoic Acid

A mixture of bromolactone (18.5 g, 71 mmol) in 300 mL of 24% HBr was heated at reflux for 1 h. The resulting solution was diluted with brine (200 mL), and was extracted with ethyl acetate (100 mL×4). The combined extracts were washed with saturated NaHCO$_3$ (100 mL×4). The aqueous solution was acidified with concentrated HCl to pH=1, which, in turn, was extracted with ethyl acetate (100 mL×4). The combined organic solution was dried over Na$_2$SO$_4$, filtered through Celite®, and evaporated in vacuo to dryness. Recrystallization from toluene afforded 10.2 g (86%) of the desired compound as colorless crystals: mp 107-109° C.; $^1$H NMR (300 MHz, DMSO-d$_6$) δ 3.63 (d, J=10.1 Hz, 1H, CHH$_a$), 3.52 (d, J=10.1 Hz, 1H, CHH$_b$), 1.35 (s, 3H, Me); IR (KBr) 3434 (OH), 3300-2500 (COOH), 1730 (C=O), 1449, 1421, 1380, 1292, 1193, 1085 cm$^{-1}$; [α]$_D^{26}$ +10.5° (c=2.6, MeOH); Anal. Calcd. for C$_4$H$_7$BrO$_3$: C, 26.25, H, 3.86. Found: C, 26.28, H, 3.75.

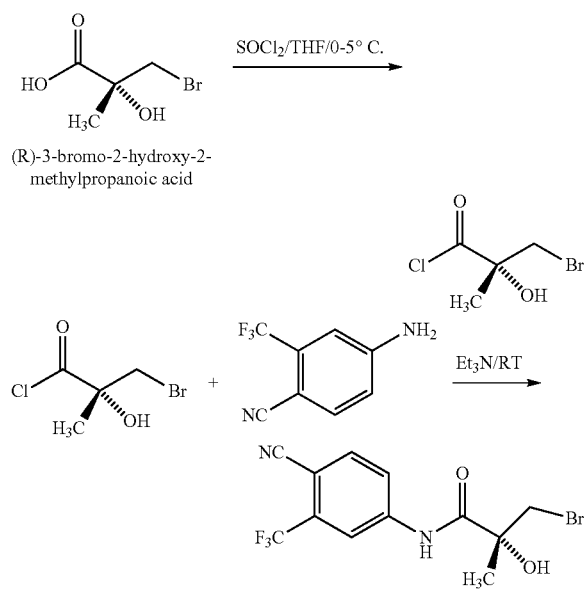

Synthesis of (2R)-3-Bromo-N-[4-cyano-3-(trifluoromethyl)phenyl]-2-hydroxy-2-methylpropanamide Thionyl chloride (46.02 g, 0.39 mol) was added dropwise to a cooled solution (less than 4° C.) of (R)-3-bromo-2-hydroxy-2-methylpropanoic acid (51.13 g, 0.28 mol) in 300 mL of THF under an argon atmosphere. The resulting mixture was stirred for 3 h under the same condition. To this was added Et$_3$N (39.14 g, 0.39 mol) and stirred for 20 min under the same condition. After 20 min, 5-amino-2-cyanobenzotrifluoride (40.0 g, 0.21 mol), 400 mL of THF were added and then the mixture was allowed to stir overnight at room temperature. The solvent was removed under reduced pressure to give a solid which was treated with 300 mL of H$_2$O, extracted with EtOAc (2×400 mL). The combined organic extracts were washed with saturated NaHCO$_3$ solution (2×300 mL) and brine (300 mL). The organic layer was dried over MgSO$_4$ and concentrated under reduced pressure to give a solid which was purified from column chromatography using CH$_2$Cl$_2$/EtOAc (80:20) to give a solid. This solid was recrystallized from CH$_2$Cl$_2$/hexane to give 55.8 g (73.9%) of (2R)-3-bromo-N-[4-cyano-3-(trifluoromethyl) phenyl]-2-hydroxy-2-methylpropanamide as a light-yellow solid.

$^1$H NMR (CDCl$_3$/TMS) δ 1.66 (s, 3H, CH$_3$), 3.11 (s, 1H, OH), 3.63 (d, J=10.8 Hz, 1H, CH$_2$), 4.05 (d, J=10.8 Hz, 1H, CH$_2$), 7.85 (d, J=8.4 Hz, 1H, ArH), 7.99 (dd, J=2.1, 8.4 Hz, 1H, ArH), 8.12 (d, J=2.1 Hz, 1H, ArH), 9.04 (bs, 1H, NH). Calculated Mass: 349.99, [M-H]$^-$ 349.0. M.p.: 124-126° C.

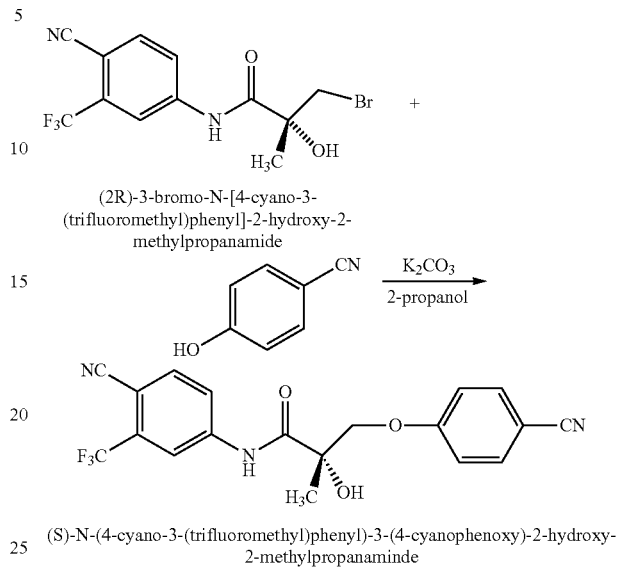

Synthesis of (S)—N-(4-Cyano-3-(trifluoromethyl) phenyl)-3-(4-cyanophenoxy)-2-hydroxy-2-methyl-propanamide A mixture of bromoamide ((2R)-3-bromo-N-[4-cyano-3-(trifluoromethyl)phenyl]-2-hydroxy-2-methylpropanamide, 50 g, 0.14 mol), anhydrous K$_2$CO$_3$ (59.04 g, 0.43 mol), 4-cyanophenol (25.44 g, 0.21 mol) in 500 mL of 2-propanol was heated to reflux for 3 h and then concentrated under reduced pressure to give a solid. The resulting residue was treated with 500 mL of H$_2$O and then extracted with EtOAc (2×300 mL). The combined EtOAc extracts were washed with 10% NaOH (4×200 mL) and brine. The organic layer was dried over MgSO$_4$ and then concentrated under reduced pressure to give an oil which was treated with 300 mL of ethanol and an activated to carbon. The reaction mixture was heated to reflux for 1 h and then the hot mixture was filtered through Celite®. The filtrate was concentrated under reduced pressure to give an oil. This oil was purified by column chromatography using CH$_2$Cl$_2$/EtOAc (80:20) to give an oil which was crystallized from CH$_2$Cl$_2$/hexane to give 33.2 g (59.9%) of (S)—N-(4-cyano-3-(trifluoromethyl) phenyl)phenyl)-3-(4-cyanophenoxy)-2-hydroxy-2-methyl-propanamide as a colorless solid (a cotton type).

$^1$H NMR (CDCl$_3$/TMS) δ 1.63 (s, 3H, CH$_3$), 3.35 (s, 1H, CH$_3$), 4.07 (d, J=9.04 Hz, 1H, CH), 4.51 (d, J=9.04 Hz, 1H, CH), 6.97-6.99 (m, 2H, ArH), 7.57-7.60 (n, 2H, ArH), 7.81 (d, J=8.55 Hz, 1H, ArH), 7.97 (dd, J=1.95, 8.55 Hz, 1H, ArH), 8.12 (d, J=1.95 Hz, 1H, ArH), 9.13 (bs, 1H, NH). Calculated Mass: 389.10, [M-H]$^-$ 388.1. Mp: 92-94° C.

Example 2

Androgenic & Anabolic Activity of Compound of Formula S-(III) in Intact and Orchidectomized (ORX) Rat Subjects Materials and Methods Male Sprague-Dawley rats weighing approximately 200 g were purchased from Harlan Bioproducts for Science (Indianapolis, Ind.). The animals were maintained on a 12 h light/dark cycle with food (7012C LM-485 Mouse/Rat Sterilizable Diet, Harlan Teklad, Madison, Wis.) and water available ad libitum. The animal protocol was reviewed and approved. Anabolic and androgenic activity of Compound of Formula S-(III) in intact animals was evaluated and also compared to oxandrolone, and the dose response in acutely orchidectomized (ORX) animals was evaluated as well. Regenerative effects of Compound S-(III) in chronically (9 days) ORX rats were also assessed.

The compound was weighed and dissolved in 10% DMSO (Fischer) diluted with PEG 300 (Acros Organics, NJ) for preparation of the appropriate dosage concentrations. The animals were housed in groups of 2 to 3 animals per cage. Intact and ORX animals were randomly assigned to one of seven groups consisting of 4 to 5 animals per group. Control groups (intact and ORX) were adminstered vehicle daily. Compound of formula S-(III) was administered via oral gavage at doses of 0.01, 0.03, 0.1, 0.3, 0.75, and 1 mg/day to both intact and ORX groups.

Castrated animals (on day one of the study) wee randomly assigned to dose groups (4-5 animals/group) of 0.01, 0.03, 0.1, 0.3, 0.75, and 1 mg/day, for dose-response evaluation. Dosing began nine days post ORX and was administered daily via oral gavage for fourteen days. The animals were sacrificed under anesthesia (ketamine/xylazine, 87:13 mg/kg) after a 14-day dosing regimen, and body weighs wee recorded. In addition, ventral prostate, seminal vesicles, and levator ani muscle were removed, individually weighed, normalized to body weight, and expressed as a percentage of intact control Student's T-test was used to compare individual dose groups to the intact control group. Significance was defined a priori as a P-value <0.05. As a measure of androgenic activity, ventral prostate and seminal vesicle weights were evaluated, whereas levator ani muscle weight was evaluated as a measure of anabolic activity. Blood was collected from the abdominal aorta, centrifuged, and sera were frozen at −80° C. prior to determination of serum hormone levels. Serum luteinizing hormone (LH) and follicle stimulating hormone (FSH) concentrations wee determined.

Results

Prostate weighs of intact rats following compound of formula S-(III) (Compound III) treatment were 111%±21%, 88%±15%, 77%±17%, 71%±16%, 71%±10%, and 87%±13% of intact controls following doses of 0.01, 0.03, 0.1, 0.3, 0.75, and 1 mg/day, respectively (FIG. 1). Similarly, seminal vesicle weights of intact rats following Compound III treatment were decreased to 94%±9%, 77%±11%, 80%±9%, 73%±12%, 77%±10%, and 88%±14% of intact controls following doses of 0.01, 0.03, 0.1, 0.3, 0.75, and 1 mg/day, respectively (FIG. 1). Significant increases were seen in levator an muscle weights of sham animals, however, in all dose groups, when compared to intact controls. Levator ani in intact rats following Compound III treatment were 120%±12%, 116%±7%, 128%±7%, 134%±7%, 125%±9%, and 146%±17% of intact controls for the 0.01, 0.03, 0.1, 0.3, 0.75, and 1.0 mg/day doses, respectively (FIG. 1).

Compound III exhibited anabolic muscle/prostate ratio in castrated rats of 7.56, 4.28, 2.21, 2.19, 1.57 and 1.75 following doses of 0.01, 0.03, 0.1, 0.3, 0.75 and 1 mg/day, respectively.

Compound III partially maintained prostate weight following orchidectomy. Prostate weight in vehicle treated-ORX controls decreased to 5%±1% of intact controls. At doses of 0.01, 0.03, 0.1, 03, 0.75, and 1.0 mg/day, Compound III maintained prostate weights at 8%±2%, 20%±5%, 51%±19%, 56%±9%, 80%±28%, and 74±12.5% of intact controls, respectively (FIG. 2).

Compound III partially maintained seminal vesicle weights in ORX animals, as well. While in castrated controls, seminal vesicle weight decreased to 13%±2% of intact controls, Compound III treated animal weighs were 12%±4%, 17%±5%, 35%±10%, 61%±15%, 70%±14%, and 80%±6% of intact controls, following doses of 0.01, 0.03, 0.1, 0.3, 0.75, and 1.0 mg/day, respectively (FIG. 2).

Figure 2:
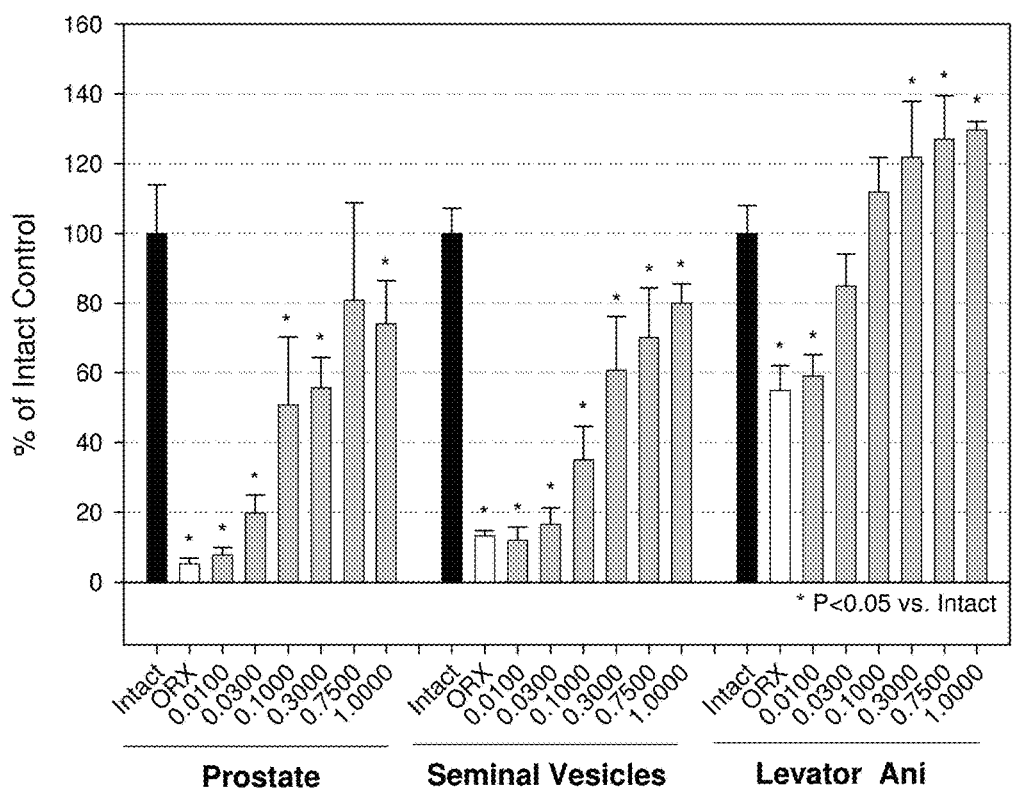
FIG. 2: Organ weights from castrated, compound of formula S-(III)-treated rats presented as a percentage of intact control. * P-value <0.05 versus intact controls.

In ORX controls the levator ani muscle weight decreased to 55%±7% of intact controls, while Compound III treated animals fully maintained and increased levator ani muscle weights at doses >0.1 mg/day, with observed muscle weights of 59%±6%, 85%±9%, 112%±10%, 122%±16%, 127±12%, and 130±2% of intact control weights for the 0.01, 0.03, 0.1, 03, 0.75, and 1.0 mg/day dose groups, respectively (FIG. 2).

Pharmacology results following 1 mg/day of Compound III exhibited that prostate weight was 87%±13% of intact control and levator ani muscle weight was 146%±17% of intact control Compound III at 1 mg/day maintained prostate weight following orchidectomy at 74±12.5% of intact controls and levator ani muscle weight at 130±2% of intact controls. 0.1 mg/day of Compound III restored 112% of levator ani muscle weight, while 51±20% of prostate weight was restored.

Figure 3:
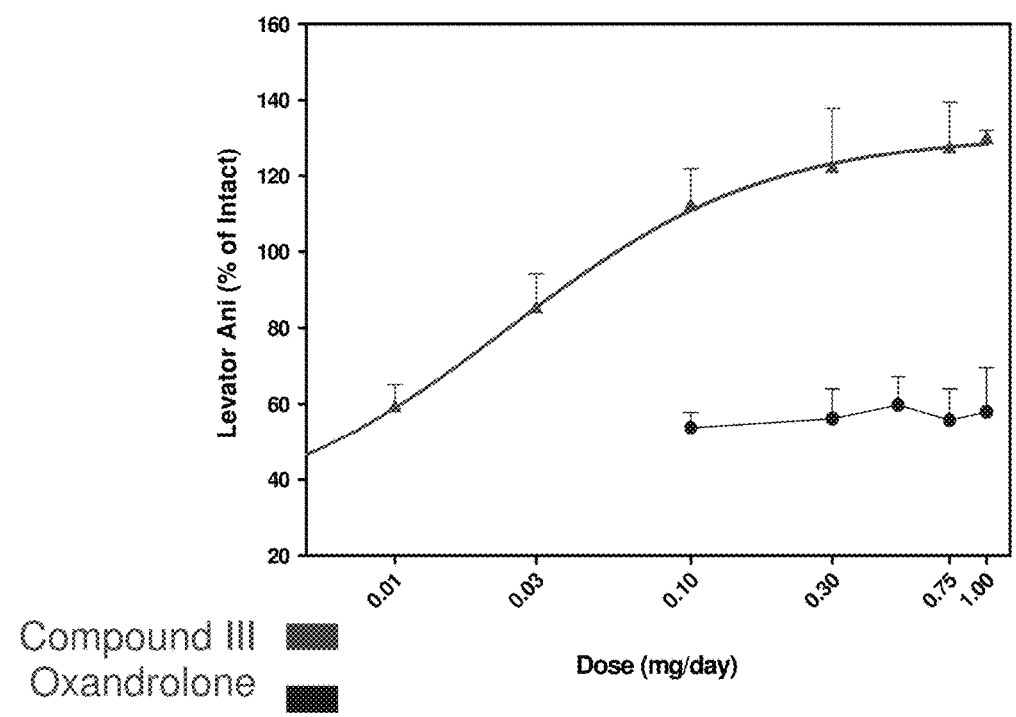
FIG. 3: Organ weight maintenance dose-response curves for compound of formula S-(III) in castrated rats compared to oxandrolone.

Oxandrolone treatment of ORX animals, was less anabolic than Compound III, with levator ani weights being 50% of intact controls, and not dosage dependent when administered at 0.1-1 mg/day (FIG. 3).

Figure 4:
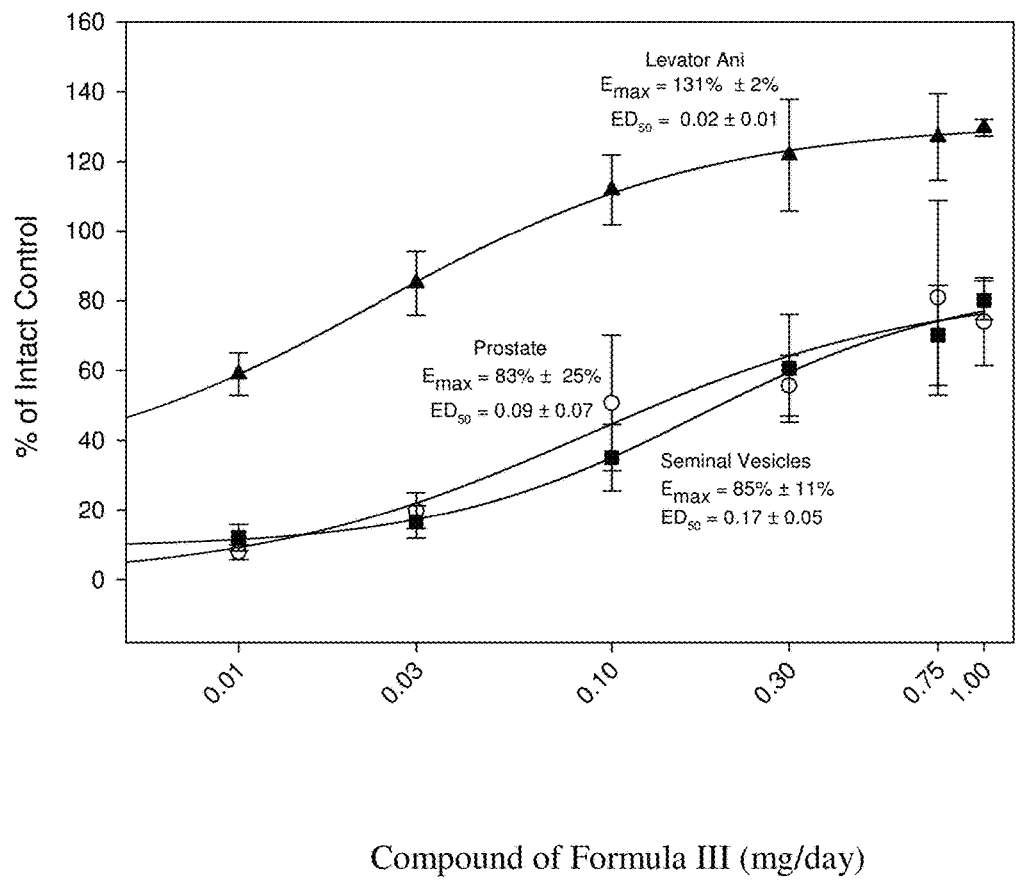
FIG. 4: Organ weight maintenance dose-response curves for compound of formula S-(III) in castrated rats. $E_{max}$ and $ED_{50}$ values for the levator ani (closed triangles), prostate (open circles), and seminal vesicles (closed squares) were obtained by nonlinear regression analysis using the sigmoid $E_{max}$ model in WinNonlin®.

$E_{max}$ and $ED_{50}$ were determined in each tissue by nonlinear regression analysis in WinNonlin® and presented in FIG. 4. $E_{D50}$ indicates the dose of Compound III resulting in 50% of the maximal response, which is the $E_{max}$. $E_{max}$ values were 83%±25%, 85%±11%, and 131%±2% for prostate, seminal vesicles, and levator ani, respectively. The $ED_{50}$ in prostate, seminal vesicles, and levator ani was 0.09±0.07, 0.17±0.05, and 0.02±0.01 mg/day, respectively.

Serum Hormone Analysis

Serum LH and FSH concentrations for the animals are presented in Table 1. LH decreased in a dose-dependent manner in both intact and castrated animals, as a function of treatment with the compound. Following doses >0.1 mg/day, LH levels were below the limit of quantitation (0.07 ng/mL). The 0.1 mg/day dose in ORX animals returned LH levels back to those seen in intact controls. Similar effects were observed with FSH. In intact animals, a significant decrease in FSH levels was observed with the 0.75 and 1 mg/day doses. In ORX animals, a dose-dependent decrease in FSH levels was observed. Doses of Compound of formula S-(III) (Compound III) >0.1 mg/day in ORX animals returned FSH levels to those of intact controls.

TABLE 1

Serum LH and FSH levels from animals in Arm 1 and Arm 2.

| Compound III (mg/day) | Luteinizing Hormone | | Follicle Stimulating Hormone | |
|---|---|---|---|---|
| | Intact (ng/ml) | ORX (ng/ml) | Intact (ng/ml) | ORX (ng/ml) |
| Vehicle | $0.281 \pm 0.126^b$ | $9.66 \pm 1.13^a$ | $6.40 \pm 1.58^b$ | $43.45 \pm 4.97^a$ |
| 0.01 | $0.195 \pm 0.106^b$ | $8.45 \pm 2.44^a$ | $5.81 \pm 0.31^b$ | $36.23 \pm 7.75^a$ |
| 0.03 | $0.176 \pm 0.092^b$ | $4.71 \pm 1.72^{a,b}$ | $5.74 \pm 0.78^b$ | $40.15 \pm 3.33^a$ |
| 0.1 | $0.177 \pm 0.058^b$ | $0.778 \pm 0.479^b$ | $6.60 \pm 1.06^b$ | $20.69 \pm 3.52^{a,b}$ |
| 0.3 | <LOQ | <LOQ | $5.32 \pm 1.80^b$ | $8.73 \pm 2.25^b$ |
| 0.75 | <LOQ | <LOQ | $4.30 \pm 0.62^{a,b}$ | $7.19 \pm 1.11^b$ |
| 1 | <LOQ | <LOQ | $4.38 \pm 0.42^{a,b}$ | $6.33 \pm 0.70^b$ |

[a] $P < 0.05$ vs. Intact Controls.
[b] $P < 0.05$ vs. ORX Controls.
LOQ—limit of quantitation.

Androgenic & Anabolic Activity Following Delayed Dosing

Figure 5:
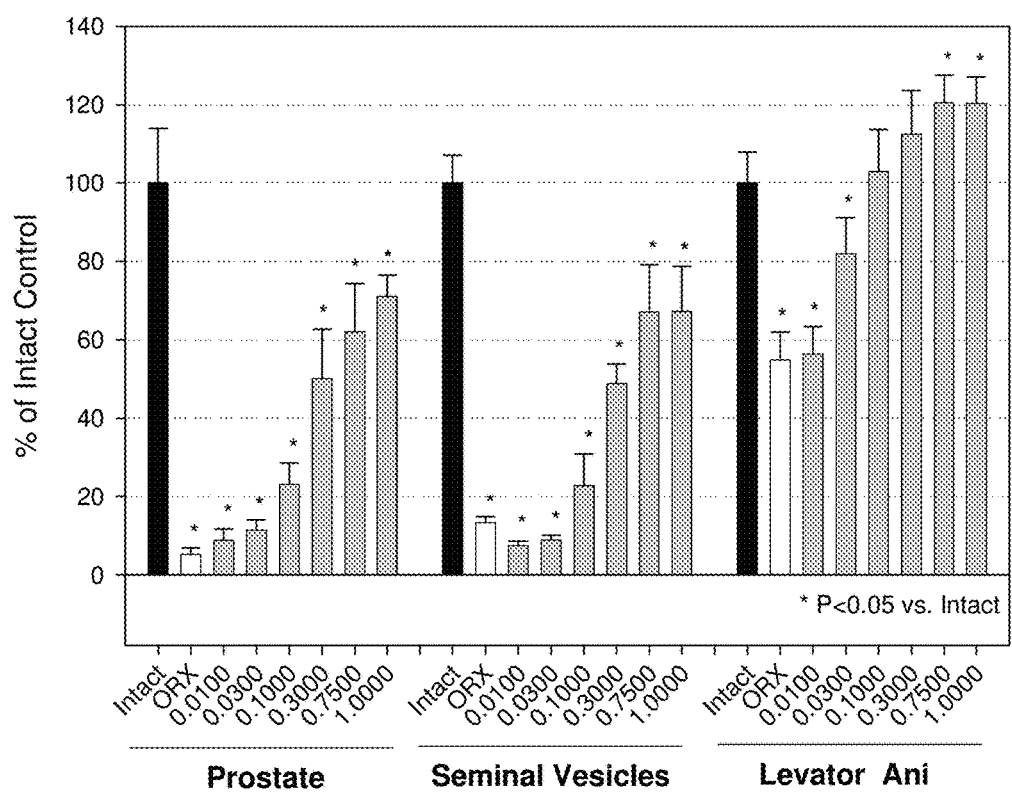
FIG. 5: Organ weights from castrated rats after delayed dosing of compound of formula S-(III) presented as a percentage of intact control. * P-value <0.05 versus intact controls.
Figure 6:
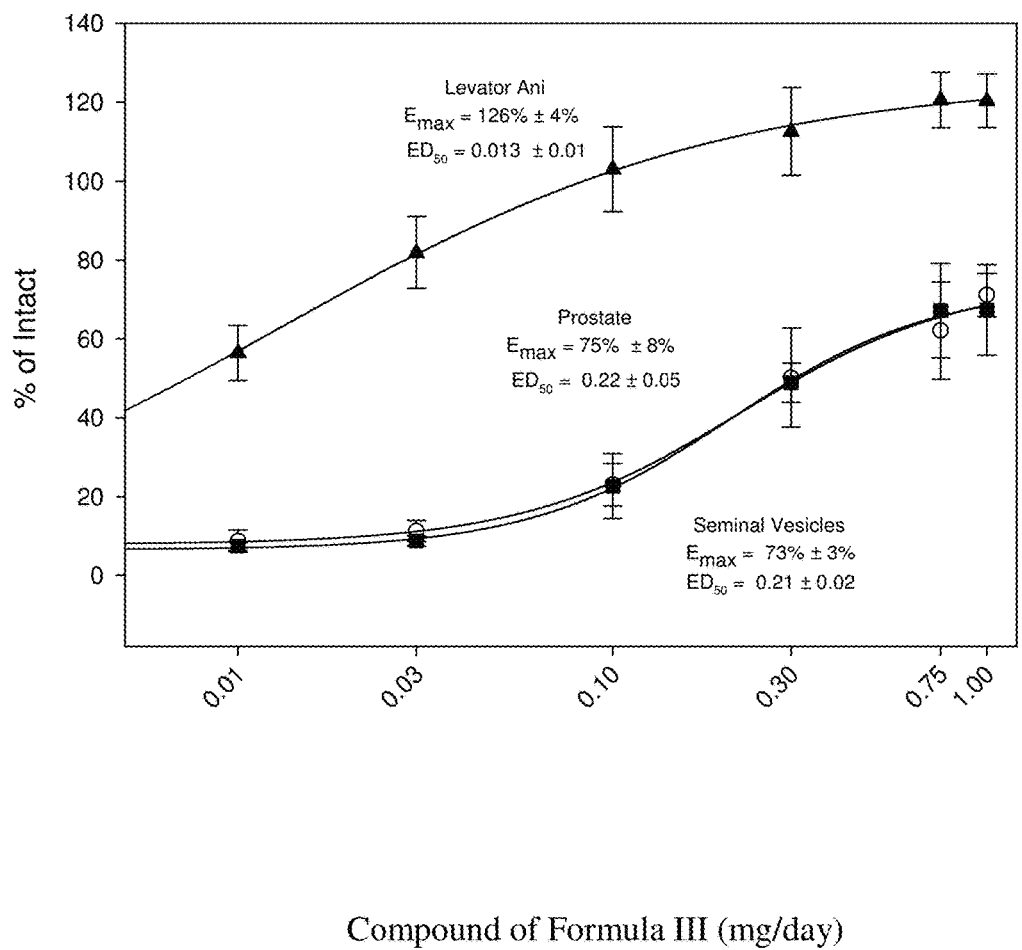
FIG. 6: Organ weight regrowth dose-response curves following delayed dosing of compound of formula S-(III) in castrated rats. $E_{max}$ and $ED_{50}$ values for the levator ani (closed triangles), prostate (open circles), and seminal vesicles (closed squares) were obtained by nonlinear regression analysis using the sigmoid $E_{max}$ model in WinNonlin®.

After a delay of 9 days following orchidectomy (chronically castrated rats), Compound of formula S-(III) (Compound III) partially restored both prostate and seminal vesicle weight in ORX animals. Prostate weights were restored to 9%±3%, 11%±3%, 23%±5%, 50%±13%, 62%±12%, and 71%±5%, while seminal vesicle weights were restored 7%±1%, 9%±1%, 23%±8%, 49%±5%, 67%±12%, and 67%±11% of intact controls for 0.01, 0.03, 0.1, 0.3, 0.75, and 1.0 mg/day dose groups, respectively. Compound III fully restored levator ani muscle weight at doses >0.1 mg/day. Levator ani muscle weights were restored to 56%±7%, 82%±9%, 103%±11%, 113%±11%, 121%±7%, and 120%±7% corresponding to doses of 0.01, 0.03, 0.1, 0.3, 0.75, and 1.0 mg/day, respectively. Results are presented graphically in FIG. 5. $E_{max}$ and $ED_{50}$ values were determined in each tissue by nonlinear regression analysis in WinNonlin® and presented in FIG. 6. $E_{max}$ values were 75%±8%, 73%±3%, and 126%±4% for prostate, seminal vesicles, and levator ani, respectively. The $ED_{50}$ in prostate, seminal vesicles, and levator ani was 0.22±0.05, 0.21±0.02, and 0.013±0.01 mg/day, respectively.

Example 3

SARM Reduction of Cholesterol Levels

Materials and Methods

One hundred Sprague Dawley rats (50 male and 50 female) were divided into five groups (n=10 per gender per group), representing vehicle only (PEG300:40% Cavasol® [75/25 (v/v)]), and four dose groups of Compound of formula S-(III) (Compound III). Animals were administered Compound III once daily by oral gavage according to their most recent body weight with doses of either 0, 3, 10, 30 or 100 mg/kg. During the study period, rats had access to water and a standard laboratory diet of Harlan Taklad Rodent Chow ad libitum. After 28 consecutive days of dosing, animals were fasted overnight, blood samples were collected and serum was obtained. Serum levels of total cholesterol were determined using an automated laboratory assay method.

Results

Figure 7:
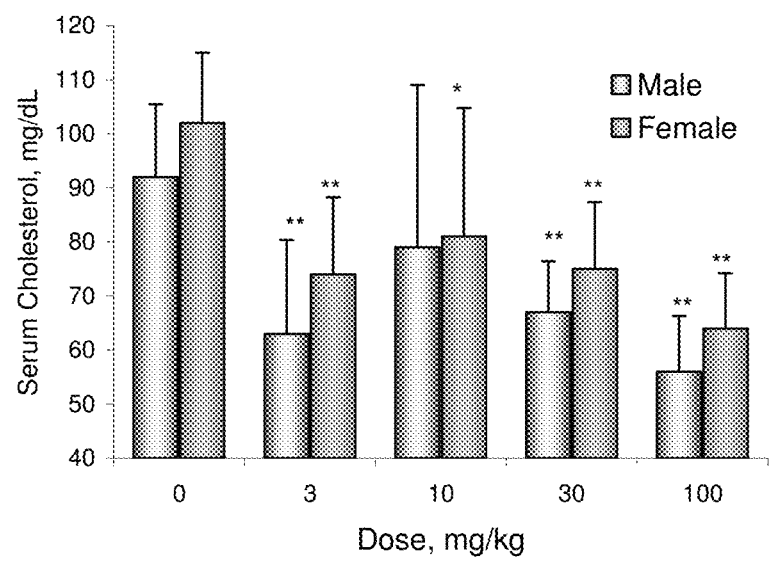
FIG. 7: Cholesterol reduction by compound of formula S-(III) in rats.

The male and female rats in the vehicle only group (0 mg/kg) had serum total cholesterol values of 92±13.5 and 102±13 mg/dL respectively. These values are considered within the normal historical range for the testing laboratory. Daily oral doses of Compound III at or above 3 mg/kg caused a significant reduction in total cholesterol levels in both male and female rats. At 3 mg/kg, compared to vehicle control animals, an approximate 30% reduction in total cholesterol was noted where males and females had 63±17.4 and 74±14.2 mg/dL respectively. Although a slightly greater effect was noted at the highest dose group (100 mg/kg per day), in general, a dose-response relationship was not observed in the reduction of total cholesterol levels in the Sprague Dawley rat. Results are presented graphically in FIG. 7.

Example 4

SARM Promotion of Lean Mass and Reduction of Fat Mass in Human Clinical Trials Five groups of 24 human subjects per group (12 males and 12 females) of 60 elderly men (age >60) and 60 postmenopausal women (not hypogonadal, not osteoporotic, no exercise program, no controlled diet) were dosed each in a randomized, double-blind study design. Each subject received 0.1 mg, 0.3 mg, 1 mg, or 3 mg Compound III (or placebo of equal volume) in solution or in experimental capsules for 90 days treatment. Total lean body mass (DEXA=dual energy x-ray absorptiometry), fat mass and performance were analyzed.

Results

Total Lean Mass (DEXA) Effects

Figure 8:
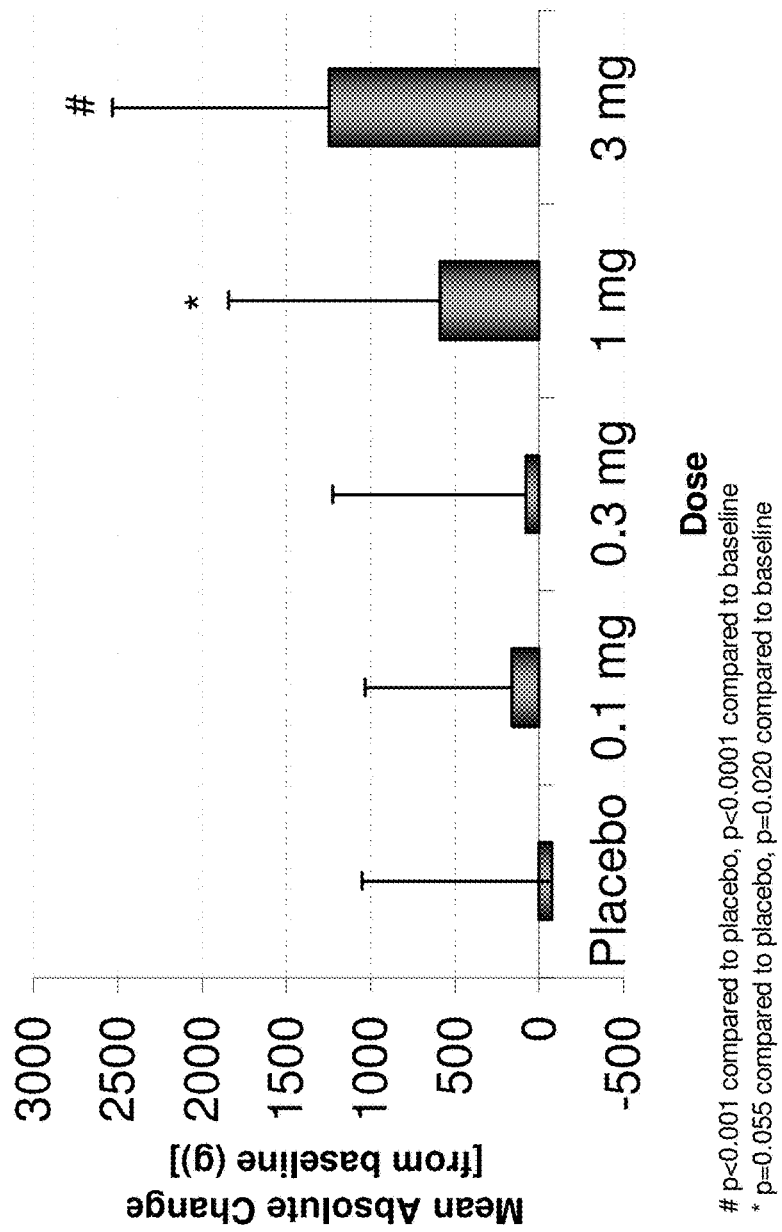
FIG. 8: Total lean mass increase of all subjects with 0.1 mg, 0.3 mg, 1 mg, and 3 mg dose of Compound S-(III).

All subjects (average age=64 years)(n=114) exhibited a dose-dependent increase in Lean Body Mass (LBM) following treatment with 0.1 rag, 0.3 mg, 1 mg and 3 mg of Compound of formula S-(III) (Compound III) (FIG. 8).

Treatment with 3 mg Compound III exhibited LBM increase of about 3.1±3.4% compared to baseline with a p<0.0001 (ANOVA). The 1 mg dose of Compound III exhibited an increase of 1.3±2.7% compared to baseline with a p=0.020 (ANOVA) (Table 2).

TABLE 2

|  | Placebo | 0.1 mg | 0.3 mg | 1 mg | 3 mg |
|---|---|---|---|---|---|
| Baseline Mean ± SD (g) | 44615 ± 96.7 | 46400 ± 9350 | 45258 ± 10103 | 48154 ± 10590 | 45031 ± 10255 |
| Mean absolute change from baseline ± SD (g) | −73.2 ± 1126.8 | 164.0 ± 868.2 | 78.0 ± 1150.3 | 588.7 ± 1257.5 | 1246.3 ± 1288.0 |
| p-value (compared to placebo) |  | 0.474 | 0.651 | 0.055 | <0.001 |
| p-value (compared to baseline) | 0.754 | 0.838 | 0.741 | 0.020 | <0.0001 |
| Mean % change from baseline ± SD | 0.1 ± 2.7 | 0.3 ± 2.0 | 0.4 ± 2.7 | 1.3 ± 2.7 | 3.1 ± 3.4 |

Females (average age 63 years)(n=56) exhibited a dose-dependent increase in LBM when administered a 3 mg dose of Compound III, with an increase of 1.7 kg compared to baseline and an increase of 1.4 kg compared to placebo with a p=0.02 (ANOVA). Females administered the 1 mg dose of Compound III exhibited an increase of 0.4 kg compared to baseline and no changes compared to placebo with a p=0.884 (ANOVA).

Males (Average age 66 years) (n=58) exhibited a dose-dependent increase in LBM when administered a 1 mg dose of Compound III, with an increase of 0.7 kg compared to baseline and an increase of 1.2 kg compared to placebo with a p=0.03 (ANOVA). Males administered the 3 mg dose of Compound III exhibited an increase of 1 kg compared to baseline and an increase of 1.4 kg compared to placebo with a p=0.005 (ANOVA).

Fat Mass (DEXA) Effects

Figure 9:
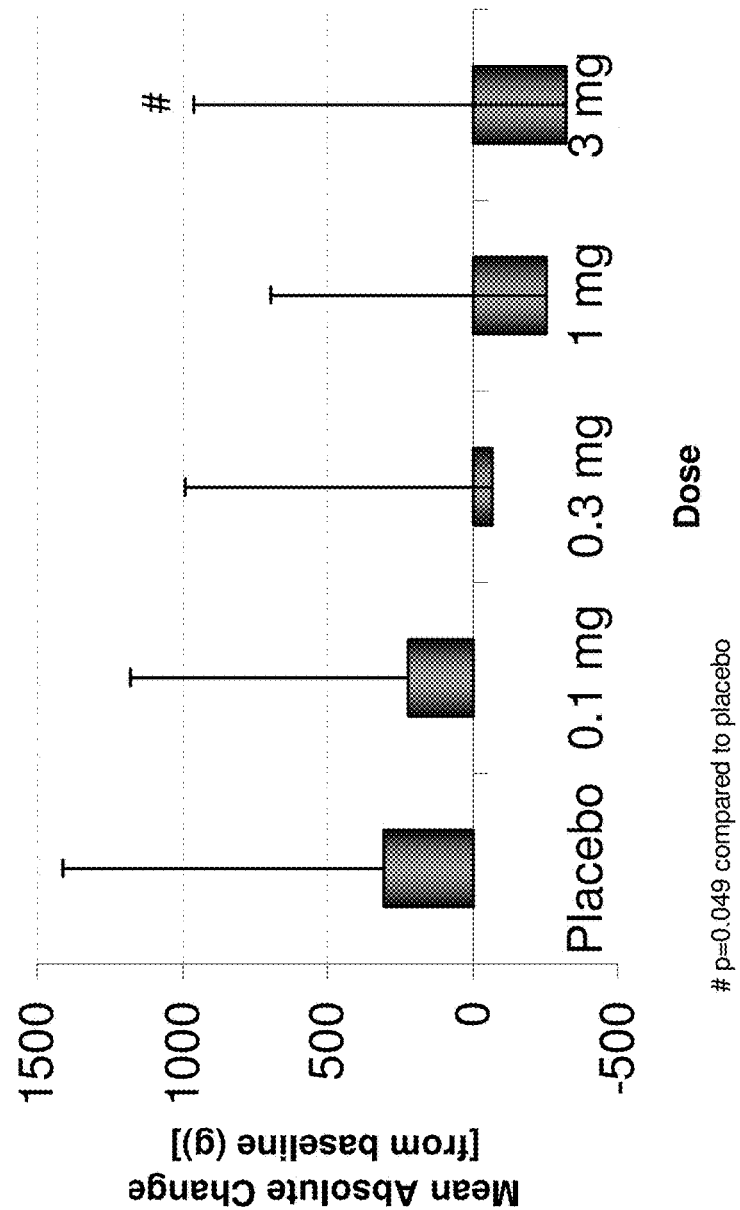
FIG. 9: Total fat mass change of all subjects with 01 mg, 0.3 nag, 1 mg, and 3 mg dose of Compound S-(III).

All subjects exhibited a dose-dependent decrease in total fat for the 0.3 mg, 1 mg and 3 mg doses of Compound III with p=0.242, 0.085 and 0.049 respectively. All subjects exhibited an increase in fat mass for the 0.1 mg (FIG. 9). At 3 mg, the loss was 0.6 kg compared to placebo and 0.3 kg (0.4%) from baseline with a p=0.049 (Table 3).

TABLE 3

|  | Placebo (gr) | 0.1 mg (gr) | 0.3 mg (gr) | 1 mg (gr) | 3 mg (gr) |
|---|---|---|---|---|---|
| Baseline Mean ± SD (g) | 20807 ± 8689 | 23355 ± 6019 | 21555 ± 6694 | 22561 ± 5659 | 20493 ± 6932 |
| Mean absolute change from baseline ± SD (g) | 304.7 ± 1105.2 | 222.47 ± 958.0 | −65.4 ± 1055.0 | −255.1 ± 948.0 | −321.9 ± 1282.0 |
| p-value (compared to placebo) |  | 0.793 | 0.242 | 0.085 | 0.049 |
| Mean % change from baseline ± SD | 1.3 ± 7.1 | 1.3 ± 5.1 | 0.2 ± 5.1 | −1.3 ± 4.4 | −0.4 ± 6.9 |

The site of fat loss was different among males and females. Males tended to lose from the trunk/abdomen about 1.4 kg compared to the placebo (and 0.5 kg from baseline) with 3 mg (p=0.237) and 1.7 kg compared to the placebo (and 0.8 kg from baseline) with 1 mg (p=0.810) doses. Females tended to lose from the thigh and legs about 1 kg compared to the placebo (and 0.5 kg from baseline) with 1 mg (p=0.038) and 3 mg (p=0.212) doses (Table 4).

TABLE 4

|  | Placebo | 1 mg | 3 mg |
|---|---|---|---|
| Females (g) | 529 ± 1210 | −514 ± 941<br>0.038 | −50.2 ± 909<br>0.212 |
| Males (g) | 91.8 ± 1013 | −8.26 ± 949<br>0.810 | −540 ± 1486<br>0.237 |

Total tissue percent fat, relative to lean muscle mass decreased in a dose-dependent fashion, at the 1 mg dose achieving p=0.02 (ANOVA) and at 3 mg, achieving p=0.006 (ANOVA) for all subjects. The decrease in tissue percent fat in women administering 3 mg was highest, compared to administering 1 mg of Compound III, and compared to men administered the same doses.

Performance Effects

In order to analyze the physical performance (which reflects the gain of quality LBM), a stair climb (time and power) study was conducted. Subjects climbed 12 stairs and data was collected as a function of time (speed) and power.

Speed: A dose-dependent decrease in the time needed to climb 12 stairs was observed with the 3 mg dose of Compound of formula S-(III) (Compound III) showing a 15.5% decrease in time (p=0.006, ANOVA).

Power Exerted: A dose-dependent increase in power was observed. In subjects with the 3 mg dose of Compound III, there was 25.5% more power observed than in the placebo group (p=0.005, ANOVA). An increase of 62 watts is approximately 8 times what is considered clinically significant in a middle-aged to elderly non-athlete.

Thus, Compound III built lean body mass in both men and women and lowered the percent body fat. This lean body mass improvement translated to improved performance and power on a stair climb, which indicates, inter alia, that Compound III improves strength and provides a clinical benefit in the elderly and in persons where a condition such as cancer or chronic kidney disease has caused or may cause muscle wasting.

Bone Mass Effects

Bone Mineral Density (BMD) (DEXA): BMD measurements in treated patients were not different from baseline or from placebo. This was not unexpected since 90 days of dosing and measurement is insufficient time to observe meaningful changes in BMD. Bone resorption and turnover markers: In preclinical in vitro and in vivo models of osteoporosis tested, Compound III demonstrated both anabolic and antiresorptive activity affecting both the osteoblasts and osteoclasts.

Safety

Adverse Events (AEs) and Severe Adverse Events (SAEs)—

Compound III was shown to be safe and well tolerated. There were no trends in AEs and there were no SAEs reported during 90 day study period.

Hepatic Effects

It is well known that natural anabolic steroids and synthetic anabolic steroids induce elevations in liver transaminases, in particular ALT and AST. Compound III, in contrast, appeared to minimally affect ALT and AST levels. Of the 120 patients evaluated, 1 female patient exhibited an isolated ALT elevation with no other clinically meaningful changes including no changes in alkaline phosphatase, GTT, and total bilirubin levels. Of the 114 patients that completed the trial, there were no clinically meaningful changes in ALT, AST, alkaline phosphatase, GGT, or bilirubin levels at 3 months post-initiation.

Lipid Profile Effects

Circulating cholesterol, LDL, VLDL, triglyceride and HDL levels were analyzed: High dose testosterone and other anabolic steroids have the ability to reduce cholesterol and profoundly reduce HDL (60-80%). Compound III reduced total cholesterol, LDL, VLDL, and triglycerides in a dose-dependent manner. A dose-dependent reduction in HDL was seen, as well, however not of the magnitude of other orally administered anabolic agents. LDL/HDL ratios, which are a well established way to identify cardiovascular risk, revealed that Compound III treated subjects and placebo groups were in the low or below cardiovascular risk category at all doses.

Body Weight Effects

All subjects total body weight was measured post-administration of Compound III. A dose-dependent change in total body weight of all subjects given a 0.1 mg, 0.3 mg, 1 mg and 3 mg dose of Compound III was observed. Treatment with 0.3 mg or 3 mg Compound III exhibited an increase of 1 kg compared to placebo (and 0.9 kg, from baseline), with a p=0.196 and 0.178 respectively, (ANOVA) (Table 5).

TABLE 5

|  | Placebo | 0.1 mg | 0.3 mg | 1 mg | 3 mg |
| --- | --- | --- | --- | --- | --- |
| Baseline Mean ± SD (kg) | 68.0 ± 72.0 | 72.5 ± 10.6 | 68.6 ± 15.9 | 72.9 ± 13.7 | 62.5 ± 13.5 |
| Mean absolute change from baseline ± SD (kg) | −0.1 ± 2.3 | 0.4 ± 1.3 | 0.9 ± 4.9 | 0.3 ± 1.7 | 0.9 ± 1.7 |
| p-value (compared to placebo) |  | 0.510 | 0.196 | 0.550 | 0.178 |
| p-value (compared to baseline) | 0.791 | 0.504 | 0.121 | 0.568 | 0.105 |
| Mean % change from baseline ± SD | −0.1 ± 3.5 | 0.5 ± 1.8 | 3.1 ± 15.0 | 0.4 ± 2.3 | 1.7 ± 2.7 |

A dose-dependent change in total body weight of women given a 3 mg dose of Compound III was observed, with an increase of 0.8 kg compared to placebo (and 1.63 kg from baseline; Table 6) with a p=0.279 (ANOVA) and with the 1 mg dose a decrease of 0.9 kg compared to the placebo with a p=0.215 (ANOVA).

A dose-dependent change in total body weight of men with the 3 mg dose of Compound III was observed, with an increase of 0.7 kg compared to placebo with a p=0.277 (ANOVA) and with the 1 mg dose an increase of 1 kg compared to the placebo with a p=0.193 (ANOVA).

TABLE 6

|  | Placebo | 1 mg | 3 mg |
| --- | --- | --- | --- |
| Females (kg) | 0.850 ± 2.09 | −0.080 ± 1.02 | 1.63 ± 1.10 |
|  |  | 0.215 | 0.279 |
| Males (kg) | −0.375 ± 1.45 | 0.655 ± 2.18 | 0.383 ± 1.85 |
|  |  | 0.193 | 0.277 |

Hormonal Effects

Testosterone and other anabolic steroid agents suppress LH secretion by feedback inhibition on the pituitary. Less LH leads to lower endogenously produced testosterone. LH levels (U/L) changed relative to placebo groups, as a function of treatment with Compound III.

Administration of 0.1 mg to women led to a 1.2±1.14 U/L increase (p=0.01) in LH, and to a 0.8±1.14 U/L decrease (p=0.466) in men.

Administration of 0.3 mg to women led to a 1.8±1.09 U/L decrease (p=0.403) in LH, and to a 0.1±1.19 U/L increase (p=0.834) in men.

Administration of 1 mg to women led to a 2.6±1.19 U/L decrease (p=0.780) in LH, and to a 0.7±1.14 U/L decrease (p=0.476) in men.

Administration of 3 mg to women led to a 6.4±1.14 U/L reduction (p=0.039) in LH, and to a 0.5±1.09 U/L decrease (p=0.543) in men (Table 7).

TABLE 7

|  |  | Placebo | 0.1 mg | 0.3 mg | 1 mg | 3 mg |
|---|---|---|---|---|---|---|
| FEMALES | Change in LS mean from baseline ± SE (U/L) | −3.1 ± 1.14 | 1.2 ± 1.14 | −1.8 ± 1.09 | −2.6 ± 1.19 | −6.4 ± 1.14 |
|  | p-value (compared to from placebo) |  | 0.010 | 0.403 | 0.780 | 0.039 |
| MALES | Change in LS mean from baseline ± SE (U/L) | 0.4 ± 1.09 | −0.8 ± 1.14 | 0.1 ± 1.19 | −0.7 ± 1.14 | −0.5 ± 1.09 |
|  | p-value (compared to from placebo) |  | 0.466 | 0.834 | 0.476 | 0.543 |

SHBG is a sensitive marker of anabolic activity. Anabolic agents lower SHBG levels. In this study, consistent with its anabolic activity, Compound III exhibited a dose-dependent, profound reduction of SHBG levels. Administration of 0.1 mg, 0.3 mg, 1 mg or 3 mg Compound III resulted in reduction of SHBG levels in men and women (Table 8).

TABLE 8

|  |  | Placebo | 0.1 mg | 0.3 mg | 1 mg | 3 mg |
|---|---|---|---|---|---|---|
| Females | Change in LS mean from baseline ± SE (nmol/L) | −16.5 ± 5.82 | −1.1 ± 5.82 | −21.2 ± 5.57 | −55.8 ± 6.11 | −52.9 ± 5.82 |
|  | p-value (compared to from placebo) |  | 0.064 | 0.564 | <0.001 | <0.001 |
| Males | Change in LS mean from baseline ± SE (nmol/L) | −10.0 ± 5.57 | −6.1 ± 5.82 | −12.4 ± 6.11 | −19.1 ± 5.82 | −25.8 ± 5.57 |
|  | p-value (compared to from placebo) |  | 0.627 | 0.775 | 0.265 | 0.048 |

Endogenous free testosterone levels decreased relative to placebo groups post-administration of 0.1 mg, 0.3 mg or 1 mg to women, and had no change relative to placebo post administration of 3 mg Compound III (Table 9).

Free testosterone levels in men increased relative to placebo groups post administration of 0.1 mg, 0.3 or 3 mg of Compound III and had almost no change relative to placebo groups post administration of 1 mg Compound III.

TABLE 9

|  |  | Placebo | 0.1 mg | 0.3 mg | 1 mg | 3 mg |
|---|---|---|---|---|---|---|
| Females | Change in LS mean from baseline ± SE (pmol/L) | −0.5 ± 2.80 | −2.0 ± 2.99 | −1.0 ± 2.50 | −0.9 ± 2.64 | −0.5 ± 3.23 |
|  | p-value (compared to from placebo) |  | 0.718 | 0.887 | 0.922 | 0.995 |
| Males | Change in LS mean from baseline ± SE (pmol/L) | −11.2 ± 2.64 | 0.5 ± 2.80 | 2.7 ± 2.80 | −11.0 ± 2.54 | −8.2 ± 2.50 |
|  | p-value (compared to from placebo) |  | 0.003 | <0.001 | 0.966 | 0.413 |

A potential side effect of testosterone and other androgenic anabolic steroids is stimulation of the prostate. Measurement of serum PSA is a sensitive measure of stimulation of the prostate gland. Compound III had no effect on serum PSA levels at any dose tested.

Androgenic steroids stimulate sebaceous glands, which play a role in producing sebum and hair. Compound III did not show any significant changes in hair growth in women. Increased sebum production can lead to acne and oily skin, an unwanted side effect. Sebum production was measured in both men and women. Compound III did not affect sebum production in men or women compared to placebo, had no virilization effect and did not cause acne in men and women.

Compound III: a) built lean body mass in both men and women and lowered the percent body fat, b) improved performance and power on a stair climb, thus improving strength and providing a clinical benefit in the elderly and in people where a condition such as cancer or chronic kidney disease has caused or may cause muscle wasting, c) was minimally androgenic thus diminishing risks of hirsitism and prostate cancer currently associated with non-specific androgenic agents, and d) was well tolerated with no serious adverse events reported.

In addition, there were reductions in total cholesterol, LDL and HDL levels. There were no AEs or detrimental changes in other cardiovascular risk factors as measured in the study (such as blood pressure, insulin sensitivity). The data shows that there is a 20% decline in HDL while LDL, triglycerides and total cholesterol are lowered in the presence of increased muscle and decreased body fat.

A 1.5 kg (3.3 lb) improvement in lean body mass is clinically meaningful and consistent with what is seen with other anabolic agents. As men lose a ½ lb. per year this would represent reversing 7 years of muscle loss in 3 months. The lean body mass improvement translates to an improvement in function and muscle power. The improvement was seen in both men and women at the same dose that improved muscle mass. This indicates that if the SARM compound of formula S-(III) delivers the same lean body mass improvement in the elderly population or those people suffering from conditions which accelerate muscle wasting then it would also provide a functional benefit and improved quality of life.

Example 5

Compound of Formula S-(III)-Mediated Reduction of Glucose and Insulin Levels

Five groups of 24 human subjects per group (12 males and 12 females) of 60 elderly men (age >60) and 60 postmenopausal women (not hypogonadal, not osteoporotic, no exercise program, no controlled diet) were dosed each in a randomized, double-blind study design. Each subject received 0.1 mg, 0.3 mg, 1 mg, and 3 mg Compound of formula S-(III) (Compound III) (or placebo of equal volume) in solution or in experimental capsules for 90 days treatment. Glucose and insulin levels were analyzed.

Results

The subjects exhibited dose-dependent decreases in total circulating insulin levels post-administration of 0.3 mg, 1 mg or 3 mg of Compound III for all subjects (all fasting subjects). Treatment with 3 mg Compound III exhibited decrease in insulin levels of about 17.6-43.5 pmol/L compared to baseline with a p=0.043 (ANOVA). The 1 mg dose of Compound III exhibited decrease of 5.43*16.7 pmol/L compared to baseline with a p=0.143 (ANOVA) (Table 10).

TABLE 10

|  | Placebo | 0.1 mg | 0.3 mg | 1 mg | 3 mg |
|---|---|---|---|---|---|
| Baseline Mean ± SD (pmol/L) | 43.3 ± 21.3 | 44.1 ± 26.1 | 38.1 ± 26.6 | 56.6 ± 37.1 | 52.9 ± 48.5 |

TABLE 10-continued

|  | Placebo | 0.1 mg | 0.3 mg | 1 mg | 3 mg |
|---|---|---|---|---|---|
| Mean absolute change from baseline ± SD (pmol/L) | −0.32 ± 14.5 | 4.96 ± 21.0 | −1.30 ± 19.0 | −5.43 ± 16.7 | −17.6 ± 43.5 |
| p-value |  | 0.169 | 0.423 | 0.143 | 0.043 |
| Mean % change from baseline ± SD | 0.5 ± 31.9 | 19.2 ± 49.7 | 5.9 ± 44.2 | −6.9 ± 24.9 | −17.6 ± 37.0 |

All subjects (all fasting) exhibited dose-dependent decreases in total glucose levels post-administration of 0.3 mg, 1 mg or 3 mg of Compound III. Treatment with 3 mg Compound III exhibited decrease in glucose levels of 11.1±7.4% compared to baseline. The 1 mg dose of Compound III exhibited decrease of 3.5-6.3% compared to baseline with a p=0.764 (ANOVA) (Table 11).

TABLE 11

|  | Placebo | 0.1 mg | 0.3 mg | 1 mg | 3 mg |
|---|---|---|---|---|---|
| Baseline Mean ± SD mmol/L | 5.09 ± 0.44 | 5.17 ± 0.50 | 4.85 ± 0.41 | 5.29 ± 0.39 | 5.22 ± 0.51 |
| Mean absolute change from baseline ± SD Mmol/L | −0.19 ± 0.35 | 0.2 ± 0.42 | −0.01 ± 0.42 | −0.19 ± 0.33 | −0.60 ± 0.44 |
| p-value |  | 0.039 | 0.064 | 0.481 | <0.001 |
| Mean % change from baseline ± SD | −3.5 ± 6.5 | 0.7 ± 8.2 | 0.3 ± 9.9 | −3.5 ± 6.3 | −11.1 ± 7.4 |

Females exhibited a dose-dependent decrease in total glucose levels post-administration of 1 mg or 3 mg of Compound III, with the 1 mg dose achieving p=0.343 (ANOVA) and the 3 mg achieving p=0.012 (ANOVA). Males exhibited a dose-dependent decrease in total glucose levels post-administration of 1 mg or 3 mg doses of Compound III, with the 1 mg dose achieving p=0.998 (ANOVA) and the 3 mg dose achieving p=0.247 (ANOVA) (Table 12).

TABLE 12

|  | Placebo | 1 mg | 3 mg |
|---|---|---|---|
| All subjects Absolute change from baseline | −1.4 ± 5.2 (mg/dL) | −2.5 ± 6.2 (mg/dL) 0.470 | −8.6 ± 9.1 (mg/dL) 0.004 |
| Females Absolute change from baseline | −1.2 ± 5.6 (mg/dL) | −4.5 ± 7.5 (mg/dL) 0.343 | −11.4 ± 10.0 (mg/dL) 0.012 |
| Males Absolute change from baseline | −1.5 ± 5.0 (mg/dL) | −1.6 ± 5.6 (mg/dL) 0.998 | −4.9 ± 6.7 (mg/dL) 0.247 |

The decrease in the concentration of glucose in women, post-administration of Compound III was twice as high as that in men.

Example 6

Compound of Formula S-(III)-Mediated Reduction of Insulin Resistance (HOMA-IR)

Five groups of 24 human subjects per group (12 males and 12 females) of 60 elderly men (age >60) and 60 postmenopausal women (not hypogonadal, not osteoporotic, no exercise program, no controlled diet) were dosed each in a randomized, double-blind study design. Each subject received 0.1 mg, 0.3 mg, 1 mg, and 3 mg Compound of formula S-(III) (Compound III) (or placebo of equal volume) in solution or in experimental capsules for 90 days treatment. Insulin resistance was analyzed, calculated from the mean fasting glucose and insulin levels.

Results

The subjects (all fasting subjects) exhibited dose-dependent decreases in insulin resistance levels post-administration of 0.3 mg, 1 mg or 3 mg of Compound III for all subjects after 86 days. Treatment with 3 mg Compound III exhibited decrease in insulin resistance levels of about 27% compared to baseline (Table 13).

TABLE 13

|  | Placebo | 0.1 mg | 0.3 mg | 1 mg | 3 mg |
|---|---|---|---|---|---|
| Baseline Mean ± SD | 1.42 ± 0.73 | 1.51 ± 1.04 | 1.16 ± 0.70 | 1.96 ± 1.47 | 1.84 ± 1.97 |
| Mean absolute change from baseline ± SD | −0.06 ± 0.50 | 0.18 ± 0.78 | −0.01 ± 0.51 | −0.24 ± 0.60 | −0.79 ± 1.80 |

TABLE 13-continued

|  | Placebo | 0.1 mg | 0.3 mg | 1 mg | 3 mg |
|---|---|---|---|---|---|
| p-value | | 0.112 | 0.364 | 0.145 | 0.037 |
| Mean % change from baseline ± SD | −2.7 ± 32.5 | 21.3 ± 52.9 | 6.9 ± 48.0 | −10.1 ± 25.6 | −26.8 ± 33.4 |

Figure 10:
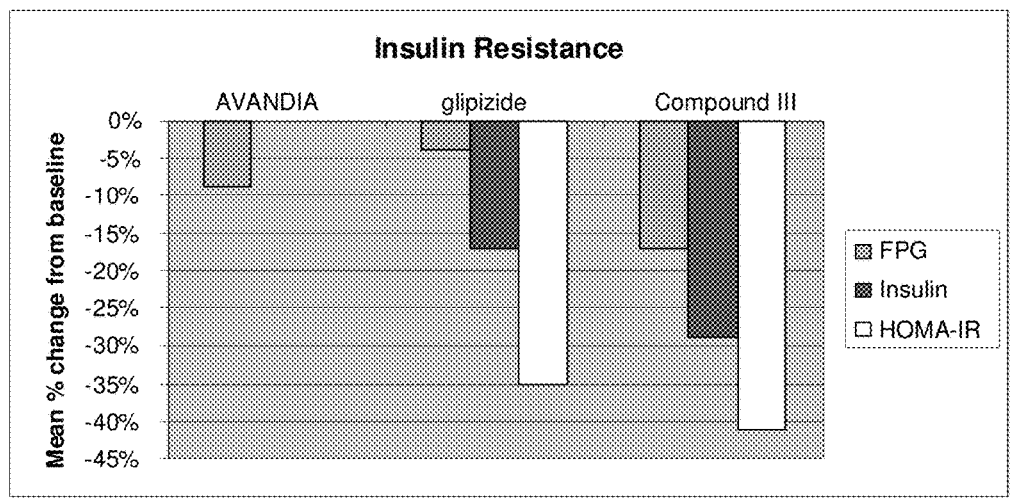
FIG. 10: Insulin resistance results (including insulin, glucose and HOMA-IR levels) of Avandia®, glipizide and compound of formula S-(III).

The levels of fasting plasma glucose (FPG), insulin and homeostasis insulin resistance (HOMA-IR) following administration of Avandia®, glipizide and Compound III exhibited the highest mean % changes from baseline with Compound III. Compound III exhibited −40% mean change from baseline of HOMA-IR, −30% mean change from baseline of insulin and −17% mean change from baseline of FPG, as presented in FIG. 10.

Example 7

Compound of Formula S-(III) Improves Soleus Strength in Rats

Materials and Methods

Female Sprague Dawley rats were divided into three groups, representing sham (vehicle) treated, ovariectomized (OVX), sham treated, and OVX animals receiving 3 mg/day Compound of formula S-(III) (Compound III). Compound III and vehicle were administered once daily by oral gavage. After 42 consecutive days of dosing, animals were sacrificed, the left hind limb soleus muscle was dissected and tested for strength analysis. The ratio between $P_0$, the peak titanic tension (N), and CSA, the cross sectional area ($cm^2$), was determined.

Results

Figure 11:
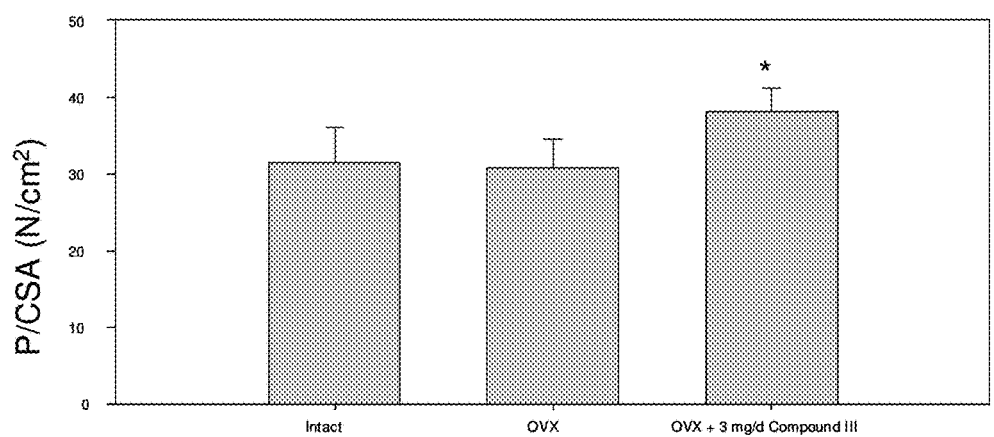
FIG. 11: Improvement of soleus strength in ovariectomized (OVX) rats treated with compound of formula S-(III).

Female rats exhibited improvement in soleus strength. Sham treated and ovariectomized (OVX) sham treated animals exhibited a strength of about 30 N/cm², while OVX-Compound III treated animals exhibited a strength of about 40 N/cm². Results are presented graphically in FIG. 11.

Example 8

SARM Bone Effects Alone and in Combination with the Anti-Resorptive Agent, Alendronate Materials and Methods Sixty female, virgin, intact Sprague-Dawley rats were obtained from Charles River Laboratories (Wilmington, Mass.) and aged to 23 wks. The animals were housed 2-3 per cage and acclimated to a 12-h light/dark cycle. Food (7012C LM-485 Mouse/Rat Sterilizable Diet, Harlan Teklad, Madison, Wis.) and water were provided ad libitum. The Institutional Animal Care and Use Committee of the University of Tennessee reviewed and approved the animal protocol for this study.

Sham surgeries or ovariectomies were performed on Day 0. The study was comprised of eight treatment groups as follows: (1) intact+vehicle, (2) intact+Compound III, (3) OVX+vehicle (4) OVX+Compound III, (5) OVX+DHT, (6) OVX+E2, (7) OVX+alendronate, (8) OVX+alendronate+Compound III. Doses were administered daily via oral gavage in a vehicle of DMSO:PEG300 (10:90) beginning on Day 1. Animals were sacrificed on Day 45 of the study. Femurs were removed, cleared of soft tissue, and stored in saline soaked gauze at −20° C. until analysis. Nine animals died during the course of the study. These deaths were attributed to surgical complications arising from the ovariectomies and technical errors during oral dosing (i.e., dosing solution delivered into the lungs). Dose groups are listed in the Table 14:

TABLE 14

| Group | Gonadal Status | Treatment | Dose | Animals/group |
|---|---|---|---|---|
| 1 | Intact | Vehicle | N/A | 9 |
| 2 | Intact | COMPOUND III | 3 mg/day | 9 |
| 3 | OVX | Vehicle | N/A | 7 |
| 4 | OVX | COMPOUND III | 3 mg/day | 8 |
| 5 | OVX | Alendronate | 1 mg/day | 10 |
| 6 | OVX | Alendronate/ COMPOUND III | 1 and 3 mg/day | 8 |

The left femurs were sent to SkeleTech Inc. (Bothell, Wash.) for biomechanical strength (three point bending) and pQCT analysis. A Stratec XCT RM and associated software (Stratec Medizintechnik GmbH, Pforzheim, Germany. Software version 5.40 C) were used for the pQCT analysis. The femur was analyzed at both the mid-shaft and distal regions. The mid-shaft analysis was performed on the region at 50% of the length of the femur. The distal analysis was performed on the region at 20% of the length of the femur starting at the distal end. One 0.5 mm slice perpendicular to the long axis of the femur was used for analysis. Total bone mineral content, total bone area, total bone mineral density, cortical bone mineral content, cortical bone area, cortical bone mineral density, cortical thickness, periosteal perimeter (circumference) and endosteal perimeter were determined at the mid-shaft of the femur. At the distal femur, total bone mineral content, total bone area, total bone mineral density, trabecular bone mineral content, trabecular bone area and trabecular bone mineral density were determined. Following pQCT analysis, the femoral strength was determined by a three-point bending test. The anterior to posterior diameter (APD) (unit: mm) at the midpoint of the femoral shaft was measured with an electronic caliper. The femr was placed on the lower supports of a three-point bending fixture with the anterior side of the femur facing downward in an Instron Mechanical Testing Machine (Instron 4465 retrofitted to 5500)(Canton, Mass.). The length (L) between the lower supports was set to 14 mm. The upper loading device was aligned to the center of the femoral shaft. The load was applied at a constant displacement rate of 6 mm/min until the femur broke. The mechanical testing machine directly measured the maximum bad ($F_u$) (unit: N), stiffness (S) (units: N/nm), and energy absorbed (W) (unit: mJ). The axial area moment of inertia (I) (unit: $mm^4$) was calculated by the software during the pQCT analysis of the femoral mid-shaft. Stress (σ) (units: $N/mm^2$), elastic modulus (E) (unit: Mpa), and toughness (T) (units: $mJ/m^3$) were calculated by the following formulas: stress: $\sigma=(F_u*L*(a/2))/(4*I)$; elastic modulus: $E=S*L^3/(48*I)$; and toughness: $T=3*W*(APD/2)^2/(L*I)$.

Statistical analysis was performed by Student's T-test. P-values of less than 0.05 were considered as statistically significant differences.

Male rats were subjected to orchidectomy (ORX), and on days 1-119 were administered peroally by gavage a vehicle, different doses of Compound III (0.1, 1, and 3 mg/d), with or without alendronate (1 mg/d), and alendronate alone. After sacrifice at the indicated times, mice were sacrificed, femurs removed and subjected to pQCT analysis and a 3-point bending assay. Vertebra were harvested as well, and crush assay of LS was conducted. Tibias were subjected to static and dynamic histomorphometry (calcein).

Results

Figure 12A:
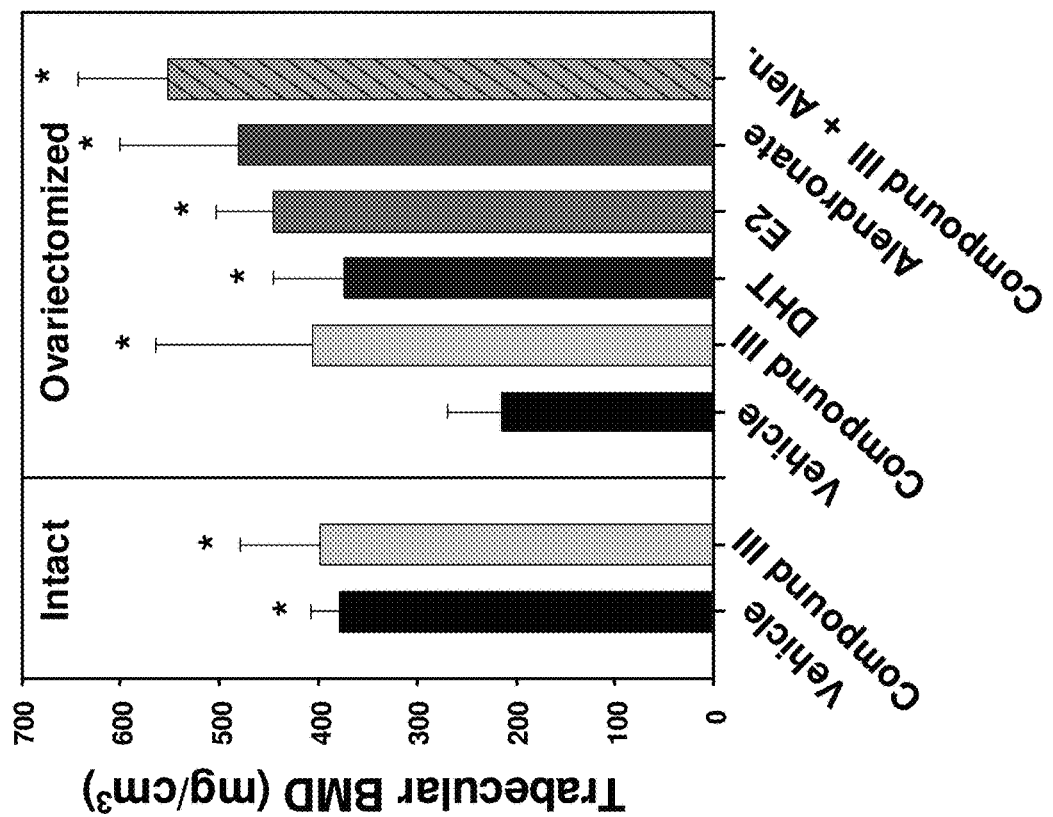
FIGS. 12A-12D: Trabecular bone mineral density determined by pQCT analysis of the distal femur 12A. Rat distal femur representative reconstructions 12B. BV/TV analysis of the distal femur 12C. Trabecular number of the distal femur 12D.

Trabecular bone mineral density was analyzed by pQCT at the distal femur. Results are shown in FIG. 12A. Significant trabecular bone loss was observed following OVX. Trabecular bone density decreased from 379 to 215 mg/mm³ in the intact and OVX vehicle control groups, respectively. In intact animals treated with Compound III, a slight increase in trabecular bone density to 398 mg/mm³ was observed. In OVX animals treated with Compound III, a significant increase was observed over the OVX vehicle control group to 406 mg/mm³. DHT increased trabecular bone density over the OVX vehicle control group to 360 mg/mm³ and estradiol (E2) increased trabecular bone density to 415 mg/mm³. Alendronate increased trabecular bone density to 480 mg/mm³. The combination therapy of alendronate and Compound III showed additive effects increasing trabecular bone density to 552 mg/mm³.

Figure 12B:
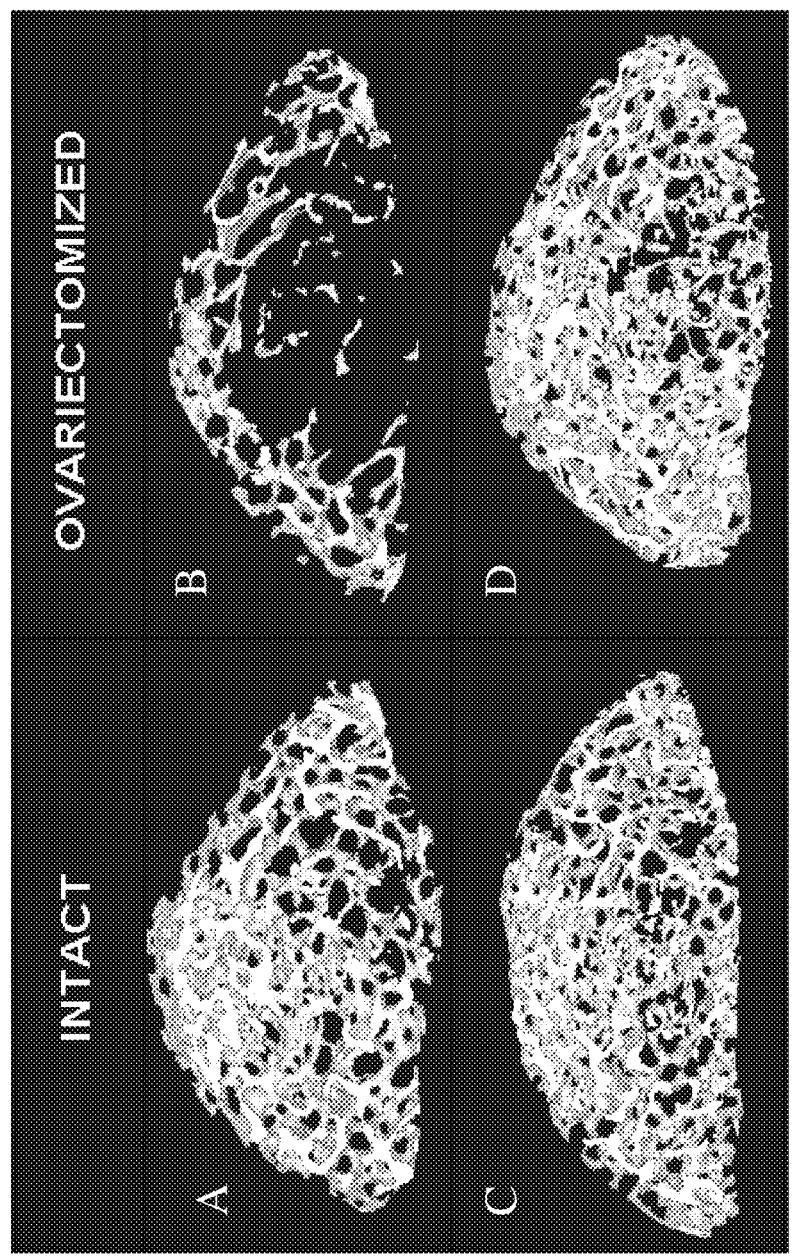

Rat distal femur representative reconstructions were prepared by standard methodology. As seen in FIG. 12B, while OVX animals show pronounced loss of normal architecture (panel B), OVX Compound III-treated animals provided a structure comparable to intact controls (panel D).

Ovariectomized animals may serve as a model for females suffering from ADIF, and as such, one embodiment of this invention is treatment thereof, for example, via administration of Compound III as exemplified herein.

Figure 12C:
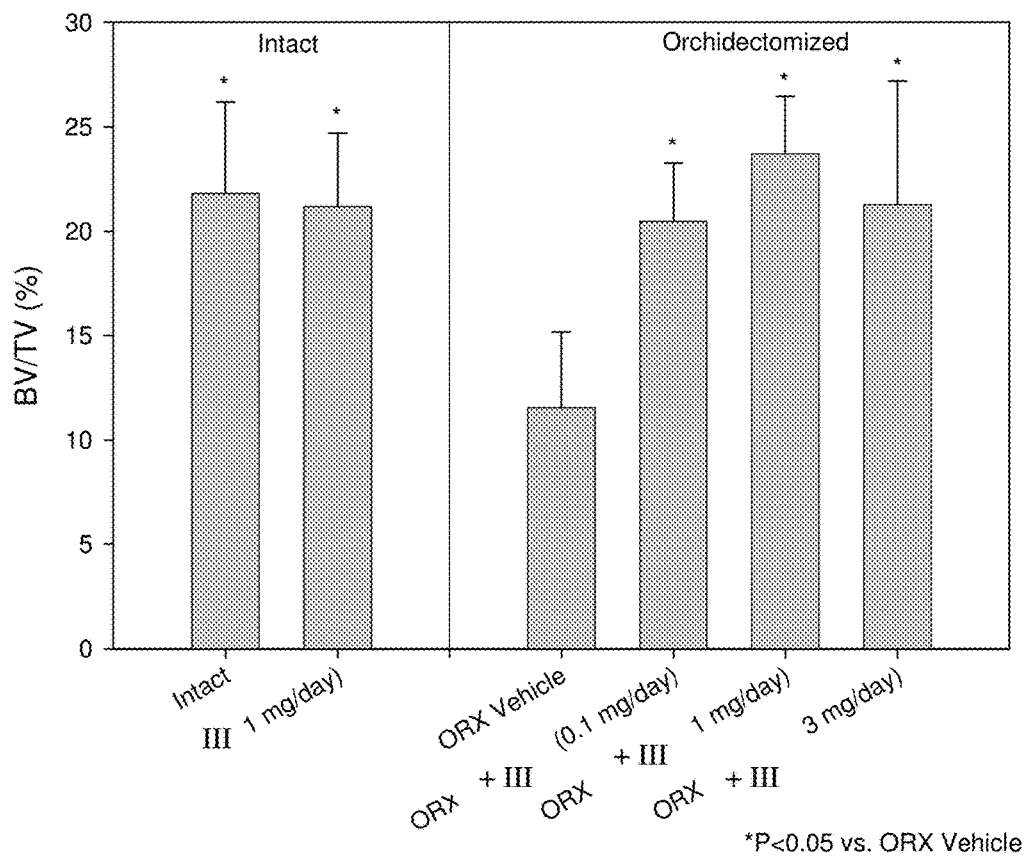
Figure 12D:
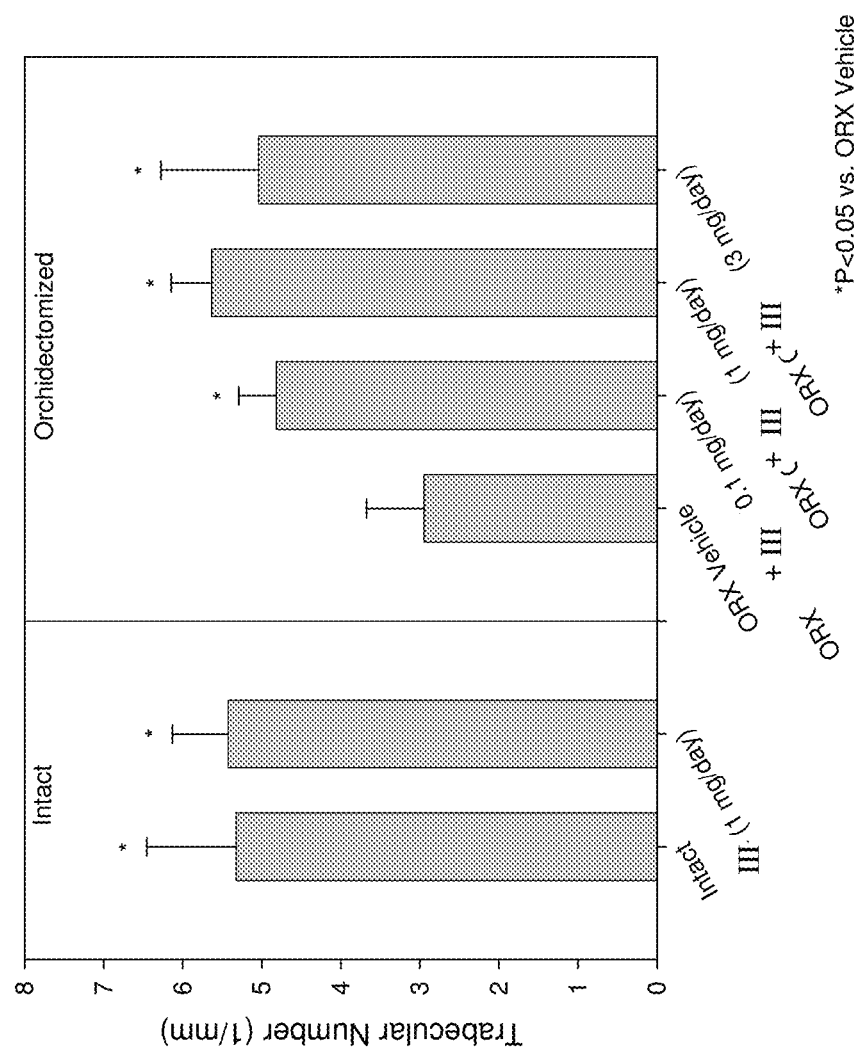

As evident from FIGS. 12C (BV/TV) and 12D (trabecular number), Compound III prevented gonadectomy-induced losses in trabecular bone in males, as well.

Example 9

Pharmacokinetics of Compound of Formula S-(III)

Figure 13:
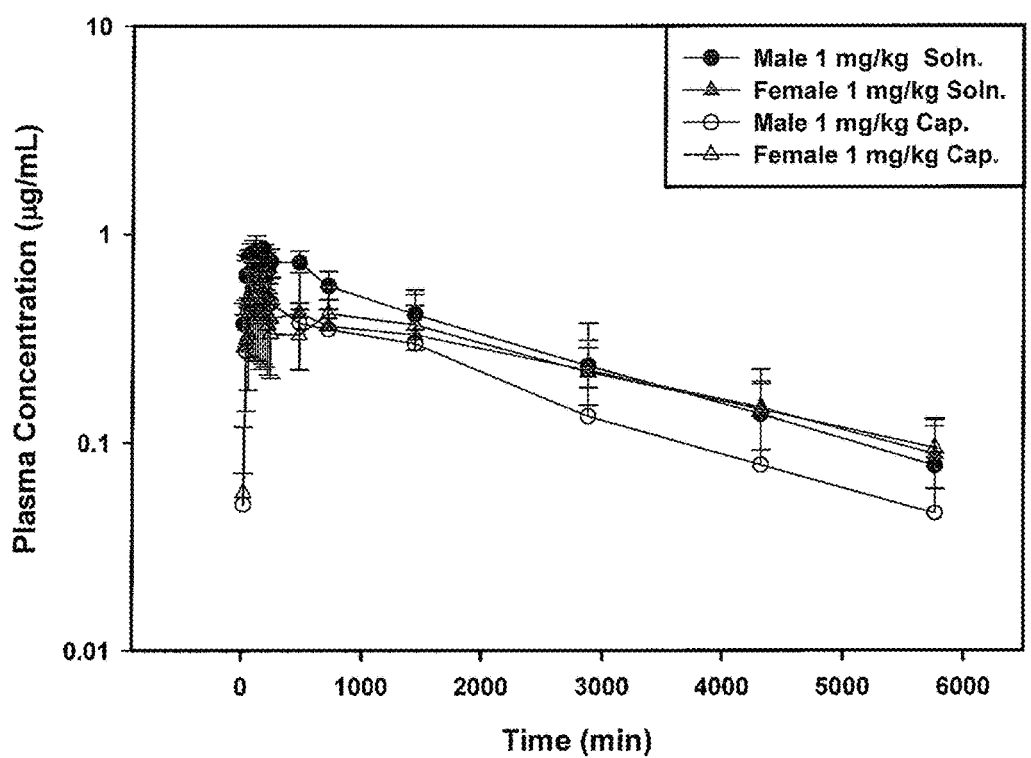
FIG. 13: plots circulating levels of compound of formula S-(III) in plasma in nude and female dogs.

In order to determine the pharmacokinetics of Compound of formula S-(III) (Compound III), the compound was administered to beagle dogs perorally, and circulating plasma levels, $C_{max}$, $t_{max}$, $t_{1/2}$, AUC and F % (FIG. 13 and the Table 15 below, respectively) were determined. Compound III was rapidly and completely absorbed.

TABLE 15

|  | Male 1 mg/kg Soln. | Female 1 mg/kg Soln. | Male 1 mg/kg Cap. | Female 1 mg/kg Cap. |
| --- | --- | --- | --- | --- |
| $C_{max}$ (mg/mL) | 0.91 ± 0.1 | 0.56 ± 0.26 | 0.59 ± 0.16 | 0.58 ± 0.06 |
| $t_{max}$ (min) | 250 ± 161 | 165 ± 211 | 120 ± 37 | 250 ± 313 |
| $t_{1/2}$ (hr) | 24.3 | 35.5 | 21.0 | 35.5 |
| AUC min * mg/mL | 1.96 ± 0.72 | 1.66 ± 0.70 | 1.22 ± 0.34 | 1.71 ± 0.43 |
| F % | 104% | 73.5% | 64.8% | 75.6% |

Example 10

Mapping of AR Binding Sites

Materials and Methods

Reagents

AR and SHC-1 antibodies were obtained from Upstate Biotechnology (Lake Placid, N.Y.), SRC-1 antibody was obtained from Santacruz Biotechnology (Santa Cruz, Calif.). Protein A Sepharose was obtained from Amersham Pharmacia (Piscataway, N.J.). WTS reagent was purchased from Roche (Nutley, N.J.). All cell culture medium was obtained from Invitrogen (Carlsbad, Calif.) and the serum for cell culture obtained from Atlanta Biologicals (Atlanta, Ga.). All other reagents used were analytical grade.

Cell Culture

LNCaP, prostate cancer cells, were obtained from ATCC (Manassas, Va.). The cells were grown in RPMI 1640 (containing 2 mM L-glutamine, 10 mM HEPES, 1 mM sodium pyruvate, penicillin and streptomycin) supplemented with 10% fetal bovine serum (FBS). For the ChIP assays, cells were plated in 150 mm dishes at 10 million cells per dish in RPMI 1640 supplemented with 1% charcoal stripped FBS. The cells were maintained in 1% csFBS for 6 days to reduce basal occupancy of promoters with medium changed on days 1 and 3 and before treatment on day 6.

Chromatin Immunoprecipitation Assay (ChIP)

ChIP assays were perfumed as described earlier (Narayanan, R. et al., 2005). The proteins were cross-linked by incubation with 1% formaldehyde (final concentration) at 37° C. for 10 min. The cells were washed with 1×PBS twice, scraped in 1 ml of PBS containing protease inhibitors ([1 mg each of aprotinin, leupeptin, antipain, benzamidine HCl, and pepstatin/ml], 0.2 mM phenylmethylsulfonyl fluoride, and 1 mM sodium vanadate), pelleted, and resuspended in SDS lysis buffer (1% SDS, 10 mM EDTA, 5 mM Tris-HC [pH 8.1]). After lysis on ice for 10 min, the cell extract was sonicated (Branson sonifer 250) in a cold mom eight times for 10 s each at constant duty cycle, with an output of 3 and with incubation on ice after every sonication. The debris was pelleted at 13,000 rpm for 10 min at 4° C., and the supernatant was diluted 10-fold with ChIP dilution buffer (0.01% SDS, 1.1% Triton X-100, 1.2 mM EDTA, 16.7 mM Tris HQ [pH 8.1], 167 mM NaCl). The proteins were precleared with 50 µl of 1:1 protein A-Sepharose beads in TE, 300 µl was reserved as input, and the remaining was incubated with 5 µg of AR or SRC-1 antibody or IgG (negative control) and 2 µg of sheared salmon sperm DNA (Stratagene, La Jolla, Calif.) rotating to overnight at 4° C. The protein-DNA-antibody complex was precipitated by incubating with 100 µl of 1:1 protein A-Sepharose beads and 2 µg of salmon sperm DNA at 4° C. for 2 h. The beads were pelleted and washed three times with low-salt wash buffer (0.1% sodium dodecyl sulfate [SDS], 1% Triton X-100, 2 mM EDTA, 20 mM Tris HCl [pH 8.1], 0.15 M NaCl), and twice with 1×TE (10 mM Tris HCl, 1 mM EDTA; pH 8.0). The DNA-protein complex was obtained by extracting the beads with 50 µl of freshly prepared extraction buffer (1% SDS, 0.1 M NaHCO$_3$) three times. The cross-linking of the DNA protein complex was reversed by incubating at 65° C. for 6 h. The DNA was extracted with a QIAquick PCR purification kit (QIAGEN, Valencia, Calif.) in 25 µl final volume of TE.

Real-Time PCR

The realtime PCR was performed on an ABI 7300 (Applied Biosystems) using TaqMan PCR master mix at universal condition. The numbers on the y axis of the ChIP assay results were obtained by dividing the arbitrary quantitative PCR numbers obtained for each sample by the respective input. All promoter array results were validated using primers and taqman probes (Biocource, CO) given in the following Table 16.

TABLE 16

Realtime PCR primers for ChIP assay

| Primer Name | Sequence | SEQ. ID No. |
|---|---|---|
| MSX-1 Forward Primer | AACCCAGCCACAGACTAAAGA | 1 |
| MSX-1 Reverse Primer | TCCCTTGTTCTCGTTCCTC | 2 |
| MSX-1 Taqman Primer | AAAGAGGAGCGGAAAAGAGGGCTG | 3 |
| APIG1 Forward Primer | GGGTCCGAGTTCTTGGATAA | 4 |
| APIG1 Reverse Primer | ATCCTGAGGAAGGAGGGAT | 5 |
| APIG1 Taqman Primer | GGACAGGGAGCGAAGTTTCCTCAA | 6 |
| AXIN-1 Forward Primer | ATTCCAAGGACCTGCAACG | 7 |
| AXIN-1 Reverse Primer | GAGAGGGCGTGGTCAGTG | 8 |
| AXIN-1 Taqman Primer | CGCCTCTCCCACTCCGCTCT | 9 |
| BATF-1 Forward Primer | CTGGACTTAAGGGGTGAGGA | 10 |
| BATF-1 Reverse Primer | GGAGAGGACAACCAGGAAAA | 11 |
| BATF-1 Taqman Primer | TGAGCAGCTGCTTTCGGCTGAA | 12 |
| SHC-1 Forward Primer | TAACTCGGGAAAGTGGGAAG | 13 |
| SHC-1 Reverse Primer | AGCTTAGGTTACCGCTCCAA | 14 |
| SHC-1 Taqman Primer | AATAAAGTTTCTCCAGGGAGGCAGGG | 15 |
| NFkB1 Forward Primer | CTCGAGAGAGTATGGACCGCATGACTCTATCA | 16 |
| NFkB1 Reverse Primer | ACGCGTAGAGAGAGCATACAGACAGACGGACA | 17 |
| PCBP2 Forward Primer | AGATGATGGGAGGTTTGGAG | 18 |
| PCBP2 Reverse Primer | GCCTAAACCAGAAACCAAGG | 19 |
| PCBP2 Taqman Primer | ATTTGGGGTAAGGGAGGTGAAGGAGG | 20 |
| PSA Forward Primer | GCCTGGATCTGAGAGAGATATCTC | 21 |
| PSA Reverse Primer | ACACCTTTTTTTTTGGATTGTTG | 22 |
| PSA Taqman Primer | TGCAAGGATGCCTGCTTTACAAACATCC | 23 |

Promoter Array

H20K promoter array from AVIVA systems biology (San Diego, Calif.) was used for these experiments. The array consists of 20,000 probe pairs mapped to about 19,600 unique proximal promoter regions. Proximal promoter regions between −1.0 KB to +300 bp were spotted on this array. Before hybridization, the efficiency of the ChIP assay was tested on PSA enhancer using quantitative PCR. Manufacturer's protocol was followed for the hybidization using Cy5 label for the immunoprecipitated samples and Cy3 label for total input DNA. The hybridized slides were scanned using a Gene Pix 4 scanner. Resulting background subtracted median intensities for both the Cy3 and the Cy5 channels were used to calculate normalized log$_2$ (Cy5/Cy3) or M values in the limmaGUI[42] package developed for the R statistical language. In limmaGUI, background subtraction was set to minimum replacing confounding negative or zero intensities with very small positive numbers. Default settings were used for spot quality weighting and all arrays were within-array normalized using the global-loss function and between-array normalized using the aquantile method as needed. A one-tailed students t-test was used to determine significance (P<0.05) of treatment hybridization versus vehicle control where the mean of replicate normalized M-values was greater in treatment than in control.

Gene Ontology (GO) Functional Analyses

The software package ErmineJ[43] was used to mine statistically overrepresented GO terms from each experimental group and successfully mapped 80% of array targets to their GO annotation. An implementation of the receiver operator characteristic (ROC) method was used in ranking—log(p-values) (NLP) of all genes showing recruitment and performing the wilcoxon rank sum test to examine significance of gene sets (minimum size 20) associated with GO terms containing a greater number of high ranking genes than would be expected if rankings were randomly distributed amongst all gene sets. Only the most significant NLP of replicates within each array were considered, p<0.05 (uncorrected for multiple comparisons) were reported. Gene product: Go term associations used were retrieved using SOUCE and the GO database (Ashburner, M. et al. 2000)

Orthlogous Promoter Determination and Retrieval

All human-mouse orthologs were determined using NCBI's Homologene[41]. Using only orthologous Reference Sequences (RefSeq), 5000 base pairs upstream of the transcription start site (TSS) and 2000 base pairs down stream were retrieved using UCSC's Genome Browser (*H. Sapiens* and *M. musculus* NCBI Build 35). 50-60% (712 genes) of the genes of interest contained the complete annotation described and were searched.

Animal Experiments

Rive male Sprague Dawley rats per group (300 g) from Harlan (Indianapolis, Ind.) were housed with three animals per cage and were allowed free access to tap water and commercial rat chow (Harlan Teklad 22/5 rodent diet—8640). During the course of the study, the animals were maintained on a 12 hr light:dark cycle. This study was reviewed and approved by the Institutional Laboratory Care and Use Committee of The University of Tennessee. The animals were dosed daily for 15 days with 3 mg/day of SARM or DHT or vehicle (Polyethylene Glycol). Dosing solutions were prepared daily by dissolving drug in dimethyl sulfoxide (DMSO) and diluting in polyethylene glycol 300 (PEG 300). At the end of 15 days, the animals were sacrificed and the weights of prostate and levator an measured.

Bone Marrow Culture

Cell culture materials were obtained from Invitrogen (Carlsbad, Calif.). The femurs were first rinsed in 70% ethanol and were then washed three times with 5 ml each of penicillin and streptomycin. Both ends of the femurs were snapped and the bone marrow cells were flushed with 15 mil of MEM with penicillin, streptomycin and fungizone into a 50 ml conical tube and stored on ice. The bone marrow cells were pooled and were centrifuged at 1000 rpm for 5 min in a clinical centrifuge. The cells were resuspended in phenol red-free MEM supplemented with 10% charcoal-stripped serum, penicillin, streptomycin and fungizone. The cells were triturated though a 22 g needle, counted under microscope, and were plated at 1.5 million cells per well of a 6 well plate in phenol red-free MEM supplemented with 15% charcoal-stripped serum, penicillin, streptomycin, 300 ng/ml fungizone, 0.28 mM ascorbic acid, and 10 mM β-glycerophosphate to differentiate towards the fibroblast/osteoblast lineage. In separate wells, 2.5 million cells per well were plated in 24 well plates in phenol red-free MEM supplemented with 10% charcoal stripped serum, penicillin, streptomycin, and 300 ng/ml fungizone to differentiate towards the osteoclast lineage. The medium was changed on day 2 and the cells were treated with the compound of interest. Osteoclast cultures were performed in the presence of RANK Ligand (50 ng) and GM-CSF (10 ng) to induce osteoclastogenesis. Medium was completely changed every third day for osteoclast cultures. For fibroblast cultures, half the culture medium was changed every third day to leave the growth factors secreted by the cells.

Staining of Cells

At the end of 12 days, the cells were fixed in 10% buffered formalin for fibroblast cultures and in 4% formaldehyde in PBS for osteoclast cultures. The fibroblasts were stained for alkaline phosphatase activity and the O.D. at 405 nm was measured using a spectrophotometer as described earlier. The osteoclasts were stained for Tartarate Resistant Acid Phosphatase Activity (TRAP) and cells having 2 or more nuclei were counted under the microscope.

RNA Analysis and Reverse Transcriptase Polymerase Chain Reaction

LNCaP cells were plated at 700,000 cells per well of a 6 well plate in RPMI supplemented with 1% csFBS or in full serum. The cells were maintained for 3 days and were treated with vehicle, DHT or SARM. RNA was isolated using Trizol (Invitrogen) and the expression of various genes measured using TaqMan prime probe mix from Applied Biosystems using one step rtPCR master mix on an ABI 7300 realtime PCR machine. The expression of individual gene is normalized to 18S rRNA levels.

Growth Assay

LNCaP cells were plated at 10,000 cells per well of a 96 well plate in RPMI supplemented with 1% csFBS. The cells were treated for 72 hrs with the indicated concentrations of DHT or SARM. The cell viability at the end of 72 hrs measured using WTS assay reagent.

Co-Immunoprecipitation

LNCaP cells were plated at 4 million cells per 10 cm dish in RPMI supplemented with 1% csFBS. The cells were maintained in 19% csFBS containing medium for 2 days. The medium was changed and were treated with vehicle, 100 nM DHT or SARM for 1 hr. Protein was extracted in Homogenization buffer (0.05 M potassium phosphate, 10 mM sodium molybdate, 50 mM sodium fluoride, 2 mM EDTA, 2 mM EGTA, and 0.05% monothioglycerol [pH 7.4] containing 0.4 M NaCl and the protease inhibitors mentioned above) by three freeze thaw cycles in dry ice ethanol bath. Equal amounts of protein (100 µg) were immunoprecipitated with SHC-1 antibody or IgG over nigh rotating at 4° C. The protein antibody complex was precipitated by the addition of protein A sepharose for 2 hrs. The beads were pelleted and washed three times with low salt wash buffer and twice with TE. The proteins were extracted from the beads by boiling for 10 min with 2× Laemmli buffer. The protein extracts were fractionated on a 6.5% SDS-PAGE, transferred to a nitrocellulose and western blotted with SRC-1 antibody.

Results

Mapping of AR Binding Sites in Response to DHT and SARM

Figure 14A:
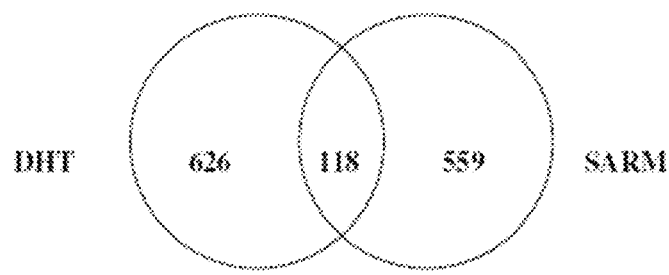
FIGS. 14A-14C: depict recruitment of AR in response to DHT or SARM.
Figure 14B:
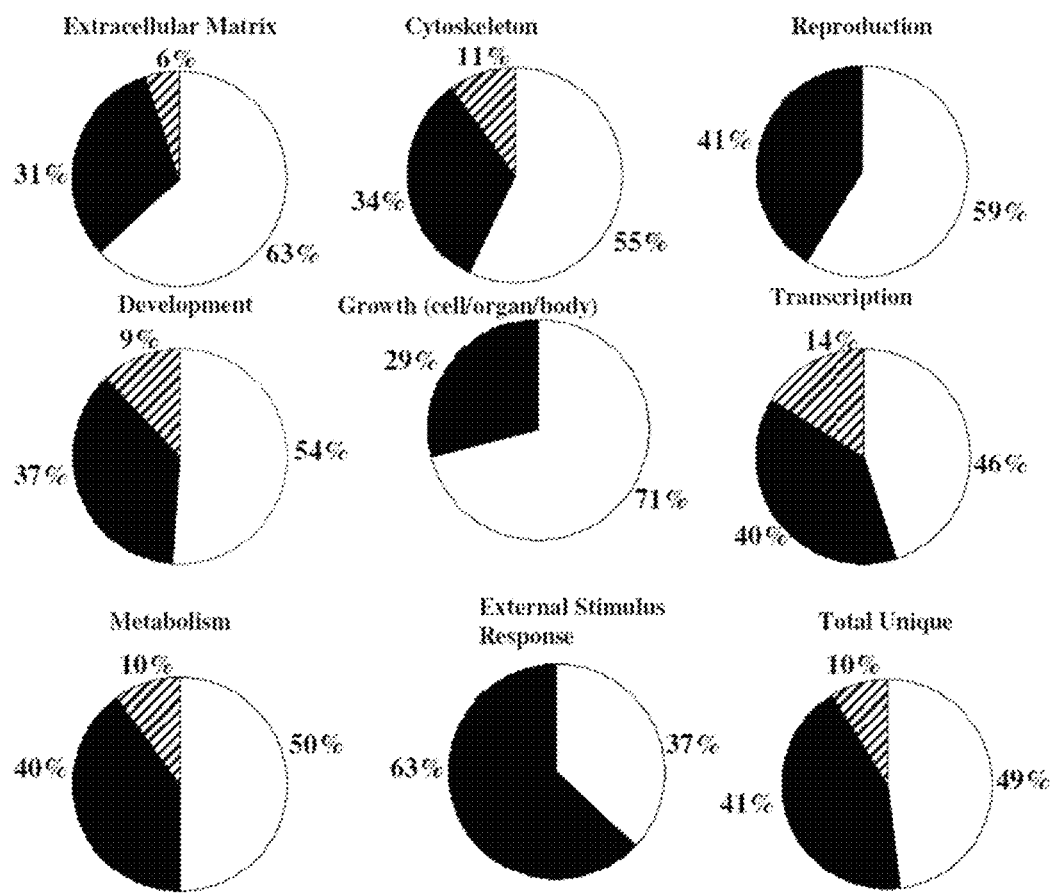
Figure 14C:
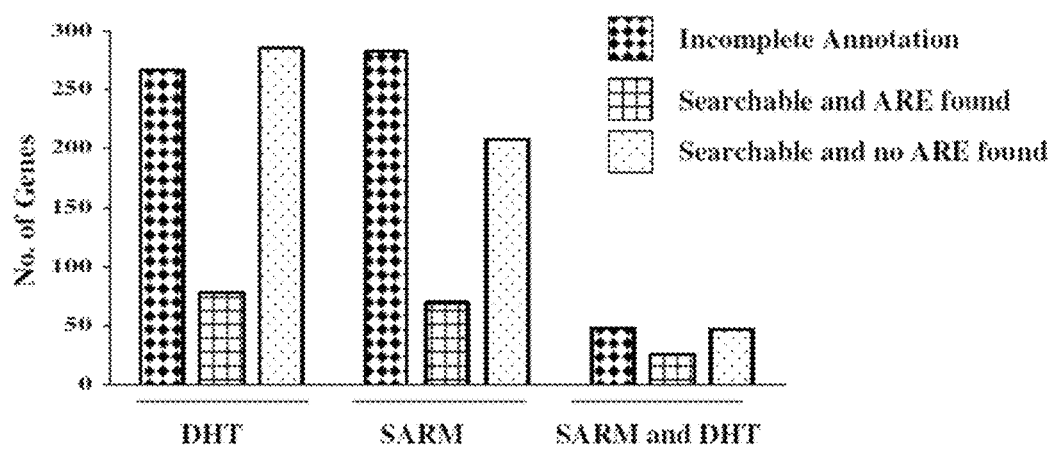

A chromatin immunoprecipitation assay (ChIP) assay was coupled with DNA microarray to determine the genome wide-binding of AR to various proximal promoter regions. LNCaP cells were treated with DHT or SARM, and equal amounts of DNA were hybridized to the transcription factor promoter array. AR significantly associated with 1303 of the promoter regions for known protein-coding genes in the presence of DHT or SARM (FIG. 14A). AR bound to nearly 6.5% of the promoters spotted on the array. Although DHT and SARM stimulated the recruitment of AR to a similar number of gene promoters, only 118 of the 1303 promoters were shared. In response to DHT, 626 promoters were uniquely occupied, while in response to SARM, 559 promoters were uniquely occupied by AR. Functional analysis of the genes revealed profound differences in the functional activity of these genes (FIG. 14B). DHT promoted recruitment of the AR to 71% and 63% of the genes associated with cell growth and extracellular matrix, respectively, while only 29% and 31%, respectively of these promoters were occupied by the AR in response to SARM. In contrast, SARM stimulated recruitment of the AR to 63% of the genes associated with an external stimulus (eg. intracellular signaling pathways). Genes associated with cytoskeleton, reproduction, development, transcription and metabolism were associated about equally with DHT and SARM treatment. A comparative genomics search was used to identify the presence of AREs in the 1303 gene promoters. Totally 712 of the 1303 gene promoters were sufficiently annotated in the human and mouse database for this search. 78 of 350 searched promoters recruiting AR in response to DHT contained AREs, whereas 69 of 277 SARM-responsive promoters were classified as ARE positive (FIG. 14C).

Mapping of SRC-1 Binding Sites in Response to DHT and SARM

Figure 15D:
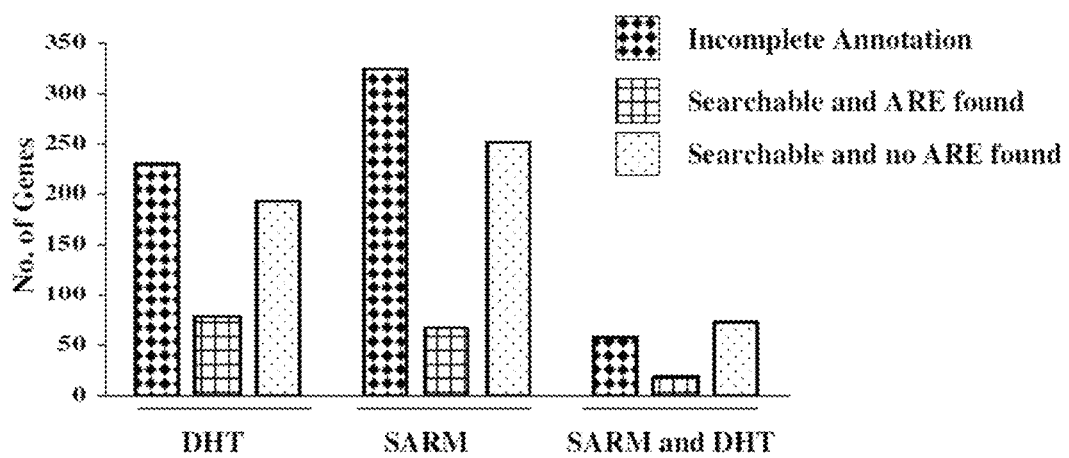

SRC-1 was efficiently recruited in the presence of DHT and SARM (FIG. 15A). Using promoter array and identical conditions to that used for AR, we mapped SRC-1 binding to 285 promoters (FIG. 15B). DHT recruited SRC-1 to 498 promoters, SARM recruited SRC-1 to 640 promoters and DHT or SARM commonly recruited SRC-1 to 147 promoters. Functional analysis of the genes revealed some significant differences in the functional activity of these genes (FIG. 15C). DHT promoted recruitment of SRC-1 to 67% and 28% of the genes associated with reproduction and cytoskeleton, respectively, while 33% and 55%, respectively of the promoters were occupied by SRC-1 in response to SARM. Genes associated with other classes were associated equally with DHT and SARM. A comparative genomics search similar to that performed with AR was performed with the list of promoters occupied by SRC-1 to identify the presence of AREs. FIG. 15D shows that 77 of the 269 searched promoters recruiting SRC-1 in response to DHT contained AREs, whereas 66 of 317 SARM-responsive promoters were classified as ARE positive. Array results were validated by performing realtime PCR on the DNA pool obtained from ChIP experiments in LNCaP cells using SRC-1 antibody.

The tissue selective responses of the compounds of this invention may be a result of their interaction with a particular androgen receptor subtype, as a function of tissue expression, or in some embodiments, as a function of tissue distribution of the particular compound, or tissue distribution of a metabolite thereof, or a function of the interaction of the compound with a 5α-reductase, or by any other mechanism.

In some embodiment, tissue selectivity is a function of the ligand affinity, or in some embodiments, intrinsic activity of the compound, for example, in terms of the ligand-induced receptor conformational change. In some embodiments, the tissue selectivity is a function of the efficacy of the compound in provoking a response in terms of effects on gene expression, regulator recruitment, interactions with components of the transcriptional machinery, or others.

In this context, Compound III has been shown herein to bind the androgen receptor ($K_i$=10.5 nM), as well as the serotonin transporter ($K_i$=2.55 μM).

Validation of Promoter Array

Figure 16A:
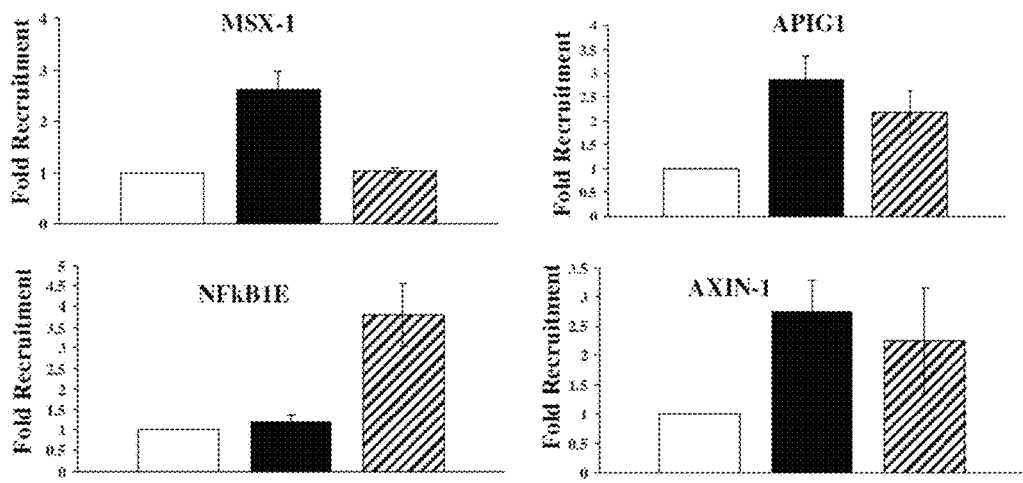
FIGS. 16A-16B: Validation of promoter array.

To validate the array results, ChIP assays were performed in LNCaP cells with primers flanking the promoters of representative genes to which the AR was recruited in the presence of DHT (MSX-1), DHT and SARM (APIG1, AXIN1) or SARM (NFkB1E). FIG. 16A shows successful validation of the array results.

Figure 16B:
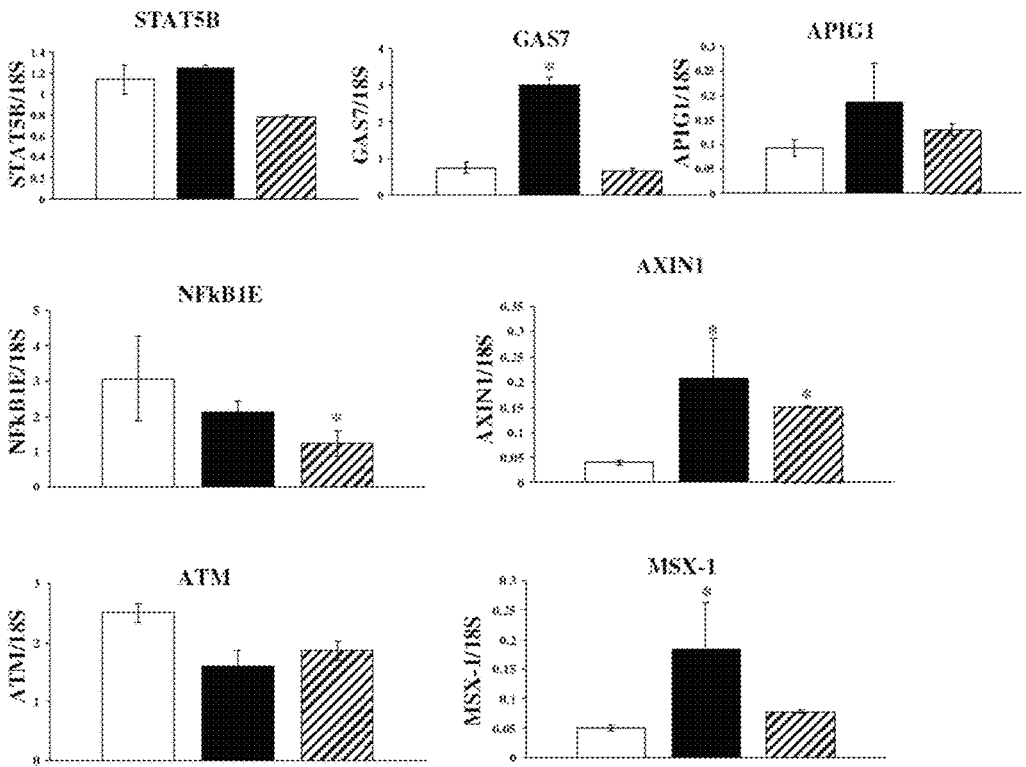
Figure 16B:
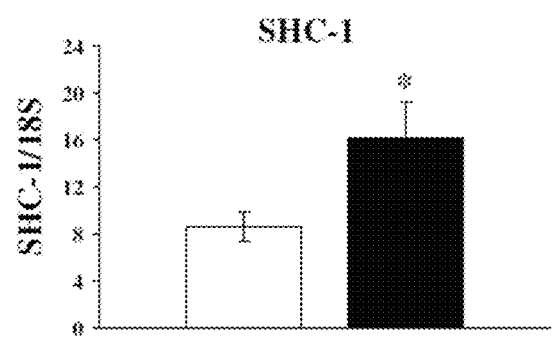

Androgen receptor (AR) is known to be involved in both gene activation and repression. As such, the transcriptional status of genes was examined to which AR was recruited. RNA from LNCaP cells treated with vehicle, DHT or SARM were quantified using rtPCR. FIG. 16B shows the transcription of several (SHC-1, MSX-1, AXIN1, NFkB1E and GAS7).

Example 11

Effect of Compound of Formula S-(III) on Muscle Wasting and Physical Function in Patients with Cancer Materials and Methods Eligible patients were men aged >45 years and postmenopausal women who were non-obese, defined as a body mass index (BMI) ≤35 kg/m². Additional inclusion criteria included 22% weight loss in the 6 months before screening, life expectancy >6 months, and an Eastern Cooperative Oncology Group (ECOG) score of ≤1. Patients must have been diagnosed with non-small cell lung cancer (Stage 2, 3, or 4), colorectal cancer (Stage 2, 3, or 4), non-Hodgkin lymphoma, chronic lymphocytic leukemia, or breast cancer (Stage 3 or 4), and had not yet begun chemotherapy or were between chemotherapy cycles. Key exclusion criteria included a history of active/uncontrolled congestive heart failure, hypertension, chronic hepatitis, hepatic cirrhosis, or infection with human immunodeficiency virus or hepatitis A, B, or C. Patients with aspartate aminotransferase/alanine aminotransferase (ALT) levels >3× the upper limit of normal (ULN) or total bilirubin levels >2 mg/dL were excluded. Patients currently taking testosterone, oxandrolone, or testosterone-like agents (e.g., dehydroepiandrosterone, androstenedione and other androgenic compounds, including herbals) within the past 30 days (or 6 months if long-term depot), megestrol acetate, dronabinol, or any prescription medication intended to increase appetite or treat unintended weight loss were also excluded.

Study Design

A randomized, double-blind, placebo-controlled, multi-center efficacy and safety study of Compound of formula S-(III) (Compound III) in patients with cancer was conducted. Eligible patients were randomized in a 1:1:1 ratio to receive Compound III 1 or 3 mg or matching placebo orally once daily for up to 113 days. Randomization was stratified to balance the treatment groups by cancer diagnosis.

Results

Patient Disposition and Demographics

A total of 159 patients were randomized and received ≥1 dose of study drug (placebo, n=52; Compound III 1 mg, n=53; or Compound III 3 mg, n=54). Among these patients in the intent-to-treat (ITT)/safety population (N=159), 53 discontinued treatment. The most common reason for discontinuation was the occurrence of an AE (n=18; 11.3%). There were no significant between-group differences in the rate of or reasons for discontinuation. The percentage of patients who had an on-study DXA scan and were included in the modified ITT (MITT) population (n=114) was similar between the placebo (73.1%) and Compound III 3-mg (75.9%) groups, but was slightly lower in the Compound III 1-mg group (66.0%). Baseline demographic and clinical characteristics were generally similar across treatment groups (Table 17). Among patients in the safety population, mean age was 65.9 years and the majority of patients were male (64.8%) and Caucasian (89.9%). At baseline, mean weight loss in the 6 months before screening was substantial (~9%) in all treatment groups. In both the safety and MITT populations, there were no statistically significant differences from placebo in the percentage of weight loss in the previous 6 months, total LBM, or hand grip strength in Compound III 1- or 3-mg treatment groups (Table 17).

TABLE 17

Patient Demographic and Clinical Characteristics

| Characteristic | Placebo Safety (n = 52) | Placebo MITT (n = 38) | Compound III 1 mg Safety (n = 53) | Compound III 1 mg MITT (n = 35) | Compound III 3 mg Safety (n = 54) | Compound III 3 mg MITT (n = 41) |
|---|---|---|---|---|---|---|
| Mean age, y (range) | 66 (41-83) | 65 (41-83) | 66 (43-87) | 65 (43-87) | 66 (39-82) | 68 (39-81) |
| Sex, n (%) | | | | | | |
| Men | 35 (67) | 25 (66) | 34 (64) | 19 (54) | 34 (63) | 24 (58) |
| Women | 17 (33) | 13 (34) | 19 (36) | 16 (46) | 20 (37) | 17 (42) |
| Race, n (%) | | | | | | |
| Caucasian | 47 (90.4) | 34 (89.5) | 45 (84.9) | 29 (82.9) | 51 (94.4) | 38 (92.7) |
| Other | 5 (9.6) | 4 (10.5) | 8 (15.1) | 6 (17.1) | 3 (5.6) | 3 (7.3) |
| Cancer type, n (%) | | | | | | |
| NSCLC | 21 (40.4) | 12 (31.6) | 21 (39.6) | 9 (25.7) | 19 (35.2) | 15 (36.6) |
| Colorectal | 21 (40.4) | 17 (44.7) | 21 (39.6) | 19 (54.3) | 20 (37.0) | 13 (31.7) |
| Other[a] | 10 (19.2) | 9 (23.7) | 11 (20.8) | 7 (20.0) | 15 (27.8) | 13 (31.7) |
| Mean (SD) weight change, % | −8.7 (5.0) | nd | −8.9 (4.8) | nd | −9.0 (5.7) | nd |
| Mean (SD) BMI, kg/m$^2$ | 24.1 (4.6) | 24.5 (5.0) | 23.5 (4.8) | 23.5 (4.6) | 24.0 (3.9) | 23.7 (3.9) |
| Mean (SD) LBM, kg | 47.0 (10.4) | 46.9 (10.8) | 42.8 (9.1) | 42.5 (9.1) | 45.3 (9.4) | 45.6 (9.6) |
| Mean (SD) stair climb power, watts (stairs 1-12) | 85.3 (30.5) | 85.7 (30.8) | 69.4 (34.6) | 69.1 (35.1) | 82.6 (37.9) | 78.0 (33.3) |
| Mean (SD) grip strength, kg | 29.0 (11.3) | 29.1 (11.7) | 26.7 (15.2) | 26.4 (15.4) | 29.1 (16.2) | 29.5 (17.9) |

Abbreviations:
BMI, body mass index;
LBM, lean body mass;
MITT, modified intent-to-treat;
NSCLC, non-small cell lung cancer;
nd, not determined.
[a]Includes non-Hodgkin's lymphoma, chronic lymphocytic leukemia, and breast cancer.

Efficacy

There was a statistically significant increase from baseline to Day 113/EOS in total LBM in patients who received Compound III 1 mg (P<0.001) and Compound III 3 mg (P=0.046), but not in those who received placebo (Table 18). The difference between the Compound III 3-mg group and the placebo group was statistically significant (mean change, P=0.041; percentage change, P=0.023). Patients who received Compound III 1 rag also had an increase in total LBM compared with patients receiving placebo, although this difference was not statistically significant. In addition to the pre-specified local reads of DXA scans, a post hoc analysis of the DXA scans was also conducted by a central radiology group. These results were consistent with those of the primary local read (data not shown).

TABLE 18

Change in Total Lean Body Mass: MITT Population

|  | Placebo | Compound III 1 mg | Compound III 3 mg | P value* Placebo vs Compound III | |
|---|---|---|---|---|---|
|  | (n = 38) | (n = 35) | (n = 41) | 1 mg | 3 mg |
| Change to Day 113/EOS | | | | | |
| N | 34 | 32 | 34 | | |
| Mean, g | 106.9 | 1492.4 | 1274.3 | 0.066 | 0.041 |
| SD | 2674.0 | 2734.4 | 3477.6 | | |
| P value† | 0.879 | 0.001 | 0.046 | | |
| Percentage change to Day 113/EOS | | | | | |
| N | 34 | 32 | 34 | | |
| Mean, % | 0.29 | 3.61 | 2.82 | 0.053 | 0.023 |
| SD | 5.80 | 6.53 | 7.18 | | |

Abbreviations:
EOS, end of study;
MITT, modified intent-to-treat.
*P values are from an Exact Wilcoxon rank-sum test with cancer type as the strata, except for analyses within a single cancer diagnosis.
†P values are from an Exact Wilcoxon signed rank test.

In the MIT population, an increase (~1 kg) in scale weight was observed by Day 113/EOS in all treatment groups (1.2%±1.5% change from baseline). Compared with placebo, patients who received Compound III 1 or 3 mg had numerically greater gains in scale weight from baseline to Day 29 (0.59 and 0.88 kg, respectively, vs 0.49 kg) and Day 57 (1.17 and 1.31 kg, respectively, vs 0.5 kg). These data are consistent with the changes seen in total LBM in these treatment groups.

Figure 17:
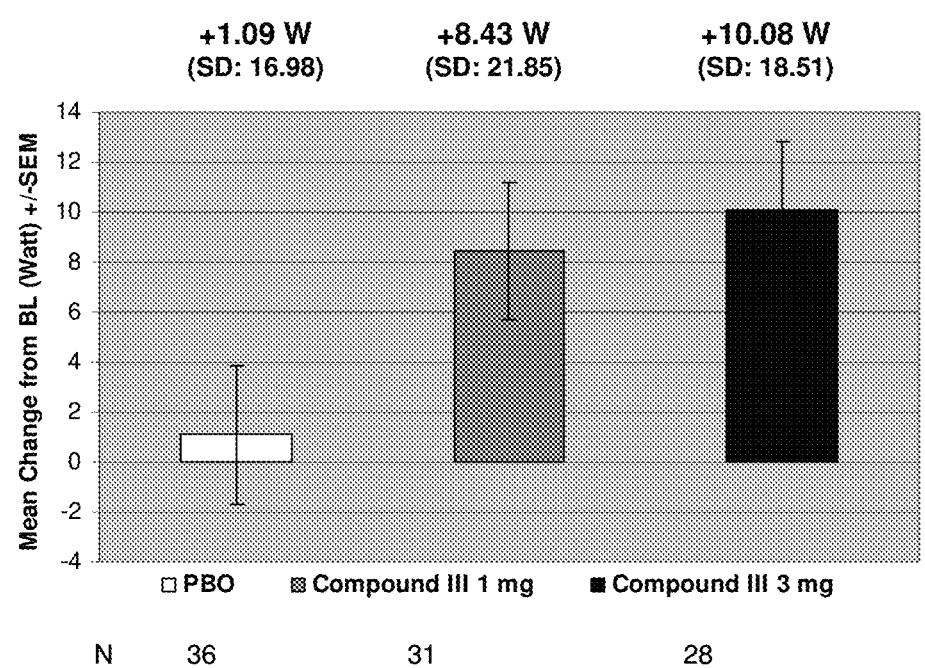
FIG. 17: Change from baseline to Day 113/EOS in stair climb power: MITT population.
EOS=end of study; MITT=modified intent-to-treat.
Figure 18:
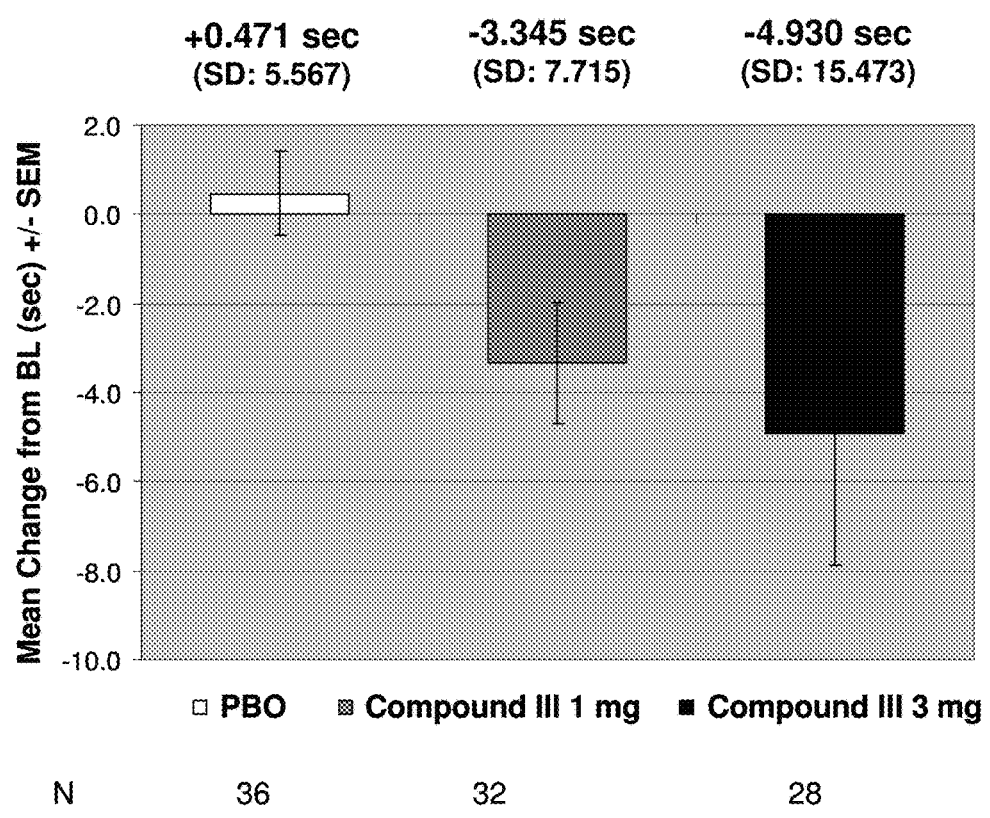
FIG. 18: Change from baseline to Day 113/EOS in stair climb time: MITT population. EOS=end of study; MITT=modified intent-to-treat.

There was a significant increase from baseline to Day 113/EOS in stair climb power among patients who received Compound III 1 or 3 mg (P≤0.002, stairs 1-12), but not those who received placebo (FIG. 17). This increase was significantly different from placebo in the Compound III 1-mg group (P=0.034), but not in the Compound III 3-mg group (P=0.058). A similar trend was observed for each set of stairs, with significant differences between the Compound III 1-mg and placebo groups for stairs 1-4, stairs 4-8, and stairs 8-12 (P≤0.036 for all comparisons). The time required to climb all 12 stairs increased slightly from baseline to Day 113/EOS in patients who received placebo, but was significantly decreased (P≤0.008) in both of the Compound III treatment groups (FIG. 18). These changes were significantly different compared with placebo in the Compound III 1-mg (P=0.007) and Compound III 3-mg (P=0.028) treatment groups.

The percentage changes from baseline to Day 113/EOS in hand grip strength (both hands) increased in both Compound III treatment groups (1 mg, 15.06%; 3 mg, 4.93%). Patients in the placebo group experienced a decrease in hand grip strength (−1.07% from baseline to Day 113/EOS). Compared with placebo, there was a significant difference in the percentage change from baseline in the Compound III 1-mg group (P=0.05).

A post hoc analysis demonstrated a significant and clinically meaningful improvement in QoL parameters in patients that showed a ≥1-second improvement in stair climb time compared with patients who did not show this improvement (P≤0.028). A similar statistically significant improvement in QoL measurements from baseline to Day 113/EOS was seen in patients who had an increase in stair climb power of >9.8 watts compared with patients without this change (P≤0.016).

Compound III is well tolerated and safe in patients with cancer cachexia and resulted in significant increases in LBM and improvements in physical function. Importantly, this study provides evidence of clinically meaningful improvements in QoL among patients who experienced improvements in physical function (as assessed by stair climb power) with Compound III treatment. The use of Compound III at an earlier stage of disease, possibly as a first-line treatment, may allow for a greater clinical benefit.

Example 12

Effect of Compound of Formula S-(III) on Physical Function in Patients with Non Small Cell Lung Cancer (NSCLC)

This randomized, double-blind, placebo-controlled, multicenter phase II trial evaluated the efficacy and safety of Compound III, a selective androgen receptor modulator, in cancer patients with muscle wasting.

Patients and Methods:

Eligible patients were non-obese men aged >45 years or postmenopausal women with cancer (colorectal, NSCLC, non-Hodgkin's lymphoma, chronic lymphocytic leukaemia and breast cancer) and 22% weight loss in the previous 6 months. Patients (N=159) received Compound III 1 mg, 3 mg, or placebo orally once daily for up to 113 days. Total LBM was evaluated as the primary endpoint using dual energy x-ray absorptiometry. The primary endpoint was change in lean body mass measured by dual energy x-ray absorptiometry. Secondary endpoints included QoL and physical function with clinical benefit defined as 10% improvement in physical function assessed by stair climb power (responder analysis). LBM, physical function and QoL were further assessed in the subset of NSCLC subjects (N=61).

Results:

Among NSCLC subjects, 28 were included in the physical function analysis (MITT). Total LBM and stair climb power increased in Compound III treated subjects compared to baseline (Table 19). LBM improved by a median of 0.99% from baseline to Day 113/end of study with Compound III (N=21, MITT; P=0.272) and decreased by 0.83% in placebo (N=10, MITT). Stair climb power increased by a median 15.15% (N=18, MITT; P=0.076) in the Compound III treated subjects compared to baseline and increased by 1.14% (N=10, MITT) in the placebo subjects.

Seventy-eight percent of NSCLC patients treated with Compound III responded, as defined by a 10% improvement in stair climb power, compared to 30% treated with placebo (P=0.02). Physical function was positively correlated with QoL as assessed by the Functional Assessment of Anorexia/Cachexia Therapy (FAACT) questionnaire further substantiating clinical benefit (Spearman correlation coefficient=0.60, P=0.001) (FIG. 19).

TABLE 19

| Treated | N Obs | Variable | N | Min | Median | Max | Mean | Std Dev | Pvalue |
|---|---|---|---|---|---|---|---|---|---|
| Placebo | 12 | LBM | 10 | −5.72 | −0.83 | 4.35 | −0.54 | 2.71 | |
| | | stair power_1_12 | 10 | −10.45 | 1.14 | 26.80 | 2.73 | 12.15 | |
| Compound III | 24 | LBM | 21 | −4.84 | 0.99 | 6.81 | 0.37 | 2.70 | 0.272 |
| 1 mg/3 mg | | stair power_1_12 | 18 | −81.58 | 15.15 | 38.19 | 8.52 | 25.79 | 0.076 |

Example 13

Effect of Compound of Formula S-(III) on Overall Survival in Patients with Cancer Cachexia Subjects (n=159) were randomized to oral Compound of formula S-(III) (Compound III) (1 or 3 mg) or placebo (pbo) daily for 16 weeks. Subjects were males >45 y and postmenopausal females, had experienced ≥2% weight loss in the 6 months prior to randomization, had a body mass index (BMI)<35 and either NSCLC, colorectal cancer, non-Hodgkin's lymphoma, chronic lymphocytic leukemia or breast cancer.

In placebo (pbo) subjects in the intent to treat (ITT) population, overall survival was significantly (P=0.003, log rank) reduced in subjects with >8% weight loss compared to subjects with ≤8% weight loss. Among NSCLC subjects (n=61) pbo subjects with >8% weight loss demonstrated a similar survival disadvantage (P=0.04); 4 month Kaplan-Meier estimates 100% vs 49%±14.8%. In Compound III treated subjects in both the ITT and NSCLC groups, increased weight loss did not negatively affect survival.

Preceding weight loss among NSCLC patients not treated with Compound III is predictive of decreased overall survival. In this 16 week study, NSCLC subjects randomized to placebo with >8% weight loss at baseline were 2 times more likely to die than subjects with ≤8% weight loss. In the Compound III group weight loss was not predictive of overall survival. These data suggest that Compound III treatment may overcome the negative prognostic effect of >8% weight loss.

Example 14

Chemotherapeutic Agents Given in Combination with Compound of Formula S-(III) for Cancer Cachexia Clinical Trials, Distribution According to Chemotherapy Agent Class

TABLE 20

Distribution of Chemotherapy in Arms according to Chemotherapy Agent Class

| Chemo agent Class | Placebo N = 52 n (%) | Compound III Treated N = 107 | P Value[1] |
|---|---|---|---|
| Alkylating agents | 22 (42) | 47 (44) | 0.87 |
| Antibodies | 21 (40) | 40 (37) | 0.73 |
| Antimetabolites | 16 (31) | 51 (48) | 0.06 |
| Kinase Inhibitors | 4 (8) | 3 (3) | 0.22 |
| Topo II Inhibitors | 10 (19) | 22 (21) | 0.99 |
| Tubulin Antagonists | 13 (25) | 25 (23) | 0.84 |

[1]Exact Pearson's chi-square test
Percentages are rounded to nearest whole percent.

Specific chemotherapeutic agents administered to subjects receiving compound of formula S-(III) include: bendamustine, bevacizumab, bleomycin, calcium folinate, capecitabine, carboplatin, cetuximab, chlorambucil, cisplatin, cyclophosphamide, cytarabine, docetaxel, doxorubicin, erlotinib, etoposide, fludarabine, fluorouracil, gemcitabine hydrochloride, irinotecan hydrochloride, lapatinib, methotrexate, methylprednisolone acetate, mitoxantrone, mitoxantrone hydrochloride, oxaliplatin, paclitaxel, panitumumab, pemetrexed, rituximab, trastuzumab, vincristine, and vinorelbine.

Example 15

Combination Treatment of Compound of Formula S-(III) with Platinum and Taxane (Study A) and Combination Treatment of Compound of Formula S-(III) with Platinum and Non-Taxane (Study B)

Methods

A 3 mg dose of Compound III was studied in two Phase 3 clinical trials (Study A and Study B) to prevent and treat muscle wasting in patients with non-small cell lung cancer (NSCLC). In each of these placebo controlled, double blind, add-on clinical trials, approximately 325 patients with stage III or IV NSCLC were randomized to oral daily doses of placebo or Compound III 3 mg at initiation of first-line chemotherapy based upon the chemotherapy regimen prescribed; platinum+taxane (Study A, n=321) or platinum+non-taxane (Study B, n=320). Patients (males and postmenopausal females 30 y with ECOG 1) received either Compound III 3 mg combination therapy or placebo for 5 months. The platinum used was cisplatin or carboplatin. The taxane used was docetaxel or paclitaxel. The non-taxane used was gemcitabine, pemetrexed or vinorelbine.

Lean body mass (LBM) was measured by dual-energy x-ray absorptiometry (DXA) and improvement of physical function was assessed by stair climb power (SCP) at days 84 (primary endpoints) and 147 (secondary endpoints). The stair climb power was measured according to the following equation: Power=9.8 $m/s^2$×stair height [m]×weight [kg]/stair climb time [s].

Secondary endpoints also included an assessment of whether Compound III-treated patients had an improved quality of life and reduced healthcare resource utilization compared to placebo.

Overall survival is being assessed as an additional safety endpoint.

Table 21 provides the baseline characteristics of Study A (combination treatment of Compound III, platinum and taxane vs. a placebo of combination of platinum and taxane) and Study B (combination treatment of Compound III, platinum and non-taxane vs. a placebo of platinum and non-taxane).

TABLE 21

| | Baseline Characteristics | | | |
|---|---|---|---|---|
| | Study A Platinum + Taxane (N = 321) | | Study B Platinum + Non-Taxane (N = 320) | |
| Feature | Placebo (n = 161) | Compound III (n = 160) | Placebo (n = 161) | Compound III (n = 159) |
| Age (y) median (range) | 62.0 (34 to 88) | 60.5 (36 to 84) | 62.0 (40 to 81) | 60.0 (41 to 79) |
| Male | 71.4% | 73.1% | 70.2% | 71.7% |
| ECOG 1 | 68.3% | 68.8% | 68.3% | 71.1% |
| Stage | | | | |
| III | 28.0% | 28.8% | 28.0% | 27.0% |
| IV | 72.0% | 71.3% | 72.1% | 73.0 |
| Chemo regimen | | | | |
| Docetaxel | 8.7% | 9.4% | — | — |
| Paclitaxel | 91.3% | 90.6% | — | — |
| Gemcitabine | — | — | 72.1% | 72.3% |
| Pemetrexed | — | — | 16.2% | 15.7% |
| Vinorelbine | — | — | 11.8% | 12.0% |
| Baseline LBM (kg/m$^2$) adjusted for height | | | | |
| Female | 14.2 (11.6 to 19.1) | 14.6 (10.8 to 18.1) | 14.8 (12.7 to 17.5) | 14.4 (11.2 to 18.0) |
| Male | 17.1 (11.9 to 21.5) | 17.6 (11.7 to 21.6) | 17.3 (13.3 to 24.9) | 17.1 (13.1 to 22.7) |
| Baseline power (watts) | 158.3 (25.7 to 435.0) | 156.5 (46.7 to 446.8) | 161.6 (65.2 to 458.3) | 164.8 (30.1 to 485.2) |
| >5% weight loss prior 6 months | 49.1% | 42.5% | 51.3% | 49.1% |

| Baseline demographics for Study A and Study B | | | | |
|---|---|---|---|---|
| | Study A (Platinum + Taxane) | | Study B (Platinum + Nontaxane) | |
| | Placebo | Cmpd. III | Placebo | Cmpd. III |
| Age (y) | 61.9 | 61.2 | 62.2 | 61.0 |
| Male % | 71.4 | 73.1 | 70.2 | 71.7 |
| ECOG 1 (%) | 68.3 | 68.8 | 68.3 | 71.1 |
| >1 mets (%) | 37.9 | 29.4 | 41.6 | 42.1 |
| Lung (%)* | 40.4 | 37.5 | 42.9 | 44.0 |
| Liver (%)* | 14.3 | 9.4 | 14.3 | 13.2 |
| Bone (%)* | 15.5 | 11.9 | 16.1 | 19.5 |
| Lymph (%)* | 27.3 | 18.1 | 33.5 | 33.3 |
| Brain (%)* | 9.3 | 11.3 | 12.4 | 12.6 |
| >5% loss (%) | 49.1 | 42.5 | 51.3 | 49.1 |

*Referring to percentage of subject with metastases to the respective tissues.

Figure 20A:
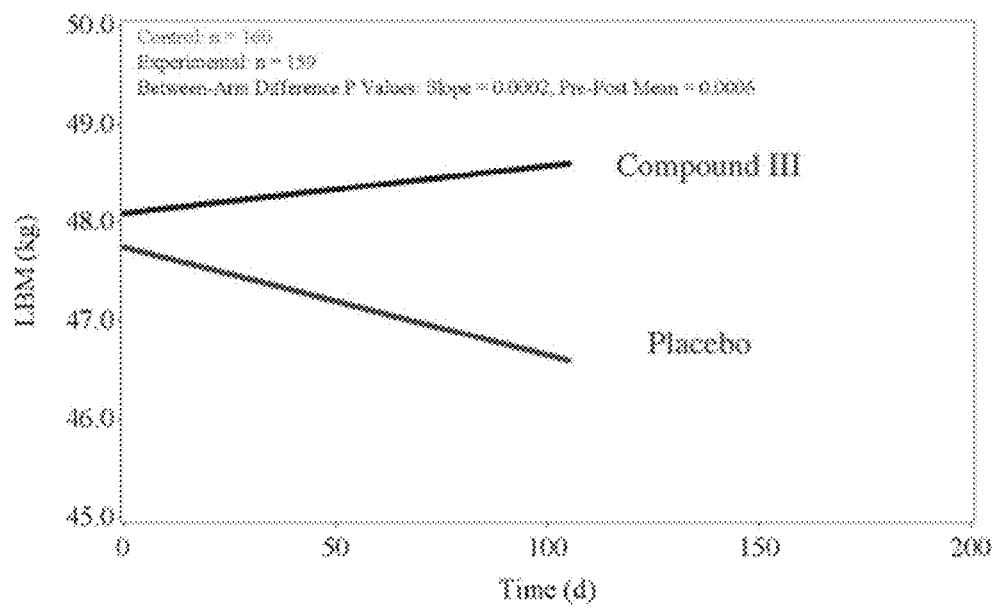
FIGS. 20A-20B depict Study A—Platinum+Taxane plus add on Lean body mass efficacy endpoint.
Figure 20B:
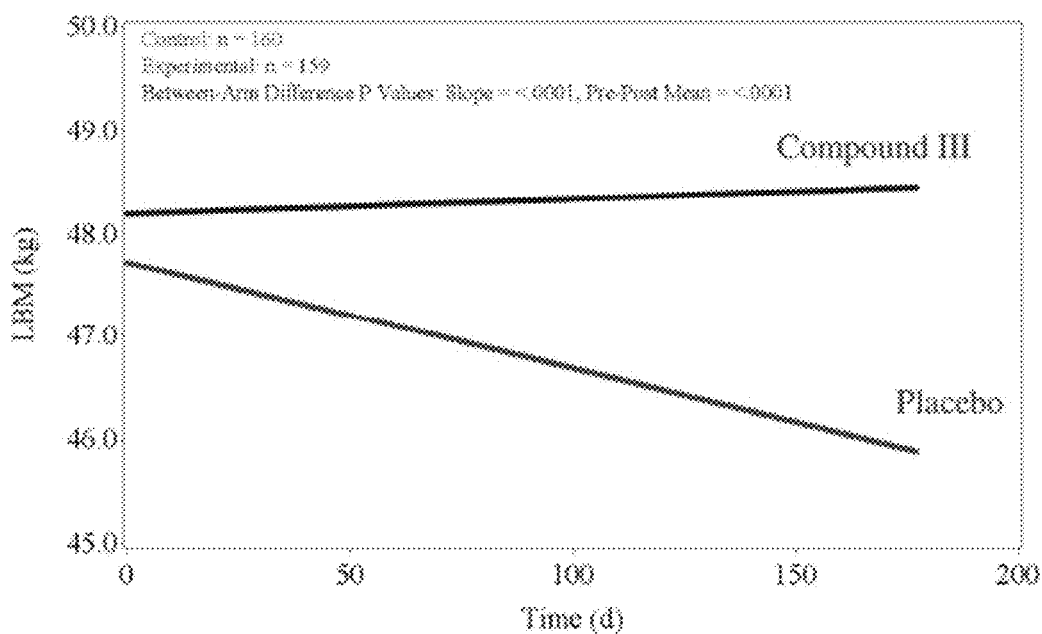
Figure 23A:
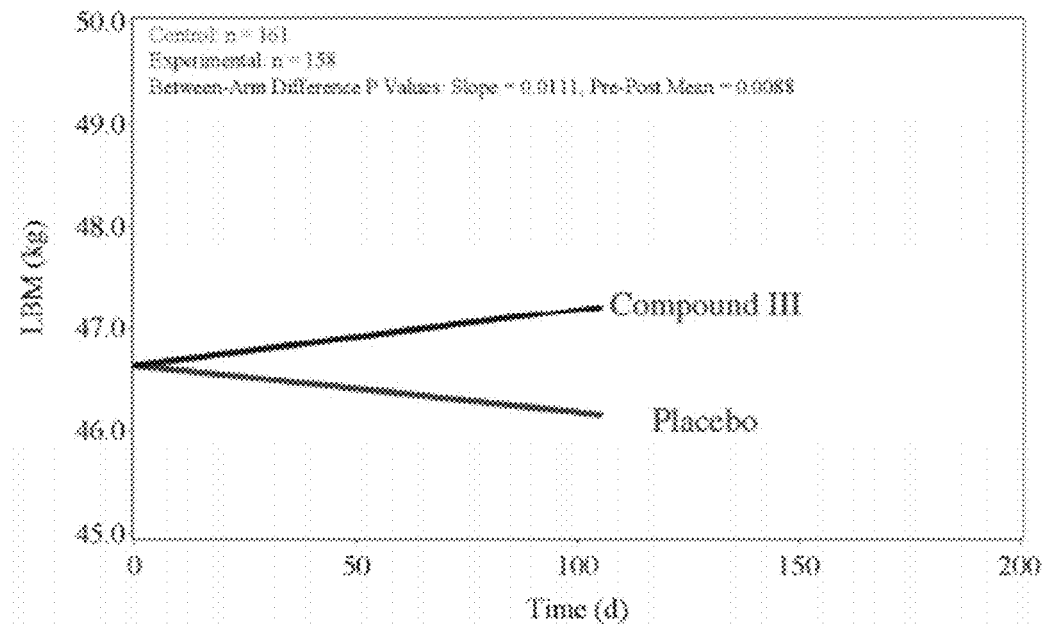
FIGS. 23A-23B depict Study B—Platinum+nontaxane plus add on lean body mass efficacy endpoint.
Figure 23B:
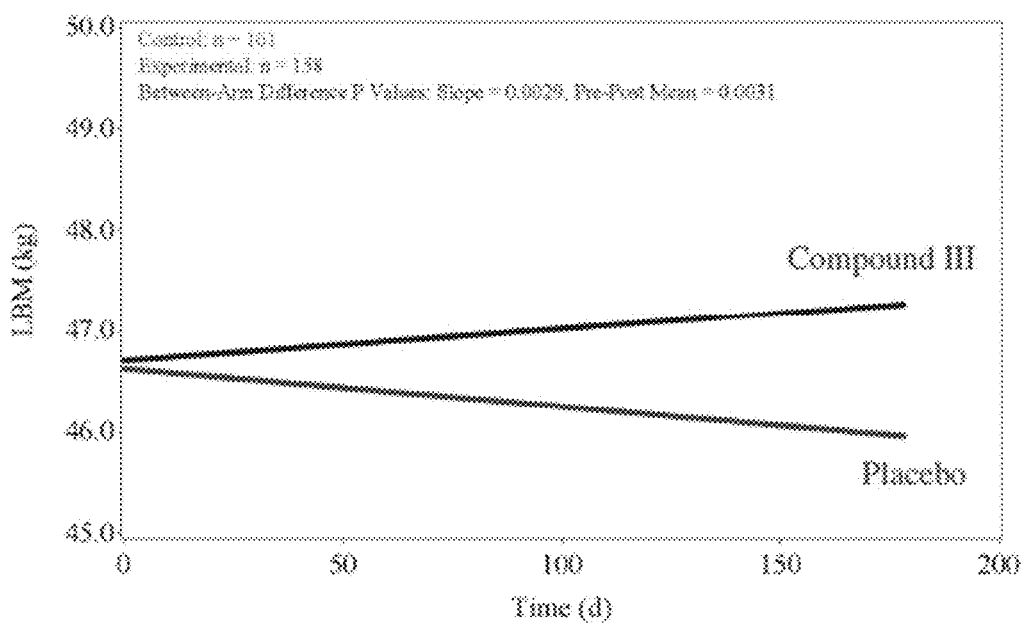

Results:

Compound III 3 mg once daily had a significant effect on LBM through Day 84 to and 147 in both studies:

Study A: p=0.0003 (day 84) and <0.0001 (day 147), as presented in Table 22B and FIGS. 20A-20B;

Study B: p=0.0227 (day 84) and 0.0036 (day 147), as presented in Table 23B and FIGS. 23A-23B, using continuous variable analyses.

By the responder* analysis, a larger proportion of patients receiving Compound III maintained or increased LBM at Day 84 and 147 in both studies (Study A: p=0.036 (Table 22A) and 0.026 (Table 22C); Study B: p=0.113 (Table 23A) and 0.013 (Table 23C)), as compared to placebo.

*Responder in this case defined as a subject that maintained or demonstrated an increase in LBM at Day 84 as compared to baseline and that demonstrated a 10% or greater increase in stair climb power [watts] at Day 84 as compared to baseline.

A non-responder is a subject who does not meet the definition of response or does not have the Day 84 assessment. Variations on the responder analyses are presented in Results of Study a (Combination Treatment of Compound III, Platinum and Taxane)

TABLE 22A

| | | Responder Analyses | | |
|---|---|---|---|---|
| | | % Responders (n) | | |
| | | Placebo (N = 161) | Compound III (N = 160) | p-value |
| LBM | Day 84 | 30.4% (49) | 41.9% (67) | 0.036 |
| SCP | Day 84 | 24.2% (39) | 29.4% (47) | 0.315 |

TABLE 22B

Mixed-effect Model Repeated Measure (MMRM) Analyses

|   | Statistical hierarchy | | MMRM Slopes | | |
|---|---|---|---|---|---|
|   |   |   | Placebo | Compound III | p-value |
| 1 | SCP | Day 84  | −0.0639 | +0.0522 | 0.0185 |
| 2 | LBM | Day 84  | −9.8357 | +4.5459 | 0.0003 |
| 3 | SCP | Day 147 | −0.0652 | −0.0166 | 0.0486 |
| 4 | LBM | Day 147 | −9.6908 | +1.2782 | <0.0001 |

TABLE 22C

Results for 5% and 10% increase in stair climb power

|   | Statistical hierarchy | | | % Responders (n) | | |
|---|---|---|---|---|---|---|
|   |   |   |   | Placebo N = 161 | Compound III N = 160 | p-value |
| 5 | SCP | 5%  | Day 84  | 32.3% (52) | 36.3 (58)  | 0.407 |
| 6 | SCP | 10% | Day 147 | 18.0% (29) | 20.6% (33) | 0.671 |
| 7 | LBM |     | Day 147 | 23.5% (38) | 35.0% (56) | 0.026 |

Figure 22A:
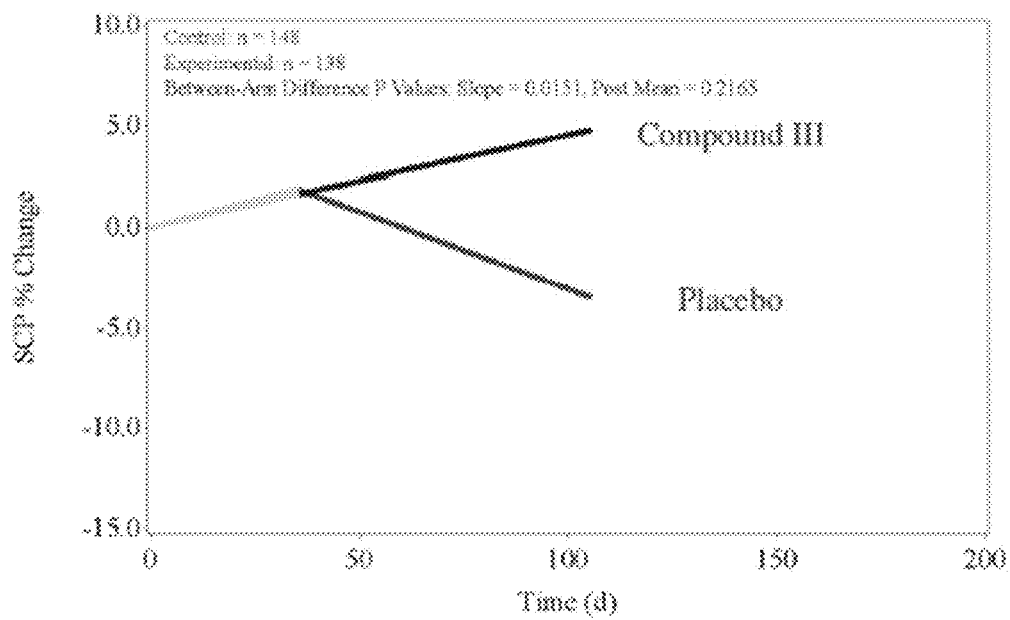
FIGS. 22A-22B depict Study A—Platinum+Taxane plus add on Stair climb test (% power change) efficacy endpoints.
Figure 22B:
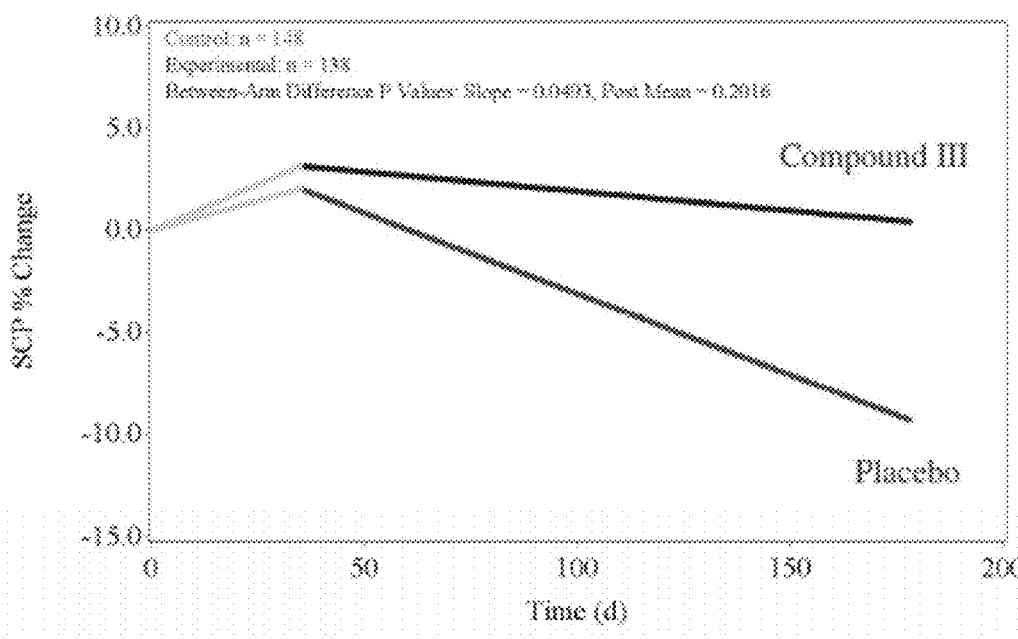

Compound III treated patients in Study A achieved the primary endpoint in SCP through Day 84 (p=0.0185) and the secondary endpoint of SCP through Day 147 (p=0.0486) (Table 22B above and FIGS. 22A-22B).

Figure 21A:
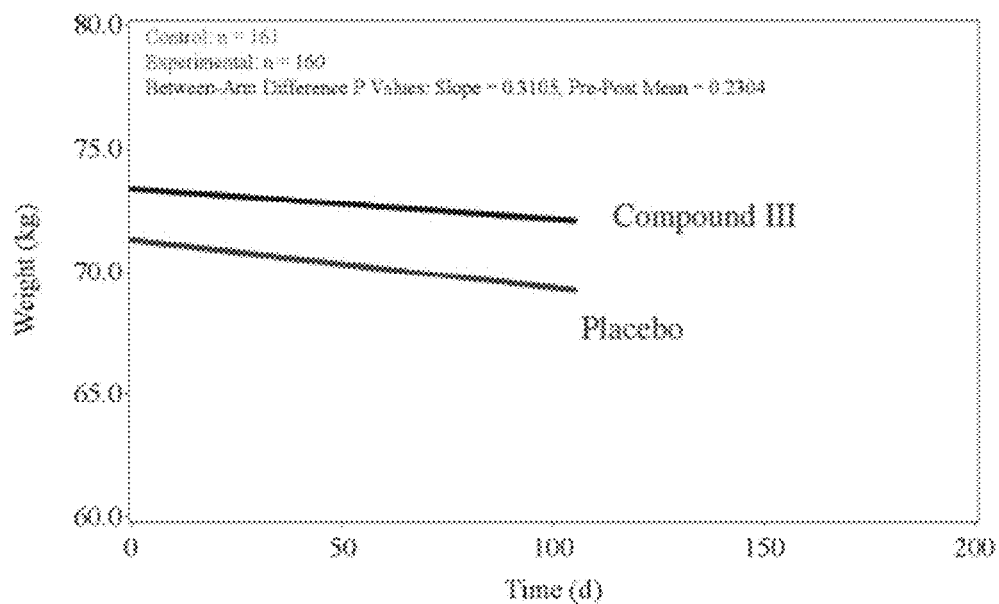
FIGS. 21A-21B depict Study A—Platinum+Taxane plus add on body weight efficacy endpoints.
Figure 21B:
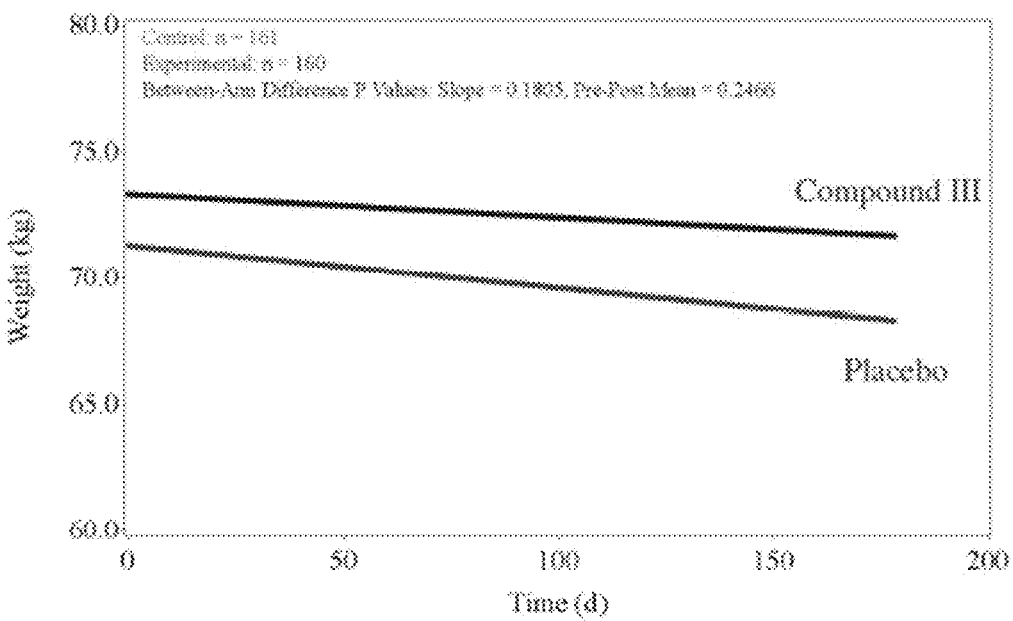

The effect on LBM in Study A was achieved despite declining of body weight (FIG. 21A-21B).

TABLE 22D

Percentage of subjects (of Study A) who had a day 84 and a day 147 response

| Stair Climb Power (% Responders) | |
|---|---|
| Placebo | 43.6% (n = 17) |
| Compound III | 57.4% (n = 27) |
| Lean Body Mass (% Responders) | |
| Placebo | 55.1% (n = 27) |
| Compound III | 67.2% (n = 45) |

TABLE 22E

Percentage in which LBM was maintained or increased and SCP was ≥10% increased (Study A)

|   | % Responder | |
|---|---|---|
|   | Day 84 | Day 147 |
| Placebo | 10.6 | 6.8 |
| Compound III | 19.4 | 12.5 |
| p value | 0.029 | 0.09 |

TABLE 22F

Percentage in which LBM was maintained or increased and SCP was maintained or increased (Study A)

|   | % Responders | |
|---|---|---|
|   | Day 84 | Day 147 |
| Placebo | 16.2 | 13.7 |
| Compound III | 30.0 | 20.0 |
| p value | 0.004 | 0.1624 |

Results of Study B (Combination Treatment of Compound III, Platinum and Non-Taxane)

Efficacy Endpoints

TABLE 23A

Responders analyses

|   |   | % Responders (n) | | |
|---|---|---|---|---|
|   |   | Placebo (N = 161) | Compound III (N = 159) | p-value |
| LBM | Day 84 | 37.9% (61) | 46.5% (74) | 0.113 |
| SCP | Day 84 | 24.8% (40) | 19.5% (31) | 0.289 |

TABLE 23B

MMRM analyses

|   | Statistical hierarchy | | MMRM slopes | | |
|---|---|---|---|---|---|
|   |   |   | Placebo | Compound III | p-value |
| 1 | SCP | Day 84  | −0.0146 | −0.0263 | 0.7923 |
| 2 | LBM | Day 84  | −5.5577 | +4.0065 | 0.0227 |
| 3 | SCP | Day 147 | −0.0050 | +0.0072 | 0.6669 |
| 4 | LBM | Day 147 | −5.2270 | +2.1192 | 0.0036 |

TABLE 23C

|   | Statistical hierarchy | | | % Responders (n) | | |
|---|---|---|---|---|---|---|
|   |   |   |   | Placebo N = 161 | Compound III N = 159 | p-value |
| 5 | SCP | 5%  | Day 84  | 33.5% (54) | 23.9% (38) | 0.054 |
| 6 | SCP | 10% | Day 147 | 21.1% (34) | 18.9% (30) | 0.679 |
| 7 | LBM |     | Day 147 | 27.9% (45) | 40.9% (65) | 0.013 |

TABLE 23D

Percentage of subjects who had a day 84 and a day 147 response

| Stair Climb Power (% Responders) | |
|---|---|
| Placebo | 57.5% (n = 23) |
| Compound III | 51.6% (n = 16) |
| Lean Body Mass (% Responders) | |
| Placebo | 62.3% (n = 38) |
| Compound III | 73.0% (n = 54) |

TABLE 23E

Percentage in which LBM was maintained or increased and SCP: ≥10% increase (Study B)

| | % Responders | |
|---|---|---|
| | Day 84 | Day 147 |
| Placebo | 14.9 | 9.3 |
| Compound III | 15.1 | 15.1 |
| p value | 0.99 | 0.126 |

TABLE 23F

Percentage in which LBM was maintained or increased and SCP was maintained or increased (Study B)

| | % Responders | |
|---|---|---|
| | Day 84 | Day 147 |
| Placebo | 24.2 | 16.8 |
| Compound III | 23.3 | 22.6 |
| p value | 0.939 | 0.2325 |

Figure 24A:
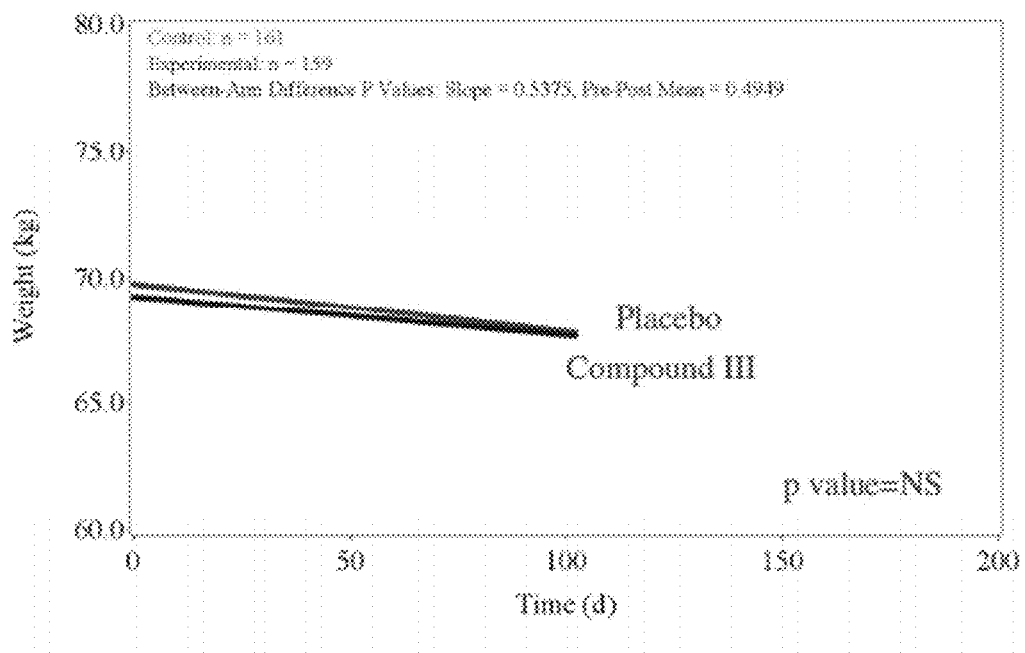
FIGS. 24A-24B depict Study B—Platinum+nonaxane plus add on body weight endpoint.
Figure 24B:
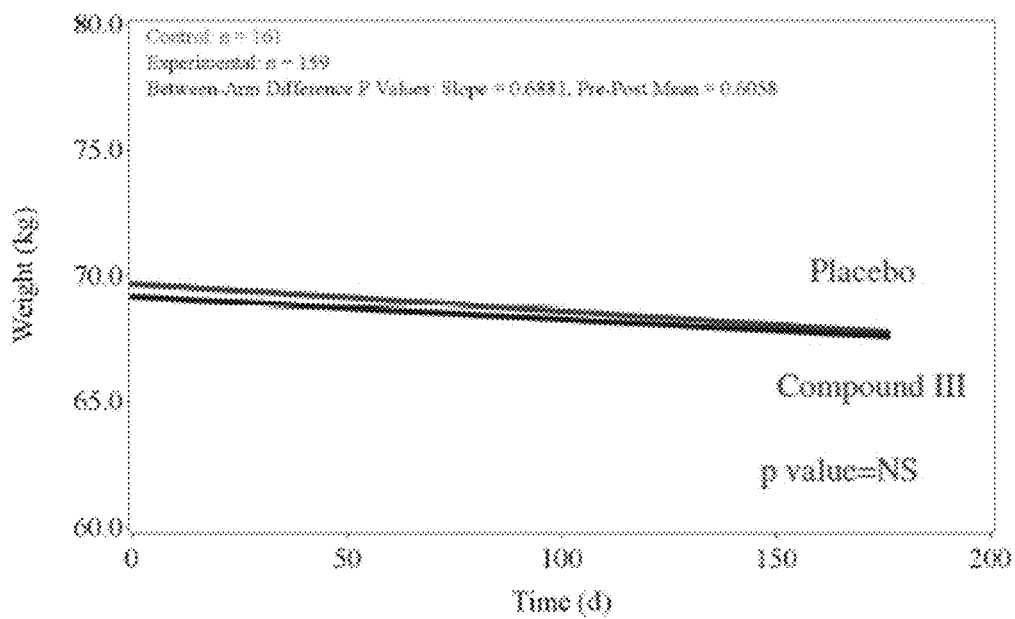
Figure 25A:
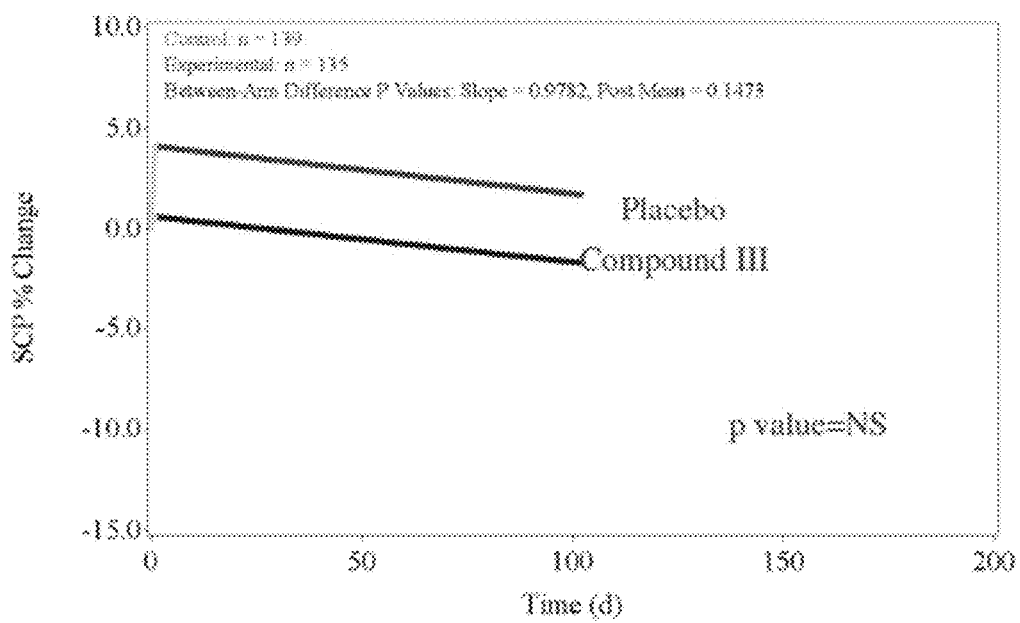
FIGS. 25A-25B depict Study B—Platinum+nonaxane plus add on stair climb test (% power change) efficacy endpoint.
Figure 25B:
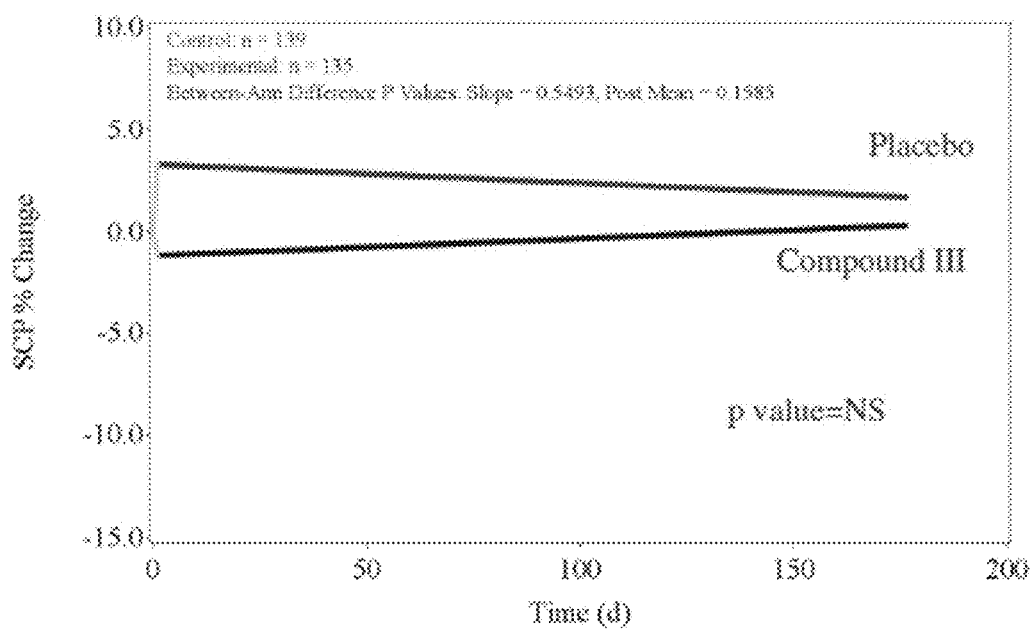

The effect on LBM in Study B was achieved despite declining of body weight (FIGS. 24A-24B).

In a post-hoc analysis, regardless of treatment, patients with a ≥1 kg increase in LBM were more likely to demonstrate at least a 10% increase in SCP compared to patients who did not have a ≥1 kg increase in LBM (Study A: 43.7% vs 29.3%, p=0.0250; and Study B: 40.5% vs 26.5%, p=0.0321) (FIGS. 35 and 36). The percentage improvement in SCP from baseline to day 84 differed significantly between patients with and without a 1 kg increase in LBM: 9.1% vs −1.0% in Study A (p=0.0022) and 7.7% vs −0.0.6% in Study B (p=0.0046).

Importantly, a larger proportion of Compound III treated patients, with 1 kg or greater increases in LBM, demonstrated at least a 10% increase in SCP (Study A: p= 0.0698, ≥1 kg 46.4%, <1 kg 29.6%; and Study B: p=0.0335, ≥1 kg 39.6%, <1 kg 20.4%), while this same trend was not observed in placebo treated patients (Study A: p=0.3149, ≥1 kg 38.7%, <1 kg 29.0%; and Study B: p=0.2852, ≥1 kg 41.5%, <1 kg 31.3%) (FIG. 36). This observation suggests that SCP improvements, in both trials, may be related to Compound III dependent increases in LBM.

Figure 31:
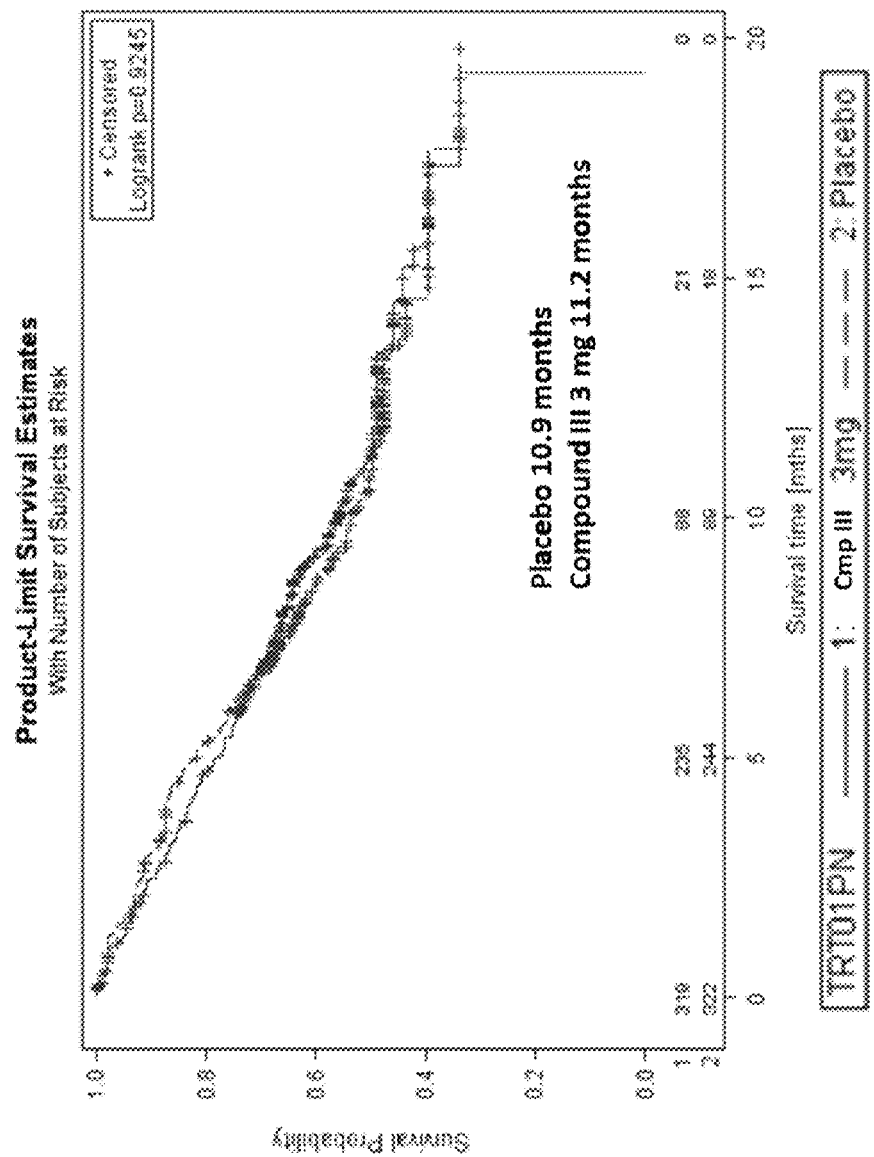
FIG. 31 depicts pooled survival analysis.
Figure 32:
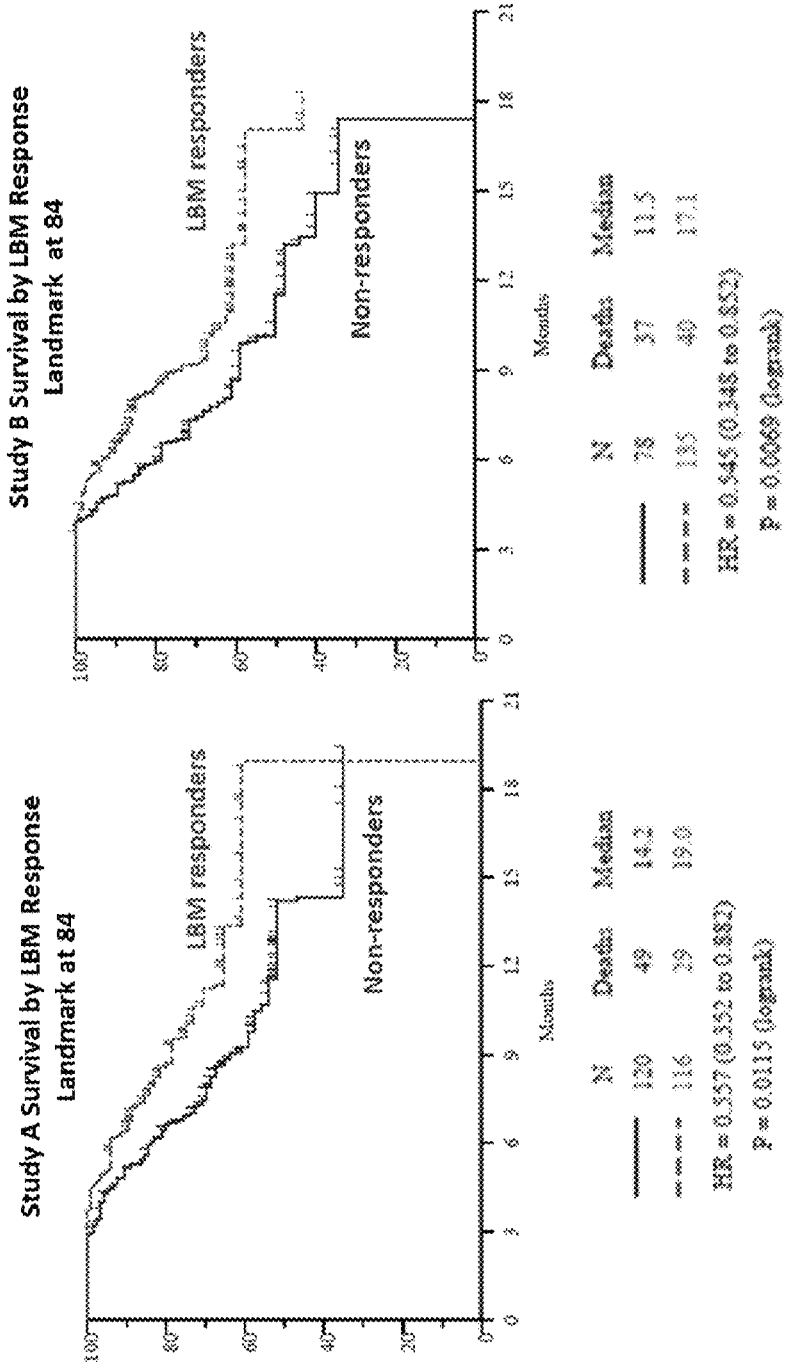
FIG. 32 shows Day 84 LBM response is associated with longer survival landmark analyses.
Figure 33:
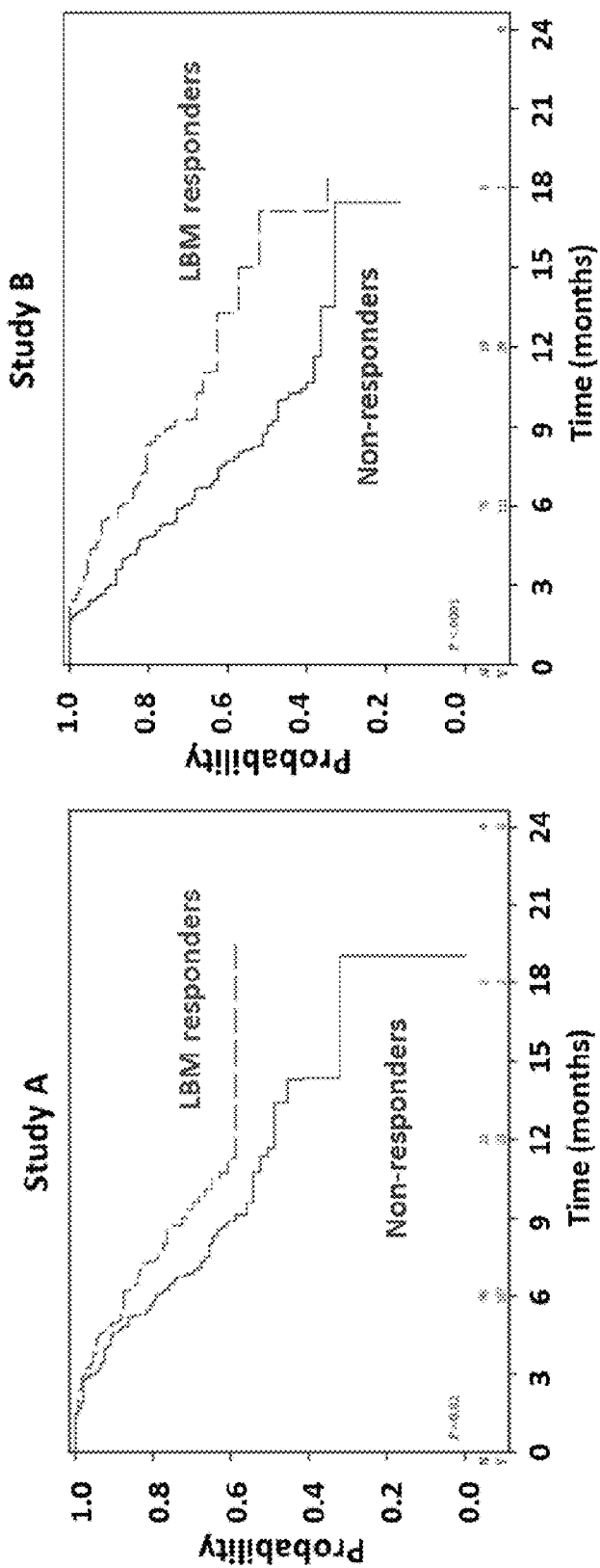
FIG. 33 shows Day 42 LBM response is associated with longer survival landmark analyses.
Figure 34:
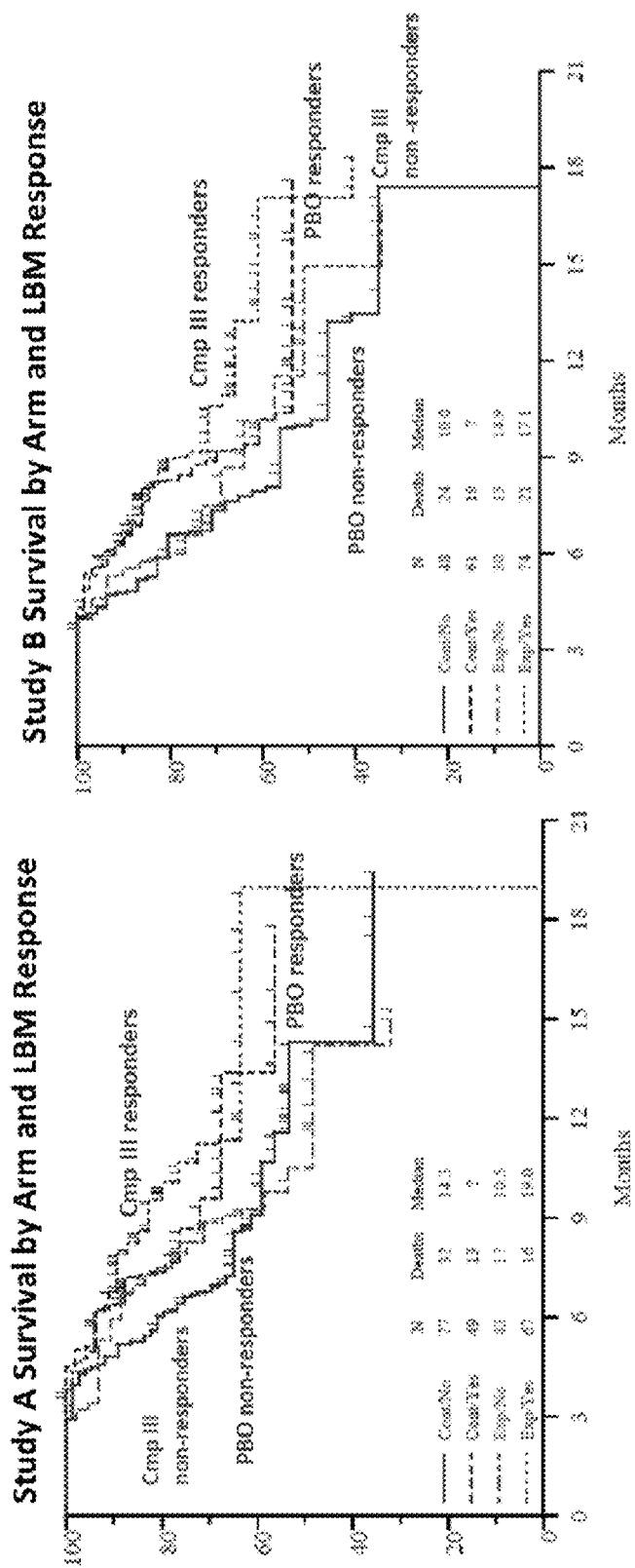
FIG. 34 depicts survival by arm and LBM response.

Post-hoc landmark survival analyses at Day 84 suggest improved survival in patients who maintained or increased LBM in both clinical trials, regardless of treatment. (FIG. 31). Published studies have reported that loss of muscle is associated with shorter survival in cancer patients. Studies A and B support these primarily retrospective analyses with a prospective assessment of the relationship between LBM and overall survival in advanced lung cancer patients (FIGS. 32-34).

Summary and Conclusions

TABLE 24

Summary of adequate, well controlled clinical studies for Compound III for the prevention and treatment of muscle wasting in patients with advanced NSCLC.

| | Study (Duration) | | | | | |
|---|---|---|---|---|---|---|
| | Results from Study disclosed in Examples 11 and 12 hereinabove | | | Phase 3 Study A (20 weeks) | | Phase 3 Study B (20 weeks) | |
| | (16 weeks) | | | Placebo | 3 mg | Placebo | 3 mg |
| | Placebo | 1 mg | 3 mg | (Day 84) | (Day 84) | (Day 84) | (Day 84) |
| LBM change (Muscle) | 0.02 kg | 1.5 kg | 1.0 kg | −9.8357 slope | +4.5459 slope | −5.5577 slope | +4.0065 slope |
| SCP change (Function) | +4.8% | +18.0% | +21.7% | −0.0639 slope | +0.0522 slope | −0.0146 slope | −0.0263 slope |
| Safety | | + | + | | + | | + |
| Survival (HR) | N/A | 0.80 | 0.70 | 0.54* | 0.38* | 0.6* | 0.37* |
| Population type | NSCLC, colorectal, NonHodgkins, CLL, Breast cancers- Chemo not controlled: | | | NSCLC Chemo controlled: Platinum + Taxane | | NSCLC Chemo controlled: Platinum + Nontaxane | |
| N | 159 | | | 321 | | 320 | |

NSCLC patients on first line platinum doublet chemotherapy have accelerated muscle loss and physical function decline in a background of progressive weight loss. Compound III maintained or improved muscle mass while subjects on chemotherapy alone continued to lose muscle mass over a relatively short period of time (3 months). Compound III stopped the physical function decline while subjects on chemotherapy alone continued to decline in physical function. Prevention and treatment of muscle loss was demonstrated in both Study A and Study B clinical trials.

Lean body mass was observed to be an important prognostic indicator for increased survival in both chemotherapy and chemotherapy plus Compound III NSCLC patients. Compound III maintained and built muscle better than chemotherapy alone.

In Study A and Study B, declines in both lean body mass and stair climb power were observed in placebo group.

Statistically and clinically meaningful differences between Compound III (Study A) and placebo were observed for both lean body mass (muscle) and stair climb test (physical function).

Statistically and clinically meaningful differences between Compound III (Study B) and placebo were observed for lean body mass (muscle).

The effect on LBM in Study A and Study B was achieved despite declining body weights (FIGS. 21A-21B and 24A-24B).

Different populations and chemotherapy side effects (anemia & vomiting (See Example 16)) in Study B appear to explain physical function responses. Evidence suggests longer duration of therapy or increasing Compound III dose may overcome these side effects of chemotherapy Compound III was very well tolerated in both Study A and Study B. In general, patients that maintained or increased LBM had greater increases in SCP and survived longer.

Example 16

Adverse Events of Study A and Study B

Table 24 provides treatment emergent adverse events of subjects treated with the combination of Compound III, platinum and taxane (Study A) and subjects treated with Compound III, platinum and non-taxane (Study B).

Based on the results, adverse events were observed in ≥5% subjects with a difference of ≥22% between placebo and Compound III.

TABLE 25

Differences in selected AEs between the Studies

| Adverse Event | STUDY A (Platinum + Taxane) | | STUDY B (Platnium + Nontaxane) | |
|---|---|---|---|---|
| | Placebo | Cmpd III | Placebo | Cmpd III |
| Anemia | 27.3% | 28.8% | 47.9% | 50.9% |
| Neutropenia | 18.6% | 12.5% | 33.9% | 30.9% |
| Leukopenia | 3.1% | 3.8% | 17.0% | 15.8% |
| Thrombocytopenia | 5.6% | 3.8% | 17.6% | 18.8% |
| Nausea | 32.3% | 35.6% | 44.2% | 44.8% |
| Vomiting | 16.1% | 18.1% | 29.1% | 27.3% |
| Constipation | 8.6% | 10.6% | 15.2% | 12.7% |
| Asthenia | 12.4% | 20.6% | 16.4% | 15.2% |
| Decreased appetite | 16.8% | 6.9% | 17.0% | 19.4% |
| Arthralgia | 13.7% | 16.9% | 2.4% | 1.8% |
| Alopecia | 32.3% | 33.8% | 10.3% | 10.9% |
| Diarrhoea | 14.9% | 11.3% | | |

TABLE 25-continued

Differences in selected AEs between the Studies

| Adverse Event | STUDY A (Platinum + Taxane) | | STUDY B (Platnium + Nontaxane) | |
|---|---|---|---|---|
| | Placebo | Cmpd III | Placebo | Cmpd III |
| Dyspnoea | 7.5% | 13.1% | 6.7% | 12.7% |
| Peripheral Sensory Neuropathy | 5.6% | 11.9% | | |
| Pneumonia | 8.7% | 5.0% | | |
| Haemoptysis | 8.7% | 4.4% | 6.7% | 3.6% |
| Pain in Extremity | 5.6% | 8.1% | | |
| Chest pain | | | 7.3% | 3.6% |
| Cough | | | 9.1% | 11.5% |
| Hypokalemia | | | 7.3% | 3.0% |
| Blood creatinine increased | | | 9.1% | 13.9% |

Figure 26:
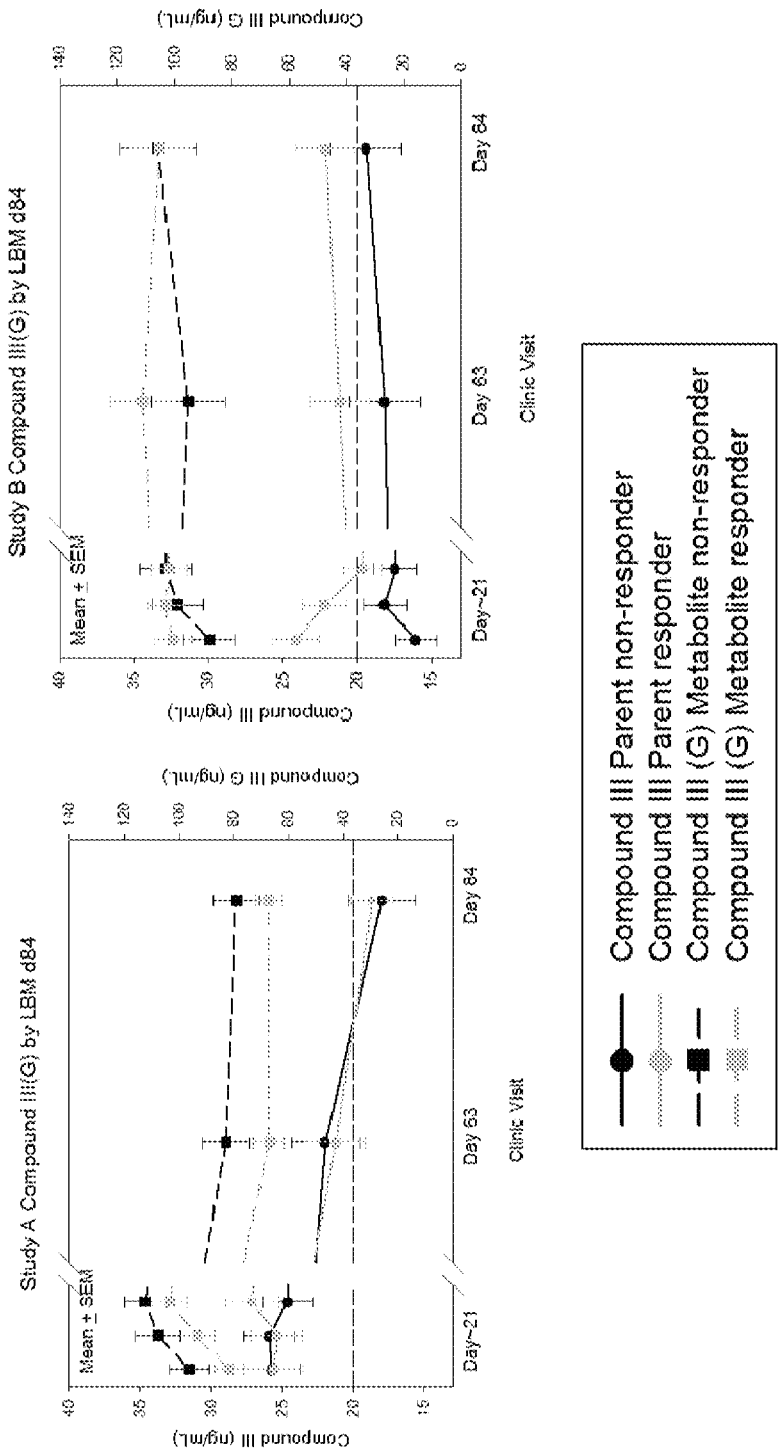
FIG. 26 shows plasma concentrations of compound III were lower in Study B LBM nonresponders.
Figure 27:
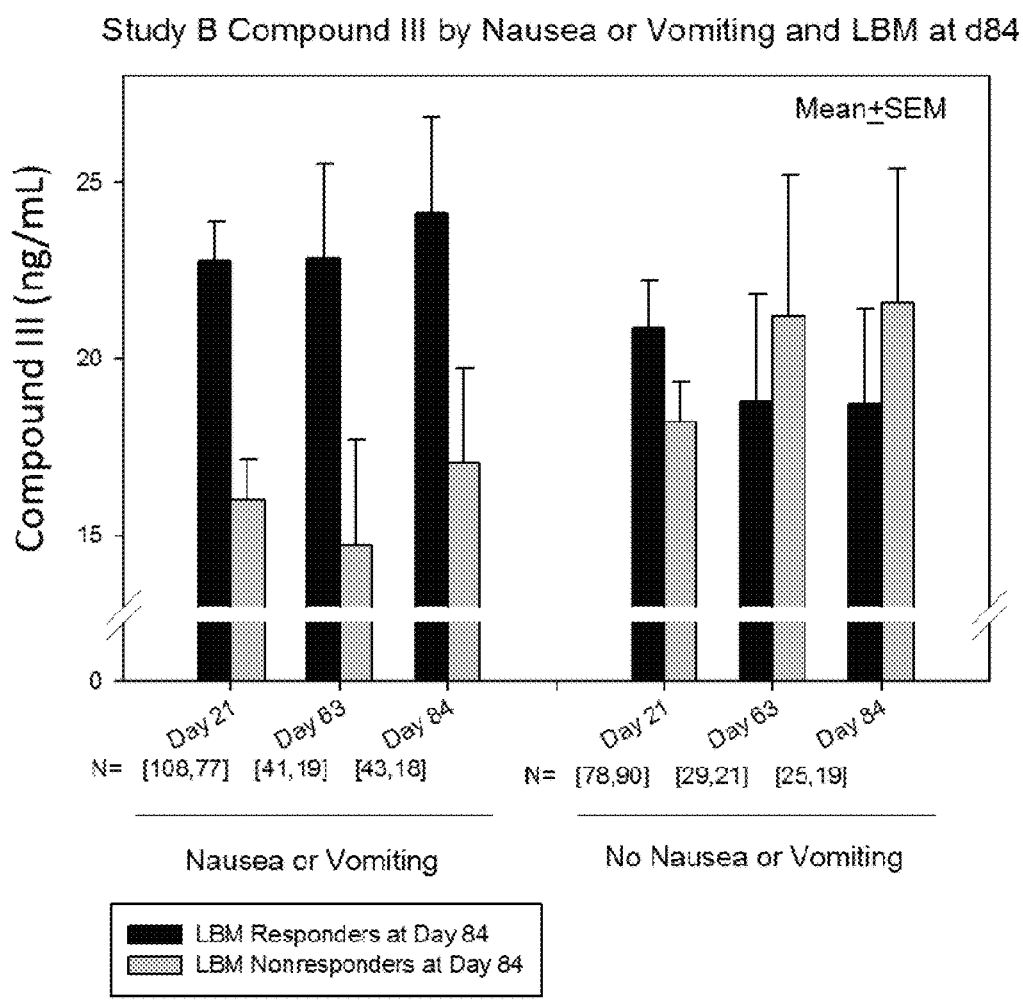
FIG. 27 shows LBM nonresponders who reported nausea and vomiting had lower Compound III levels in Study B. Compound S-(III) levels were similar in LBM responders and non-responders who did NOT report nausea and vomiting

The non responders also had adverse effects as demonstrated in FIGS. 26 and 27.

FIG. 26 demonstrates that the plasma concentrations of Compound III were lower in Study B LBM nonresponders. FIG. 27 (left panel) demonstrates that LBM nonresponders who reported nausea and vomiting had lower Compound III levels in Study B. FIG. 27 (right panel) demonstrates that Compound III levels were similar in LBM responders and non-responders who did not report nausea and vomiting.

Only minor differences in adverse events were observed between the groups treated with Compound III 3 mg and placebo in the Study A and Study B, however, there were notable differences in the adverse event profile between studies with anemia and other hematologic toxicities more prevalent in the Study B (platinum plus non-taxane) clinical trial.

Example 17

Hemoglobin Concentrations Following Study A and Study B

Figure 28:
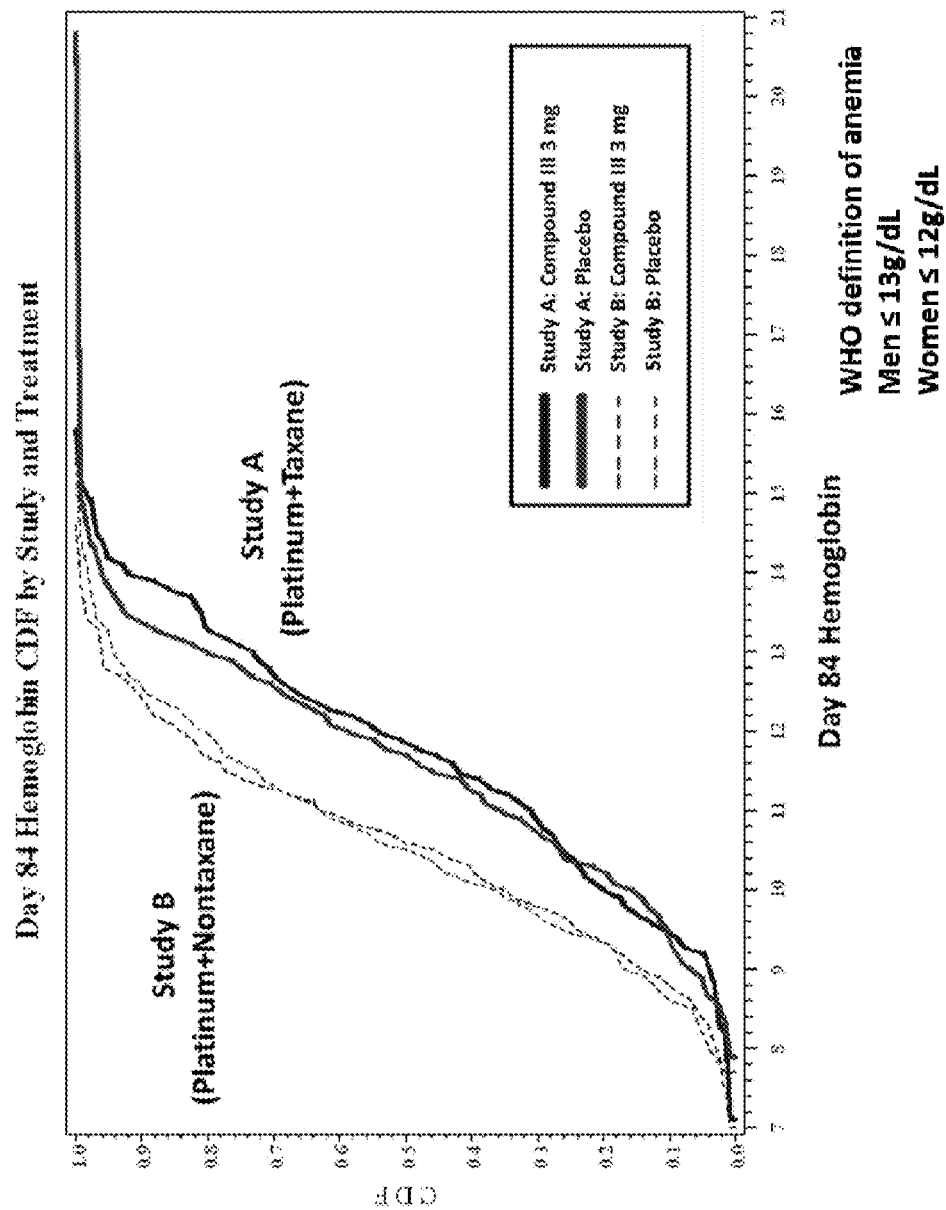
FIG. 28 shows Study B Platinum+Nontaxane subjects had lower hemoglobin levels. WHO definition of anemia Men ≤13 g/dL; Women ≤12 g/dL.
Figure 29:
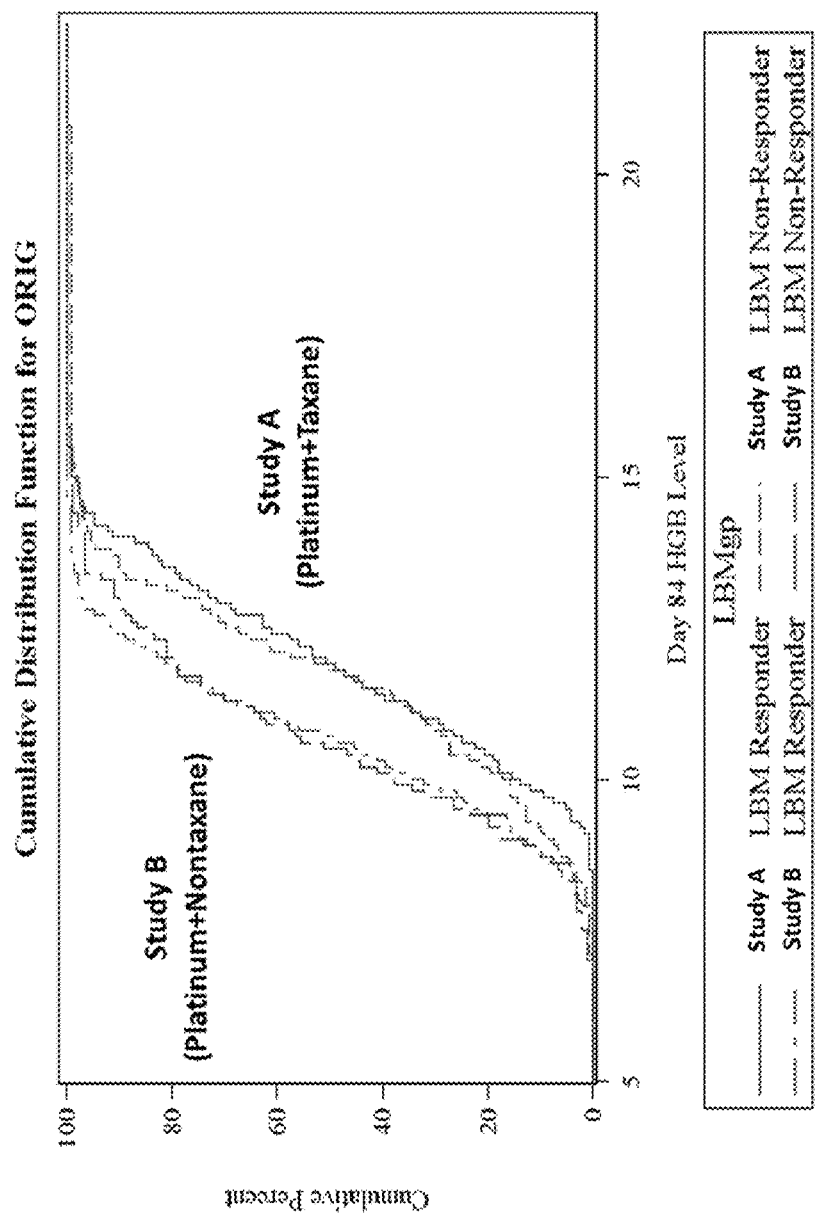
FIG. 29 depicts LBM benefit not affected by hemoglobin concentrations.

FIG. 28 shows that Study B (platinum+nontaxane) subjects had lower hemoglobin levels. However, the hemoglobin levels did not affect LBM response (Table 26 and FIG. 29). Current understanding of the ability of Compound III to build or maintain LBM is not thought to rely on sufficient hemoglobin for muscle oxygenation and respiration.

TABLE 26

Responders analyses: Lean Body Mass (LBM) maintain or increase

| | Hemoglobin (g/dL), median (range) | | |
|---|---|---|---|
| Study A | Nonresponders (n = 132) | Responders (n = 116) | p-value |
| Day 84 | 11.80 (7.10-20.80) | 11.90 (8.5-15.80) | 0.2587 |

| | Hemoglobin (g/dL), median (range) | | |
|---|---|---|---|
| Study B | Nonresponders (n = 90) | Responders (n = 134) | p-value |
| Day 84 | 10.50 (7.00-15.50) | 10.70 (7.70-14.60) | 0.7845 |

Figure 30:
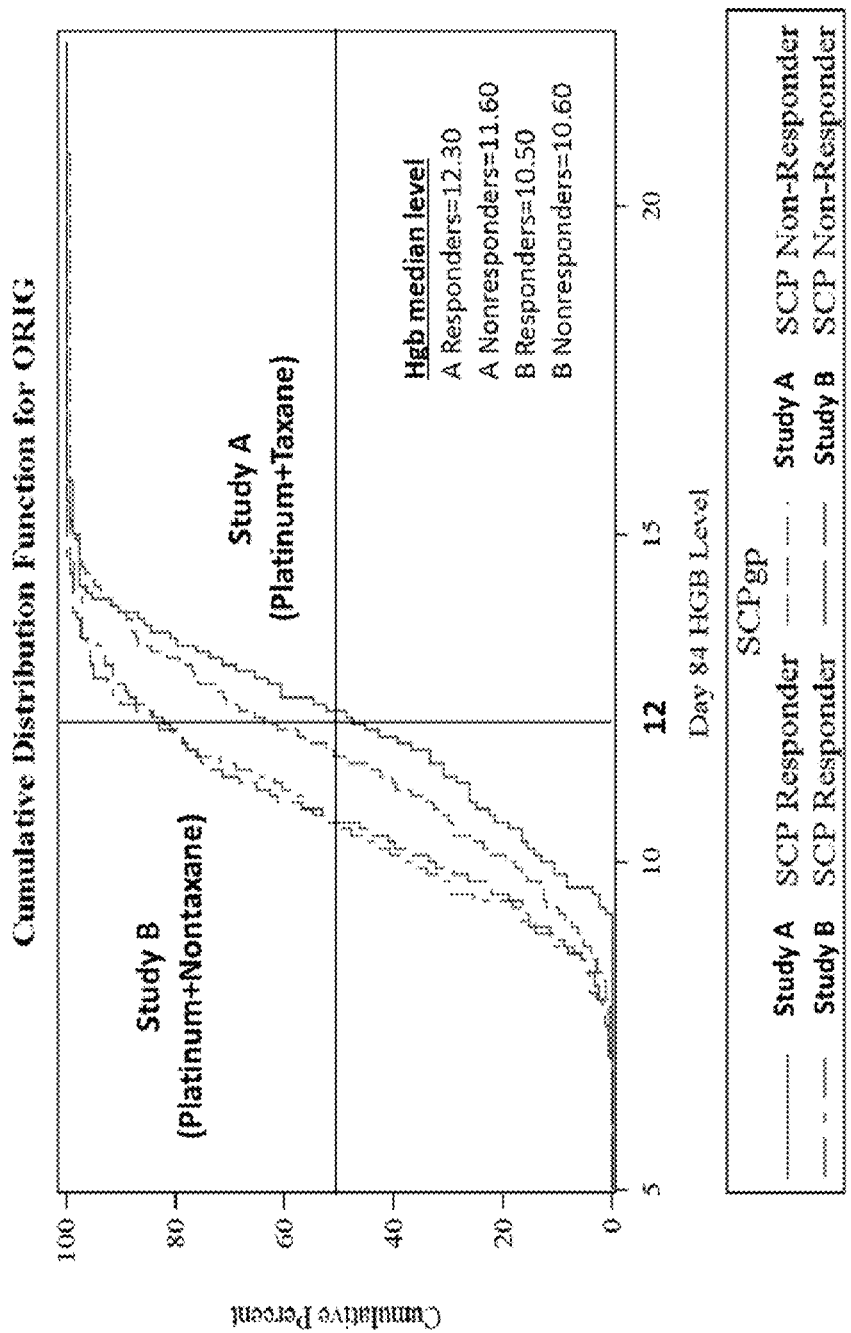
FIG. 30 shows physical function benefit of new muscle is associated with hemoglobin concentrations.

However, hemoglobin levels were related to the ability of LBM responders to have a stair climb test benefit (Table 27 and FIG. 30). Anemia, manifest in this case as a reduction in hemoglobin, is a well-established cause of weakness, fatigue, deconditioning, and loss of physical function which could influence the results of a functional endpoint such as SCP in response to maintained or increased LBM. The overall lower hemoglobin levels in Study B relative to Study A suggest that LBM responders in Study B may have lacked sufficient hemoglobin to translate drug mediated LBM effects into SCP performance.

TABLE 27

Responders analyses: Stair Climb Power (SCP) ≥10% increase

| Study A | Hemoglobin (g/dL), median (range) | | |
|---|---|---|---|
| | Nonresponders (n = 174) | Responders (n = 86) | p-value |
| Day 84 | 11.60 (7.10-20.80) | 12.30 (9.20-15.80) | 0.0152 |

| Study B | Hemoglobin (g/dL), median (range) | | |
|---|---|---|---|
| | Nonresponders (n = 158) | Responders (n = 71) | p-value |
| Day 84 | 10.60 (7.00-15.50) | 10.50 (7.70-14.60) | 0.8250 |

Example 18

Studies of Compound of Formula S-(III) on Knockout Mice

Dystrophin (DMD) homozygous null nice (−/−) and utrophin (UTRN) heterozygous mice (+/−) were obtained from JAX labs. The animals were used to breed DMD (−/−) UTRN (+/+) and DMD (−/−) UTRN (−/−) mice.

When mice attained 4-6 weeks of age, male mice were castrated and treated as indicated in Table 28.

TABLE 28

Study Design

| Group No. | Mice | Treatment | Duration | N |
|---|---|---|---|---|
| 1 | DMD (−/−) UTRN (−/−) | Vehicle | 12 weeks | 8 |
| 2 | DMD (−/−) UTRN (−/−) | 10 mg/kg/day S-(III) | 12 weeks | 8 |
| 3 | DMD (−/−) UTRN (−/−) | 10 mg/kg/day S-(V) | 12 weeks | 8 |
| 4 | DMD (−/−) UTRN (−/−) | 10 mg/kg/day S-(IV) | 12 weeks | 8 |
| 5 | Wildtype | Vehicle | 12 weeks | 8 |
| 6 | Wildtype | 10 mg/kg/day S-(III) | 12 weeks | 8 |
| 7 | Wildtype | 10 mg/kg/day S-(V) | 12 weeks | 8 |
| 8 | Wildtype | 10 mg/kg/day S-(IV) | 12 weeks | 8 |
| 9 | DMD (−/−) UTRN (−/−) | Vehicle | till death (~20 weeks) | 8 |
| 10 | DMD (−/−) UTRN (−/−) | 10 mg/kg/day S-(III) | till death (~20 weeks) | 8 |
| 11 | DMD (−/−) UTRN (−/−) | 10 mg/kg/day S-(V) | till death (~20 weeks) | 8 |
| 12 | DMD (−/−) UTRN (−/−) | 10 mg/kg/day S-(IV) | till death (~20 weeks) | 8 |
| 13 | DMD (−/−) UTRN (+/+) | Vehicle | 12 weeks | 8 |
| 14 | DMD (−/−) UTRN (+/+) | 10 mg/kg/day S-(III) | 12 weeks | 8 |
| 15 | DMD (−/−) UTRN (+/+) | 10 mg/kg/day S-(V) | 12 weeks | 8 |
| 16 | DMD (−/−) UTRN (+/+) | 10 mg/kg/day S-(IV) | 12 weeks | 8 |

Figure 38A:
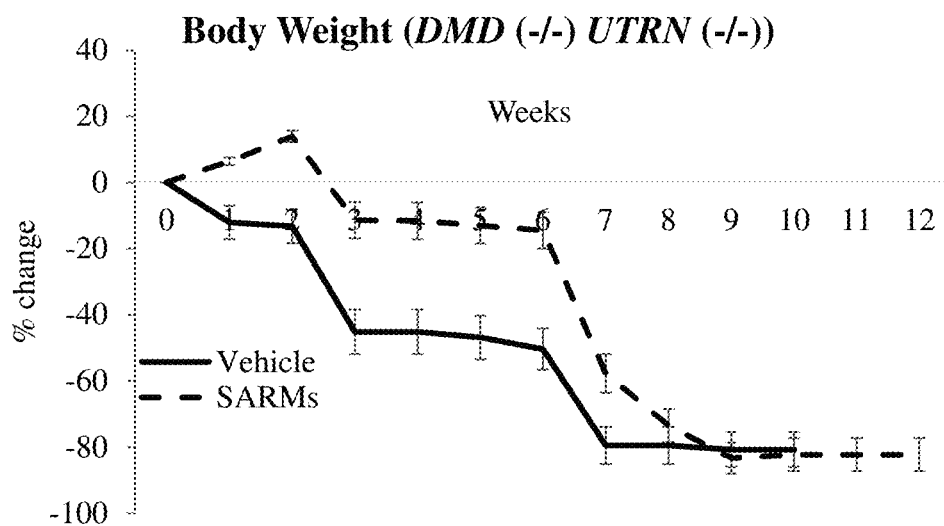
FIGS. 38A-38C show the effects of 'SARMs' in the double knock-out mouse model.
Figure 38B:
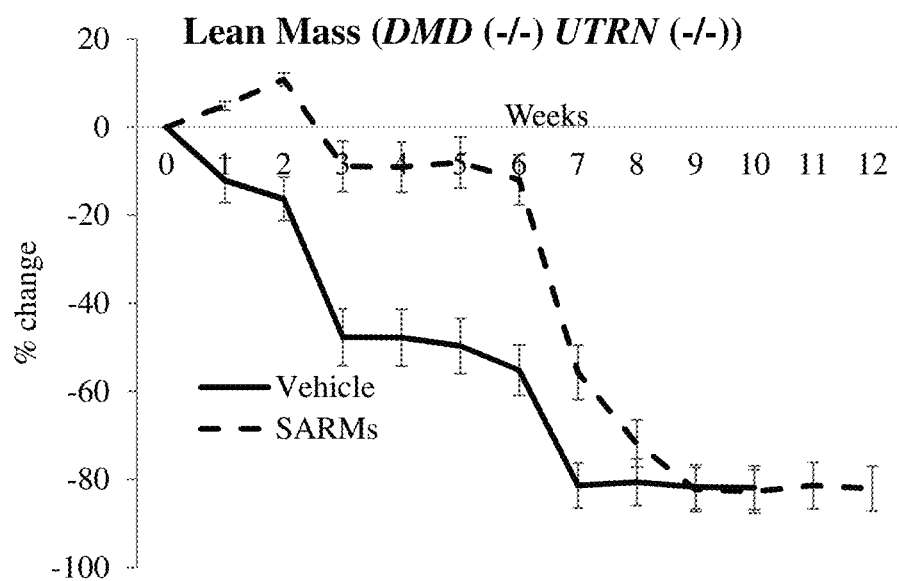
Figure 38C:
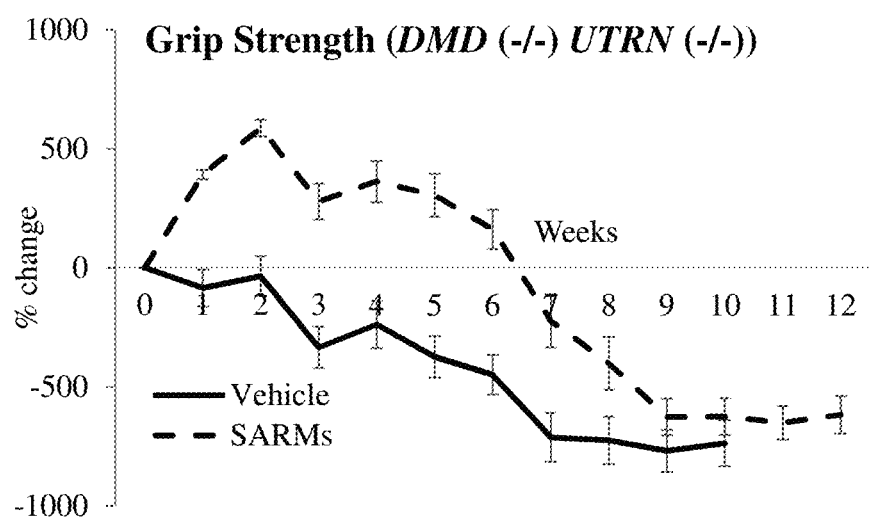
Figure 39A:
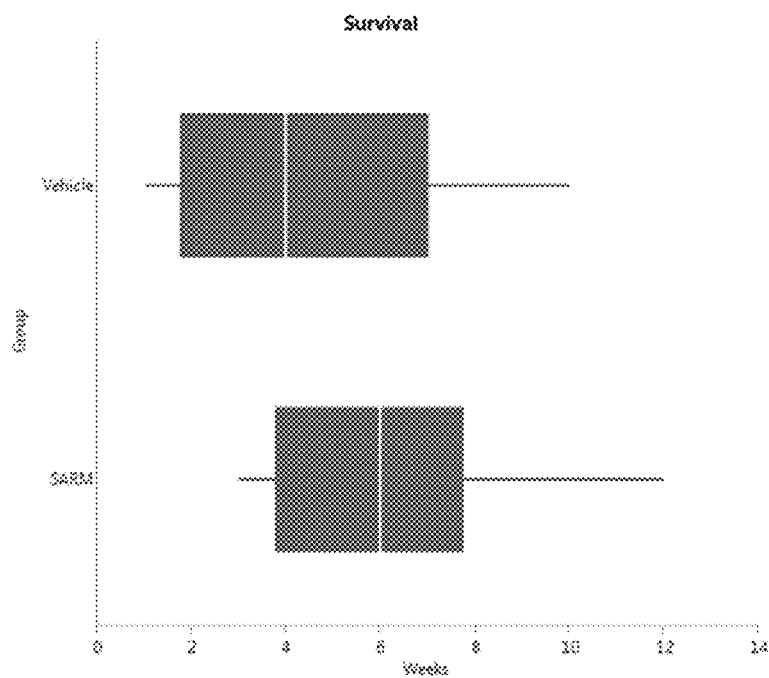
FIGS. 39A and 39B show that compounds of formulas S-(III) or S-(V) (combined data labeled as 'SARM') and S-(III), respectively, increased the survival by 50-70% in DMD (−/−) UTRN (−/−) double knockout mice.

Compounds of formulas S-(III), S-(VI), and S-(V) were used at 10 mg per kg per day subcutaneously (mpk/day s.c.). Compound of formula S-(III) is the S-isomer of Compound III or (S)—N-(4-cyano-3-(trifluoromethyl)phenyl)-3-(4-cyanophenoxy)-2-hydroxy-2-methylpropanamide. Compound of formula S-(IV) is (S)—N-(3-chloro-4-cyano-phenyl)-3-(4-cyanophenoxy)-2-hydroxy-2-methylpropanamide. Compound of formula S-(V) is (S)—N-(4-cyano-3-(trifluoromethyl)phenyl)-3-(4-cyano-3-fluorophenoxy)-2-hydroxy-2-methylpropanamide. In FIGS. 38A-38C, 'SARMs' is cumulative data across groups 2, 3, and 4. In FIG. 39A, the labeling as 'SARM' indicates cumulative data across groups 2 and 4. One set of UTRN wildtype mice (i.e., the mdx model or DMD (−/−) UTRN (+/+) mice) were also used (i.e., groups 13-16) to evaluate the effect of S-(III) (and other SARMs) on Duchenne muscular dystrophy through UTRN up-regulation.

Weekly body weight, MRI measurements, and grip strengths were measured (body weight: biweekly; MRI scan: once every 2 weeks or once every week; and grip strength: Once every 2 weeks or once every week).

Groups 1-8 and 13-16 were sacrificed after 12 weeks of treatment and various tissues were excised, weighed, and stored appropriately for further analysis. At sacrifice, blood was collected for serum biochemical markers (ALT, AST, glucose, cholesterol creatinine, creatine kinase, pyruvate, and others). Echocardiogram was performed in one set of knockout mice. As inflammation is considered as one of the primary pathogenic mechanisms, a serum inflammatory marker panel was evaluated. Organs (prostate, seminal vesicles, levator ani, soleus, gastrocnemious, heart, lungs, and liver) were weighed and stored for gene expression studies and histology. Levator ani, soleus, extensor digitorum longus (EDL), and gastrocnemious muscles were processed to measure the tension (if possible), histology and gene expression.

Figure 37A:
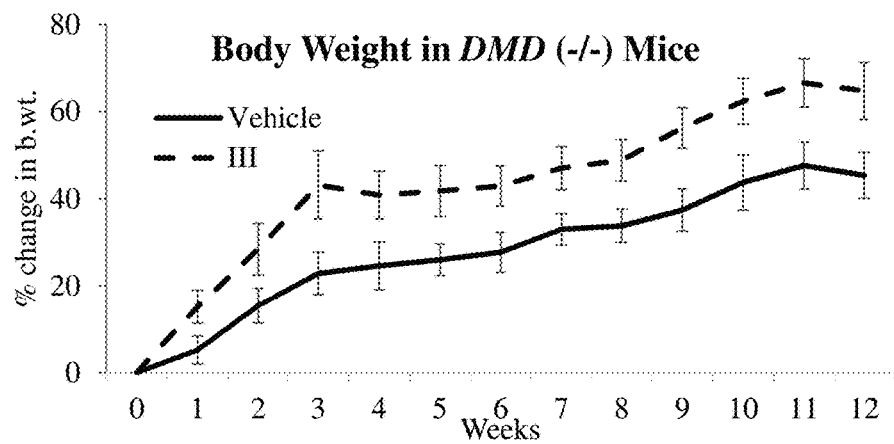
FIGS. 37A-37D show that compound of formula S-(III) in the DMD single knockout or mdx mouse model (DMD (−/−) UTRN (+/+)), e.g., increased body weight and lean mass of DMD knockout mice.
Figure 37B:
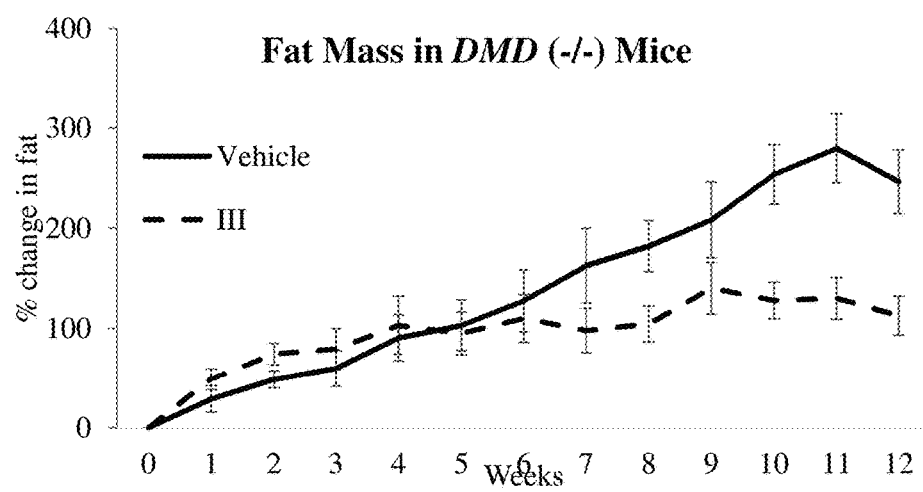
Figure 37C:
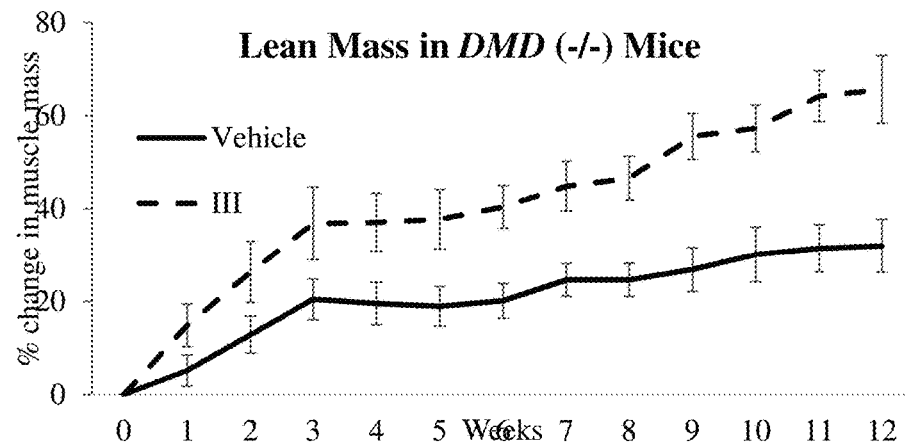
Figure 37D:
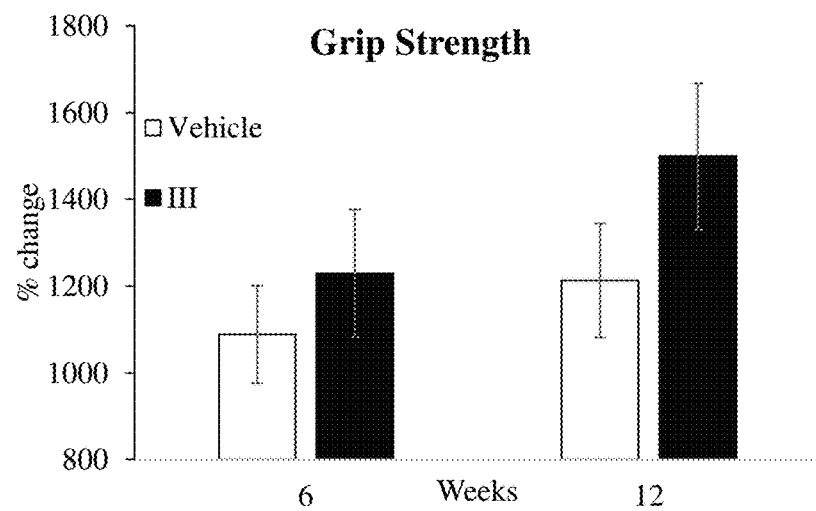

FIGS. 37A-37D show that DMD (−/−) UTRN (+/+) mice when treated with S-(III) demonstrated a significant increase in body weight (FIG. 37A), lean [muscle] mass (FIG. 37C), and grip strength (FIG. 37D), and also a decrease in fat mass (FIG. 37B).

FIGS. 38A-38C show that double knock out mice (DMD (−/−) UTRN (−/−)) when treated with vehicle significantly and rapidly lost their body weight, lean [muscle] mass, and grip strength. However, 'SARMs' (S-(III), S-(VI), and S-(V); data shown is cumulative across groups 1-4) delayed the deterioration of these measurements significantly. Further, 'SARMs' enhanced the ability of these mice to be ambulatory.

Figure 39B:
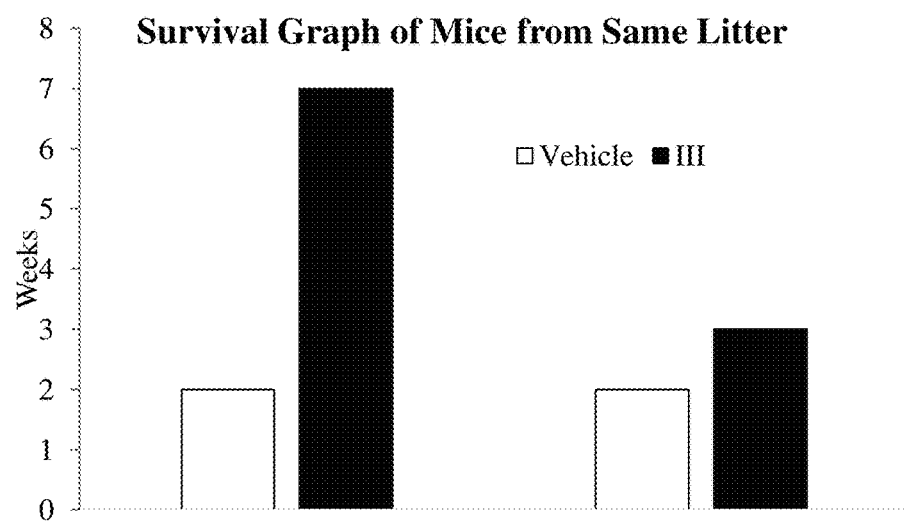
Figure 40A:
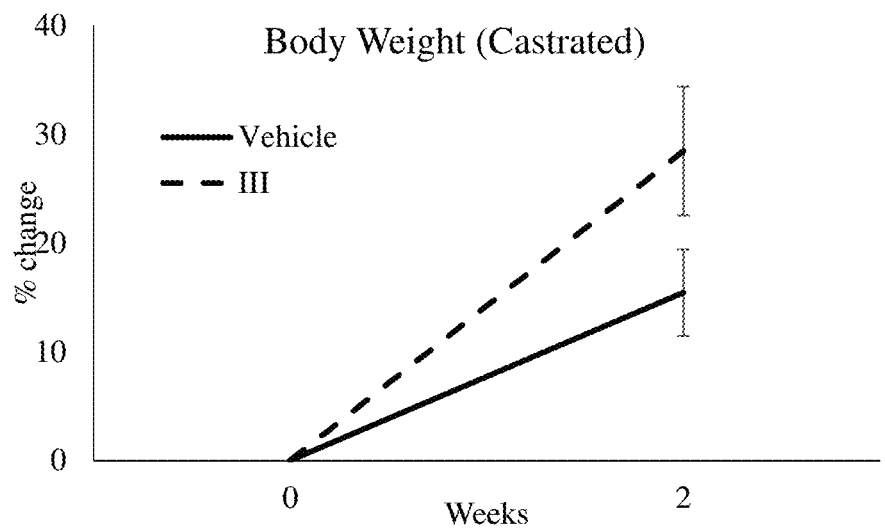
FIGS. 40A and 40B allow the comparison of the castrated mdx mice to intact control mdx mice in terms of body weight.
Figure 40B:
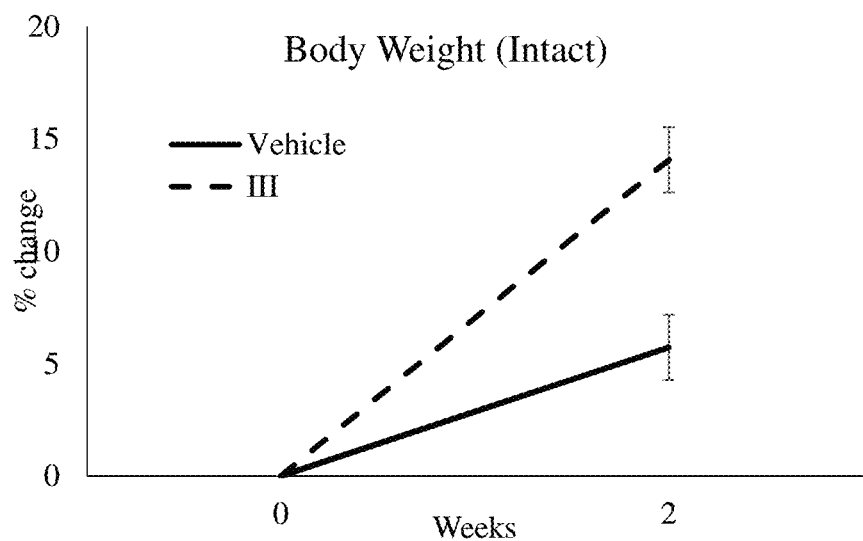
Figure 41A:
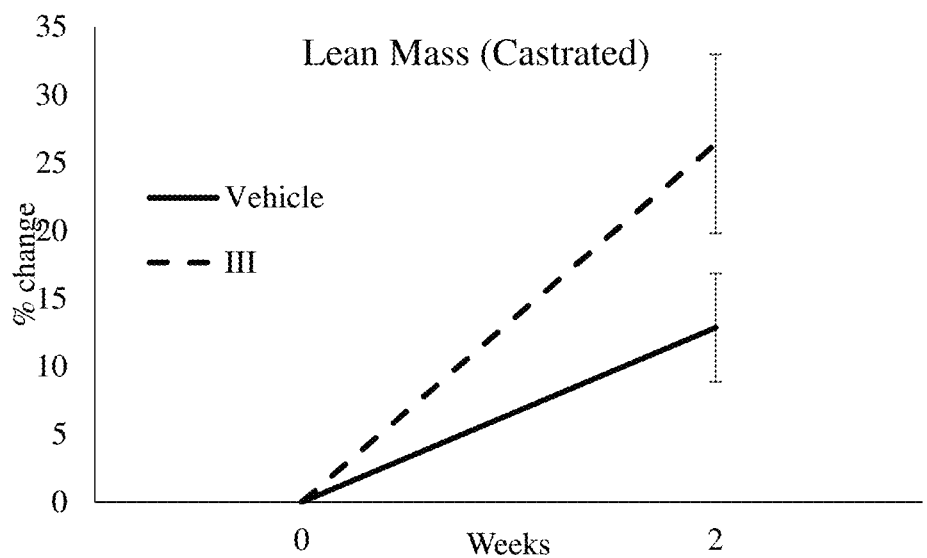
FIGS. 41A and 41B allow the comparison of the castrated mdx mice to intact control mdx mice in terms of lean mass.
Figure 41B:
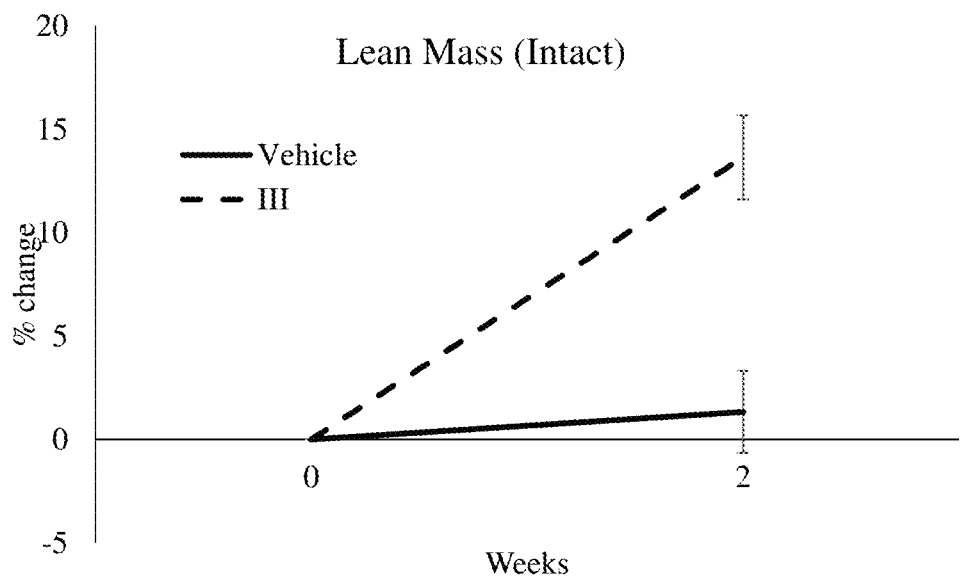

DMD (−/−) UTRN (−/−) male mice were castrated and treated with vehicle or a compound of this invention at 10 mpk s.c. The number of weeks the mice survived was recorded and expressed. The 'SARM' treated group combines the data for S-(III) and S-(V) treated animals together. Animals from the same litter are shown in FIG. 39B. FIGS. 39A (cumulative data for S-(III) and S-(V) and 39B (S-(III)) show that due to enhancement in body weight and lean

[muscle] mass, the [castrated] DMD (−/−) UTRN (−/−) mice treated with the indicated compounds of the invention lived longer by approximately 40-50% compared to [castrated] vehicle-treated control mice from the same litter, suggesting the result is not due to genetic variation but drug efficacy. Cumulatively, this suggests that patients with Duchenne muscular dystrophy treated with S-(III) (or another SARM of this invention) are expected to not only benefit from improved growth and strength (e.g., improved physical function and quality of life such as longer ambulation) but also may live longer lives. A possible explanation for the survival benefit may be due, in part, to improved cardiac function.

FIGS. 40A and 40B and FIGS. 41A and 41B show that intact and castrated mdx mice, i.e., DMD (−/−) UTRN (+1+), were both effected by S-(III) treatment. The effects of S-(III) reported above for castrated mdx mice were also seen in intact mdx mice. E.g., S-(III) increased body weight (FIGS. 40A-40B) and lean mass (FIGS. 41A-41B) in castrated and intact mdx mice. This suggests that the therapeutic effects for Duchenne muscular dystrophy were not an artifact of the use of castrated animals to model the disease.

It will be appreciated by a person skilled in the art that the present invention is not limited by what has been particularly shown and described hereinabove. Rather, the scope of the invention is defined by the claims that follow.

What is claimed is:

1. A method of treating, reducing the severity, reducing the incidence, or reducing cardiovascular failure in a subject suffering from Duchenne muscular dystrophy, comprising the step of administering to said subject a selective androgen receptor modulator (SARM) compound represented by the structure of formula S-(III):

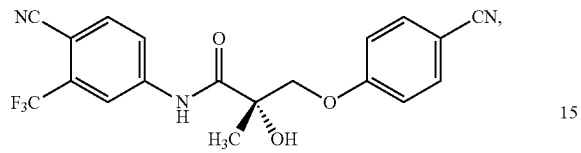

S-(III)

or its pharmaceutically acceptable salt.

2. The method of claim 1, wherein said method further increases the physical function of said subject.

3. The method of claim 1, wherein said method further increases the quality of life of said subject.

4. The method of claim 1, wherein said method increases the survival of said subject.

5. The method of claim 1, wherein said method further delays onset or improves symptoms of respiratory function.

* * * * *

SEQUENCE LISTING

```
<160> NUMBER OF SEQ ID NOS: 23

<210> SEQ ID NO 1
<211> LENGTH: 21
<212> TYPE: DNA
<213> ORGANISM: Artificial Sequence
<220> FEATURE:
<223> OTHER INFORMATION: MSX-1 Forward Primer

<400> SEQUENCE: 1
aacccagcca cagactaaag a                                             21

<210> SEQ ID NO 2
<211> LENGTH: 20
<212> TYPE: DNA
<213> ORGANISM: Artificial Sequence
<220> FEATURE:
<223> OTHER INFORMATION: MSX-1 Reverse Primer

<400> SEQUENCE: 2
tcccttgttc tcgttccttc                                               20

<210> SEQ ID NO 3
<211> LENGTH: 24
<212> TYPE: DNA
<213> ORGANISM: Artificial Sequence
<220> FEATURE:
<223> OTHER INFORMATION: MSX-1 TaqMan Probe

<400> SEQUENCE: 3
aaagaggagc ggaaaagagg gctg                                          24

<210> SEQ ID NO 4
<211> LENGTH: 20
<212> TYPE: DNA
<213> ORGANISM: Artificial Sequence
<220> FEATURE:
<223> OTHER INFORMATION: APIG1 Forward Primer

<400> SEQUENCE: 4
gggtccgagt tcttggataa                                               20

<210> SEQ ID NO 5
<211> LENGTH: 20
<212> TYPE: DNA
<213> ORGANISM: Artificial Sequence
<220> FEATURE:
<223> OTHER INFORMATION: APIG1 reverse Primer

<400> SEQUENCE: 5
atcctgagga aggagggagt                                               20
```

```
<210> SEQ ID NO 6
<211> LENGTH: 24
<212> TYPE: DNA
<213> ORGANISM: Artificial Sequence
<220> FEATURE:
<223> OTHER INFORMATION: APIG1 TaqMan Probe

<400> SEQUENCE: 6
ggacagggag cgaagtttcc tcaa                                              24

<210> SEQ ID NO 7
<211> LENGTH: 19
<212> TYPE: DNA
<213> ORGANISM: Artificial Sequence
<220> FEATURE:
<223> OTHER INFORMATION: AXIN-1 Forward Primer

<400> SEQUENCE: 7
attccaagga cctgcaacg                                                    19

<210> SEQ ID NO 8
<211> LENGTH: 18
<212> TYPE: DNA
<213> ORGANISM: Artificial Sequence
<220> FEATURE:
<223> OTHER INFORMATION: AXIN-1 Reverse Primer

<400> SEQUENCE: 8
gagagggcgt ggtcagtg                                                     18

<210> SEQ ID NO 9
<211> LENGTH: 20
<212> TYPE: DNA
<213> ORGANISM: Artificial Sequence
<220> FEATURE:
<223> OTHER INFORMATION: AXIN-1 TaqMan Probe

<400> SEQUENCE: 9
cgcctctccc actccgctct                                                   20

<210> SEQ ID NO 10
<211> LENGTH: 20
<212> TYPE: DNA
<213> ORGANISM: Artificial Sequence
<220> FEATURE:
<223> OTHER INFORMATION: BATF-1 Forward Primer

<400> SEQUENCE: 10
ctggacttaa ggggtgagga                                                   20

<210> SEQ ID NO 11
<211> LENGTH: 20
<212> TYPE: DNA
<213> ORGANISM: Artificial Sequence
<220> FEATURE:
<223> OTHER INFORMATION: BATF-1 Reverse Primer

<400> SEQUENCE: 11
ggagaggaca accaggaaaa                                                   20

<210> SEQ ID NO 12
<211> LENGTH: 22
<212> TYPE: DNA
<213> ORGANISM: Artificial Sequence
<220> FEATURE:
<223> OTHER INFORMATION: BATF-1 TaqMan Probe
```

```
<400> SEQUENCE: 12
tgagcagctg ctttcggctg aa                                        22

<210> SEQ ID NO 13
<211> LENGTH: 20
<212> TYPE: DNA
<213> ORGANISM: Artificial Sequence
<220> FEATURE:
<223> OTHER INFORMATION: SHC-1 Forward Primer

<400> SEQUENCE: 13
taactcggga aagtgggaag                                           20

<210> SEQ ID NO 14
<211> LENGTH: 20
<212> TYPE: DNA
<213> ORGANISM: Artificial Sequence
<220> FEATURE:
<223> OTHER INFORMATION: SHC-1 Reverse Primer

<400> SEQUENCE: 14
agcttaggtt accgctccaa                                           20

<210> SEQ ID NO 15
<211> LENGTH: 26
<212> TYPE: DNA
<213> ORGANISM: Artificial Sequence
<220> FEATURE:
<223> OTHER INFORMATION: SHC-1 TaqMan Probe

<400> SEQUENCE: 15
aataaagttt ctccagggag gcaggg                                    26

<210> SEQ ID NO 16
<211> LENGTH: 32
<212> TYPE: DNA
<213> ORGANISM: Artificial Sequence
<220> FEATURE:
<223> OTHER INFORMATION: NFkB1 Forward Primer

<400> SEQUENCE: 16
ctcgagagag tatggaccgc atgactctat ca                             32

<210> SEQ ID NO 17
<211> LENGTH: 32
<212> TYPE: DNA
<213> ORGANISM: Artificial Sequence
<220> FEATURE:
<223> OTHER INFORMATION: NFkB1 Reverse Primer

<400> SEQUENCE: 17
acgcgtagag agagcataca gacagacgga ca                             32

<210> SEQ ID NO 18
<211> LENGTH: 20
<212> TYPE: DNA
<213> ORGANISM: Artificial Sequence
<220> FEATURE:
<223> OTHER INFORMATION: PCBP2 Forward Primer

<400> SEQUENCE: 18
agatgatggg aggtttggag                                           20

<210> SEQ ID NO 19
```

```
<211> LENGTH: 20
<212> TYPE: DNA
<213> ORGANISM: Artificial Sequence
<220> FEATURE:
<223> OTHER INFORMATION: PCBP2 Reverse Primer

<400> SEQUENCE: 19
gcctaaacca gaaaccaagg                                          20

<210> SEQ ID NO 20
<211> LENGTH: 26
<212> TYPE: DNA
<213> ORGANISM: Artificial Sequence
<220> FEATURE:
<223> OTHER INFORMATION: PCBP2 TaqMan Probe

<400> SEQUENCE: 20
atttggggta agggaggtga aggagg                                   26

<210> SEQ ID NO 21
<211> LENGTH: 25
<212> TYPE: DNA
<213> ORGANISM: Artificial Sequence
<220> FEATURE:
<223> OTHER INFORMATION: PSA Forward Primer

<400> SEQUENCE: 21
gcctggatct gagagagata tcatc                                    25

<210> SEQ ID NO 22
<211> LENGTH: 25
<212> TYPE: DNA
<213> ORGANISM: Artificial Sequence
<220> FEATURE:
<223> OTHER INFORMATION: PSA Reverse Primer

<400> SEQUENCE: 22
acaccttttt ttttctggat tgttg                                    25

<210> SEQ ID NO 23
<211> LENGTH: 28
<212> TYPE: DNA
<213> ORGANISM: Artificial Sequence
<220> FEATURE:
<223> OTHER INFORMATION: PSA TaqMan Probe

<400> SEQUENCE: 23
tgcaaggatg cctgctttac aaacatcc                                 28
```